United States Patent
Liu et al.

(10) Patent No.: US 11,257,350 B2
(45) Date of Patent: Feb. 22, 2022

(54) SYSTEM AND METHOD FOR OPPORTUNITY-BASED REMINDING OR COMPLIANCE WITH ONE OR MORE HEALTH PROTOCOLS

(71) Applicant: Microsensor Labs, LLC, Chicago, IL (US)

(72) Inventors: Peng Liu, Chicago, IL (US); Yang Liu, Chicago, IL (US); Jiapeng Huang, Louisville, KY (US); Darius Cepulis, Forest Park, IL (US)

(73) Assignee: Microsensor Labs, LLC, Chicago, IL (US)

( * ) Notice: Subject to any disclaimer, the term of this patent is extended or adjusted under 35 U.S.C. 154(b) by 0 days.

(21) Appl. No.: 16/895,435

(22) Filed: Jun. 8, 2020

(65) Prior Publication Data

US 2020/0302775 A1 Sep. 24, 2020

Related U.S. Application Data

(60) Continuation-in-part of application No. 16/557,191, filed on Aug. 30, 2019, now Pat. No. 10,748,410, and
(Continued)

(51) Int. Cl.
*G08B 21/24* (2006.01)
*G06K 7/10* (2006.01)
(Continued)

(52) U.S. Cl.
CPC ....... *G08B 21/245* (2013.01); *G06K 7/10366* (2013.01); *G16H 40/20* (2018.01); *G01H 1/00* (2013.01); *G01P 15/18* (2013.01)

(58) Field of Classification Search
CPC .. G08B 21/245; G06K 7/10366; G16H 40/20; G01P 15/18; G01H 1/00
See application file for complete search history.

(56) References Cited

U.S. PATENT DOCUMENTS

| | | |
|---|---|---|
| 5,870,015 A | 2/1999 | Hinkel |
| 6,028,520 A | 2/2000 | Maehre |

(Continued)

FOREIGN PATENT DOCUMENTS

| | | |
|---|---|---|
| EP | 3118828 A1 | 1/2017 |
| WO | 2012037192 A1 | 3/2012 |

(Continued)

OTHER PUBLICATIONS

International Search Report for PCT Application No. US2018/026238, dated Jul. 23, 2018.
(Continued)

*Primary Examiner* — Hongmin Fan
(74) *Attorney, Agent, or Firm* — Lempia Summerfield Katz LLC

(57) ABSTRACT

A system and method for opportunity-based hygiene monitoring and/or reminding is disclosed. Healthcare providers may have various opportunities to interact with a patient. As such, an opportunity-based focus in managing a healthcare environment may assist in assessing the various opportunities when interacting with the patient. For example, an opportunity-based analysis may be used for protocol compliance, such as compliance with hand hygiene protocols and/or PPE protocols. Further, infection analysis, patient care billing, staff locating, or workload analysis may be opportunity based in order to more efficiently manage the healthcare environment.

24 Claims, 70 Drawing Sheets

Related U.S. Application Data a continuation-in-part of application No. PCT/US2019/025751, filed on Apr. 4, 2019, and a continuation-in-part of application No. 16/148,683, filed on Oct. 1, 2018, now Pat. No. 10,679,488, said application No. 16/557,191 is a division of application No. 15/946,537, filed on Apr. 5, 2018, now Pat. No. 10,403,121, said application No. 16/148,683 is a continuation-in-part of application No. 15/946,537, filed on Apr. 5, 2018, now Pat. No. 10,403,121.

(60) Provisional application No. 62/482,146, filed on Apr. 5, 2017.

(51) Int. Cl.
*G16H 40/20* (2018.01)
*G01P 15/18* (2013.01)
*G01H 1/00* (2006.01)

(56) References Cited

U.S. PATENT DOCUMENTS

| | | |
|---|---|---|
| 6,417,773 B1 | 7/2002 | Vlahos et al. |
| 6,937,155 B2 | 8/2005 | Ballard |
| 8,648,724 B2 | 2/2014 | Forsberg et al. |
| 8,698,637 B2 | 4/2014 | Raichman |
| 9,135,805 B2 | 9/2015 | Freedman et al. |
| 9,483,930 B1 | 11/2016 | Haaland |
| 9,695,981 B2 | 7/2017 | Au |
| 9,747,760 B2 | 8/2017 | Fletcher |
| 9,773,402 B2 | 9/2017 | Raichman |
| 2006/0191068 A1 | 8/2006 | Vlahos et al. |
| 2008/0131332 A1 | 6/2008 | Nguyen |
| 2009/0195385 A1 | 8/2009 | Huang |
| 2010/0073162 A1 | 3/2010 | Johnson et al. |
| 2010/0164728 A1 | 7/2010 | Plost |
| 2011/0193703 A1 | 8/2011 | Payton |
| 2011/0254682 A1 | 10/2011 | Sigrist |
| 2012/0062382 A1 | 3/2012 | Taneff |
| 2012/0256742 A1 | 10/2012 | Snodgrass |
| 2012/0268277 A1 | 10/2012 | Best |
| 2013/0300572 A1 | 11/2013 | Mould-Millman |
| 2014/0266692 A1 | 9/2014 | Freedman |
| 2014/0313055 A1 | 10/2014 | Warkentin et al. |
| 2014/0345726 A1 | 11/2014 | Seggio et al. |
| 2015/0278456 A1 | 10/2015 | Rodriguez |
| 2016/0140832 A1* | 5/2016 | Moore .................... G16H 40/20 340/573.1 |
| 2016/0180695 A1* | 6/2016 | Levchenko .............. G07C 9/28 340/573.1 |
| 2016/0324460 A1 | 11/2016 | Kusens |
| 2016/0379456 A1 | 12/2016 | Nongpiur et al. |
| 2017/0004287 A1 | 1/2017 | O'Toole |
| 2017/0018167 A1 | 1/2017 | Dey |
| 2017/0084161 A1 | 3/2017 | Dey |
| 2017/0294106 A1 | 10/2017 | Thyroff |
| 2017/0372216 A1 | 12/2017 | Awiszus |
| 2018/0122214 A1 | 5/2018 | Freedman |
| 2018/0151054 A1 | 5/2018 | Pi |
| 2018/0357886 A1* | 12/2018 | Tavori ..................... G06F 1/163 |
| 2019/0314843 A1 | 10/2019 | Nour-omid |
| 2020/0321104 A1* | 10/2020 | Lindstrom ............. G16H 40/63 |

FOREIGN PATENT DOCUMENTS

| | | |
|---|---|---|
| WO | 2015179262 A1 | 11/2015 |
| WO | 2017011911 A1 | 1/2017 |
| WO | 2017094016 A1 | 6/2017 |

OTHER PUBLICATIONS

PCT International Preliminary Report on Patentability and Written Opinion of International Searching Authority, corresponding to PCT International Application No. PCT/US2018/026238 dated Oct. 8, 2019.
PCT International Search Report and Written Opinion of International Searching Authority, corresponding to PCT International Application No. PCT/US2019/025751 dated Sep. 11, 2019.
Search Report issued in European Application No. 18722785.5, dated Oct. 13, 2020.
U.S. Office Action for U.S. Appl. No. 15/946,537 dated Oct. 18, 2018.
Wijayasingha, et al.: "A wearable sensing framework for improving personal and oral hygiene for people with developmental disabilities", 2016 IEEE Wireless Health (WH), IEEE, Oct. 25, 2016.
Written Opinion of the International Searching Authority for PCT Application No. US2018/026238, dated Jul. 23, 2018.
International Preliminary Report on Patentability issued in related application No. PCT/US2019/025751, dated Apr. 15, 2021 (16 pages).

* cited by examiner

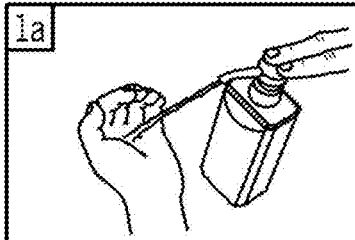 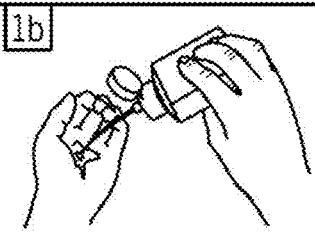 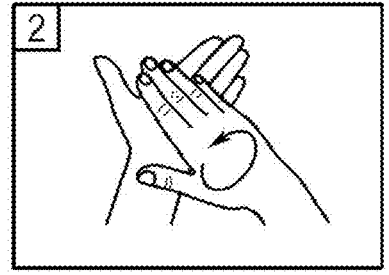

Apply a palmful of the product in a cupped hand, covering all surfaces;

Rub hands palm to palm;

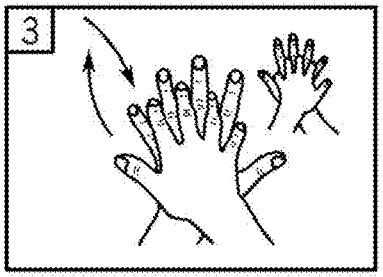 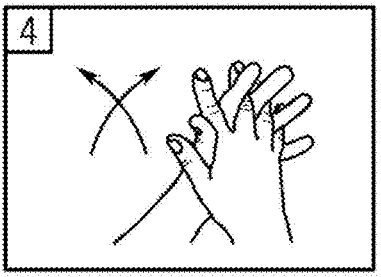 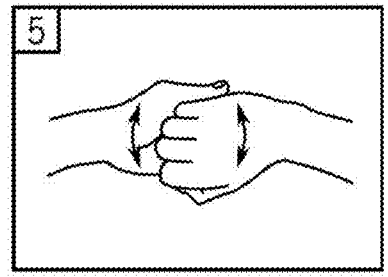

Right palm over left dorsum with interlaced fingers and vice versa;

Palm to palm with fingers interlaced;

Backs of fingers to opposing palms with fingers interlocked;

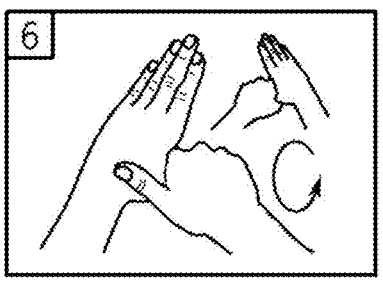 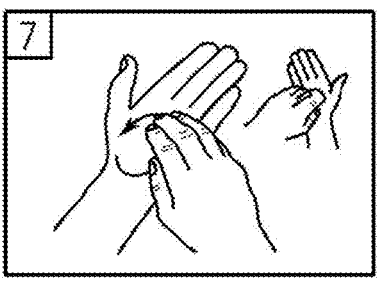 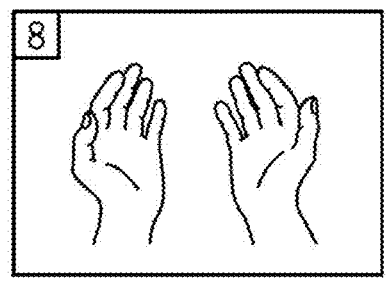

Rotational rubbing of left thumb clasped in right palm and vice versa;

Rotational rubbing, backwards and forward with clasped fingers of right hand in left palm and vice versa;

Once dry; your hands are safe.

FIG. 10A

CLEANWORKS     ▵ MARSHALL JEFFERSON ▽ ⟵ LOGOUT

▵ MANAGER OF CCU
      ▵ NURSE AT CCU

- TODAY
- LAST WEEK
- CUSTOMS
- ⚙ ROOM PRECAUTIONS

| CCU-01 | CCU-02 | CCU-03 |
|---|---|---|
| CONTACT × DROPLET × | STANDARD | CONTACT ENTERIC × |

| CCU-04 | CCU-05 | CCU-06 |
|---|---|---|
| CONTACT | STANDARD | CONTACT × |

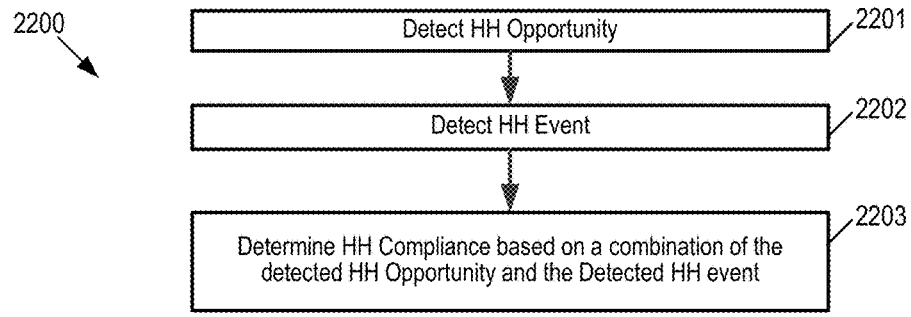
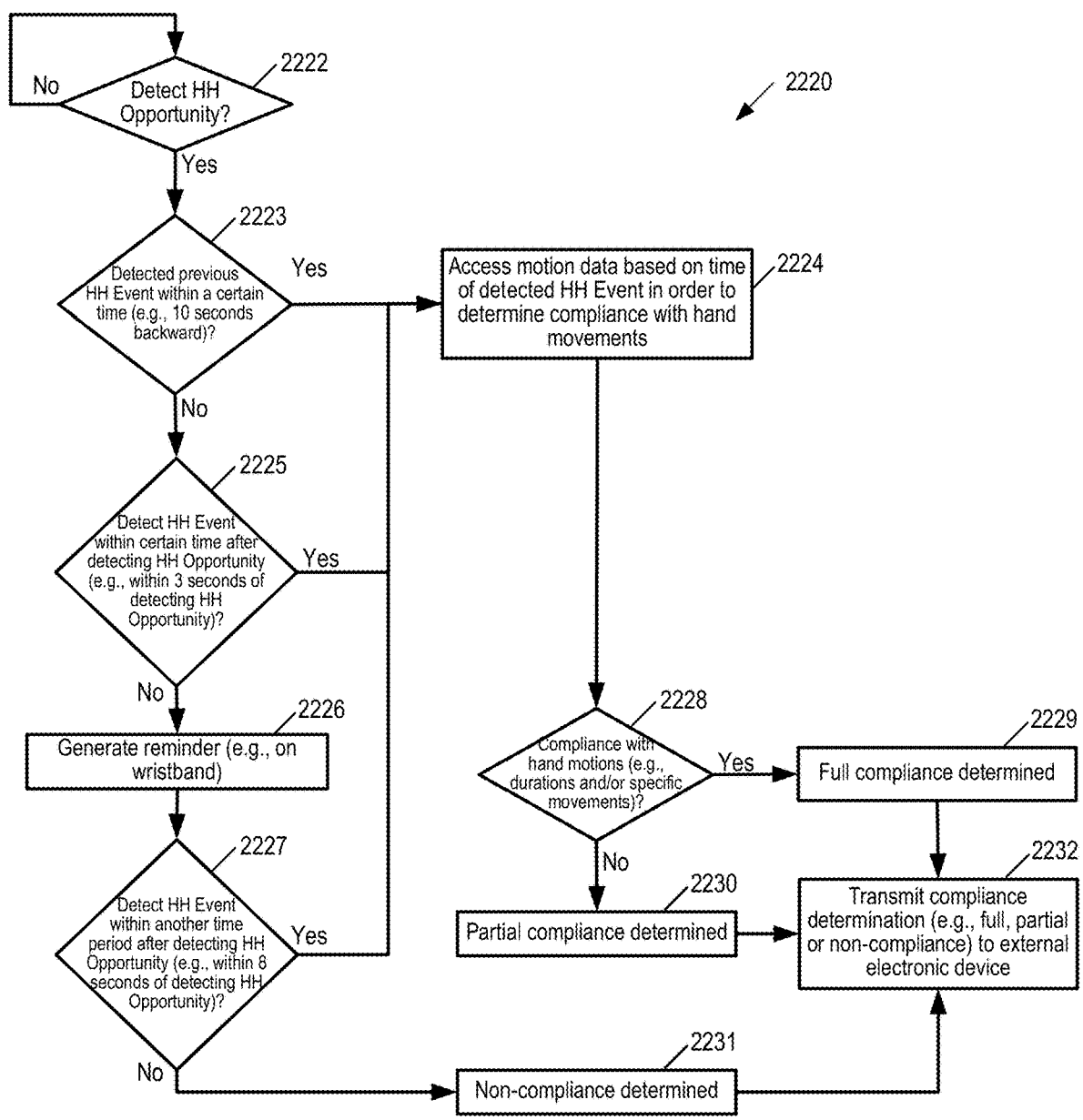
FIG. 22A
FIG. 22B

Infection Spread Analysis

Infection Room
5W Neuro 01

Room Precautions
Gloves, Gown, Mask

Confirmation Date
3/20/2020

Search Start
03/20/2020

Search End
03/27/2020

| Staff | Local Rank | Hand Hygiene | PPE | Total Visit Duration |
|---|---|---|---|---|
| arogers@hospital.com | 0.99 | 65.80% | xx.xx% | 1h 13m |
| lkafer@hospital.com | 0.89 | 71.47% | xx.xx% | 1h 16m |
| jowens@hospital.com | 0.77 | 82.70% | xx.xx% | 1h 38m |
| lsaffell@hospital.com | 0.77 | 76.15% | xx.xx% | 1h 16m |
| sibarra@hospital.com | 0.68 | 78.52% | xx.xx% | 1h 13m |
| mprisco@hospital.com | 0.63 | 90.49% | xx.xx% | 2h 03m |
| dsmith@hospital.com | 0.60 | 70.79% | xx.xx% | 0h 50m |
| tbeach@hospital.com | 0.45 | 0.00% | xx.xx% | 0h 12m ~ |
| kmallard@hospital.com | 0.45 | 0.00% | xx.xx% | 0h 12m ~ |

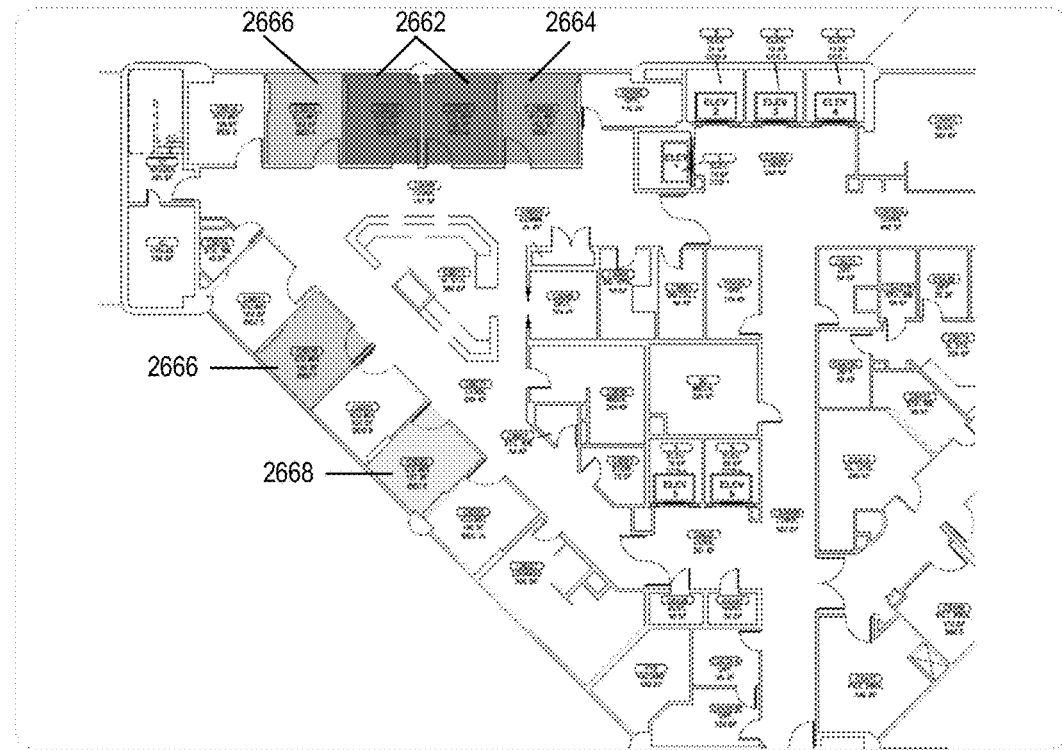

FIG. 26E

SYSTEM AND METHOD FOR OPPORTUNITY-BASED REMINDING OR COMPLIANCE WITH ONE OR MORE HEALTH PROTOCOLS

REFERENCE TO RELATED APPLICATIONS

This application is a continuation in part of U.S. patent application Ser. No. 16/148,683 (now U.S. Pat. No. 10,679,488) filed on Oct. 1, 2018, which is a continuation in part of U.S. patent application Ser. No. 15/946,537 (now U.S. Pat. No. 10,403,121) filed on Apr. 5, 2018, which claims priority to US Provisional Patent Application No. 62/482,146 filed on Apr. 5, 2017. This application also claims priority to and is a continuation in part of PCT Application No. PCT/US19/25751 filed on Apr. 4, 2019 (published as WO 2020/072096 A1). This application further is a continuation in part of U.S. patent application Ser. No. 16/557,191 filed on Aug. 30, 2019, which is a division of U.S. patent application Ser. No. 15/946,537 (now U.S. Pat. No. 10,403,121) filed on Apr. 5, 2018, which claims priority to U.S. Provisional Patent Application No. 62/482,146 filed on Apr. 5, 2017. Each of U.S. patent application Ser. No. 16/148,683 (now U.S. Pat. No. 10,679,488), U.S. patent application Ser. No. 15/946,537 (now U.S. Pat. No. 10,403,121), U.S. Provisional Patent Application No. 62/482,146, U.S. patent application Ser. No. 16/557,191, and PCT Application No. PCT/US19/25751 (published as WO 2020/072096 A1) are incorporated by reference herein in their entirety.

GOVERNMENT LICENSE RIGHTS

This invention was made with United States government support under grant number 1R43NR017373-01A1 and grant number 1R44AG060848-01 awarded by the National Institutes of Health (NIH) Small Business Innovation Research (SBIR). The United States Government has certain rights in the invention.

BACKGROUND

Healthcare-Associated Infections (HAIs) imposes devastating medical and economic consequences. Severe HAIs lead to extended hospital stays, lasting side effects and ultimately increased costs and risks of mortality. Treating these infections costs the healthcare system billions of dollars every year.

A good personal protective equipment practice is important to reduce transmission of pathogenic microorganisms to patients and to protect workers (e.g., pursuant to Occupational Safety and Health Administration (OSHA) standards). For example, healthcare providers may wear various types of personal protective equipment, such as any one, any combination, or all of: gloves, mask, gown, or protective eyewear. Typically, the personal protective equipment is placed outside of a patient's room for the healthcare provider to wear.

BRIEF DESCRIPTION OF THE DRAWINGS

The accompanying drawings, which are incorporated in and constitute a part of this specification, illustrate various aspects of the invention and together with the description, serve to explain its principles. Wherever convenient, the same reference numbers will be used throughout the drawings to refer to the same or like elements.

FIG. 10A illustrates a series of pictures which highlights the recommended hand rubbing techniques with alcohol-based formulation in World Health Organization (WHO) guidelines on hand hygiene in healthcare, with the duration of the hand hygiene motions (picture #2-7) recommended to last 20-30 seconds. Thus, the alcohol-based hand rub (ABHR) is one example of a hand hygiene technique. Another example of a hand hygiene technique is using soap (or other type of cleanings product) and water.

FIGS. 12F-I illustrate various screens of a hand hygiene/PPE compliance system

FIG. 22A is a flow diagram for detecting both the HH opportunity and the HH event and determining HH compliance based on a combination of the detected HH opportunity and the HH event.

FIG. 22B is a flow diagram of one example of determining whether there is sufficient connection between the detected HH event and the detected HH opportunity.

FIG. 26E is an illustration of an infection spread analysis that may be generated by the future cluster risk analysis methodology of FIG. 26C and/or future infection risk analysis methodology of FIG. 26D.

DETAILED DESCRIPTION OF EMBODIMENTS

Overview

Figure 1A:
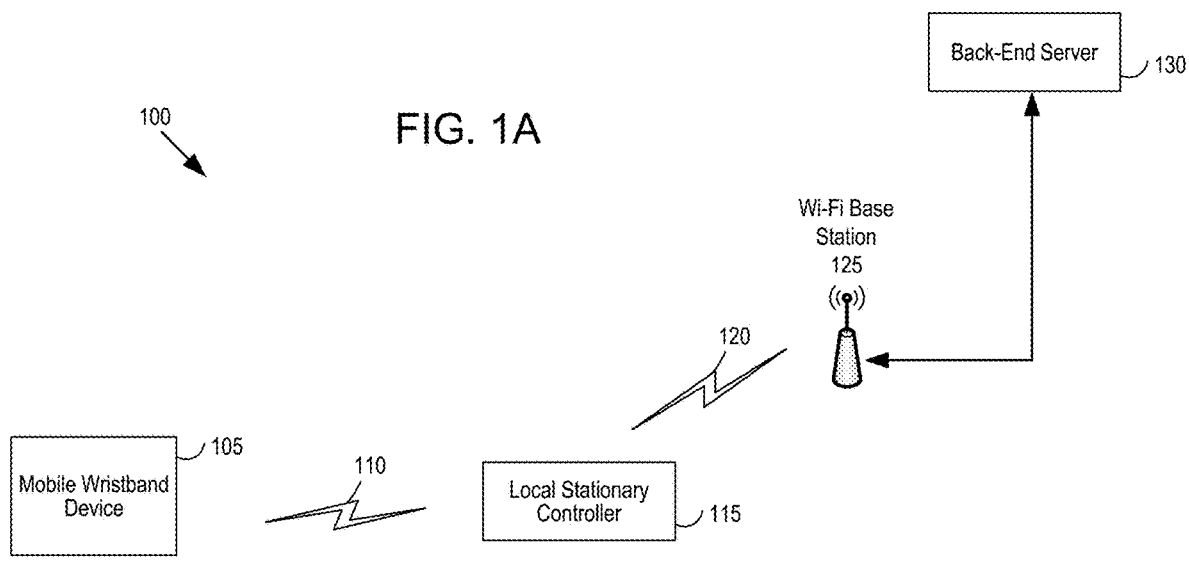
FIG. 1A is a first example block diagram of a hand hygiene and/or PPE system, with a mobile wristband device, a local stationary controller and a back-end server.

Healthcare providers often are presented with opportunities for patient interaction. For example, the WHO lists five hygiene opportunities for infection control, as discussed in more detail below. In those opportunities, the healthcare providers may need to follow one or more protocols, such as one or more hand hygiene (HH) protocols and/or patient protective equipment (PPE) protocols. Compliance may with the protocol(s) may include one or more steps. Example steps include any one, any combination, or all of: taking hand cleaning agent (e.g., taking hand sanitizer); taking PPE (e.g., opening a drawer or cabinet containing gloves, masks, etc.); performing one or more hand movements and/or the one or more hand movements in a sequence (e.g., performing hand rubbing for at least 20 seconds; upon entrance to a patient area, first cleaning hands prior to donning PPE; etc.). These steps are merely listed by way of example. Other steps are contemplated. Any one, any combination, or all of those steps may be used to identify a hygiene event, such as one or both of a HH event or a PPE event. As one example, taking sanitizer from a dispenser may be a trigger identifying a HH event. As another example, opening a drawer that contains gloves may be a trigger identifying a PPE event. Thus, in a more specific embodiment, the trigger for the hygiene event may comprise a predicate step (such as an initial step) in order for the healthcare provider to comply with the protocol (e.g., the healthcare provider performing the predicate step of taking sanitizer in preparation for rubbing hands to comply with the HH protocol; the healthcare provider performing the predicate step of opening the drawer containing gloves in preparation for putting on the gloves in order to comply with the PPE protocol).

However, identifying and detecting a hygiene event may occur at different times (e.g., identifying the hygiene opportunity may occur before or after detecting the hygiene event), thereby complicating matters. As discussed in more detail below, the hygiene opportunity may comprise an opportunity for practicing proper hygiene with a patient that may be identified based on identifying behavior indicative of patient interaction associated with one or more hygiene opportunities. Further, as discussed in more detail below, a hygiene event comprises an event for performing proper hygiene. The hygiene event may be detected in one of several ways, such as by sensing one or more of the acts for complying with the hygiene event, including by: detecting sanitizer being dispensed from a dispenser; detecting opening/taking of PPE from a PPE container. By way of example, a healthcare worker may potentially have dozens or hundreds of interactions with others in the course of a single day. In order to focus the compliance analysis, a subset of those interaction are identified as being hygiene opportunities, which may be those interactions where guidelines, such as the WHO guidelines, are to be followed. The hygiene events, with the various steps following those guidelines, may, in turn, be used to determine compliance.

In one or some embodiments, reminders may be generated for healthcare workers according to any one, any combination, or all of the following: responsive to identifying a hygiene opportunity; responsive to identifying a hygiene event; responsive to identifying both a hygiene opportunity and a hygiene event; responsive to detecting a hygiene opportunity and responsive to a determination of compliance or non-compliance with the hygiene opportunity (e.g., providing a reminder as feedback indicating non-compliance (e.g., failure to take sanitizer), indicating partial compliance (e.g., taking sanitizer but failing to perform the requisite 20 seconds of hand rubbing required by the HH protocol); and/or indicating full compliance (e.g., full compliance with one or both HH protocol or PPE protocol); or responsive to detecting a hygiene event and responsive to a determination of compliance or non-compliance with the hygiene event.

As one example, in one or some embodiments, a reminder may be generated immediately responsive to identifying the hygiene opportunity. In one particular example, an area, such as a patient room, may have associated with it a hygiene protocol (such as a HH protocol and/or a PPE protocol), with the hygiene protocol either being non-changing or changing. Responsive to identifying the opportunity (and before any determination of partial or full compliance), an output may be generated to remind the healthcare worker as to the hygiene protocol associated with the area. In another particular example, the area may have a changing hygiene protocol (e.g., the hygiene protocol(s) associated with the patient room change based on the diagnosis of the patient assigned to the patient room). Rather than relying on a handwritten note at the entrance to the patient room and the healthcare worker seeing the handwritten note, responsive to identifying the opportunity (such as responsive to identifying an exit opportunity from the patient room), a reminder may be output as to the changing hygiene protocol (e.g., responsive to identifying the healthcare worker exiting the patient room, generating an output as to the HH protocol to use soap/water to clean hands (the HH protocol associated with the patient room due to a diagnosis of the patient in the patient room)). Alternatively, the reminder may be generated responsive to identifying the opportunity and responsive to meeting one or more other criteria (e.g., only output the reminder responsive to identifying the opportunity and based on the status of the healthcare worker, such outputting the reminder if the healthcare worker is a trainee; only output the reminder responsive to identifying the opportunity and if there has been a change in the protocol associated with the patient area (e.g., the HH protocol has changed within X days of the identification of the opportunity); only output the reminder responsive to identifying the opportunity and based on the whether the specific healthcare worker has or has not been reminded of the protocol associated with the patient area (e.g., if the healthcare worker has already been reminded of the protocol associated with the patient area, such as having been reminded within X amount of time, do not generate the reminder responsive to identifying the opportunity); alternatively, responsive to the healthcare worker not having already been reminded of the protocol associated with the patient area, such as not having been reminded within X amount of time, generating the reminder responsive to identifying the opportunity).

Alternatively, the reminder may be associated with or dependent on compliance with the hygiene opportunity (e.g., a failure to take sanitizer within 3 seconds of identifying the HH opportunity results in an output being generated indicating non-compliance, as discussed below; compliance with taking sanitizer within 3 seconds of identifying the HH opportunity results in an output being generated indicating compliance). As one example, responsive to a failure to detect the predicate step within a certain time period of identifying the HH opportunity (whether before or after identifying the HH opportunity) results in generating an output indicative of a reminder to perform the predicate step (e.g., an output indicative to "take sanitizer"). As another example, responsive to failure to detect a step in the compliance process (separate from the predicate step), an output may be generated (e.g., failure to detect hand rubbing for at least 20 seconds required by the hand hygiene protocol results in an output being generated indicative to the healthcare provider to rub for at least 20 seconds; failure to detect a certain hand rubbing motion required by the hand hygiene protocol results in an output being generated indicative to the healthcare provider to perform the certain hand rubbing motion; failure to detect a proper sequence (e.g., failure to perform hand sanitizing/PPE in proper sequence); etc.). As discussed further, the output may be generated on a mobile electronic device associated with the healthcare provider (e.g., a wristband) and/or on a stationary controller associated with the patient area, as discussed further below.

Alternatively, or in addition to generating reminders (as discussed herein), in one or some embodiments, compliance determination(s) may be performed according to any one, any combination, or all of the following: responsive to identifying a hygiene opportunity; responsive to identifying a hygiene event; or responsive to identifying both a hygiene opportunity and a hygiene event.

In one or some embodiments, a method and system are disclosed that detects hand hygiene compliance and in turn, addresses hospitals' needs to reduce HAI rates and re-admission rates, improve patient care and decrease HAI-related costs.

Alternatively, or in addition, a method and system are disclosed that detects personal protective equipment compliance and in turn, addresses hospitals' needs to reduce HAI rates and re-admission rates, improve patient care and decrease HAI-related costs. As discussed in further detail below, the detection of hand hygiene compliance and the detection of personal protective equipment compliance may be performed separately from one another, or may be performed in combination with one another. For example, in one implementation, the system may only detect hand hygiene compliance (without detecting personal protective equipment compliance). In another implementation, the system may only detect personal protective equipment compliance (without detecting hand hygiene compliance). In still another implementation, the system may detect both hand hygiene compliance and personal protective equipment compliance. In a specific implementation, the detection of the hand hygiene (HH) compliance and the detection of personal protective equipment (PPE) compliance may at least be partly dependent on one another, as discussed in further detail below. As one example, the trigger to detect HH compliance and PPE compliance may be dependent on one another (e.g., a common trigger for both HH compliance and PPE compliance; a trigger for HH compliance in turn results in a trigger for PPE compliance; a trigger for PPE compliance in turn results in a trigger for HH compliance). As another example, the detection of movements for HH compliance and PPE compliance may be dependent on one another (e.g., movements are checked for HH compliance and thereafter movements are checked for PPE compliance; movements are checked for PPE compliance and thereafter movements are checked for HH compliance).

By way of background, both the World Health Organization (WHO) and the Centers for Disease Control (CDC) provide detailed hand hygiene techniques and durations in their guidelines that are intended to be implemented in all healthcare settings. For instance, in WHO guidelines on hand hygiene in healthcare, hand hygiene with alcohol-based formulation is recommended for routine hygienic hand antisepsis with various hand-rubbing motions lasting for 20-30 seconds. One example hand hygiene technique is handwashing using soap and water. Another hand hygiene technique is hand rubbing, such as with alcohol-based formulations. As used herein, any discussion for hand hygiene is applicable to both handwashing and hand rubbing. Likewise, any discussion regarding hand rubbing is applicable to handwashing, and any discussion regarding handwashing is applicable to hand rubbing.

Figure 10B:
FIG. 10B illustrates a series of pictures which highlights the recommended hand washing techniques with soap and water in WHO guidelines on hand hygiene in healthcare, with the duration of the procedure recommended to last 40-60 seconds.

An example of this is illustrated in FIG. 10A. In particular, FIG. 10A illustrates the recommended hand rubbing techniques with alcohol-based formulation in WHO guidelines on hand hygiene in healthcare, with the duration of the hand hygiene motions (as shown in pictures #2-7 of FIG. 10A) that is recommended to last 20-30 seconds. In contrast, handwashing with soap is recommended for cleaning soiled hands, with the same hand-rubbing motions plus extra steps of rinsing and drying, for a total duration of 40-60 seconds. An example of this is illustrated in FIG. 10B. Thus, in one implementation, the hand movements associated with cleaning hands using the alcohol based-formulation is the same as the hand movements associated with cleaning hands using soap/water (e.g., pictures #2-7 of FIG. 10A). Alternatively, different hand movements are required for cleaning hands using the alcohol based-formulation versus using soap/water.

Separate from, or in combination with, movements may be monitored for compliance with one or more PPE protocols. As discussed above, to reduce the spread of diseases, healthcare providers may don personal protective equipment (e.g., gloves, gown, mask, protective eyewear). The wearing of the personal protective equipment may be dictated by the one or more PPE protocols. In this regard, compliance with PPE protocols may be recommended in certain situations when interacting with patients. Further, any discussion herein regarding compliance by and/or reminders to a healthcare provider may equally apply to other types of workers, such as construction workers, factory workers, or the like.

Figure 10C:
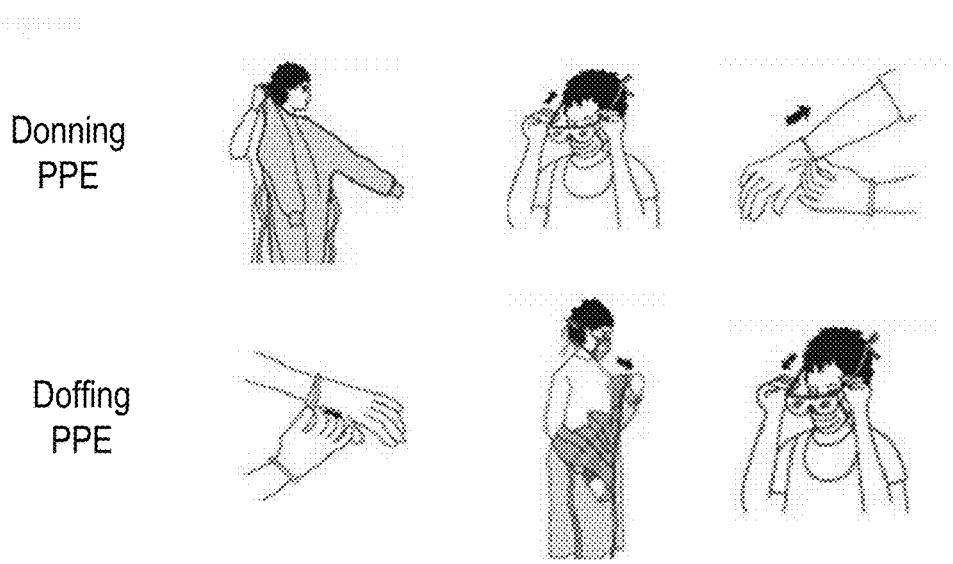
FIG. 10C illustrates a series of pictures which highlights the donning and doffing of personal protective equipment (PPE).

FIG. 10C illustrates a series of pictures which highlights best practices for donning and doffing of personal protective equipment (PPE). Examples are illustrated at http://www.nipcm.hps.scot.nhs.uk/appendices/appendix-6-best-practice-putting-on-and-removing-ppe/. As shown in FIG. 10C, donning PPE may include first putting on a gown, then putting on protective face wear (e.g., first a mask and then google), and finally putting on gloves, while doffing PPE includes first removing the gloves, then removing the gown, and finally removing the protective face wear. Combinations of PPE types (e.g., gloves, masks, goggle, respirator, gown or apron) are available to protect all or parts of the healthcare provider from contact with potentially infectious material. For instance, gloves protect the hands; gowns or aprons protect the skin and/or clothing; masks and respirators protect the mouth and nose; goggles protect the eyes; and face shields protect the entire face. The selection of PPE may be determined by the isolation precautions required for the patient and/or the nature of the patient contact. The Centers for Disease Control and Prevention (CDC) have suggested steps for donning and removing PPEs. Specifically, the CDC recommends donning or doffing PPEs in the proper steps to prevent contamination of skin and clothing.

Alternatively, protocols may be issued by another governing body, such as the Occupational Safety and Health Administration (OSHA). As one example, OSHA (or another governing body) may issue protocols for: eye and face protection; respiratory protection; head protection; foot protection; electrical protective devices; and hand protection. In this regard, any discussion regarding compliance with hand hygiene and/or personal protective equipment may likewise be applied to compliance with any type of protocol. As one specific example, OSHA promulgates protocols for training, such as for hazardous material handling. As another specific example, OSHA may require compliance with wearing of protective equipment. In this regard, the systems and methods used for training and/or monitoring in hand hygiene or personal protective equipment compliance may likewise be applied to training and/or monitoring for other protocols, such as OSHA training protocols.

In one implementation, a hand hygiene monitoring system and method is disclosed. The hand hygiene monitoring system may be used in various settings, such as in a hospital setting, a nursing home setting, a home setting, or the like. In a first specific implementation, the hand hygiene monitoring system comprises one or more mobile electronic devices and one or more stationary electronic devices. The mobile electronic device may be configured to be attached or associated (such as by the shape of the mobile electronic device or a hook or clip associated with the electronic device) with a person, such as a healthcare provider, a child, an elderly person, or the like. As discussed in more detail below, the mobile electronic device in one implementation may comprise a wristband electronic device configured to be worn on a person's wrist. Alternatively, the mobile electronic device may be attached to other parts of the person's body. The stationary electronic device may be fixedly attached to a part of a premises. The part of the premises may be itself stationary (such as a stationary hand cleaning agent dispenser) or may move (such as a door or a drawer). For example, as discussed in more detail below, the stationary electronic device may be fixedly attached in relation to a hand cleaning agent dispenser (e.g., as part of (or within) the hand cleaning agent dispenser or in fixed relation and proximate to or adjacent to the hand cleaning agent dispenser). In a second specific implementation, the hand hygiene monitoring system comprises one or more mobile electronic devices, one or more stationary electronic devices, and central analytics. The central analytics may be configured to analyze one or more aspects of the hand hygiene monitoring system, as discussed further below.

Figure 2:
FIG. 2 is a fourth example block diagram of a hand hygiene system, with a mobile wristband device and a local stationary controller.
Figure 1B:
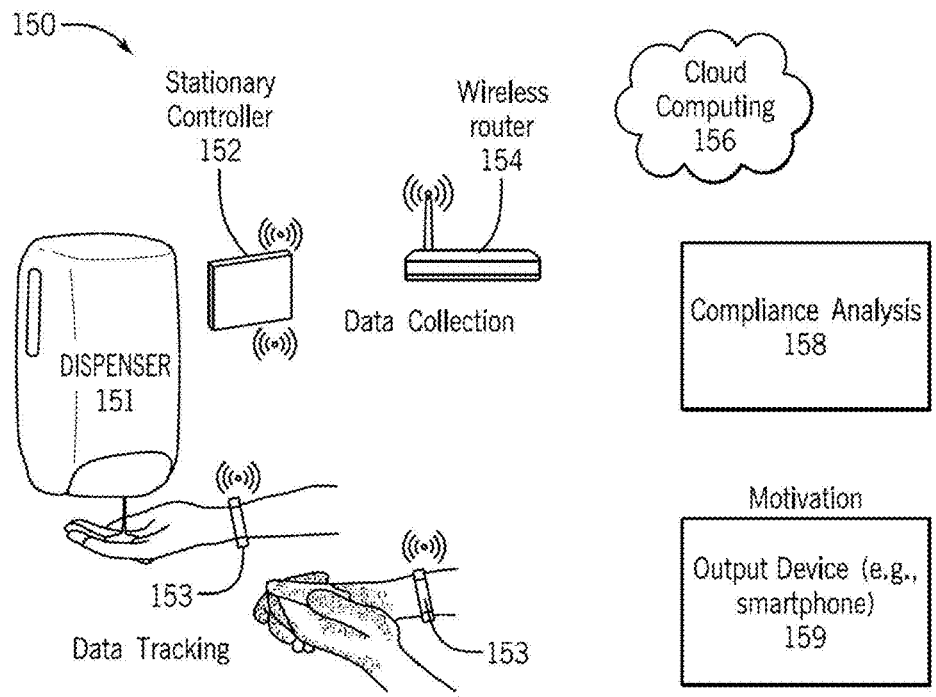
FIG. 1B is a second example block diagram of a hand hygiene system, with a mobile wristband device, a dispenser, a local stationary controller, compliance analysis, one or more output devices, and cloud computing.

Thus, in one implementation, the hand hygiene monitoring system may comprise a hand hygiene compliance system configured for use in a hospital setting or other healthcare setting, whereby one or more healthcare providers wear wristbands and whereby stationary controllers may be associated with a dispenser (e.g., mounted proximate to (such as within sound sensor range or ultrasonic sensor range) or within the dispenser) and/or an entrance to a room, and back-end analytics (such as cloud computing). Examples of this are illustrated in FIGS. 1A-C. Alternatively, the hand hygiene compliance system includes the wristband and a stationary controller, an example of which is illustrated in FIG. 2.

As discussed in more detail below, a mobile electronic device is configured with one or more sensors that measure movement of a person, such as the healthcare provider. The mobile electronic device may include a housing that is attached or somehow associated with the person. As one example, the mobile electronic device may comprise a wristband electronic device, whereby the wristband electronic device is affixed to the wrist of the person. In one specific example, the wristband electronic device fully encircles the wrist of the healthcare provider. In another specific example, the wristband electronic device only partly encircles the wrist of the healthcare provider. Alternatively, the mobile electronic device may be clipped or strapped to the wrist of the healthcare provider (such as tying a strap to the wrist of the healthcare provider). Discussed below are various applications of the wristband. Any discussion below regarding the wristband comprises a wristband electronic device, and may likewise be applied to any other type of electronic device, such as another type of wearable electronic device, that can be attached or otherwise associated with the person that may measure hand movements or other type of body movements of the healthcare provider. Further, any discussion regarding the mobile electronic device, such as the wristband, may likewise be applied to a PPE compliance system. In this regard, any discussion herein regarding the mobile electronic device, including tracking movements or the electronics therein, for use in a hand hygiene compliance system may likewise be applied to a PPE compliance system and/or to a hand hygiene/PPE compliance system.

The wristband may record sensor data from one or more sensors. In one implementation, the wristband includes a single motion sensor. In an alternate implementation, the wristband includes multiple motion sensors, such as a first type of motion sensor and a second type of motion sensor, with the first type of motion sensor being different than the second type of motion sensor. In a first specific implementation, the first type of motion sensor is configured to sense a first type of movement, and the second type of motion sensor is configured to sense a second type of movement.

For example, the first type of motion sensor comprises a micro-vibration sensor configured to sense basic movement, and the second type of motion sensor comprises an accelerometer configured to sense acceleration in one, two, or three axes. One example of a micro-vibration sensor comprises a Sensolute Version MVS0608.02 micro-vibration sensor. The micro-vibration sensor may be omnidirectional with sensitivity independent of sensor orientation and may be suitable for basic motion-detection, whereas the accelerometer is configured to detect more advanced motions, such as acceleration. In operation, the wristband may operate in low power mode, such that one or more sections of the wristband do not draw power (or draw less power than in normal operation) and other sections of the wristband draw power and are in normal operation mode. When the wristband is in low power mode, example sections subject to low power mode comprise the controller and the accelerometer (or other type of motion sensor configured to sense more complex motions) and an example section of the wristband that draws power and in normal mode may comprise the micro-vibration sensor. Further, in operation, the micro-vibration sensor may sense basic motions, and responsive to detecting the basic motions, may wake-up the wristband from low power mode (such as resuming normal operation of the accelerometer and the controller). In this way, the wristband may conserve power by operating in low power mode, and may use a combination of motion sensors to sense a hand washing event (such as by resuming normal mode (and waking up the accelerometer) triggered by the output of the micro-vibration sensor and by sensing the hand washing motions using the accelerometer).

In still an alternate implementation, the wristband includes three or more motion sensors, such as a first type of motion sensor, a second type of motion sensor, and a third type of motion sensor, with each type being different from the other. As discussed further below, the wristband may include any one, any two, any three, or all four of: a micro-vibration sensor; an accelerometer; a gyroscope; and a magnetometer.

Responsive to the one or more sensors generating sensor data, the sensor data may be analyzed. In one implementation, the wristband analyzes the sensor data, with the wristband making the determination, based on the analysis, whether the hand movements were sufficient or insufficient according to the guidelines. Thereafter, the wristband may output the determination (e.g., generating an output indicative of the sufficiency and/or insufficiency of the hand movements according to the guidelines, whether for hand hygiene and/or PPE) and may transmit the determination (e.g., sufficiency and/or insufficiency of hand movements according to the guidelines) to an external device, such as the stationary controller and/or the back-end analytics. In another implementation, the stationary controller receives the sensor data from the wristband and analyzes the sensor data, thereby making the determination as to sufficiency and/or insufficiency of hand movements. Thereafter, the stationary controller transmits the determination (e.g., sufficiency and/or insufficiency of hand movements according to the guidelines) to an external device, such as the wristband (for outputting an indication of sufficiency and/or insufficiency according to the guidelines) or the back-end analytics. Alternatively, or in addition, the stationary controller may determine both whether hand cleaning agent (such as sanitizer, soap, or the like) has been dispensed and whether the hand movements were sufficient to meet compliance. In still an alternate implementation, the stationary controller may determine whether a PPE garment (e.g., mask, gown, or the like) has been dispensed or removed and whether the hand movements were sufficient to meet compliance with putting on the PPE garment. In still another implementation, the back-end analytics receives the sensor data from the wristband and analyzes the sensor data, thereby making the determination as to sufficiency and/or insufficiency of hand movements according to the guidelines. Thereafter, the back-end analytics may transmit the determination (e.g., sufficiency and/or insufficiency of hand movements) to an external device, such as the wristband (for outputting an indication of sufficiency and/or insufficiency) or the stationary controller.

Alternatively, more than one device may determine hand hygiene and/or PPE compliance. As one example, the wristband and the stationary controller, in combination, may determine hand hygiene and/or PPE compliance. Specifically, the stationary controller may determine whether hand cleaning agent (such as sanitizer, soap, or the like) has been dispensed, and the wristband may determine whether the hand movements were sufficient (e.g., the hand movements were for at least a predetermined amount of time; the hand movements were at least a certain level of vigorousness (e.g., as measured by an accelerometer); or the hand movements with a certain level of vigorousness were for at least the predetermined amount of time). As another example, the wristband and the back-end analytics, in combination, may determine hand hygiene and/or PPE compliance. In particular, the wristband may send the movements (e.g., the hand movements, the PPE movements, or both the hand movements and the PPE movements) to a server, with the server configured to analyze the movements for compliance (e.g., analyze the hand movements for hand hygiene compliance, analyze the PPE movements for PPE compliance, or analyze both the hand movements and the PPE movements for hand hygiene and PPE compliance). Alternatively, or in addition, the stationary controller may send data (such as sound data regarding whether the hand cleaning agent has been dispensed) to the server, with the server analyzing the data. Thus, any discussion herein with regard to determination of compliance resident in the wristband and/or in the stationary controller (whether hand hygiene compliance, PPE compliance, or hand hygiene and PPE compliance in combination) may likewise be applied to a server performing those determinations of compliance. Alternatively, the stationary controller may determine whether the PPE garment (such as the mask, gown, gloves, etc.) has been dispensed and/or removed, and the wristband may determine whether the hand movements were sufficient (e.g., the hand movements indicate that the PPE garment was put on. As another example, the wristband and the back-end analytics, in combination, may determine PPE compliance. In still an alternate implementation, more than one device may determine both hand hygiene and PPE compliance.

As discussed above, the analytics may analyze the sensor data in one or more respects to determine hand hygiene and/or PPE compliance. In one implementation, the analytics may determine whether or not the person performed any act related to hand washing (such as whether the hand cleaning agent was dispensed from the dispenser) and/or any act related to PPE (such as whether the PPE garment was dispensed). In another implementation, the analytics may determine a duration of the hand hygiene motions and/or a duration of the PPE motions. As discussed in more detail below, the wristband (and/or the stationary controller) may analyze sensor output from the motion sensor(s) (such as the accelerometer) to determine whether the sensor output is indicative of hand hygiene motions (as opposed to other hand motions) and/or PPE motions for a predetermined amount of time (e.g., for 20 seconds). In a more specific implementation, the analytics may sum the amount of time that the sensor data is indicative of the hand hygiene motion(s) and/or PPE motion(s) in a predetermined time window. For example, responsive to the wristband being triggered by the stationary controller to monitor hand hygiene motion(s) and/or PPE motion(s), the wristband may track the hand hygiene motion(s) and/or PPE motion(s) for the subsequent 60 seconds, one example of the predetermined time window. In that 60 seconds, the wristband may analyze the sensor data generated by the accelerometer and/or gyroscope and/or magnetometer for the hand hygiene motion(s) and/or PPE motion(s). In practice, the user may start and stop the hand hygiene motion(s) and/or PPE motion(s), such as a starting time at time=1 second to time=10 seconds perform the hand hygiene motion(s), stop performing the hand hygiene motion(s) from a stopping time of time=11 seconds to time=14 seconds, and resume the hand hygiene motion(s) from a restarting time of time=15 seconds to time=28 seconds. The wristband may track that from time=1-10 a total of 9 seconds of hand hygiene motion(s) were performed (with the wristband incrementing a counter so that the value of the counter is indicative of 9 seconds of hand hygiene motion(s)), from time=11-14, may track no hand hygiene motion(s) were performed (so that the counter is not incremented such that the value of the counter remains indicative of 9 seconds of hand hygiene motion(s)), and may track at least from time=15-26 seconds of hand hygiene motion(s) (for a total of 20 seconds of hand hygiene motion(s)). In this way, the wristband may determine that the minimum amount of time (e.g., 20 seconds) of hand hygiene motion(s) and/or PPE motion(s) was performed within the predetermined time window, even though the user started and stopped the hand hygiene motion(s) and/or PPE motion(s). Further, in one implementation, once the wristband tracks the minimum amount of time (e.g., 20 seconds) of hand hygiene motion(s) and/or PPE motion(s), the wristband may return to sleep mode. Alternatively, the wristband may track a total amount of time of hand hygiene motion(s) and/or PPE motion(s) within the predetermined time window.

In another implementation, the analysis of the sensor data may be configured to identify a plurality of discrete motions. As illustrated in FIG. 10A, the WHO recommends a plurality of discrete motions, such as the 6-step hand hygiene technique as indicated in steps 2-7. The analytics may determine whether the sensor data is indicative of any one, any combination, or all of a set of discrete motions, such as the motions as indicated in steps 2-7. In one implementation, the analytics may determine whether all of the motions in the discrete set of motions were performed regardless of sequences (e.g., steps 2-7 are performed in sequence; steps 2, 4, 6, 3, 5, 7). In an alternate implementation, the analytics may determine whether all of the motions in the discrete set of motions were performed in a predetermined sequence (e.g., steps 2-7 are performed in sequence). Further, in one implementation, the analytics may track an amount of time (such as a minimum amount of time) that each of the motions in the discrete set of motions is performed. By way of example, the analytics may determine "sufficient" hand hygiene motions if each of steps 2-7 is performed for 3 seconds each. Alternatively, the analytics may determine "sufficient" hand hygiene motions if each of steps 2-5 is performed for 3 seconds each and steps 6-7 are each performed for 4 seconds. The analytics may track whether the total amount of time for each of the steps tracked is at least the predetermined amount (e.g., either 3 or 4 seconds). As another example, there may be a predetermined sequence in which to put on and/or to take off PPE garments. The analytics may determine whether the sensor data is indicative of any one, any combination, or all of a set of discrete motions, such as a specific sequence of motions for putting on PPE garments in a predetermined putting-on sequence and/or for removing PPE garments in a predetermined removal sequence. In one implementation, the analytics may determine whether all of the motions in the discrete set of motions were performed regardless of sequences. In an alternate implementation, the analytics may determine whether all of the motions in the discrete set of motions were performed in a predetermined sequence (e.g., in a PPE putting on movement, discussed below, determines whether the gloves are put on after other putting on movements are performed). Further, the analytics may assign one or more counters to track a total amount of time for each of the steps tracked in order to account for starting/stopping of hand hygiene motions and/or PPE motion(s) for a respective step. In this way, the analytics may track the recommended different steps in order to determine whether the hand hygiene motions and/or PPE motions are sufficient.

In one implementation, the analysis of the sensor data may be directed to the vigorousness of the hand hygiene motions. As one example, the analysis may be based on frequency of at least one aspect of the sensor data. In particular, the frequency of movement of the sensor data may be analyzed, such as the peak frequency of movement. As discussed in more detail below, different body movements result in different frequencies of movement. Hand movements, such as predetermined hand movements associated with hand washing, may have a higher frequency than other body movements (such as arm swinging, walking, etc.). In this regard, the peak frequency of the movement may be analyzed in order to determine whether the movement is attributable to hand washing or to another body movement. Further, because hand washing movements may have higher frequencies than other types of movements, such as arm swinging, the analysis may use a frequency filter (e.g., use a high pass filter to filter out frequencies lower than a predetermined frequency in order to filter out frequencies due to walking or arm swinging), as discussed further below. Thus, if the wristband performs the analysis, the wristband may include a high-pass filter to filter out non-hand washing movements.

Further, in one implementation, the sensor data is analyzed in each of the three dimensions. In an alternate implementation, the sensor data is analyzed in fewer than all of the three dimensions. In a first specific implementation, the sensor data is analyzed in only two dimensions (e.g., analyzing for large acceleration in both the x- and y-axis). In a second specific implementation, the sensor data is analyzed in only one dimension (e.g., analyzing for large rotation rate along the y-axis (pitch) or for large acceleration along the z-axis).

In another implementation, the sensor data may be analyzed for power spectrum density (PSD). In one example, the PSD of the signal may describe the power present in the signal as a function of frequency, per unit frequency. In particular, the analysis may focus on peak power in determining whether the sensor data is associated with hand washing movements.

In still another implementation, the method and system limits analysis to a discrete window of sensor data. In particular, various triggering events are contemplated, such as identifying a hygiene opportunity, detecting a hygiene event, or both detecting a hygiene event and identifying a hygiene opportunity. For example, a triggering event may identify a potential hand hygiene event and/or a potential PPE event, thereby beginning the sequence of analyzing the sensor data for the hand hygiene event and/or the PPE event. As discussed in more detail below, the wristband and the stationary controller work in combination for the triggering event. In one example, the stationary controller sends a beacon. Responsive to the wristband coming within range of near-field communication (e.g., within Bluetooth communication range for at least a predetermined amount of time), the wristband may be triggered to record sensor data in order to determine whether hand hygiene movements and/or PPE movements have occurred (e.g., the wristband may be triggered to perform any one, any combination, or all of: waking up from sleep mode to begin generating motion data; begin saving the generated motion data; begin analyzing the motion data for compliance; transmit to an external device (e.g., the stationary controller and/or the server) the determination indicating whether the motion data indicates compliance, partial compliance or non-compliance). In another example, the wristband may send a beacon, such as a Bluetooth signal or RFID signal. The stationary controller may sense the signal (e.g., the stationary controller may determine, based on the strength of the beacon, how close the wristband is to the stationary controller). Responsive to the stationary controller determining that the wristband is proximate (e.g., within a predetermined distance for at least a predetermined amount of time), the stationary controller may transmit a wake-up signal to the wristband as a trigger (e.g., the wristband may be triggered to perform any one, any combination, or all of: waking up from sleep mode to begin generating motion data; begin recording or saving the generated motion data; begin analyzing the motion data for compliance; transmit to an external device (e.g., the stationary controller and/or the server). Further, the analysis of the sensor data generated within the discrete window may be based on a contrast of hand hygiene motions and/or PPE motions with other periodic motions that may occur within the discrete window. As one example, the time period associated with the discrete window may be 60 seconds from identifying the hygiene opportunity and/or detecting the triggering event (e.g., when the healthcare provider is walking into a patient's room). In that regard, the analysis may focus on contrasting hand hygiene movements and/or PPE movements with other periodic movements that may be performed within the 60 second discrete window (e.g., walking, knocking on a door, etc.). For example, the analysis may focus on frequency and/or power to differentiate hand hygiene movements and/or PPE movements with other periodic movements. In this regard, accuracy of analysis may be increased by: (1) using data in the discrete window; and (2) analyzing hand hygiene actions and/or PPE actions and contrasting those hand hygiene actions and/or PPE actions without other periodic actions (e.g., walking, knocking on door) within that discrete window.

Figure 4A:
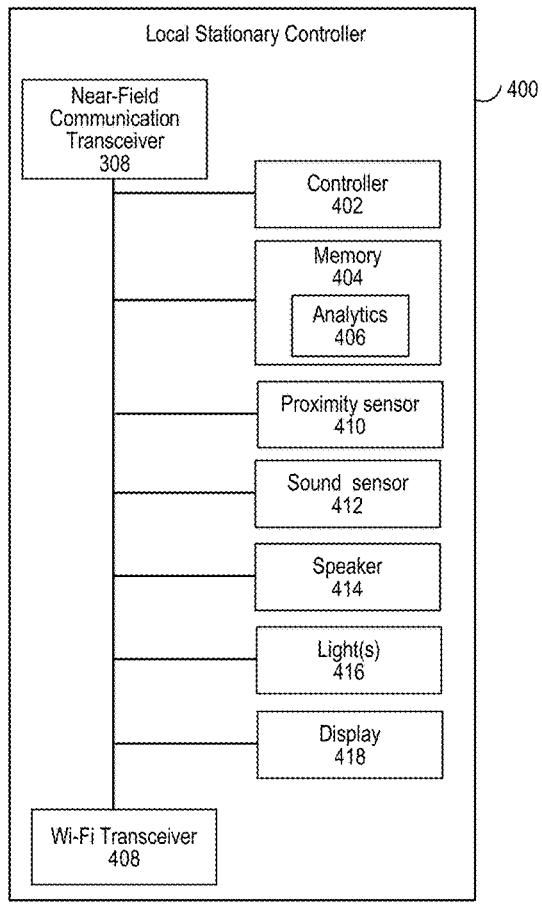
FIG. 4A is a first example block diagram of the local stationary controller.
Figure 4B:
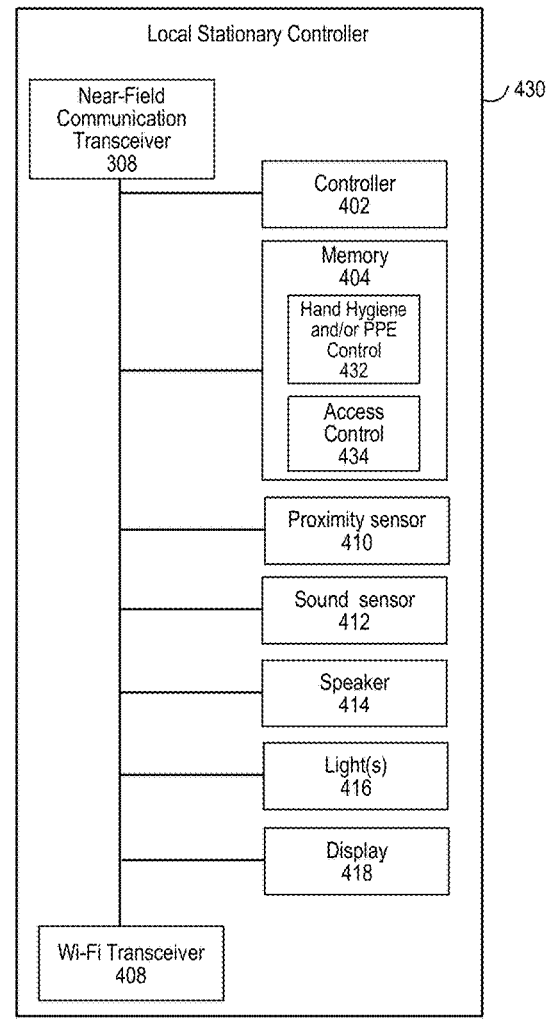
FIG. 4B is a second example block diagram of the local stationary controller.

In the present implementation, the motion sensor may operate for a very short time (~1 minute) only when a hygiene opportunity is identified and/or a hand hygiene event and/or PPE event is detected (such as by the stationary controller as illustrated in FIGS. 4A-B). For most of the time, at least a part of the wristband, such as one or more of the motion sensors within the wristband, is in sleep mode. For example, within sleep mode, power may be reduced or completely withheld from one or more parts of the wristband, such as the motion sensor. This achieves both low power dissipation and reliable hygiene compliance and/or PPE compliance detection. Selection of low-power chips further reduces the wristband's power consumption, as discussed further below. In particular, since the wristband is activated in the discrete window, the wristband may have a longer battery life, thereby reducing the burden from the healthcare provider to recharge or replace the battery as often. Further, since the wristband is activated in the discrete window, the wristband may focus on events that may occur within the window, thereby more accurately detecting compliance during a hand hygiene event and/or hygiene opportunity, and avoiding false alarms from any interfering motions (e.g., walking) or motions in a non-hygiene event and/or non-PPE event.

In one implementation, the analysis uses one or more static thresholds in analyzing whether the sensor data is indicative of hand hygiene movements and/or PPE movements. For example, the frequency and/or the power associated with the sensor data may be compared with static thresholds (e.g., use a static filter to filter periodic walking movement from hand rubbing movement and/or from donning/removing PPE garments; use a static threshold to analyze in the magnitude domain (such as power)). With regard to frequency, one or more thresholds, such as a lower threshold (to filter out other periodic movements, such as walking) and/or an upper threshold (to filter out overly vigorous hand hygiene movements and/or PPE movements) may be used. In an alternate implementation, the analysis may use one or more dynamic thresholds in order to dynamically adapt the analytics. For example, based on previous sensor data, the thresholds and/or ranges for frequency and/or power analysis may be adapted. In a particular example, the analysis may use machine learning that adapts to an individual healthcare provider's hygiene habit. For example, the individual healthcare provider may perform hand hygiene movements and/or PPE movements multiple times in a certain period (e.g., in a day, week, month, etc.). The machine learning may extract one or more characteristics associated with the hygiene habits and/or PPE habits of the individual healthcare provider and then store those parameters correlated to this individual healthcare provider. Thus, the thresholds, such as the frequency and/or magnitude for analysis, may be tailored to the individual healthcare provider.

As discussed in more detail below, the wristband may operate in a lower power mode. In one implementation, the wristband may operate in a discrete window (such as for 60 seconds) in order to detect the hand hygiene movements and/or PPE movements. Within this discrete window, one or more operations of the wristband, such as the motion sensor(s), are awakened for recording sensor data.

Further, in one implementation, the wristband may operate in a sleep mode (in which a part of the electronics within the wristband are turned off or are consuming less power) and may operate in a normal mode (in which some or all of the electronics within the wristband that are turned off or are consuming less power in sleep mode are turned on or consume a greater amount of power). As one example, the wristband may include one or more sensors, with some or all of the sensors being turned off or inactive in sleep mode, and some or all of the sensors being turned on or active in normal mode.

The wristband may be triggered to exit from sleep mode in one of several ways. In one way, the wristband may make the decision to exit sleep mode on its own and without any input from an external device. For example, the wristband may have one or more sensors that remain active in sleep mode, with the data generated by the one or more sensors active in sleep mode being used to determine whether to exit sleep mode. In particular, the wristband may include a micro-vibration sensor. The micro-vibration sensor draws less power than other motion sensors, such as accelerometers or gyroscopes. Responsive to the micro-vibration sensor, active in sleep mode, indicating motion, the wristband may wake-up the microcontroller and/or other sensors on the wristband, such as the accelerometer and/or gyroscope and/or magnetometer, thereby exiting sleep mode. In another way, the wristband may make the decision to exit sleep mode based on input from another electronic device. For example, the wristband may work in combination with an external device, such as the stationary controller, in order to determine when a hand hygiene event begins (and, in turn, when for the wristband is to "wake up"). As discussed above, the wristband may send a beacon to the stationary controller, or may receive a beacon from the stationary controller in order to trigger the wake up of the wristband. After which, the wristband may generate and record sensor data. After identification of the hygiene opportunity and/or detection of the hygiene event (e.g., the hand hygiene event and/or PPE event) (e.g., after no more than 60 seconds), the wristband may go back into sleep mode (either due to determining that the hygiene opportunity and/or the hygiene event (e.g., the hand hygiene event and/or PPE event) is successful or not).

In still another implementation, one or more operations of hand hygiene and/or PPE monitoring may be divided amongst the wristband and the stationary controller. As discussed in more detail below, the stationary controller may be associated with the dispenser (e.g., antibacterial dispenser) and/or the entrance of the room. For example, one operation of hand hygiene and/or PPE monitoring is a trigger for beginning the hand hygiene and/or PPE monitoring. In this example, one of the wristband or the stationary controller may send a beacon, and another of the wristband or the stationary controller may detect the beacon, thereby triggering the beginning of the hand hygiene and/or PPE monitoring. In particular, the wristband may send an RFID or Bluetooth signal, which may be sensed by the stationary controller. In the example of Bluetooth, the stationary controller, based on the signal strength of the Bluetooth signal and/or the time elapsed of receiving the Bluetooth signal, may determine the closeness of the devices to one another. In response to the stationary controller determining that the wristband is within a predetermined distance for a predetermined period of time, the stationary controller may send a wake-up signal to the wristband to begin monitoring for hand hygiene and/or PPE movements. In another implementation, the stationary controller may transmit a beacon, which upon receipt by the wristband wakes up at least a part of the wristband, such as the motion sensor(s) on the wristband. More specifically, in one implementation, responsive to the wristband sensing the beacon signal from the stationary controller for a predetermined amount of time, the wristband may wake-up the motion sensor(s) on the wristband. Alternatively, or in addition, identification of a hygiene opportunity (such as by the wristband and/or the stationary controller) may trigger the wake-up of the wristband and/or the stationary controller.

Alternatively, or in addition, the hand hygiene and/or PPE monitoring system may generate one or more outputs associated with the hand hygiene and/or PPE monitoring. A first output may be generated to alert the healthcare provider to perform the hand hygiene and/or PPE movements (e.g., responsive to identifying a hygiene opportunity and/or a hygiene event). A second output may be generated to alert the healthcare provider as to whether the hand hygiene and/or PPE movements were sufficient and/or insufficient. In one implementation, the stationary controller may generate the alert to the healthcare provider to perform the hand hygiene and/or PPE movements, and the wristband may generate the alert to the healthcare provider as to whether the hand hygiene and/or PPE movements were sufficient and/or insufficient. Alternatively, the wristband may generate the alert to the healthcare provider to perform the hand hygiene and/or PPE movements, and the stationary controller may generate the alert to the healthcare provider as to whether the hand hygiene and/or PPE movements were sufficient and/or insufficient. In either implementation, the alerts may be divided amongst the stationary controller and the wristband. In still another implementation, only one device (e.g., either the stationary controller or the wristband) generates both the alert to the healthcare provider to perform the hand hygiene and/or PPE movements, and the alert to the healthcare provider as to whether the hand hygiene and/or PPE movements were sufficient and/or insufficient.

Generally speaking, the analytics may determine any one, any combination, or all of: compliance; partial compliance; or non-compliance. Further, the analytics may determine any one, any combination or all of: whether the user took hand cleaning agent and/or whether the user took the PPE garment(s); whether the user performed hand movements indicative of hand hygiene and/or whether the user performed hand movements indicative of putting on and/or taking off PPE garment(s); whether the user performed hand movements indicative of hand hygiene and/or PPE for at least a predetermined amount of time; whether the user performed a series of hand movements indicative of hand hygiene and/or PPE; whether the user performed a series of hand movements indicative of hand hygiene and/or PPE each for a respective period of time; and whether the data was indeterminate of compliance.

Responsive to the determination of the analytics, one or more outputs may be generated using output functionality. In one implementation, the wristband may generate one or more outputs based on a determination of any one, any combination, or all of: compliance, partial compliance and/or non-compliance. The one or more outputs from the wristband may comprise audio and/or visual outputs, such as sound(s) (such as different sounds), light(s) (such as different lights or different combinations of lights), vibration(s) (such as different patterns of vibrations), or the like. For example, a first sound may be indicative of compliance and a second sound, different from the first sound, may be indicative of non-compliance. As another example, a first sound may be indicative of compliance, a second sound may be indicative of partial compliance, and a third sound may be indicative of non-compliance. As still another example, a first light may be indicative of compliance (e.g., a green colored light) and a second sound (e.g., a red colored light) may be indicative of non-compliance. As yet still another example, the wristband may escalate the outputs based on a determination of partial compliance and/or non-compliance. In particular, the wristband may initially output a sound and/or light responsive to determining a hand hygiene event and/or PPE event. Responsive to determining non-compliance (and/or partial compliance) with the identified hygiene opportunity and/or the hygiene event (e.g., the hand hygiene event and/or PPE event), the wristband may generate a different type of output, such as a louder sound (e.g., louder than the output responsive to determining a hand hygiene event and/or PPE event) and/or a brighter light (e.g., brighter lights or a greater number of lights than the output responsive to determining a hand hygiene event and/or PPE event).

Alternatively, or in addition, the stationary controller may generate one or more outputs based on a determination of any one, any combination, or all of: compliance, partial compliance and/or non-compliance. The one or more outputs from the stationary controller may comprise audio and/or visual outputs, such as sound(s), light(s), or the like. Alternatively, or in addition, an electronic device separate from the wristband and the stationary controller may generate one or more outputs based on a determination of any one, any combination, or all of: compliance, partial compliance and/or non-compliance. In one implementation, the determination as to compliance, partial compliance and/or non-compliance, either transmitted to or determined by the back-end analytics, may result in the back-end analytics transmitting an alert to a separate electronic device. For example, the separate electronic device (e.g., a smartphone) may be associated with the user who is the subject of the compliant, partial compliant and/or non-compliant hygiene opportunity and/or the hygiene event (e.g., hand hygiene event). As another example, the separate electronic device may be associated with a third party separate from the user subject to the identified hygiene opportunity and/or the hygiene event (e.g., the hand hygiene event and/or PPE event). In particular, the separate electronic device may be associated with an administrator tasked with hand hygiene and/or PPE compliance in a hospital setting or a responsible administrator for a section of the hospital (e.g., the head nurse in the ICU).

Alternatively, or in addition, one or more aspects of the wristband, the stationary controller or the back-end analytics may change responsive to a determination of any one, any combination, or all of: compliance; partial compliance; or non-compliance. As one example, responsive to a determination of partial and/or non-compliance, the wristband and/or stationary controller may modify its operation responsive to a new hand hygiene event and/or PPE event. In one implementation, the outputs generated by the wristband and/or stationary controller may be different than those outputs during a previous wristband event. As one example, the audio outputs generated by the wristband and/or stationary controller may be louder than those outputs during the previous wristband event responsive to determination of partial compliance and/or non-compliance. As another example, an output, not generated during the previous identified hygiene opportunity and/or the previous hygiene event (e.g., the previous hand hygiene event and/or previous PPE event), may be generated in a subsequent identified hygiene opportunity and/or subsequent hygiene event (e.g., subsequent hand hygiene event and/or subsequent PPE event) based on compliance, partial compliance, and/or non-compliance. In particular, responsive to determining that the user partially complied and or non-complied during the previous identified hygiene opportunity and/or the previous hygiene event (e.g., the previous hand hygiene event and/or previous PPE event), a display on the wristband may be activated to output a countdown of 20 seconds. In this way, the user may receive more guidance to wash for a predetermined amount of time (e.g., 20 seconds) responsive to determination of partial or non-compliance. Alternatively, or in addition, the analytics to determine compliance may be different than the analytics used during the previous wristband event and/or previous wristband opportunity. For example, the analytics may be stricter (e.g., requiring a longer time to detect hand hygiene and/or PPE motions for determining compliance) than previously used analytics.

Alternatively, or in addition, the hand hygiene and/or PPE monitoring system may track the dispensing of hand cleaning agent from the dispenser and/or removal of PPE garment(s). In one implementation, the stationary controller tracks at least one aspect related to the dispensing and/or removal. In a more specific implementation, the stationary controller tracks the operation of the dispenser as opposed to hand movement. For example, the stationary controller may include a sensor, such as a sound sensor, to determine whether the dispenser has dispensed the hand cleaning solution. In particular, the sound sensor may record data that the stationary controller may later analyze to determine whether the dispenser has performed an internal movement that is indicative of dispensing hand cleaning solution (e.g., whether the data recorded from the sound sensor is indicative of a motor on the dispenser dispensing hand cleaning agent). For example, the stationary controller may perform frequency domain analysis to determine whether the motor has dispensed hand cleaning solution. One or both of graphs of background sound (FIG. 6E) and dispensing sound (FIG. 6F) may be used by the stationary controller to perform the frequency domain analysis for the determination. Alternatively, the stationary controller may examine output generated by an ultrasonic sensor in order to determine whether hand cleaning solution has been dispensed. In another specific implementation, the stationary controller tracks the operation of the removal of the garment as opposed to hand movement(s). For example, the stationary controller may include a sensor, such as a sound sensor, to determine whether a sound indicates the removal from a container of gowns, masks or the like (and/or the throwing away in the instance of removal the PPE garment(s)). Alternatively, a sensor may indicate whether there is movement near the container to indicate the removal of the PPE garment (e.g., a sensor may indicate that a drawer housing the PPE garment has been opened).

In an alternate implementation, multiple types of hand cleaning solution may be dispensed. One type comprises an alcohol-based cleaning solution, which is dispensed from a first dispenser. Another type comprises a soap-based cleaning solution, which is dispensed from a second dispenser. In one implementation, one or more stationary controllers may determine whether the respective dispenser (alcohol-based cleaning solution dispenser or soap dispenser) has dispensed cleaning agent. For example, one or more sound sensors may generate sound data for the sound from the respective dispenser, with the sound data being analyzed to determine whether the sound is more closely related to the sound when dispensing the alcohol-based cleaning solution from the alcohol-based cleaning solution dispenser or more closely related to the sound when dispensing the soap-based cleaning solution from the soap-based cleaning solution dispenser. In this regard, the stationary controller may record the sound, and determine whether the sound is indicative of dispensing from the first dispenser (and thus dispensing the alcohol-based cleaning solution) or is indicative of dispensing from the second dispenser (and thus dispensing the soap-based cleaning solution). Alternatively, multiple indicators (such as multiple sounds) may indicate compliance with the hand hygiene protocol. As discussed above, one hand hygiene protocol comprises using soap and water. In this way, one or more sound sensors may sense first sound data emanating from the dispenser (such as the soap dispenser) and sense second sound data emanating from the faucet (to determine whether water is flowing from the faucet). Responsive to determining that the first sound data is indicative of dispensing from the soap dispenser and second sound data is indicative of water flow, the stationary controller may determine compliance with the soap/water protocol. In this way, the stationary controller may determine, based on sound, which of the multiple types of hand cleaning solution were dispensed. This determination may be used particularly when the hand hygiene protocol may change in a patient area, such as a patient room. For example, responsive to changing the protocol from using hand sanitizer to using soap/water, the stationary controller may determine whether the healthcare worker complied with the new protocol (e.g., taking soap rather than sanitizer). Alternatively, or in addition, multiple PPE garments may be dispensed, such as masks, gowns, etc. In one implementation, one or more stationary controllers may determine whether the respective container (mask container containing masks or gown container containing gowns) has movement and/or sound indicating removal of a respective PPE garment. Again, responsive to changing the PPE protocol, the stationary controller may determine whether the healthcare worker complied with the new PPE protocol.

Alternatively, the wristband, via a microphone resident on the wristband, may input sound data and may determine itself whether the sound data is indicative of the sound of the motor dispensing hand cleaning agent and/or removal of the PPE garment from the container. Or, in the instance of multiple types of hand cleaning solution, the wristband may determine, from analysis of the sound, which dispenser dispensed the hand cleaning agent, and in turn the type of hand cleaning agent. In this regard, the wristband may determine whether hand cleaning agent has been dispensed, triggering a hand hygiene event. Alternatively, or in addition, in the instance of multiple types of PPE garments, the wristband may determine, from analysis of the sound, from which container the PPE garment was removed, and in turn the type of PPE garment subject to removal. As another example, the stationary controller may be integrated with the electronics of the dispenser such that a signal from the dispenser motor, which is configured to dispense hand cleaning solution, may be input to the stationary controller. In that regard, responsive to the signal from the dispenser motion indicating that the motor dispensed hand cleaning solution, the stationary controller may determine that hand cleaning solution has been dispensed.

In still another implementation, the system may include a back-end electronic device, such as a server, that performs analytics, as discussed above. The analytics may be configured to perform any one, any combination, or all of: determine compliance (e.g., full, partial or non-compliance); generate compliance reports, to identify trends based on time of shift, protocols, and other desired metrics; identify patients and/or healthcare providers that are the source of cross-contamination; generate alerts responsive to compliance determinations, identifying trends, identifying patients and/or healthcare providers that are the source of cross-contamination, or the like; generating displays or other types of graphical users interfaces to output statistics based on one or more criteria, such as based on an event (e.g., full, partial, or non-compliance), based on people (e.g., analysis based on all doctors, all nurses, or individuals), and/or based on location (e.g., based on the particular floor of a hospital, the particular wing of a hospital, based on a department of the hospital (e.g., ICU-A, ICU-B, ICU-C)).

In one implementation, one or more electronic devices may work in combination with the wristband in order to instruct a user as to proper hand hygiene and/or PPE compliance. For example, a user may follow instructions of requested movements that are output (e.g., displayed on a display) on an electronic device. The wristband, worn by the user, may register movements of the user. The electronic device may compare the requested movements with the registered movements in order to provide feedback to the user. In a first implementation, the user may comprise an adult healthcare provider, with the feedback to the user for instructional purposes. The feedback may comprise instructions as to one or more of the following: information as to deficiencies in hand hygiene movements and/or PPE movements (e.g., whether the proper movements were performed or were performed in the proper sequence); or information as to deficiencies in the amount of time of hand hygiene and/or in the amount of time in putting on PPE garment(s). The feedback may include a score, with the score based on improvement or worsening of the hand hygiene and/or PPE compliance (e.g., improvement or worsening based on a previous training session). In a second implementation, the user may comprise a child, with the feedback to the user for instructing the child on hand hygiene. The feedback may take one or more forms. In one form, the feedback may be similar to the feedback to educate a healthcare provider. Alternatively, or in addition, the form of the feedback may be in the form of scoring for a video game type output or gamification. As one example, the feedback may be in the form of a score, which may be translated in a video game type feedback. As another example, the gamification may use game-design elements and game principles in non-game contexts, such as in the context of teaching hand hygiene.

In still another implementation, hand hygiene and/or PPE monitoring may be integrated with another type of system, such as an access control system. Various types of access control systems are contemplated. In one example, the access control may comprise physical access, such as access to a premises. In another example, the access control may comprise information access, such as computer access to a resource, such as information. In either type, the access control system may determine whether a user is authorized for access.

In one implementation, the access control may be determined based on an identification code associated with the user. Various types of identification codes may be used. In a first type, the identification code may be transmitted via radio frequency. In particular, radio frequency identification (RFID) technology may be used. RFID may use electromagnetic fields to automatically identify a user. For example, RFID tags may contain electronically-stored information indicative of an identification code of the user. Different types of RFID tags may be used. One type of RFID tag comprises a passive RFID tag, which collects energy from a nearby RFID reader's interrogating radio waves. Another type of RFID tag comprises an active RFID tag, which has a local power source (such as a battery). In this regard, an RFID tag may be used or incorporated within or somehow associated with the wristband. Thus, the wristband may be held within a certain distance of the RFID reader to authenticate the user. In another type, the identification code may be transmitted via a communication protocol, such as near-field communication (e.g., Bluetooth) and/or Wi-Fi.

In a first specific implementation, the access control system and the hand hygiene and/or PPE system may operate independently of one another, with the wristband including both types of functionality (e.g., hand hygiene and/or PPE functionality including one or more motion sensors and/or hand hygiene and/or PPE analytics and access control functionality including access control identification (e.g., RFID tag), with the hand hygiene and/or PPE functionality and access control functionality operating independently of one another). In a second specific implementation, hand hygiene and/or PPE monitoring and access control may be integrated. In one aspect, both hand hygiene and/or PPE monitoring and access control may be analyzed in order to determine whether to grant access to a person, such as a healthcare provider, to a premises, such as a room, a floor, a building, or the like. The analysis may comprise: (1) whether the hand hygiene and/or PPE monitoring system has determined that the person has sufficiently met hand hygiene protocol(s) and/or PPE protocols (e.g., the person has taken sanitizer; whether the person performed a hand hygiene rubbing motion (such as for at least a predetermined time); whether the person performed a set of predetermined rubbing motions; the person has taken the PPE garment(s) in the proper sequence; whether the person performed the hand movements indicating proper putting on of the PPE garment(s) in the proper sequence; whether the person has performed the hand hygiene and PPE compliance in the proper combination); and (2) whether the access control system has determined that the person is authorized to enter (e.g., the identification code associated with the person indicates access to premises should be granted). Performing (1) and (2) may be in any sequence in order to determine whether to grant access, such as: first (1) and then (2); first (2) and then (1); or both (1) and (2) are examined simultaneously.

Further, different devices may perform (1) and/or (2). In one implementation, the wristband may perform (1) and an external device, such as a stationary RFID local access control panel or a central RFID control system, may perform (2). In another implementation, the stationary controller may perform (1) and an external device, such as a stationary RFID local access control panel or a central RFID control system, may perform (2). In still another implementation, a hand hygiene and/or PPE central monitoring system may perform (1) and an external device, such as a stationary RFID local access control panel or a central RFID control system, may perform (2).

As discussed above, the wristband may include functionality for both monitoring hand hygiene and/or PPE and for access control (e.g., monitoring hand hygiene and access control; monitoring PPE and access control, monitoring hand hygiene, PPE, and access control). In one implementation, the wristband may include one or more sensors for monitoring hand hygiene and/or PPE (and optionally functionality for determining whether the hand hygiene and/or PPE was sufficient), and may include functionality for the identification code associated with the person (e.g., an RFID tag that is associated with the person; an identification code that may be transmitted via Bluetooth or Wi-Fi or the like). In this regard, the information (such as identification code and the hand hygiene and/or PPE information) may be transmitted via different protocols (e.g., RFID vs. Bluetooth or Wi-Fi) or may be transmitted via the same protocol (e.g., Bluetooth or Wi-Fi). Further, the wristband may transmit the information in a predetermined sequence. As one example, the wristband may transmit the identification code and the hand hygiene and/or PPE information independent of one another. As another example, the wristband may transmit the identification code and the hand hygiene and/or PPE information dependent on one another, such as transmitting the identification code only in response to the wristband determining that the hand hygiene and/or PPE is sufficient.

In still another implementation, a proximity sensing-output generating device is disclosed. In a specific implementation, the proximity sensing-output generating device may be positioned in different sections of a premises, and may be configured to sense one or more events or tasks. For example, the proximity sensing-output generating device may be fixedly attached to a part of the premises, such as to a wall, a door, a drawer, an electrical appliance (e.g., a refrigerator), or the like. The events or tasks may comprise leaving a premises, entering a premises, preparing food, using the toilet, using the faucet, or the like. These events or tasks may not follow a predefined schedule and may thus be difficult to track.

The proximity sensing-output generating device may identify the event or task based on one or more sensors resident in the proximity sensing-output generating device. In one implementation, the one or more sensors comprise one or more motion sensors (e.g., micro-vibration sensor, accelerometer, gyroscope). The motion sensor(s) may sense movement of the part of the premises to which the proximity sensing-output generating device is attached (e.g., sense movement of the door, the drawer, etc.) or may sense movement proximate to the proximity sensing-output generating device (e.g., in a hallway of the premises). In one implementation, the motion sensor(s) sense direction of opening (such as whether a door is being opened or closed; drawer/cabinet is being opened or closed). As discussed further below, the motion sensors may sense whether an event or a task will happen, or whether an event or a task is happening. As one example, responsive to the motion sensor sensing that a door to the bathroom has opened, the proximity sensing-output generating device may determine that the person is using the bathroom. As another example, responsive to the motion sensor sensing that a door to the residence has opened, the proximity sensing-output generating device may determine that the person is exiting the residence. As still another example, responsive to the motion sensor sensing that a drawer, a cabinet, and/or an appliance in the kitchen has been opened, the proximity sensing-output generating device may determine that the person is using the kitchen.

Alternatively, or in addition, the proximity sensing-output generating device may include a sound sensor (e.g., a microphone or the like) configured to sense one or more sounds in the premises in order to determine whether the event or task is occurring. Responsive to the sensor(s) determining that an event or task is occurring or will occur, the proximity sensing-output generating device may take one or more actions. In one implementation, the proximity sensing-output generating device may wake-up at least a part of the proximity sensing-output generating device. As one example, the sound sensor may sense one aspect in order to wake up in anticipation of monitoring an event or a task. In particular, the sound sensor may sense a toilet flushing or a person walking in the vicinity in order to wake up one or more circuits in the proximity sensing-output generating device. As another example, the micro-vibration sensor may sense vibration in order to wake up at least a part of the proximity sensing-output generating device.

Alternatively, or in addition, the proximity sensing-output generating device may generate an output. For example, responsive to the sound sensor detecting an event or a task, such as a door opening, a cabinet opening, or the like, the proximity sensing-output generating device may generate an output (e.g., responsive to sensing that the bathroom door opening, the proximity sensing-output generating device may generate an audio output reminding to "flush the toilet after use"; responsive to the sound sensor sensing that the toilet has flushed, the proximity sensing-output generating device may generate an audio output reminding to "wash hands in the sink"; etc.).

As another example, responsive to the sound sensor not detecting an event or a task, such as not detecting that the water in the bathroom has been shut off, the proximity sensing-output generating device may generate an output (e.g., responsive to the sound sensor continuing to sense for greater than a predetermined amount of time that the faucet is still running water, the proximity sensing-output generating device may generate an audio output reminding to "shut off the faucet in the bathroom").

As still another example, responsive to the motion sensor detecting an event or task, the proximity sensing-output generating device may generate an output (e.g., responsive to the door sensor detecting the opening of the front door, the proximity sensing-output generating device may generate an audio output reminding to "take your mobile phone and identification with you").

Further, the proximity sensing-output generating device may sense a series of sounds and/or a series of movements in sequence (including the presence/absence of a sound, and/or the presence/absence of a movement). In the example of monitoring the event or task of using the restroom, the proximity sensing-output generating device may monitor the series of sounds including: (1) toilet flushing (e.g., the presence of a sound that the toilet has flushed); and (2) the absence of water running (or first the presence of water running indicating that the faucet has been used, and thereafter the absence of water running to monitor that the faucet has been turned off). Responsive to monitoring each of the series of sounds, the proximity sensing-output generating device may generate an output.

Thus, at any point in the detected event or task, the proximity sensing-output generating device may generate one or more outputs. The outputs may take one of several forms, including an aural output (such as via a speaker), a visual output (such as via display), or a combination thereof. Further, the outputs may be generated in anticipation of reminding a person of an expected event or task, or reminding a person in case the event or task has not occurred.

The aural outputs may be pre-recorded sound. For example, the proximity sensing-output generating device may include a button or trigger in order to input the aural output so that a familiar voice, such as from a family member, may be output as a reminder.

A series of proximity sensing-output generating devices may be positioned in various parts of a residence, such as in the kitchen, in the entranceway, in the bathrooms, or the like. Further, the proximity sensing-output generating devices may communicate with one another and/or with a central hub via wireless communication (e.g., Wi-Fi communication). In this regard, the proximity sensing-output generating devices may communicate with other proximity sensing-output generating devices locally (e.g., point-to-point) or with a hub centrally (e.g., hub and spoke). In this regard, one proximity sensing-output generating device may sense an event and may communicate with the hub and/or another proximity sensing-output generating device in order for the output to be generated by another proximity sensing-output generating device. As discussed above, in the context of a faucet running in the bathroom, since the person has left the bathroom and the faucet running, the proximity sensing-output generating device positioned near or in the bathroom may communicate (either directly or via a hub) with another proximity sensing-output generating device. The another proximity sensing-output generating device may then generate an output in order to remind the resident to turn the faucet off in the bathroom. Alternatively, or in addition, the proximity sensing-output generating device positioned near or in the bathroom may communicate (either directly or via a hub) with an electronic device external to the premises (e.g., sending an alert to a central authority, which in turn relays the alert to a mobile phone of a family member of the resident, or sending the alert to the mobile phone of the family member directly) alerting the electronic device of the event (e.g., the failure to turn off the faucet or the exit of the resident from the residence).

The proximity sensing-output generating device may take one of several forms, such as a small form factor for placement on a door, a wall, a drawer (e.g., such as in the shape of a pull-knob for a drawer), an appliance, or the like. Further, the proximity sensing-output generating device may include a multi-position switch in order to indicate the placement of the proximity sensing-output generating device. As one example, the proximity sensing-output generating device may include a 3-position switch, with a first position indicative of bathroom placement, a second position indicative of kitchen placement, and a third position indicative of entranceway placement. Responsive to the position of the switch, the proximity sensing-output generating device may activate different modes in the device (e.g., a kitchen mode in order to sense events related to the kitchen and generate outputs thereto, a bathroom mode in order to sense events related to the bathroom and generate outputs thereto, and an entranceway mode in order to sense events related to the entranceway and generate outputs thereto).

In yet another implementation, the wristband may include multiple monitoring functionalities, such as hand hygiene and/or PPE monitoring functionality and non-hand hygiene or non-PPE monitoring (e.g., fitness monitoring). As discussed above, the wristband may monitor one or more activities, which may relate to any one, any combination, or all of: hand hygiene; PPE; or fitness monitoring. The wristband may include algorithms that distinguish between the hand hygiene and/or PPE motions and other fitness type motions, such as walking. For example, the wristband may include separate algorithms that analyze the hand hygiene and/or PPE motions and other fitness type motions, such as walking. As another example, the wristband may include a single algorithm that analyzes both the hand hygiene and/or PPE motions and other fitness type motions in combination. In this regard, the wristband, which includes multiple functionalities (including two functionalities, such as hand hygiene and fitness, PPE and fitness, or three functionalities, such as hand hygiene, PPE and fitness), may act synergistically to analyze the hand hygiene and/or PPE motions and the non-hand hygiene or non-PPE motions (such as walking or stepping).

Thus, in one implementation, the sensor-based system, discussed in more detail below, is configured to track and analyze the HH and/or PPE of healthcare providers (e.g., provide 24 hours a day and 7 days a week monitoring, and provide real-time intervention and feedback).

In one implementation, a PPE monitoring system and method is disclosed. Similar to the HH monitoring system, the PPE system may be used in various settings, such as in a hospital setting, a nursing home setting, a home setting, or the like. In a first specific implementation, the PPE monitoring system comprises one or more mobile electronic devices and one or more stationary electronic devices. The mobile electronic device may be configured to be attached or associated (such as by the shape of the mobile electronic device or a hook or clip associated with the electronic device) with a person, such as a healthcare provider, a child, an elderly person, or the like. As discussed in more detail below, the mobile electronic device in one implementation may comprise a wristband electronic device configured to be worn on a person's wrist. Alternatively, the mobile electronic device may be attached to other parts of the person's body. The stationary electronic device may be fixedly attached to a part of a premises. The part of the premises may be itself stationary (such as a stationary hand cleaning agent dispenser proximate to or associated with an entrance or an exit to a patient area (such as a patient room)) or may move (such as a door or a drawer). For example, as discussed in more detail below, the stationary electronic device may be fixedly attached in relation to a hand cleaning agent dispenser (e.g., as part of (or within) the hand cleaning agent dispenser or in fixed relation and proximate to or adjacent to the hand cleaning agent dispenser). In a second specific implementation, the PPE monitoring system comprises one or more mobile electronic devices, one or more stationary electronic devices, and central analytics. The central analytics may be configured to analyze one or more aspects of the PPE monitoring system, as discussed further below.

Thus, in one implementation, the PPE monitoring system may comprise a PPE compliance system configured for use in a hospital setting or other healthcare setting, whereby one or more healthcare providers wear wristbands and whereby stationary controllers may be associated with an entrance and/or exit to a room, and back-end analytics (such as cloud computing). Though disclosed in the context of a HH monitoring system, examples of this are likewise illustrated in FIGS. 1A-C. Alternatively, or in addition, the PPE compliance system includes the wristband and a stationary controller, an example of which is illustrated in FIG. 2.

Similar to HH monitoring, the mobile electronic device is configured with one or more sensors that measure movement of a person, such as the healthcare provider, and may comprise a wristband electronic device, whereby the wristband electronic device is affixed to the wrist of the person. Any discussion below regarding a wristband for HH monitoring may likewise be applied to PPE monitoring. As merely one example, the wristband may record sensor data from one or more sensors, with the wristband including a single motion sensor, or multiple motion sensors (e.g., a first type of motion sensor and a second type of motion sensor, with the first type of motion sensor being different than the second type of motion sensor).

Similar to the discussion for the wristband monitoring HH movement, the first type of motion sensor comprises a micro-vibration sensor configured to sense basic movement, and the second type of motion sensor comprises an accelerometer configured to sense acceleration in one, two, or three axes. In still an alternate implementation, the wristband includes three or more motion sensors, such as a first type of motion sensor, a second type of motion sensor, and a third type of motion sensor, with each type being different from the other. As discussed further below, the wristband may include any one, any two, any three, or all four of: a micro-vibration sensor; an accelerometer; a gyroscope; and a magnetometer.

Responsive to the one or more sensors generating sensor data, the sensor data may be analyzed for PPE compliance. In one implementation, the wristband analyzes the sensor data, with the wristband making the determination, based on the analysis, whether the PPE movements were sufficient or insufficient according to the PPE protocols. Thereafter, the wristband may output the determination (e.g., generating an output indicative of the sufficiency and/or insufficiency of the PPE movements according to the PPE protocols) and may transmit the determination (e.g., sufficiency and/or insufficiency of PPE movements according to the guidelines) to an external device, such as the stationary controller and/or the back-end analytics. Alternatively, or in addition, the wristband may determine compliance with multiple protocols, such as both HH protocols and PPE protocols.

In another implementation, the stationary controller receives the sensor data from the wristband and analyzes the sensor data, thereby making the determination as to sufficiency and/or insufficiency of PPE movements. Thereafter, the stationary controller transmits the determination (e.g., sufficiency and/or insufficiency of PPE movements according to the guidelines) to an external device, such as the wristband (for outputting an indication of sufficiency and/or insufficiency according to the guidelines) or the back-end analytics.

Alternatively, or in addition, the stationary controller (or alternatively multiple stationary controllers) may determine compliance with multiple protocols, such as both HH protocols and PPE protocols. The determination as to compliance with HH protocols may be achieved in one of several ways, including any one, any combination, or all of: whether hand cleaning agent (such as sanitizer, soap, or the like) has been dispensed; whether the hand movements were for a sufficient period of time; or whether the hand movements were sufficient to meet compliance. Alternatively, or in addition, the determination as to compliance with PPE protocols may occur independently of (or in dependence of) the determination of compliance with the hand hygiene opportunity and/or the hand hygiene event. As one example, the identification of the hand hygiene opportunity is independent of the identification of the PPE opportunity. As another example, the identification of the hand hygiene opportunity is dependent of the identification of the PPE opportunity (identification of one results in identification of the other). As still another example, the determination as to the hand hygiene event is independent of the determination of compliance of the PPE event. As another example, the determination as to the hand hygiene event is dependent of the determination of compliance of the PPE event (e.g., before entering the room, compliance with the hand hygiene event is first determined and thereafter compliance with the PPE event is determined; upon exiting the room, compliance with the PPE event is first determined and thereafter compliance with the hand hygiene event is determined). In still another implementation, the back-end analytics receives the sensor data from the wristband and analyzes the sensor data, thereby making the determination as to sufficiency and/or insufficiency of PPE and/or HH movements according to the guidelines. Thereafter, the back-end analytics transmits the determination (e.g., sufficiency and/or insufficiency of PPE and/or HH movements) to an external device, such as the wristband (for outputting an indication of sufficiency and/or insufficiency) or the stationary controller.

Alternatively, more than one device may determine PPE compliance. As one example, the wristband and the stationary controller, in combination, may determine PPE and HH compliance. As another example, the wristband and the back-end analytics, in combination, may determine PPE compliance.

As discussed above, the analytics may analyze the sensor data in one or more respects to determine PPE compliance. In one implementation, the analytics may determine whether or not the person performed any act related to putting on or taking off personal protective equipment (such as whether the healthcare provider put on or took off latex rubber gloves). As one example, the analysis of the sensor data may be configured to identify a plurality of discrete motions that are indicative of performing certain predetermined movements associated with putting on or taking off personal protective equipment. In one implementation, the analytics may determine whether all the predetermined PPE motions in the discrete set of PPE motions were performed in a specific sequence (e.g., motion associated with putting on gloves is detected last; motion associated with putting on gloves is detected first). In an alternate implementation, the analytics may determine whether all of the predetermined PPE motions in the discrete set of PPE motions were performed in any sequence. As discussed above, the determination of compliance with the PPE event may be independent of any determination of compliance with the HH event. Alternatively, the determination of compliance with the PPE event and the determination of compliance with the HH event are dependent on one another (e.g., first determine that hand cleaning agent has been dispensed, then determine the hand hygiene movements have occurred, then determine whether the PPE garments have been dispensed and/or movements indicating that the PPE garments have been put on).

As discussed above, various PPE protocols may be used. In one implementation, an entire area (such as a section of a floor in a hospital (e.g., Intensive Care Unit)), an entire floor, or an entire building (e.g., an entire hospital building) may be subject to the same PPE protocol. In another implementation, the PPE protocol used may depend on a specific patient area, such as a patient room. As one example, a first patient may be in a first patient area (such as a first patient room) and a second patient may be in a second patient area (such as a second patient room). The first patient may have a first illness that has associated therewith a first PPE protocol, and the second patient may have a second illness that has associated therewith a second PPE protocol, with the first PPE protocol being different from the second PPE protocol. In particular, the first PPE protocol may require gloves, and the second PPE protocol may require gloves, gown and a mask. Similarly, a patient's associated hygiene protocol may change, such as responsive to the patient being diagnosed with a new illness while in the hospital (e.g., after admittance, the patient is diagnosed with a MRSA infection, resulting in the HH protocol and/or the PPE protocol changing, so that the hygiene protocol(s) associated with the room change as well).

Further, PPE protocols may be dependent on whether a person is entering or exiting a patient area, as discussed in more detail below. Thus, one or more devices may determine whether the person (e.g., the healthcare worker) is entering or exiting a patient area (e.g., a patient room). In one implementation, one or more stationary controllers may perform the determination.

For example, a single stationary controller may be used to determine whether the person is entering or exiting the patient area (e.g., the single stationary controller may be the same stationary controller used for identifying the HH opportunity and/or HH event; alternatively, a different stationary controller may be used for identifying the HH opportunity and/or HH event). In one implementation, the stationary controller may make this determination based on timing and/or based on an identification of the person. As one example, the wristband may include a particular identification associated with the healthcare worker. A particular stationary controller, communicating with the wristband, may receive the particular identification. Responsive to the particular stationary controller determining that it has not communicated with the wristband with this particular identification within a certain period of time (e.g., 2 minutes, 5 minutes, etc.), the stationary controller may determine that the healthcare worker has entered the patient area. Responsive to the particular stationary controller determining that it has communicated with the wristband with this particular identification within the certain period of time, the stationary controller may determine that the healthcare worker is exiting the patient area.

As another example, multiple stationary controllers may be used to determine whether the person is entering or exiting the patient area. The multiple stationary controllers may be stationed in different positions relative to the patient area (e.g., a first stationary controller positioned outside of the patient area and a second stationary controller positioned inside of the patient area). In one implementation, the stationary controllers may interact with a wristband (such as via Bluetooth communication). Responsive to the interaction, the respective stationary controller may determine whether the healthcare worker (who is wearing the wristband) is entering or exiting the patient area. For example, responsive to the first stationary controller communicating via Bluetooth with the wristband for a certain period or time (or the first stationary controller communicating via Bluetooth with the wristband without the second stationary controller communicating via Bluetooth with the wristband; or the first stationary controller first communicating via Bluetooth with the wristband before the second stationary controller communicates via Bluetooth with the wristband), the first stationary controller (which is positioned outside the patient area) may determine that the healthcare worker is entering the patient area. As another example, responsive to the second stationary controller communicating via Bluetooth with the wristband for a certain period or time (or the second stationary controller communicating via Bluetooth with the wristband without the first stationary controller communicating via Bluetooth with the wristband; or the second stationary controller first communicating via Bluetooth with the wristband before the first stationary controller communicates via Bluetooth with the wristband), the second stationary controller (which is positioned inside the patient area) may determine that the healthcare worker is exiting the patient area.

In another implementation, the wristband may perform the determination as to whether the person is entering or exiting the patient area. In a first specific implementation, the wristband may analyze the sensor data (e.g., data from the gyroscope and/or accelerometer) responsive to detecting communication from a stationary controller. For example, responsive to communicating via Bluetooth with a stationary controller, the wristband may store sensor data from one or more sensors (e.g., gyroscope and/or accelerometer) and analyze the sensor data in order to determine whether the sensor data is indicative of a pulling motion or a pushing motion. Responsive to determining that the sensor data is indicative of a pulling motion and responsive to a pulling motion being indicative of entering an area (e.g., the wristband is pre-programmed to indicate that pulling motions are indicative of entering an area), the wristband and/or stationary controller may determine that the healthcare worker has entered the patient area. Responsive to determining that the sensor data is indicative of a pushing motion and responsive to a pushing motion being indicative of exiting an area (e.g., the wristband is pre-programmed to indicate that pushing motions are indicative of exiting an area), the wristband and/or stationary controller may determine that the healthcare worker has exited the patient area. In a second specific implementation, the wristband may analyze the sensor data (e.g., data from the gyroscope and/or accelerometer) continuously to determine whether a pulling motion or a pushing motion has occurred.

In yet another implementation, a device separate from the stationary controllers and the wristband may be used in determining whether the healthcare worker is entering or exiting the patient area. A proximity sensing device may be positioned in different sections of a premises (such as on or associated with a door), and may be configured to sense one or more events or tasks. For example, the proximity sensing device may be fixedly attached to a door in order to indicate whether the door is being opened or closed. The proximity sensing device may identify the event (such as the door opening and/or closing) on one or more sensors resident in the proximity sensing device. In one implementation, the one or more sensors comprise one or more motion sensors (e.g., micro-vibration sensor, accelerometer, gyroscope). The motion sensor(s) may sense movement of the part of the premises to which the proximity sensing-output generating device is attached (e.g., sense movement of the door, etc.) or may sense movement proximate to the proximity sensing device (e.g., in a hallway of the premises). In one implementation, the motion sensor(s) sense direction of opening (such as whether a door is being opened or closed). As one example, responsive to the motion sensor sensing that a door to the patient room has opened, the proximity sensing device may determine that a healthcare provider is entering the patient room. An example of the proximity sensing device is disclosed in U.S. application Ser. No. 15/946,537 (now U.S. Pat. No. 10,403,121), incorporated by reference herein in its entirety.

Thus, the proximity sensing device may be configured to indicate movement of a door, such as movement associated with opening and/or closing of the door. In one implementation, the proximity sensing and output generating device may only sense a movement (such as the door has been opened and closed), but cannot sense whether the movement is associated with an entrance or an exit. In this regard, the proximity sensing and output generating device may be used in combination with one or both of the wristband or the stationary controller in order to determine whether the person is entering or exiting the patient area. As one example, responsive to the proximity sensing and output generating device determining movement of the door, the proximity sensing and output generating device may generate an output indicative of the determination of the movement of the door. The wristband and/or the stationary controller may receive the output, and responsive to receipt, may analyze its sensor data in order to make the determination as to whether the healthcare worker is entering or exiting the patient area. For example, responsive to receiving the output, the wristband may analyze its sensor data in order to determine whether it has recorded a pulling motion or a pushing motion, and responsive to this determination, determine whether the healthcare worker is entering or exiting the patient area. As another example, the proximity sensing and output generating device may have a unique identification, and send the unique identification in the output to the stationary controller. Using the output, with the unique identification, the stationary controller may determine whether the healthcare worker is entering or exiting the patient area.

The device which makes the determination of PPE protocol compliance may receive the respective protocol in one of several ways. In the example where the wristband performs the determination as to PPE protocol compliance, the wristband may receive an indication as to the specific PPE protocol from a separate electronic device (e.g., the stationary controller and/or the backend server). In particular, a stationary controller may be associated with a specific patient area, such as first patient area or second patient area. The stationary controller may send one or both of an indication of the PPE protocol or the required movements for the PPE protocol. In the example, discussed above, responsive to the wristband being proximate to the first stationary controller, the first stationary controller may transmit to the wristband an indication of the first PPE protocol (e.g., the first PPE protocol may comprise a gown and gloves, with the first stationary controller transmitting to the wristband an indication of the gown and gloves, such as upon entering the room and indication of putting on the gown first and then the gloves).

Further, in one implementation, the sensor data for PPE movement is analyzed in each of the three dimensions. In an alternate implementation, the sensor data for PPE movement is analyzed in fewer than all of the three dimensions. In a first specific implementation, the sensor data is analyzed in only two dimensions (e.g., analyzing for large acceleration in both the x- and y-axis). In a second specific implementation, the sensor data is analyzed in only one dimension (e.g., analyzing for large rotation rate along the y-axis (pitch) or for large acceleration along the z-axis).

In still another implementation, the method and system for PPE compliance limits analysis to a discrete window of sensor data. In particular, an identification of a PPE opportunity and/or a triggering event may identify a potential PPE event, thereby beginning the sequence of analyzing the sensor data for the PPE opportunity and/or the PPE event. As discussed in more detail below, in one implementation, the wristband and the stationary controller work in combination for the triggering event. In one example, the stationary controller sends a beacon. Responsive to the wristband coming within range of near-field communication (e.g., within Bluetooth communication range for at least a predetermined amount of time), the wristband may be triggered to record sensor data in order to determine whether PPE movements have occurred. In another example, the wristband may send a beacon, such as a Bluetooth signal or RFID signal. The stationary controller may sense the signal (e.g., the stationary controller may determine, based on the strength of the beacon, how close the wristband is to the stationary controller). Responsive to the stationary controller determining that the wristband is proximate (e.g., within a predetermined distance for at least a predetermined amount of time), the stationary controller may transmit a wake-up signal to the wristband to record the sensor data for analysis. In still another example, the wristband may identify the PPE opportunity, as discussed below. Further, the analysis of the sensor data generated within the discrete window may be based on a contrast of PPE motions with other periodic motions that may occur within the discrete window. As one example, the time period associated with the discrete window may be 60 seconds when the healthcare provider is walking into a patient's room. In that regard, the analysis may focus on contrasting PPE movements with other periodic movements that may be performed within the 60 second discrete window (e.g., walking, knocking on a door, etc.). For example, the analysis may focus on frequency and/or power to differentiate PPE movements with other periodic movements. In this regard, accuracy of analysis may be increased by: (1) using data in the discrete window; and (2) analyzing PPE actions and contrasting those PPE actions without other periodic actions (e.g., walking, knocking on door) within that discrete window.

In the present implementation, the motion sensor may operate for a very short time (e.g., less than 30 seconds, between 30 seconds and 1 minute, approximately 1 minute, less than 1 minute, between 30 seconds and 1 minute 30 seconds, between 1 minute and 2 minutes, less than 2 minutes, less than 3 minutes, less than 5 minutes, etc.) only when a PPE opportunity is identified and/or a PPE event is detected. For most of the time, at least a part of the wristband, such as one or more of the motion sensors within the wristband, is in sleep mode. For example, within sleep mode, power may be reduced or completely withheld from one or more parts of the wristband, such as the motion sensor. This achieves both low power dissipation and reliable PPE compliance detection. Selection of low-power chips further reduces the wristband's power consumption, as discussed further below. In particular, since the wristband is activated in the discrete window, the wristband may have a longer battery life, thereby reducing the burden from the healthcare provider to recharge or replace the battery as often. Further, since the wristband is activated in the discrete window, the wristband may focus on events that may occur within the window, thereby more accurately detecting compliance during a PPE opportunity and/or a PPE event, and avoiding false alarms from any interfering motions (e.g., walking) or motions in a non-PPE opportunity and/or a non-PPE event.

In one implementation, the analysis uses one or more static thresholds in analyzing whether the sensor data is indicative of PPE movements. For example, the frequency and/or the power associated with the sensor data may be compared with static thresholds (e.g., use a static filter to filter periodic walking movement from PPE movement; use a static threshold to analyze in the magnitude domain (such as power)). With regard to frequency, one or more thresholds, such as a lower threshold (e.g., to filter out other periodic movements, such as walking) and/or an upper threshold (e.g., to filter out overly PPE movements) may be used. In an alternate implementation, the analysis may use one or more dynamic thresholds in order to dynamically adapt the analytics. For example, based on previous sensor data, the thresholds and/or ranges for frequency and/or power analysis may be adapted. In a particular example, the analysis may use machine learning that adapts to an individual healthcare provider's PPE habit. For example, the individual healthcare provider may perform PPE movements multiple times in a certain period (e.g., in a day, week, month, etc.). The machine learning may extract one or more characteristics associated with the PPE habits of the individual healthcare provider and then store those parameters correlated to this individual healthcare provider. Thus, the thresholds, such as the frequency and/or magnitude for analysis, may be tailored to the individual healthcare provider.

As discussed in more detail below, the wristband may operate in a lower power mode. In one implementation, the wristband may operate in a discrete window (such as any of the intervals discussed above, such as for 60 seconds) in order to detect the hand hygiene movements. Within this discrete window, one or more operations of the wristband, such as the motion sensor(s), are awakened for recording sensor data.

Further, in one implementation, the wristband may operate in a sleep mode (in which a part of the electronics within the wristband are turned off or are consuming less power) and may operate in a normal mode (in which some or all of the electronics within the wristband that are turned off or are consuming less power in sleep mode are turned on or consume a greater amount of power). As one example, the wristband may include one or more sensors, with some or all of the sensors being turned off or inactive in sleep mode, and some or all of the sensors being turned on or active in normal mode.

The wristband may be triggered to exit from sleep mode in one of several ways. In one way, the wristband may make the decision to exit sleep mode on its own and without any input from an external device. For example, the wristband may have one or more sensors that remain active in sleep mode, with the data generated by the one or more sensors active in sleep mode being used to determine whether to exit sleep mode. In particular, the wristband may include a micro-vibration sensor. The micro-vibration sensor draws less power than other motion sensors, such as accelerometers or gyroscopes. Responsive to the micro-vibration sensor, active in sleep mode, indicating motion, the wristband may wake-up the microcontroller and/or other sensors on the wristband, such as the accelerometer and/or gyroscope and/or magnetometer, thereby exiting sleep mode. In another way, the wristband may make the decision to exit sleep mode based on input from another electronic device. For example, the wristband may work in combination with an external device, such as the stationary controller, in order to determine when a PPE event begins (and, in turn, when for the wristband is to "wake up"). As discussed above, the wristband may send a beacon to the stationary controller, or may receive a beacon from the stationary controller in order to trigger the wake up of the wristband. After which, the wristband may generate and record sensor data. After the PPE event (e.g., after no more than 60 seconds), the wristband may go back into sleep mode (either due to determining that the PPE event is successful or not). Alternatively, the wristband may wake up responsive to identifying a PPE opportunity.

In still another implementation, one or more operations of PPE monitoring may be divided amongst the wristband and the stationary controller. As discussed in more detail below, the stationary controller may be associated with an entrance or exit to a room. For example, one operation of PPE monitoring is a trigger for beginning the PPE monitoring. In this example, one of the wristband or the stationary controller may send a beacon, and another of the wristband or the stationary controller may detect the beacon, thereby triggering the beginning of the PPE monitoring. In particular, the wristband may send an RFID or Bluetooth signal, which may be sensed by the stationary controller. In the example of Bluetooth, the stationary controller, based on the signal strength of the Bluetooth signal and/or the time elapsed of receiving the Bluetooth signal, may determine the closeness of the devices to one another. In response to the stationary controller determining that the wristband is within a predetermined distance for a predetermined period of time, the stationary controller may send a wake-up signal to the wristband to begin monitoring for PPE. In another implementation, the stationary controller may transmit a beacon, which upon receipt by the wristband wakes up at least a part of the wristband, such as the motion sensor(s) on the wristband. More specifically, in one implementation, responsive to the wristband sensing the beacon signal from the stationary controller for a predetermined amount of time, the wristband may wake-up the motion sensor(s) on the wristband.

Alternatively, or in addition, the PPE monitoring system may generate one or more outputs associated with the PPE monitoring. A first output may be generated to alert the healthcare provider to perform the PPE movements. A second output may be generated to alert the healthcare provider as to whether the PPE movements were sufficient and/or insufficient. In one implementation, the stationary controller may generate the alert to the healthcare provider to perform the PPE movements, and the wristband may generate the alert to the healthcare provider as to whether the PPE movements were sufficient and/or insufficient. Alternatively, the wristband may generate the alert to the healthcare provider to perform the PPE movements, and the stationary controller may generate the alert to the healthcare provider as to whether the PPE movements were sufficient and/or insufficient. In either implementation, the alerts may be divided amongst the stationary controller and the wristband. In still another implementation, only one device (e.g., either the stationary controller or the wristband) generates both the alert to the healthcare provider to perform the PPE movements, and the alert to the healthcare provider as to whether the PPE movements were sufficient and/or insufficient.

Generally speaking, the analytics may determine any one, any combination, or all of: compliance; partial compliance; or non-compliance. Further, the analytics may determine any one, any combination or all of: whether the person put on or took off the required PPE; whether the person put on or took off the required PPE in the required sequence; whether the person complied with PPE and HH protocols; or whether the person complied with PPE and HH protocols in the required sequence.

Responsive to the determination of the analytics, one or more outputs may be generated using output functionality. In one implementation, the wristband may generate one or more outputs based on a determination of any one, any combination, or all of: compliance, partial compliance and/or non-compliance. The one or more outputs from the wristband may comprise audio and/or visual outputs, such as sound(s) (such as different sounds), light(s) (such as different lights or different combinations of lights), vibration(s) (such as different patterns of vibrations), or the like. For example, a first sound may be indicative of compliance and a second sound, different from the first sound, may be indicative of non-compliance. As another example, a first sound may be indicative of compliance, a second sound may be indicative of partial compliance, and a third sound may be indicative of non-compliance. As still another example, a first light may be indicative of compliance (e.g., a green colored light) and a second sound (e.g., a red colored light) may be indicative of non-compliance. As yet still another example, the wristband may escalate the outputs based on a determination of partial compliance and/o non-compliance. In particular, the wristband may initially output a sound and/or light responsive to determining a hand hygiene event. Responsive to determining non-compliance (and/or partial compliance) with the HH opportunity and/or the HH event, the wristband may generate a different type of output, such as a louder sound (e.g., louder than the output responsive to determining a hand hygiene event) and/or a brighter light (e.g., brighter lights or a greater number of lights than the output responsive to identifying the HH opportunity and/or detecting a HH event).

Alternatively, or in addition, the stationary controller may generate one or more outputs based on a determination of any one, any combination, or all of: compliance, partial compliance and/or non-compliance. The one or more outputs from the stationary controller may comprise audio and/or visual outputs, such as sound(s), light(s), or the like. Alternatively, or in addition, an electronic device separate from the wristband and the stationary controller may generate one or more outputs based on a determination of any one, any combination, or all of: compliance, partial compliance and/or non-compliance. In one implementation, the determination as to compliance, partial compliance and/or non-compliance, either transmitted to or determined by the back-end analytics, may result in the back-end analytics transmitting an alert to a separate electronic device. For example, the separate electronic device (e.g., a smartphone) may be associated with the user who is the subject of the compliant, partial compliant and/or non-compliant PPE event and/or PPE opportunity. As another example, the separate electronic device may be associated with a third party separate from the user subject to the PPE event and/or PPE opportunity. In particular, the separate electronic device may be associated with an administrator tasked with PPE compliance in a hospital setting or a responsible administrator for a section of the hospital (e.g., the head nurse in the ICU). As another example, the separate electronic device may be associated with a teacher tasked to train healthcare providers in PPE protocols.

Alternatively, or in addition, one or more aspects of the wristband, the stationary controller or the back-end analytics may change responsive to a determination of any one, any combination, or all of: compliance; partial compliance; or non-compliance. As one example, responsive to a determination of partial and/or non-compliance, the wristband and/or stationary controller may modify its operation responsive to a new PPE event and/or a new PPE opportunity. In one implementation, the outputs generated by the wristband and/or stationary controller may be different than those outputs during a previous wristband event. As one example, the audio outputs generated by the wristband and/or stationary controller may be louder than those outputs during the previous wristband event responsive to determination of partial compliance and/or non-compliance. As another example, an output, not generated during the previous PPE event and/or previous PPE opportunity, may be generated in a subsequent PPE event and/or subsequent PPE opportunity based on compliance, partial compliance, and/or non-compliance. In particular, responsive to determining that the user partially complied and or non-complied during the previous PPE event and/or previous PPE opportunity, a display on the wristband may be activated to output a countdown of 20 seconds. In this way, the user may receive more guidance to put on or take off the protective garments within a predetermined amount of time (e.g., 20 seconds) responsive to determination of partial or non-compliance. Alternatively, or in addition, the analytics to determine compliance may be different than the analytics used during the previous wristband event. For example, the analytics may be stricter than previously used analytics.

In still another implementation, the PPE monitoring system may include a back-end electronic device, such as a server, that performs analytics, as discussed above. The analytics may be configured to perform any one, any combination, or all of: determine compliance (e.g., full, partial or non-compliance); generate compliance reports, to identify trends based on time of shift, protocols, and other desired metrics; identify patients and/or healthcare providers that are the source of cross-contamination; generate alerts responsive to compliance determinations, identifying trends, identifying patients and/or healthcare providers that are the source of cross-contamination, or the like; generating displays or other types of graphical users interfaces to output statistics based on one or more criteria, such as based on an event (e.g., full, partial, or non-compliance), based on people (e.g., analysis based on all doctors, all nurses, or individuals), and/or based on location (e.g., based on the particular floor of a hospital, the particular wing of a hospital, based on a department of the hospital (e.g., ICU-A, ICU-B, ICU-C)).

In one implementation, one or more electronic devices may work in combination with the wristband in order to instruct a user as to proper PPE. For example, a user may follow instructions of requested movements that are output (e.g., displayed on a display) on an electronic device. The wristband, worn by the user, may register movements of the user. The electronic device may compare the requested movements with the registered movements in order to provide feedback to the user. In a first implementation, the user may comprise an adult healthcare provider, with the feedback to the user for instructional purposes. The feedback may comprise instructions as to one or more of the following: information as to deficiencies in PPE movements; or information as to deficiencies in the sequence of PPE movements. The feedback may include a score, with the score based on improvement or worsening of the PPE (e.g., improvement or worsening based on a previous training session).

Thus, in one implementation, all stages of PPE monitoring are performed independently of HH monitoring. Alternatively, any one, any combination, or all stages of PPE monitoring are performed dependently on one or more stages of HH monitoring. As one example, in one implementation, the trigger to begin PPE monitoring (e.g., to trigger the wristband to wake-up and begin monitoring movements) is independent of the trigger to begin HH monitoring. Alternatively, the trigger to begin PPE monitoring and the trigger to begin HH monitoring are dependent on one another. As one example, the same trigger is used to begin PPE monitoring as to begin HH monitoring. As another example, completion of one or more stages of HH monitoring triggers PPE monitoring. In one instance, such as upon entering the room, identifying one or both of the dispensing hand cleaning agent or the monitoring hand movements (which may be a predicate act prior to donning PPE garment(s), whether hand hygiene compliance is determined or not) may be the trigger to begin PPE monitoring. In another instance, such as upon exiting the room, identifying one or more PPE movements (which may be a predicate act prior to cleaning hands upon exit, whether PPE compliance is determined or not) may be the trigger to begin HH monitoring.

As discussed above, the WHO may issue guidelines regarding hygiene. As one example, the WHO lists five moments of hand hygiene (HH) that define five opportunities where hand hygiene should be followed. The five moments of HH opportunity include: (1) before touching a patient; (2) before clean/aseptic procedures; (3) after body fluid exposure/risk; (4) after touching a patient; and (5) after touching patient surroundings. In this way, the different moments of HH opportunity represent different situations in which to check for HH compliance. Further, as discussed above, a hand hygiene event may be identified or detected based on one or more steps in order to perform hand hygiene compliance (e.g., an event triggered by the dispensing of hand cleaning agent (e.g., hand sanitizer or soap)). Likewise, there may be instances of PPE opportunity and instances of a PPE event (which may be associated with and triggered by a HH event and/or may be triggered by a separate event, such as opening a drawer or a cabinet).

In one or some embodiments, the system may be opportunity-dependent, such as dependent on a patient area hygiene opportunity (e.g., the patient area hygiene opportunity indicative of interaction with a patient in the patient area, such as a HH opportunity associated with a patient area and/or a PPE opportunity associated with the patient area), in order to determining any one, any combination, or all of: monitoring compliance; determining whether and/or how to output reminders; staff locating; or patient care billing (e.g., physician billing).

With regard to an opportunity-dependent compliance system, various types of analysis may be dependent on identifying the patient area hygiene opportunity, such as any one, any combination, or all of: the HH opportunity; the PPE opportunity, or the HH/PPE opportunity. In one or some embodiments, compliance with the patient area hygiene opportunity (such as the HH and/or PPE opportunity) may comprise: (i) identifying the patient area hygiene opportunity; and (ii) determining compliance with the patient area hygiene opportunity.

As discussed in more detail below, the patient area hygiene opportunity may be identified in one of several ways, such as based on tracking movement of the healthcare provider and/or based on determining interaction with a patient. In one or some embodiments, determining compliance with the opportunity may comprise determining whether a compliant event is sufficiently related to the identified patient area hygiene opportunity. In one or some embodiments, compliance with the hygiene opportunity is the same for different patient areas. In this regard, the same hygiene protocol(s) may be used responsive to identifying the hygiene opportunity (with one or more hygiene events being detected to determine compliance with the same hygiene protocol(s)). Alternatively, for patient areas with different compliance requirements, responsive to identifying the patient area hygiene opportunity, the patient area hygiene protocol(s) (e.g., one or both of HH protocol and/or PPE protocol for the specific patient area) may be identified, and compliance with the patient area hygiene protocol(s) may be determined in order to determine compliance with the patient area hygiene opportunity (with one or more hygiene events being detected to determine compliance with the patient area hygiene protocol(s)). As discussed here, the patient area hygiene protocol(s), which may be specific to the patient area, may be determined in one of several ways (e.g., at the server level; at the patient area level; or at the server level and the patient area level) and with one or more devices (e.g., by any one, any combination, or all of: the server; the stationary controller; or the mobile electronic device).

Thus, in one or some embodiments, determining compliance with the patient area hygiene opportunity may be dependent on: (a) detecting an event (with the event being at least one step to comply with the protocol(s) associated with the patient area, such as detecting a HH event; a PPE event; or a HH/PPE event); (b) determining whether there is a detected event sufficiently related to the identified patient area hygiene opportunity (e.g., determining whether the detected HH event is sufficiently close in time to be related to the identified patient area hygiene opportunity); and (c) responsive to determining whether there is a detected event sufficiently related to the identified patient area hygiene opportunity, assigning or associating the compliance determination with the detected event (or lack thereof) to the identified patient area hygiene opportunity (e.g., a compliance or non-compliance determination).

Thus, in one or some embodiments, a method and system are disclosed that determine whether a healthcare provider is complying with defined healthcare protocols, such as compliance with any one, any combination, or all of a plurality of HH opportunities (such as the WHO five moments of hand hygiene opportunity). Alternatively, a method and system are disclosed that determine whether a healthcare provider is complying with defined healthcare protocols, such as compliance with any one, any combination, or all of a plurality of PPE opportunities. Still alternatively, a method and system are disclosed that determine whether a healthcare provider is complying with defined healthcare protocols, such as compliance with any one, any combination, or all of a plurality of HH opportunities and a plurality of PPE opportunities.

In particular, a system and a computer-implemented method is disclosed for determining compliance by a person with one or both of a HH opportunity or a PPE opportunity, including: determining whether there is one or both of a HH event or a PPE event that is sufficiently associated in time or in space with the one or both of the HH opportunity or the PPE opportunity; responsive to determining that there is the one or both of the HH event or the PPE event that is sufficiently associated in time or in space with the one or both of the HH opportunity or the PPE opportunity: determining compliance with the one or both of the HH event or the PPE event; and attributing the determined compliance with the one or both of the HH event or the PPE event to the one or both of the HH opportunity or the PPE opportunity; and responsive to determining that there is no HH event or PPE event that is sufficiently associated in time or in space with the identified one or both of the HH opportunity or the PPE opportunity, determining non-compliance for the one or both of the HH opportunity or the PPE opportunity. Further, identifying the one or both of the HH opportunity or the PPE opportunity may occur either prior to or after detecting the one or both of the HH event or the PPE event. In addition, whether the one or both of the HH event or the PPE event is sufficiently associated in time may comprise whether an act associated with the HH event (e.g., the dispensing of hand cleaning agent or the completion of hand movements, which may comprise the trigger to detect the HH event) or the PPE event (e.g., the taking of PPE or the completion of the PPE movements, which may comprise the trigger to detect the PPE event) is within a time period of the one or both of the HHE opportunity or the PPE opportunity.

Thus, in one or some embodiments, the method and system include identifying one or more HH opportunities, and determining compliance with the identified one or more HH opportunities. As discussed in more detail below, identifying a HH opportunity may be determined in one of several ways. In one way, identifying movement of a healthcare provider relative to a patient area (such as into a patient area, out of a patient area, within a patient area, etc.) may be used to identify the HH opportunity. As one example, to identify moment (1), which is before touching a patient, the healthcare provider's movement may be tracked into a patient area, such as any one, any combination, or all of: tracking movement toward a defined border of a patient area; tracking movement crossing the border of the patient area; or tracking movement within the patient area after crossing the border of the patient area. As another example, in order to identify moments (4) and (5), which is after touching a patient and after touching patient surroundings, respectively, the healthcare provider's movement may be tracked out of a patient area, such as any one, any combination, or all of: tracking movement toward a defined border of a patient area; tracking movement crossing the border of the patient area; tracking movement outside the patient area after crossing the border of the patient area.

Further, tracking the healthcare provider's movement may be performed in one of several ways. In one way, external sensors (e.g., sensors that are not associated with the healthcare provider, such as not resident on the wristband associated with the healthcare provider) may be used to determine movement of the healthcare provider into and/or out of the patient area. For example, one or more ultrasonic sensors, statically positioned in different parts of the patient area (e.g., at an entrance to the patient area and/or in one or more sections in an interior of the patient area) may be used to track whether the healthcare provider is moving into or out of the patient area. In another way, a mobile electronic device (such as a wristband) associated with or attached to the healthcare provider may be used to determine movement into, inside and/or out of the patient area. For example, the mobile electronic device may communicate with one or more electronic devices associated with the patient area, such as one or more stationary controllers positioned external, at a border and/or interior to the patient area. The mobile electronic device, using communications with the one or more stationary controllers, may determine whether the electronic device (and in turn the healthcare provider wearing the electronic device) is moving toward or away from the patient area. In this regard, the tracking may be performed either external to a wristband (or other mobile electronic device) associated with the healthcare provider and/or may be performed by the wristband (or other mobile device) associated with the healthcare provider.

Associated with identifying a HH opportunity is determining compliance with the HH opportunity. As discussed in more detail below, compliance may comprise compliance with the HH event (e.g., determining whether hand cleaning agent has been dispensed and/or the required duration of movements and/or specific movements are performed). However, the events or actions to determine compliance with the HH opportunity (e.g., compliance with the hand hygiene event) may start before or after identifying the respective HH opportunity, thereby complicating matters. This is due to hand cleaning agent dispensers potentially being located outside and/or inside a patient area (e.g., at the entrance to a patient room and inside the patient room).

As one example, a healthcare provider may walk into the patient room (which may be indicative of HH opportunity moment (1), discussed above) and thereafter take hand sanitizer (or some other hand cleaning agent) from a dispenser positioned within the patient room. In such an example, the identification of the HH opportunity (e.g., due to tracking the healthcare provider) may occur before detecting the HH event (e.g., due to detecting dispensing of hand cleaning agent from a dispenser located within the patient room). As another example, the healthcare provider may take hand sanitizer (or some other hand cleaning agent) outside of the patient room, thereby triggering the HH event, in a hallway external to a patient's room before the HH opportunity is identified. In such an instance, the healthcare provider may either enter the patient's room or may continue to walk down the hallway. The former case (the healthcare provider entering the patient's room), in certain circumstances, may be a HH opportunity (e.g., moment (1)). In a first instance, the healthcare provider may immediately (or within a certain time period) enter the patient's room, thereby sufficiently connecting the HH event with the HH opportunity. In a second instance, the healthcare provider may wait an excessive amount (e.g., greater than the certain time period) to enter the patient's room, thereby decoupling the HH event from the HH opportunity and rendering any determination of compliance with the HH event as not being applicable to the identified HH opportunity (e.g., due to the elapsed time between the HH event and the HH opportunity, there is an increased likelihood that the healthcare provider has interacted with someone or something else prior to entering or exiting the patient area, thereby rendering compliance with the decoupled HH event as not being applicable to the HH opportunity). Though, the healthcare provider may have already taken sanitizer and began rubbing hands before the healthcare provider's movement into the patient room is detected (and thus before the HH opportunity is identified). As another example, the healthcare provider's taking of sanitizer from a dispenser inside the patient room and subsequently waiting an excessive amount before leaving the room may likewise decouple any HH event compliance determination with the HH opportunity of moments (4) and (5).

The latter case (the healthcare provider takes hand cleaning agent outside of the patient's room and continues to walk down the hallway) again may or may not be a HH opportunity depending on what occurs thereafter. In particular, if the healthcare provider takes the sanitizer and continues to walk down the hallway rubbing hands, but does not perform any action that indicates a HH opportunity within a certain period of time (e.g., the healthcare provider does not walk into a patient's room within 10 seconds), the determination of HH compliance (e.g., determination of compliance with the HH event) may be considered in certain embodiments to be too remote to be associated with any HH opportunity.

Various criteria may be used to determine closeness and/or remoteness of the HH opportunity with the HH event. Criteria include, for example, time and/or distance. As discussed below, the criteria of time may be static (e.g., a predetermined time period between one aspect of the HH event and one aspect of the HH opportunity) and/or may be dynamic (e.g., based on any one, any combination, or all of: the protocol(s) to be followed; positioning of dispensers; or the behavior of the healthcare provider). The HH opportunity may have an identified start time (e.g., identified based on tracking the movement of the healthcare provider) and/or an identified end time. Likewise, the HH event may have an identified start time (e.g., identified based on the HH predicate act of dispensing of hand cleaning agent) and/or an identified end time (e.g., based on completion of compliance with the HH event). Thus, the criteria (e.g., time) may be measured between one aspect or one act of the HH event (such as the beginning of the HH event and/or the completion of the HH event) with one aspect of the HH opportunity (such as the identified start and/or end of the HH opportunity).

Thus, in one or some embodiments, responsive to the timing of one aspect of the HH event being within the timing of one aspect of the HH opportunity, the determination regarding compliance (e.g., compliant, non-compliant, partially compliant) with the HH event may be ascribed to the HH opportunity. In an example where detecting the dispensing of hand cleaning agent is indicative of the HH event, a dispensing time at which the hand cleaning agent is dispensed from the dispenser is determined, and may be either before or after identifying the HH opportunity. If the dispensing time is within a first period of time before identifying the HH opportunity or is within a second period of time after identifying the HH opportunity, the HH event is sufficient tied in time to the HH opportunity. Otherwise, if the dispensing time is not within a first period of time before identifying the HH opportunity or is not within a second period of time after identifying the HH opportunity, the HH event is not sufficiently tied in time to the HH opportunity. In one embodiment, the first time period is different from the second time period, as discussed below. Alternatively, the first time period is the same as the second time period.

In one or some embodiments, the timing may be static and predetermined (e.g., 8 seconds after identifying the HH opportunity until detecting the HH event or 10 seconds after detecting the HH event until identifying the HH opportunity, as discussed further below). Alternatively, the timing may be dynamic based on any one, any combination, or all of: the protocol(s) to be followed (e.g., healthcare provider is required to follow HH protocol versus PPE protocol (with less time given between the aspect of the HH event and the aspect of the HH opportunity as opposed to more time given between the aspect of the PPE event and the aspect of the PPE opportunity since complying with the HH protocol is quicker); healthcare provider is required to follow only one protocol versus two protocols (with less time given between the aspect of the HH event and the aspect of the HH opportunity as opposed to more time given between the aspect of the HH/PPE event and the aspect of the HH/PPE opportunity since complying with two protocols such as HH and PPE, takes longer); the behavior of the healthcare provider (e.g., the backend server may analyze the behavior of a specific healthcare provider in order to determine the typical time the specific healthcare provider takes between an event (such as a HH and/or PPE event) and an opportunity (e.g., between the HH event and the HH opportunity); or the positioning of hardware (e.g., the position of dispensers in a healthcare setting (with more time given for dispensers placed further from the entrance of a patient area).

For example, a specific HH event may be triggered when sanitizer dispensing is detected; even if the duration and/or movements render the specific HH event "compliant", that compliance is not associated with any specific HH opportunity if the compliant HH event is too remote in time (there has been too much time elapsed that can lead to subsequent hand contamination of the healthcare provider, between the triggering of the specific HH event and/or the completion of the duration and/or movements of the specific HH event to an identified HH opportunity). As such, any compliance determination with the HH event may be deemed too remote (such as too remote in time and/or too remote in distance) as to render the HH opportunity compliant as well. In this regard, there are instances where a HH event is not tied at all or not sufficiently tied to a HH opportunity.

By way of example, a configuration with a hand cleaning agent dispenser at the entrance to the room and in the interior of the room is considered. In particular, when entering, the healthcare provider may first take hand cleaning agent from the dispenser at the entrance, and then walk into the room. In this instance, the HH event is detected (e.g., by detecting the dispensing event) prior to identifying the HH opportunity (e.g., by tracking the movement into the patient room). In another instance when entering, the healthcare provider may first walk into the room (triggering identification of the HH opportunity) and then take hand cleaning agent from the dispenser in the interior of the patient room (triggering detection of the HH event). Similarly, when exiting, the healthcare provider may take hand cleaning agent from the dispenser in the interior of the patient room (triggering detection of the HH event) prior to leaving the patient room (which may trigger identification of the HH opportunity). Conversely, when exiting, the healthcare provider may first leave the patient room (triggering identification of the HH opportunity) and then take hand cleaning agent from the dispenser at the entrance of the patient room (triggering detection of the HH event). Thus, the HH event may begin before or after identifying the HH opportunity. Further, responsive to determining that the HH event and the HH opportunity are sufficiently close to one another (e.g., sufficiently close in time and/or in space), the determination of compliance of the HH event is imputed or associated with the identified HH opportunity. For example, closeness in time may be determined whether the HH event is detected before or after identifying the hand hygiene opportunity (e.g., the HH opportunity is identified within X seconds of detecting the HH event; the HH event is detected within Y seconds of identifying the HH opportunity). In this way, determining compliance with the HH opportunity may be based on the both: (i) determining whether there is a sufficient connection of the identified HH opportunity with a specific HH event; and (ii) determining compliance with the specific HH event. This is in contrast to merely focusing on compliance with HH events completely divorced from any identified HH opportunity.

In one or some embodiments, the HH opportunity may be accompanied by a PPE opportunity. For example, in certain circumstances, a PPE opportunity may be present when the healthcare provider enters or exits the patient room, as discussed above. In a particular example, when entering the patient area, the PPE is typically outside of the patient area (such as near the entrance to the patient area and near the hand cleaning agent dispenser outside of the patient area). In this regard, the typical protocol prior to entry of the patient area is for the healthcare provider to clean hands first, and then put on PPE. As such, the initial trigger for checking for PPE may be the dispensing of hand cleaning agent (with the HH opportunity confirmed responsive to tracking the movement of the healthcare provider into the patient room within a certain period of time). In one or some embodiments, the PPE opportunity may be tied or connected to the HH opportunity. As one example, prior to entering the patient area, a healthcare provider may first clean hands and then don PPE. As another example, prior to exiting the patient area, a healthcare provider may first doff PPE and then clean hands. Thus, the PPE opportunity may be connected to the HH opportunity.

However, complicating matters is identifying an actual PPE opportunity from amongst the general behavior of a healthcare provider. As discussed above, a healthcare provider may take sanitizer from the dispenser outside of the patient room, thereby triggering a HH event. Likewise, a healthcare provider may take PPE, such as gloves or a mask, from a cabinet positioned outside of the patient room, thereby potentially triggering a PPE event (discussed below). After taking sanitizer or taking PPE, the healthcare provider may enter the patient room, or may continue to walk down the hallway. In order to better monitor compliance with a PPE opportunity, a trigger for determining a PPE opportunity is disclosed. Various triggers are contemplated. As one example, the trigger to detect a PPE event is the same as for a HH event (e.g., triggering detection of a PPE event is the same as the trigger to detect a HH event, such as based on detecting dispensing of hand cleaning agent). Further, the trigger to identify the PPE opportunity is the same as for the trigger to identify the HH opportunity (e.g., a HH opportunity is based on tracking movement of the healthcare provider into and/or out of the patient area).

Alternatively, the trigger for checking for a PPE event may be different than for a HH event. As discussed above, upon entry, the proximity sensing-output generating device may be attached to a cabinet or a door, and may generate data responsive to opening the cabinet or door. Thus, when PPE is housed in a cabinet or in a drawer, the proximity sensing-output generating device may be attached thereto and may generate a sensor output when the cabinet or door is opened, thereby triggering detection of the cabinet/drawer containing PPE opening (thus leading to the conclusion that the healthcare provider is donning PPE prior to entering the patient area (e.g., the proximity sensing-output generating device, either directly or via the stationary controller, sends a communication to the wristband to monitor PPE movements). Further, upon exit, the trigger for monitoring a PPE event may comprise movement, such as moving past a beam, as discussed below.

As one example, when entering a patient room, the trigger for the HH event may comprise the taking of hand cleaning agent (e.g., the stationary controller may determine that hand cleaning agent was dispensed, and then send a message to the wristband(s) in the dispensing messaging zone to monitor hand movements associated with hand hygiene) whereas the trigger for the PPE event may comprise the taking of PPE (e.g., the proximity sensing-output generating device, discussed herein, may be attached to a cabinet or a door housing PPE, and may generate data responsive to opening the cabinet or door; responsive to generating the data from the proximity sensing-output generating device, a message, routed directly or via a stationary controller, may be sent to the wristband to monitor hand movements associated with PPE). As another example, when exiting a patient room, the trigger for the PPE event may comprise movement toward the exit (such as breaking an ultrasonic beam, discussed below) whereas the trigger for the HH event may comprise the taking of hand cleaning agent.

Alternatively, or in addition to opportunity-based monitoring, generating reminders for persons, such as the healthcare provider, visitors, patients, or the like, may be opportunity-based. Thus, in one or some embodiments, separate from, or in addition to, monitoring compliance with a hygiene opportunity (such as a HH opportunity and/or a PPE opportunity), a healthcare provider is provided reminder(s) as to the protocol(s) to comply with the hygiene opportunity. For example, reminders may be generated for healthcare workers according to any one, any combination, or all of the following: responsive to identifying a hygiene opportunity (e.g., responsive to identifying a HH opportunity and/or a PPE opportunity); responsive to detecting a hygiene event (e.g., responsive to detecting a HH event and/or a PPE event); responsive to identifying both a hygiene opportunity and a hygiene event; responsive to detecting a hygiene opportunity and responsive to a determination of compliance or non-compliance with the hygiene opportunity; or responsive to detecting a hygiene event and responsive to a determination of compliance or non-compliance with the hygiene event.

As discussed above, there are various contexts in which people may be reminded of protocols, such as HH and/or PPE protocols. In one or some embodiments, the reminders associated with a patient area may be responsive to and dependent on one or both of identifying the patient area hygiene event (e.g., the patient area hygiene event follows one or both of a HH protocol for a HH event or a PPE protocol for a PPE event) or on identifying the patient area hygiene opportunity (e.g., the HH opportunity and/or the PPE opportunity). Responsive to identifying one or both of the patient area hygiene event or the patient area hygiene opportunity, patient area protocol(s) (such as one or both of patient area PPE protocol or patient area HH protocol) are determined and an output for the patient area protocol(s) are generated. As discussed above, identifying the patient area hygiene opportunity may be performed in one of several ways, such as by tracking the movement of a healthcare provider. Further, the patient hygiene event may be determined based on detecting at least one action of the healthcare provider (e.g., taking sanitizer from a dispenser; taking PPE from a cabinet/drawer or other type of PPE dispenser; throwing away PPE into a trash can; interaction of a mobile electronic device (such as a wristband) with a stationary controller). In this way, by making the reminders opportunity-based (e.g., determining whether to generate a reminder based on an identified opportunity), the reminders may be generated in a more intelligent manner.

Further, reminders may be generated at any stage of determination of compliance (or lack thereof), thereby providing feedback to the healthcare provider as to the adequacy (or inadequacy) of compliance. For example, responsive to detecting an error in compliance (such as for hand hygiene any one, any combination, or all of: failing to take hand cleaning agent; failing to rub a sufficiently long time; or failing to perform the proper requisite movements), an output may be generated indicating the deficiency. Alternatively, responsive to detecting compliance with the hygiene protocol (such as for hand hygiene any one, any combination, or all of: taking hand cleaning agent; rubbing a sufficiently long time; or performing the proper requisite movements), an output may be generated indicating compliance.

As discussed above, data relating to HH and/or PPE compliance (such as any one, any combination, or all of HH event compliance, HH opportunity compliance, PPE event compliance, or PPE opportunity compliance) may be analyzed in order to perform one or both of: identifying provider(s) who may have contributed to an identified infection; or identifying potential future infection risks. For example, the analytics may determine who are the person(s) that contributed to infections and/or which patients are at risk of infection. Complicating matters is identifying whether the protocols were not followed upon entry of the patient area (thereby potentially resulting in infection of the patient in the patient area) and/or upon exit from an infected patient area (thereby potentially resulting in infection of the patient in a subsequently visited patient area). Thus, back-end analytics, such as one or more servers, may be used to perform the data analysis, as discussed above. Various types of analysis are contemplated, including any one, any combination, or all of: infection root cause analysis; cluster root cause analysis; future cluster risk analysis and future infection risk analysis. In this way, one may identify healthcare providers that contribute to infections and/or patients at risk of infections.

In one or some embodiments, the infection analysis may be opportunity focused, such as focused on whether there is full, partial or no compliance with a HH opportunity and/or a PPE opportunity. Underlying the opportunity-focused analysis, pathogens may be transmitted via contact, such as via the WHO opportunities discussed above. In particular, five WHO opportunities are discussed above. In one or some embodiments, some of the opportunities may be identified directly (such as by tracking the movement of the healthcare provider into and/or out of a patient area) and other opportunities may be inferred from one or more aspects of the healthcare provider (e.g., healthcare provider activity, such as duration with in the patient area and/or status of the healthcare provider).

As discussed in more detail below, various types of infection analysis are contemplated, such as infection root cause analysis, cluster root cause analysis, future cluster risk analysis and future infection risk analysis. One, some or each of those may be opportunity focused in that the underlying infection analysis is based on analyzing compliance with opportunities in order to determine the underlying cause of an infection, determining clusters of infection, or estimating future risk of infections. This opportunity-focused analysis is in contrast to typical infection analysis, which generally analyzes compliance or non-compliance with hygiene protocols but are not moored or tied to any identified opportunities. In this way, unlike typical infection analysis, the opportunity-focused analysis centers on identified interactions with patients that are identified as important, as opposed to general infection analysis that may include it its analysis irrelevant interactions, thereby resulting in erroneous results.

In this regard, an opportunity-based infection analysis system and method are disclosed, including: at least one memory configured to store hygiene opportunity compliance data, with the hygiene opportunity compliance data indicative of compliance by one or more healthcare providers of identified hygiene opportunities for interacting with a patient, the hygiene opportunities being identified based on tracking movement of the one or more healthcare providers; at least one output device; and at least one processor in communication with the memory and the output device. The processor is configured to: access the hygiene opportunity compliance data; identify some or all of the hygiene opportunity compliance data associated with a patient area during an identified period of time, with the identified hygiene opportunity compliance data being segmented into at least two separate opportunities; identify, based on the hygiene opportunity compliance data associated with the patient area during the identified period of time, the one or more healthcare providers that visited the patient area during the identified period of time; analyze, for the one or more healthcare providers that visited the patient area during the identified period of time, identified hygiene opportunity compliance data separately for the at least two separate opportunities; and generate an output based on the analysis.

For example, wherein the opportunities comprise (1) before touching a patient, (2) before clean/aseptic procedures, (3) after body fluid exposure/risk, (4) after touching a patient, and (5) after touching patient surroundings, (1) may be identified based on tracking the healthcare provider's movement into the patient area, (4) and (5) may be identified based on tracking the healthcare provider's movement into the patient area, and (2) and (3) may be estimated based on the tracking of the healthcare provider's movement. In particular, (2) and (3) may be estimated based on: determining, based on the tracking of the healthcare provider's movement, a duration within the patient area; determining a status of the healthcare provider; and estimating a number of hygiene opportunities based on the duration of the healthcare provider within the patient area and the status of the healthcare provider (e.g., the status of the healthcare provider may comprise a title or role associated with the healthcare provider, such as one of trainee, nurse, doctor, or hospital support staff (such as clinical assistants who take care of ward housekeeping, patient services assistants who bring meals and drinks, porters who take care of patient lifting and transport, volunteers who help with fundraising and ward visits, or ward clerks who staff the ward reception desks); in the example of a nurse, it is estimated that nurses touches a patient once every 5 minutes; so that, if a nurse spends 1 hour in patient room, it is estimated that there were 12 opportunities within the 1 hour spent in the patient room; in the example of a doctor, it is estimated that doctors touch patients more frequently than nurses, though this may depend on healthcare settings so that the healthcare setting may factor into the estimated number of touches in a predetermined time period). Further, based on the number of estimated hygiene opportunities, the system may then estimate a compliance rate for a specific healthcare provider with regard to the number of estimated hygiene opportunities based on historical data (e.g., examining data for a time period, such as the previous week, month, etc. a compliance rate for the specific healthcare provider).

In addition, depending on the type of analysis, different opportunities, such as different HH opportunities, may be analyzed. For example, with regard to infection root cause analysis, opportunities analyzed may, in one embodiment, consist of (1), (2) and (3) in order to perform a root cause analysis for an infection in the patient room. Specifically, the opportunities analyzed may be limited in time, such as during a predetermined number of days after confirming infection in the patient room. Thus, infection root cause analysis may be directed to a single patient area (e.g., the patient's room) where patient became infected. In this regard, infection root cause analysis may determine, from a statistical standpoint, which healthcare provider(s) contributed to the infection of the patient. Practically speaking, the patient will be in contact with several healthcare providers, some of which result in infection(s). Thus, the patient may accumulate pathogens from one or more of the several healthcare providers. The infection root cause analysis may evaluate the contribution to infection from each opportunity (and from each healthcare provider) over time. In one or some embodiments, the infection root cause analysis may then generate an output to indicate the healthcare provider(s) more likely to have caused the infection, such as generate a ranked list output of healthcare providers based on risk of having caused the infection (e.g., determine which healthcare provider made the greatest contribution to the infection, such as indicate who is the highest risk healthcare provider to cause the infection).

As another example, cluster root cause analysis may be performed. Typically, analysis only focuses on tracking a high-risk healthcare provider who traveled from room to room. However, cross contamination may occur because of any provider and not simply high-risk healthcare providers. In this regard, an analysis that only examines high risk providers may be wanting. Further, the opportunity-based focus for the analysis (rather than a person-based focus) may examine the opportunities, regardless of compliance rate, for a specific healthcare provider. For example, the specific healthcare provider may have only entered the patient area once (resulting in a healthcare opportunity), with a low compliance rate for that opportunity (e.g., zero compliance), potentially causing contamination. However, a high-risk analysis may discount such a non-compliant opportunity since the specific healthcare provider may have a high overall compliance rate. Thus, instead of focusing on overall compliance rate, focusing on different opportunities (and the associated compliance for those different opportunities) may result in more reliable contamination analysis.

Further, the opportunity-focused analysis may assist in the cross contamination analysis, particularly when opportunities are connected. For example, a healthcare provider may exit a first room (resulting in a first opportunity) and thereafter may enter a second room (resulting in a second opportunity). The healthcare provider's failure to wash hands when exiting the first room (e.g., a non-compliant first opportunity) impacts the connected second opportunity. In this way, the analysis may determine whether separate opportunities (whether those opportunities are from the same healthcare provider or different healthcare providers) are to be coupled, based on any one, any combination, or all of: (1) time (e.g., whether the two opportunities are within a certain time period of one another); (2) space (e.g., whether the two opportunities are within a certain distance from one another); or (3) compliance. For example, with regard to compliance, if a specific healthcare provider fails to comply both with the first opportunity and the second opportunity, the opportunities may be connected; otherwise, if the specific healthcare provider fails to comply with the first opportunity but complies with the second opportunity, the opportunities may be disconnected since the healthcare provider presumably remedied the previous failure with the first opportunity with compliance of the second opportunity. As another example, a first opportunity resulting from a first healthcare provider exiting the first room and thereafter returning to the nurses' station may be connected to a second opportunity from a second healthcare provider going from the nurses' station and entering a second room. More specifically, compliance failure by the first healthcare provider with the first opportunity and compliance failure by the second healthcare provider with the second opportunity may be connected. In the case of future infection risk analysis, opportunities for each room may be connected in order to determine the number and/or types of potential pathogens for each room the patient has been exposed to from the different healthcare providers. As one example, the future infection risk analysis may receive as input one or both of a date range for analysis (such as the past 24 hours, the past week, etc.) or patient area(s) (such as a specific patient room, a specific set of patient rooms, an entire healthcare facility (by default if no patient area input given), etc.). The future infection risk analysis may analyze the compliance data associated with opportunities connected to the patient area(s) in order identify a future risk of infection associated with the patient area(s). In this way, the analysis may connect opportunities (whether with the same healthcare provider or different healthcare providers).

Separate from opportunity-based analysis, the methodology used to identify an opportunity may be applied to different contexts of patient care. As one example, physician monitoring and/or billing may rely on such a methodology. Typically, physicians simply bill each patient based on an estimated time that the physician spends with a patient. As discussed in more detail below, the methodology may identify when the physician enters the patient area and exits the patient area. As such, the methodology may provide the exact visit time and/or the exact duration of the visit.

As another example, the methodology may be used for workload analysis of healthcare workers. In particular, the system may track the duration between entrance/exit opportunities with patients, thereby tallying a total time that a healthcare worker is with patients. Thus, the methodology may generally track how long a first nurse versus a second nurse has spent with patients. Further, the methodology may track any one, any combination, or all of: a total time that any healthcare worker spends with a specific patient; a total time any nurse (or any other type of healthcare worker, such as doctors) spends with a specific patient; or a total time a specific nurse (or other specific healthcare worker, such as a specific doctor) spends with a specific patient. The duration data may be used for human resources purposes and/or for workload analysis.

For example, in order to accurately analyze hygiene data, the system (such as the backend server) may store in a database hygiene records every time a healthcare provider enters and/or exits a room. In particular, the server may store each patient visit and its duration. With each stored entry being designated as a Hygiene Event. By iterating through these records sequentially and pairing enter and exit events, the system may calculate how long a provider spent in a given patient room. In one or some embodiments, a user may input the area (e.g., one or a plurality of patient rooms) subject to analysis, as well as a time period (e.g., the last week, the last month, etc.). Thus, the system may any one, any combination, or all of: fetch all Hygiene Events in the input time period for the given area; record the Hygiene Events by staff member and room (e.g., "How long did each staff member spend in each room?"); or provide a statistical summary of each room and provider, including any one, any combination, or all of: mean visit duration; total visit duration; and visit count. In this regard, analyzing opportunities, which may be used to determine a duration that a healthcare worker spends with one or more patients, may be used for one or both of workload analysis or infection analysis.

As still another example, the methodology may be used for staff locating. Every healthcare provider may be easily located using the wristband worn by the healthcare provider. The location of each healthcare worker may be displayed on monitor for review and/or a healthcare provider may be contacted via message/reminder/call on the wristband worn or nearby stationary controllers.

In one or some embodiments, assets, such as assets in a healthcare setting (e.g., hospital equipment), an office setting, a manufacturing setting, a home setting, or the like, may be tracked. Typically, an asset may be assigned a tag, such as an RFID tag, from which a beacon may be constantly sensed. In one or some embodiments, asset tracking comprises using a device attached to or associated with the asset that senses movement, and responsive thereto, wakes up in order to perform tracking functionality. After a period of time where there is no movement of the asset (e.g., 1 minute), the device may return to sleep, thereby conserving power. In this way, the device need not constantly generate a beacon for tracking.

As one example, a vibration sensor, such as a microvibration sensor, may be resident in the asset tracker in order to trigger a wake-up of at least a part of the functionality of the asset tracker. Responsive to waking up, any one, any combination, or all of the following functions may be performed: (i) determining movement and/or location of the asset (e.g., movement of the asset from one location to another, such as hospital equipment being moved from one room to another; movement of the asset itself such as where the asset is a dumbbell or other exercise equipment, monitoring movement of the dumbbell); (ii) determining who is moving the asset; determining timing of movement; (iv) determining whether operation of the asset is modified based on the movement (e.g., if the asset is in a first patient room with a first protocol (e.g., protocol for MRSA infection) to use the asset, and then the asset is moved to a second patient room with a second protocol (e.g., protocol for pneumonia) to use the asset, the operation of the asset may be modified to reflect the second protocol for the second patient room); (v) determining how long the asset has been in movement (e.g., for exercise equipment, such as dumbbells, in order to track the amount of activity a patient performs, with the data later being uploaded and then reviewed by the doctor or physical therapist); or (vi) determining whether the asset is being moved from a predefined area and sounding an alarm when that occurs (e.g., if a piece of equipment is designated to remain in a predetermined patient area, responsive to determination that the piece of equipment is being moved, an alarm may be generated indicating that the piece of equipment should not be moved).

With regard to (i), it is contemplated that movement of the asset comprises movement of the entire asset (e.g., moving a machine from a first location to a second location; moving a dumbbell). Alternatively, it is contemplated that only a part of the asset is moved (e.g., a drawer/cabinet of an asset is opened or closed in order to access medicine, PPE or the like).

With regard to (ii), there are instances where it may not be necessary to determine the person performing the movement (e.g., in a home setting or a dementia care facility, it may be presumed as to the resident or the person with dementia performing the movement).

Alternatively, there are instances where it is desired to determine who is moving the asset. For example, in a hospital or business setting, it may be desirable to determine the healthcare provider that performs the movement. The asset tracker itself or another electronic device (such as a stationary controller) working in combination with the asset tracker may determine the person performing the movement. In particular, a controller resident on the asset tracker may directly communicate with a wireless device worn by the healthcare provider (e.g., a wristband (such as mobile wristband device, discussed below), RFID tag, or some other mobile electronic device) proximate to the asset tracker to identify the wireless device (and in turn the person associated with the wireless device) moving the asset. In this way, after wake-up of the asset tracker (such as due to movement), the controller on the asset tracker may begin to scan the vicinity in order to identify the wireless device (and optionally its location). Alternatively, responsive to movement, the asset tracker may generate a beacon, which may be received by another electronic device, such as a stationary controller resident in an area (such as a patient area). After wake-up, the asset tracker may generate the beacon for a limited period of time (e.g., 5 minutes, 1 hour, etc.) and then return to sleep. In turn, the stationary controller may communicate with wristbands in its proximity in order to identify the person moving the asset. The asset, in the course of moving between different rooms, may interact with multiple stationary controllers. This multiple interaction may be recorded in order to determine the path of the asset and the ultimate destination of the asset. Alternatively, the asset tracker itself may record the path of the asset and its ultimate destination.

Thus, a method and apparatus are disclosed for tracking an asset. The method may include: sensing, using an asset tracker that is associated with, connected to or part of the asset, movement of part or all of an asset: responsive to sensing the movement of part or all of the asset, waking up communication functionality of the asset tracker from a sleep state, wherein, in the sleep state, the asset tracker reduces power to the communication functionality of the asset tracker; transmitting, using the communication functionality of the asset tracker, an asset tracker communication, the asset tracker communication comprising an asset tracker identification, the asset tracker identification indicative of one or both of the asset tracker or the asset; responsive to transmitting the asset tracker communication, transmitting, by a mobile electronic device proximate to the asset tracker, a mobile electronic device communication comprising a mobile electronic device identification that is indicative one or both of a unique identifier for the mobile electronic device or of a person assigned to the mobile electronic device; receiving, by an asset tracking server, one or more communications comprising the asset tracker identification and the mobile electronic device identification; and responsive to the asset tracker determining that the asset tracker has not been moved for a predetermined amount of time, transitioning, by the asset tracker, to the sleep state thereby disabling the communication functionality of the asset tracker. In this way, the asset tracker may communicate with the mobile electronic device either directly, or indirectly (e.g., via a stationary controller).

In communicating indirectly, the asset tracker communication (such as a beacon) from the asset tracker is received by the stationary controller, and responsive to the stationary controller receiving the asset tracker communication, the stationary controller communicates with the mobile electronic device in order to trigger the mobile electronic device to transmit the mobile electronic device communication (e.g., either the stationary controller receives the mobile electronic device communication and transmits to the asset tracking server the one or more communications indicative of the asset tracker identification, the mobile electronic device identification, and a stationary controller identification, the stationary controller identification indicative of one or both of a unique identification of the stationary controller or of the area; or the mobile electronic device, communicating with the stationary controller, transmits the asset tracker identification, the stationary controller identification, and the mobile electronic device identification). In practice, the asset may be moved proximate to multiple stationary controllers, such as a first stationary controller associated with a first area and a second stationary controller associated with a second area. In moving to each of the respective stationary controllers: the respective stationary controller receives the communication from the asset tracker; responsive to the respective stationary controller receiving the communication, the respective stationary controller communicates with the mobile electronic device in order to trigger the mobile electronic device to transmit the mobile electronic device communication; and the respective stationary controller transmits to the asset tracking server the one or more communications indicative of the asset tracker identification, the mobile electronic device identification, and a first stationary controller identification, the first stationary controller identification indicative of one or both of a unique identification of the respective stationary controller or of the respective area.

Alternatively, the asset tracker may directly communicate with the mobile electronic device. In one instance, responsive to receiving the communication from the asset tracker, the mobile electronic device may access location functionality resident on the mobile electronic device (e.g., a GPS receiver) in order to determine a current location of the mobile electronic device and transmit to the asset tracking server the one or more communications indicative of the asset tracker identification, the mobile electronic device identification, and the current location of the mobile electronic device. In this regard, location information may be sent to the asset tracking server. In another instance, where location is not needed, the mobile electronic device may receive a plurality of the communications from the asset tracker responsive to movement of the asset tracker during a time period. In response to the mobile electronic device receiving the plurality of communications, the mobile electronic device may: determine respective times at which the mobile electronic device received the plurality of communications; determine, based on the respective times at which the mobile electronic device received the plurality of communications, the time period of movement of the asset tracker; and transmit to the asset tracking server the one or more communications indicative of the asset tracker identification and the determined time period movement of the asset tracker. In this regard, the mobile electronic device is configured to determine the time period of movement of the asset tracker. This type of functionality may be used in a situation where the time period movement of the asset is desired, such as an asset comprising weights, exercise equipment or the like, in which location of the asset may not necessarily be sought but time period of movement of the asset, such as movement of weights, is desired.

Still alternatively, the asset tracker may communicate with the asset tracker server, in which the asset tracker communicates bidirectionally with the mobile electronic device in order to obtain the mobile electronic device identification from the mobile electronic device and in which the asset tracker transmits to the asset tracking server the one or more communications comprising the asset tracker identification and the mobile electronic device identification. Further, the asset tracker may obtain a current location of the mobile electronic device from the mobile electronic device and may also transmit the current location received from the mobile electronic device. Thus, one, some or all of the asset tracker, the stationary controller, or the mobile electronic device may communicate with the asset tracker server.

Various items in a hospital setting may require replenishing periodically. For example, general use supplies, such as hand cleaning agent (e.g., hand sanitizer), gloves, or other PPE may be subject to inventory management. As another example, other medical items, such as drug items, medical equipment (e.g., supplies for catheterization), may likewise require monitoring/replenishing.

The discussion below is focused on monitoring hand cleaning agent use. However, the discussion may equally be applied to other items subject to monitoring/replenishing. In particular, hand cleaning agent, such as hand sanitizer or soap, may be dispensed from dispensers. Over time, the hand cleaning agent is dispensed so that no more hand cleaning agent remains in the dispenser. One manner to track the amount of hand cleaning agent in a respective dispenser is to include a level sensor inside of the dispenser to monitor the amount of hand cleaning agent remaining in the dispenser. Alternatively, a sensor separate from or associated with the dispenser may be used. For example, in one or some embodiments, the dispenser monitoring device, which may be separate from, integrated with, or associated with a stationary controller, may be used to monitor the amount of hand cleaning agent remaining in the dispenser. As discussed above, the stationary controller may determine, such as via a sensor (e.g., an ultrasonic sensor, a sound sensor, or the like), whether hand cleaning agent has been dispensed.

In particular, hand cleaning agent may be inserted into a dispenser using a bag or the like, so that according to specifications, a certain number of unit dispensing volume of the hand cleaning agent being projected for the bag (e.g., one bag translates into 1,000 unit dispensing volume of hand cleaning agent). Thus, the dispenser monitoring device may determine whether a dispense has occur and update the amount of hand cleaning agent in the dispenser accordingly. In this regard, the dispenser monitoring device is unlike a level sensor that simply measures an amount of hand cleaning agent divorced or not triggered based on a dispensing event.

As such, after a new bag is inserted into a dispenser, the stationary controller associated with the dispenser may be reset. Resetting may be performed in one of several ways. In one way, a software reset may be performed in which a technician, when installing the bag in the dispenser, may input via an app (or other software) on a mobile device of the installation. The input to the app on the mobile device may trigger a communication to the backend server. The communication may include one or both of the following: (1) an indication that a bag has been replaced; and (2) an indication as to the dispenser whose bag has been replaced. With regard to (2), the mobile device may obtain the indication of the dispenser in one of several ways. In one way, the app may include a field for the technician to manually input the indication (which may be labeled on the dispenser). In another way, the app may include a visual layout of the patient area, such as a floor of a hospital, so that the visual layout may be displayed on the display of the mobile device. The technician may indicate on the display (such as touching a part of the layout) to indicate the dispenser subject to refilling. In still another way, the mobile device may communicate with the dispenser, such as via near-field communication, in order for the dispenser to send its indication to the mobile device (and in turn for the indication to be sent in the communication).

In response to the input, a communication, either directly to the stationary controller or routed via the backend server, may be sent to the stationary controller associated with the dispenser of the new bag and the number of dispenses in the new bag (e.g., new bag installed with 1,000 dispenses). In this way, the software reset comprises a virtual button reset. In another way, a hardware reset may be performed in which a technician, when installing the bag in the dispenser, may press a button (or the like) on the stationary controller indicating the installation of a new bag, with the pressing of the button triggering a reset of the counter on the stationary controller (e.g., reset back to 1,000) and triggering a communication to the backend server indicating that the dispenser associated with the stationary controller has had its bag replaced.

After which, the stationary controller may track the number of dispenses of hand cleaning agent. When the number of dispenses reaches a predetermined amount (or where there are less than a certain number of dispenses remaining in the bag), the stationary controller may send a communication to another electronic device, such as the backend server, in order to notify that the bag of the dispenser needs replacing. For example, the stationary controller's communication may trigger an email or other notification to the facilities manager indicating the location of the dispenser needing its bag replaced. Alternatively, or in addition, the backend server allows polling of one, some, or all of the stationary controllers distributed throughout a facility in order for the stationary controllers to respond with a percentage or indication of an amount of hand cleaning agent remaining in their associated dispensers.

As discussed above, in one or some embodiments, proximity, such as temporal proximity, is analyzed in order to determine whether compliance with the hand hygiene and/or PPE event is sufficiently related to the hand hygiene and/or PPE opportunity. Further, in one or some embodiments, the hand hygiene and/or PPE opportunity may be deemed not to require compliance based on one or more rules. As one example, one or more criteria, such as any one, any combination, or all of role/status of healthcare provider, schedule of patient or location of the opportunity, may be used to determine whether a compliance determination with the hand hygiene and/or PPE opportunity is to be used in calculating statistics for compliance. For example, the healthcare provider may be a physical therapist. In practice, the physical therapist washes hands when entering a patient room or when entering a workout facility (e.g., where the patient is working out). The physical therapist can assist the patient to move to or from a workout facility and assist the patient out of the patient room or the workout facility. In such an instance, the physical therapist may be unable to wash his/her hands since the physical therapist is assisting the patient. Under typical circumstances, when the healthcare provider leaves a patient room, the healthcare provider is required to wash hands. However, when the healthcare provider is a physical therapist and is assisting a patient (such as during a scheduled physical therapy session), the physical therapist does not need to wash hands. In this regard, the system includes one or more rules to determine when the physical therapist does and does not need to wash hands. As such, the one or more rules may be used so that compliance with a specific opportunity, such as exiting a patient room, is not to be used in calculating statistical compliance for the physical therapist (e.g., the compliance determination for the exit opportunity is not determined at all, the compliance determination is performed for the exit opportunity but is tagged to indicate that the compliance determination is not to be used to calculating statistical compliance for the physical therapist).

Merely by way of example, the rules may be applied for a physical therapist scheduled to visit a first patient in a first room for physical therapy to be performed in another room. In such an instance, the physical therapist washes his/her hands prior to or upon entering the first room, helps the first patient out of the first room to the physical therapy room (whereupon exiting the first room, there is no requirement for the physical therapist to wash his/her hands), leave the physical therapy room (where there is also no requirement for the physical therapist to wash his/her hands), enter the first patient's first room (where there is also no requirement for the physical therapist to wash his/her hands), and then leave the first patient's first room (where there is a requirement for the physical therapist to wash his/her hands). The physical therapist may have a schedule in which to perform this for multiple patients (in room #1, #5, #8, etc.) so the sequence above may be followed accordingly for each patient in the respective rooms.

As another example, certain rooms or areas in a hospital may be designed as housing contaminated equipment. For example, healthcare workers entering a soiled utility room (or "dirty" room) need not clean hands, but need to clean hands upon exiting. As such, compliance with certain opportunities associated with these certain rooms (such as entrance opportunities) need not be used to calculate compliance statistics whereas other opportunities (such as exit opportunities) may need to be used to calculate compliance statistics. In particular, responsive to identifying that a certain type of opportunity (such as an entrance opportunity) is associated with a certain room or area (whether this is performed by the mobile electronic device associated with the healthcare worker, performed by the stationary controller (programmed to indicate that the stationary controller is a "special area" not subject to compliance), or performed by the backend server), any compliance determination associated with such opportunity may be excluded from compliance statistics for the healthcare worker. Conversely, responsive to identifying that another type of opportunity (such as an exit opportunity) is associated with the certain room or area, any compliance determination associated with such opportunity is included in compliance statistics for the healthcare worker.

In one or some embodiments, the rules may be applied in real-time (as the HH and/or PPE opportunity is occurring) or thereafter (e.g., after the HH and/or PPE opportunity has ended). For example, responsive to detecting the opportunity, the system, such as any one, any combination or all of the wristband, the stationary controller or the backend server, may determine that the opportunity does not need compliance. As such, any one, any combination, or all of the following may be performed: reminders to comply are output but compliance data is not determined, not transmitted, or tagged at the backend server as not to be used for compliance statistics; reminders to comply are disabled; the wristband does not determine compliance; the wristband determines compliance but does not transmit the compliance determination; the backend server determines not to log the compliance determination; or the backend server logs the compliance determination but tags the compliance determination as a special circumstance. As another example, the backend server, after the opportunity has ended and after receiving the compliance determination, may determine that compliance with the opportunity is not needed. As such, the backend server may either determine not to log the compliance determination or may log the compliance determination but tags the compliance determination as a special circumstance. Further, the application of the rules may be applied at any one, any combination, or all of: the wristband (e.g., the wristband may be programmed with the status of the healthcare provider and the rules stored locally in the wristband, and may determine which opportunities not to factor into compliance determination); at the stationary controller (e.g., the stationary controller may communicate with the wristband to determine the status of the healthcare provider and may access the rules stored locally in the stationary controller, and may determine which opportunities not to factor into compliance determination); or the backend server (e.g., the backend server may be access a database with the status of the healthcare provider and the rules, and may determine which opportunities not to factor into compliance determination).

As discussed above, HH and/or PPE may be relevant for a variety of settings, such as healthcare settings (e.g., hospitals, nursing homes, etc.) or other businesses (e.g., restaurants, schools, etc.). As a specific example, restaurants are typically tasked with following local or regional health codes. Typically, one of those health codes is following proper hand hygiene, such as proper hand washing in various areas of a restaurant including the kitchen and/or the bathroom. In order to monitor hand hygiene, the restaurant workers, such as chefs and/or waiters/waitresses, may wear a mobile electronic device, such as a wristband or the like.

Further, various parts of the restaurant may include additional hardware including any one, any combination, or all of: stationary controller(s) associated with hand cleaning agent dispensers (such as soap dispensers); electronic devices associated with moving objects (such as movement sensor(s) associated with doors (such as kitchen doors and/or bathroom doors)); stationary controller(s) associated with kitchen appliances (such as stoves, fryers, etc.); stationary controller(s) associated with bathroom appliances (such as commodes, toilets, etc.); or sound sensors positioned in or near the kitchen and/or bathroom.

Thus, depending on the layout and size of the kitchen and/or bathroom, one or more stationary controllers may be used. For example, in a smaller bathroom, a single stationary controller may solely be used or may be used with another sensor, such as a door sensor (sensing opening and/or closing of the door to the bathroom) and/or a sensor sensing flushing of the commode (e.g., a sound sensor configured to generate a signal to the stationary controller responsive to sending the sound of flushing). Responsive to the trigger (e.g., receiving a signal that the door has been opened and/or flushing sound has been detected), the stationary controller may set a timer in which the worker is to take hand cleaning agent. As another example, in a larger kitchen or bathroom, more than one stationary controller may be used, such as one stationary controller positioned proximate to the hand cleaning agent dispenser, another stationary controller positioned proximate to the door of the kitchen or bathroom, and still stationary controller positioned proximate to a device (such as a kitchen appliance or a bathroom appliance (e.g., a commode)). In this way, movement of the worker may be tracked in order to trigger a hand hygiene opportunity. For example, tracking movement into the kitchen or movement from the bathroom appliance to the dispenser may be used to identify a hand hygiene opportunity. Responsive to identifying the hand hygiene opportunity, the worker may be given a certain amount of time in which to take hand cleaning agent. If the worker does not take the hand cleaning agent within the certain amount of time (e.g., 2 seconds from identifying the hand hygiene opportunity), a reminder may be generated by one or both of the wristband associated with the worker or the stationary controller associated with the dispenser. In the event the worker fails to take hand cleaning agent with another amount of time (e.g., 6 seconds from identifying the hand hygiene opportunity), the hand hygiene opportunity is deemed non-compliant. Further, once hand cleaning agent is dispensed, the stationary controller may send a communication to the wristband to begin monitoring hand movements in order to determine either full or partial compliance. Similar to the discussion above, after the wristband determines compliance, the wristband may send the compliance determination to an external device, such as to the stationary controller or to the backend server.

Similar to determining compliance with one or more detected WHO hand hygiene opportunities, a method and system are disclosed that determines compliance with one or more detected restaurant hand hygiene opportunities, such as entering the kitchen, beginning a task in the kitchen (such as beginning to cook), and/or exiting the bathroom. In one or some embodiments, the method and system may comprise interaction between the wristband and another electronic appliance. As one example, interaction between the wristband and a stationary controller (which may be positioned or integrated with a hand cleaning agent dispenser) may trigger determination of compliance with a hand hygiene opportunity. In particular, responsive to interaction of the wristband with the stationary controller, the wristband may be triggered to determine hand hygiene event compliance (e.g., interaction results in the wristband being triggered to determine hand hygiene compliance, such as compliance with one or both duration of hand movements or specific hand movements). Various types of interaction are contemplated, as discussed above. As one example, communication between the wristband and stationary controller may trigger the wristband to determine hand hygiene event compliance (e.g., the wristband receives a communication from the stationary controller and determines that the communication has an RSSI signal indicative of being within the connection zone). As another example, the stationary controller's determination that hand cleaning agent has been dispensed triggers the stationary controller to send a communication (such as a dispensing communication) to the wristband in order for the wristband to determine hand hygiene event compliance (e.g., the wristband receives the dispensing communication from the stationary controller and is triggered to wake up and begin monitoring hand hygiene compliance).

As still another example, determination of movement into, out of, and/or within the kitchen and/or the bathroom may trigger determination of hand hygiene opportunity. In one instance, movement may be tracked using one or more stationary controllers, which may be located in different portions of the kitchen and or bathroom, such as at an entrance and/or in one or more interior portions. In particular, in communicating with multiple stationary controllers, the wristband may determine its movement, as discussed above.

In another instance, a sensor that is attached to the door, such as a proximity sensing-output generating device discussed above, may sense movement of the door (such as whether the door has opened or closed). Responsive to the sensor sensing movement of the door (such as opening the door to the kitchen or the bathroom), the sensor may send a communication to one or both of the wristband or the stationary controller, thereby triggering the sequence of determining hand hygiene compliance. In one or some embodiments, the sensor and/or the stationary controller are typically in sleep mode. For example, the sensor may include a micro-vibration sensor to wake up other parts of the sensor (such as communication functionality) responsive to movement from the door. As another example, the stationary controller may have its communication functionality awake in sleep mode but other aspects, such as sensing dispensing of hand cleaning agent, may be turned off. Responsive to the door moving (such as opening), the sensor may wake up and send a communication to the stationary controller. In turn, the stationary controller may wake up in order to begin monitoring whether someone has taken hand cleaning agent. In this way, one or both of the door sensor or the stationary controller may be in sleep mode and thus conserve power. Further, one or both of the sensor or the stationary controller may communicate with the wristband responsive to waking up in order to identify the person associated with the wristband. For example, responsive to the sensor waking up, the sensor may send an identify communication wirelessly, such as via Bluetooth, to wristbands within a certain range. Responsive to receiving the identify communication, the wristband may send a communication with a code identifying the person associated with the wristband. As another example, responsive to the stationary controller waking up, the stationary controller may send an identify communication wirelessly to wristbands within a certain range, and receive the identifying code in response.

In still another instance, a sensor, such as an audio sensor, may be used to trigger the hand hygiene event determination. For example, a sensor may be configured to sense a predetermined sound, such as a toilet flushing. Responsive thereto, the sensor may send a communication to the wristband to begin monitoring the hand hygiene event for compliance determination (e.g., responsive to receiving the communication from the sensor, the wristband sets a timer in which the wearer of the wristband is to comply with the hand hygiene event; otherwise, the hand hygiene event is determined as non-compliant).

Alternatively, in the restaurant or hospitality-industry setting, workers may typically be tasked with cleaning hands at a predetermined schedule (such as every 30 minutes). Thus, in one or some embodiments, a single device, such as a mobile electronic device associated with the worker, may be used to: (1) determine whether there is a hygiene opportunity; (2) detect whether hand cleaning agent has been dispensed; (3) detect hand movements; and (4) detect whether the hand movements are sufficient for hygiene compliance. With regard to (1), the mobile electronic device may include a timer, which indicates the schedule at which the hygiene opportunities are determined (e.g., time set to 30 minutes to indicate a hygiene opportunity every 30 minutes). In one embodiment, an output, such as an output generated by the mobile electronic device, may be generated when a hygiene opportunity is determined. Alternatively, no output is generated responsive to determining a hygiene opportunity. With regard to (2), the mobile electronic device may include one or more sensors whose data may be analyzed by a processor in the mobile electronic device in order to detect whether hand cleaning agent has been dispensed. In one example, the mobile electronic device may include a sound sensor, which may generate sound data at, approximately before, or approximately after the hygiene opportunity is determined. The processor on the mobile electronic device may analyze the sound data generated at, approximately before, or approximately after the hygiene opportunity is determined in order to determine whether the sound data is indicative of hand cleaning agent being dispensed. In another example, the mobile electronic device may include a motion sensor, which may generate motion data at, approximately before, or approximately after the hygiene opportunity is determined. The processor on the mobile electronic device may analyze the motion data generated at, approximately before, or approximately after the hygiene opportunity is determined in order to determine whether the motion data is indicative of a hand movement where the palm of a hand is moved to face upward or positioned to face upward, in turn indicating that the hand is positioned or has moved to receive hand cleaning agent from a dispenser.

With regard to (3) and (4), the mobile electronic device may include one or more sensors whose data may be analyzed by a processor in the mobile electronic device in order to detect whether hand movements are sufficiently performed. For example, the mobile electronic device may include one or more motion sensors, which may generate motion data at, approximately before, or approximately after detecting dispensing of hand cleaning agent. The processor on the mobile electronic device may analyze the motion data generated at, approximately before, or approximately after detecting dispensing of hand cleaning agent in order to determine whether the motion data is indicative of sufficient hand cleaning (e.g., at least a certain period of time, such as 20 seconds, of hand movement; at least one or more predetermined hand motions; etc.). In this way, the mobile electronic device need not rely on any external electronic device in order to perform each of (1), (2), (3), and (4).

Alternatively, or in addition, reminders may be generated for the worker and/or for patrons of the restaurant to see and/or hear. As discussed above, outputs may be generated at various stages for the worker, such as reminder(s) to perform certain actions, feedback as to whether the worker complied or did not comply with the protocol at various stages, etc. In one or some embodiments, the output may be generated for someone other than the worker or the healthcare provider. As discussed above, hospitality workers, such as restaurant workers, serve patrons. Those patrons may be interested in knowing whether a hospitality worker serving them has complied with HH protocol(s). As such, the output, such as whether the hospitality worker complied or did not comply with the HH protocol(s), may be generated responsive to interaction of the hospitality worker with patron(s). In one or some embodiments, the mobile electronic device, such as the wristband, may be triggered to output the compliance determination responsive to the mobile electronic device, on its own, identifying an opportunity associated with interacting with a patron. As discussed above, there are various ways in which the mobile electronic device may identify approaching a patron, such as approaching a patron area. Likewise, in response to the mobile electronic device identifying a patron interaction (such as tracking the worker's movement into a designated dining area, the mobile electronic device may generate the output (such as a red LED light activated to indicate non-compliance and a green LED light activated to indicate compliance). Alternatively, the mobile electronic device may be triggered to output the compliance determination responsive to interaction with another electronic device, such as a stationary controller. For example, a stationary controller may be positioned proximate to a patron (such as at a dining table of the patron). Responsive to the mobile electronic device interacting with the stationary controller (e.g., the mobile electronic device communicates with the stationary controller via near-field communication), one or both of the mobile electronic device or the stationary controller may generate the output indicative of compliance (e.g., the wristband may generate an output and/or the stationary controller may generate the output). In this way, the output generated may be triggered based on interaction with the patron, thus being personalized to the patron.

As discussed above, an electronic device, such as a wristband, may be associated with a person, such as a healthcare provider. Assigning of the electronic device, such as a wristband, to a specific person, such as a specific healthcare provider, may be performed in one of several ways. As discussed above, the wristband may have wireless communication functionality, such as any one, any combination, or all of: Bluetooth communication functionality; Wi-Fi communication functionality; cellular communication functionality; or the like. The wristband, using the wireless communication functionality, may communicate with a remote server (such as via the Internet). In turn, the remote server may determine any one or both of the following: (1) who is currently assigned the wristband; and (2) assign (or reassign) the wristband to a specific person.

For example, the wristband may have a code (e.g., XYZA). The remote server may correlate that code in a database to an identification of the specific person (e.g., code XYZA is correlated to "Jane Doe"). In practice, the wristband may send, via its wireless communication functionality, its code to a local mobile controller (e.g., the wristband uses its near-field communication functionality to communicate with the local mobile controller). In turn, the mobile controller sends, via the Internet, the code to the remote server. The remote server may then access the database to determine the specific person assigned the wristband. With regard to assigning or reassigning, the remote server may simply reprogram the database so that a specific code is correlated to a different person (e.g., change correlation of XYZA to "Jane Doe" to XYZA to "John Roe"). Various communication protocols are contemplated. As one example, the remote server and the mobile controller may communicate with one another using web sockets technology. In this way, assigning, or reassigning, of the wristbands may be performed quickly and easily.

FIG. 1A is a first example block diagram of a HH and/or PPE system 100, with a mobile wristband device 105, a local stationary controller 115 and a back-end server 130. As discussed above, the mobile wristband device 105 and the local stationary controller 115 may communicate wirelessly, such as via 110. Example wireless protocols may comprise near-field communication protocols, such as RFID, Bluetooth, ZigBee or the like. The local stationary controller 115 may likewise communicate with back-end server 130. As shown in FIG. 1A, the communication between the local stationary controller 115 and back-end server 130 is wireless 120 via a Wi-Fi base station 125. Other methods of communication are contemplated.

FIG. 1B is a second example block diagram of a HH system 150, with a mobile wristband device 153, a dispenser 151, a local stationary controller 152, wireless router 154 (e.g., Wi-Fi transceiver), cloud computing 156, compliance analysis 158, and output device 159 (e.g., smartphone or tablet). The HH system 150 is configured to perform any one, any combination, or all of the following four functions: data tracking, data collection, data analysis and healthcare provider motivation. Each healthcare provider wears a wristband 153 with built-in motion sensors, discussed in more detail below. In one implementation, each wristband is assigned to and worn by only one person (e.g., healthcare provider). Further, there is a one-to-one mapping between the person's information (e.g., name, role, etc.) and the MAC address of the wristband. As discussed further below, stationary controllers (e.g., positioned inside and/or outside a patient room) may be mapped to a particular area (e.g., a room location).

When the healthcare provider approaches the entrance of a patient's room, the wristband sensor on wristband 153 detects the beacon from the controller 152 installed close to, adjacent to, proximate to, or integrated with the sanitizer dispenser 151 and send a hand hygiene alert to the healthcare provider. Alternatively, the wristband 153 may transmit a beacon to the controller 152, which in turn may detect the wristband 153, with the controller 152 sending a signal to wristband 153, as discussed above. The wristband sensor in wristband 153 records the healthcare provider's hand motion data during the HH event, which is transmitted via the controller 152 and wireless router 154 to cloud computing 156, which may comprise a hospital server.

As discussed above, controller 152 may be mounted proximate to dispenser 151, such as within or less than 1 inch, within or less than 2 inches, within or less than 3 inches, etc. of dispenser 151. Controller 152 may include electronics that performs one or more functions. For example, controller 152 may generate a beacon (or other wireless signal) that is received by the wristband 153. As discussed above, in response to receiving the beacon, the wristband 153 is configured to generate an output indicative of the hand hygiene alert (e.g., an audible output and/or a visual output indicative to the healthcare provider to perform the hand cleaning process). In this regard, the controller 152 generates the beacon that begins the hand hygiene notification process. Alternatively, controller 152 may receive a beacon from wristband 153, such as a Bluetooth signal. In response, controller 152 may determine a proximity to wristband 153, and if sufficiently proximate, send a wake-up signal to wristband 153 to begin motion sensor monitoring.

As another example, the controller 152 may monitor one or more operations related to dispenser 151. In one implementation, the controller 152 may monitor at least one aspect of the dispenser 151 itself. For example, the controller 152 may monitor an internal operation of the dispenser 151. In a first specific implementation, the controller 152 may include a sensor, such as a sound sensor, that may monitor the internal operation of dispenser 151 (e.g., a sound sensor that senses sound generated by a motor within dispenser 151 that dispenses antibacterial product into the hand of the healthcare provider). Thus, in the first specific implementation, the controller 152 may monitor the dispenser 151, as opposed to movement of the healthcare provider. In a second specific implementation, the controller 152 may include a sensor, such as an infrared sensor, that may monitor the movement of the healthcare provider in an area proximate to the dispenser 151. In a third specific implementation, the controller 152 may include multiple sensors that monitor the internal operation of the dispenser 151 and the movement of the healthcare provider in an area proximate to the dispenser 151.

Responsive to the controller 152 determining that the monitored aspect of the dispenser 151 has occurred (e.g., the controller 152 determining that the dispenser 151 has dispensed the antibacterial product and/or the controller 152 determining that the healthcare provider is proximate to the dispenser 151), the controller 152 may send a communication to the wristband 153. Responsive to the communication, the wristband 153 may begin to track the hand movements of the healthcare provider and/or may generate one or more outputs in order to provide instruction to comply with protocol(s) (such as hand hygiene protocols). For example, the wristband may generate the one or more outputs responsive to receiving the communication and/or responsive to determination of compliance or non-compliance (e.g., responsive to determination of non-compliance (such as not rubbing for at least the predetermined amount of time and/or not performing the proper hand movements, the wristband may generate the output indicating the deficiency). Alternatively, the wristband 153 may begin to track the hand movements responsive to receiving the beacon from the controller 152.

The wristband 153 may thus record the healthcare provider's hand motion data during the HH event. In one implementation, the wristband 153 may analyze the hand motion data locally (within the wristband 153), and transmit the analysis (and/or the hand motion data) to the controller 152. Alternatively (or in addition), the wristband 153 may transmit the hand motion data to controller 152 for analysis by the controller 152 and/or for analysis by cloud computing 156.

After the analysis of the hand motion data (either by wristband 153, controller 152 and/or cloud computing 156), an indication of the results of the analysis may be transmitted to the healthcare provider. In one implementation, the indication may be output on wristband 153. In one example, the wristband 153 may perform the analysis and may output the indication of the results of the analysis (e.g., whether the healthcare provider adequately cleaned his/her hands; whether the healthcare provider inadequately cleaned his/her hands; an indication how to improve hand cleaning (e.g., aurally outputting to the healthcare provider to clean the hands for a longer period of time, such as for 10 more seconds responsive to determining that the healthcare provider rub his/her hands for 10 seconds less than the hand hygiene protocol dictates)). In another example, the controller 152 may perform the analysis and may transmit to the wristband 153 the indication for output by the wristband 153 of the indication of the results of the analysis. In still another example, the controller 152 may perform the analysis and may transmit to cloud computing 156 the indication, which may transmit to (or may available for download by) a mobile app running on a mobile electronic device associated with the healthcare provider. In yet another example, cloud computing 156 may perform the analysis using compliance analysis 158 (e.g., a computer associated with the infection control team may analyze hand hygiene data) and may transmit to (or may available for download by) a mobile app running on a mobile electronic device associated with the healthcare provider (e.g., output device 159).

In this way, separate from feedback from the wristband 153, each healthcare provider may also check his/her performance through the mobile app on output device 159, thereby being provided motivation to comply with hygiene standards.

In one implementation, the hygiene protocol, including the HH protocol, is standard and consistent for different locations within a premises. Generally speaking, the hygiene protocol may include any one, any combination, or all of the following: HH protocol; mask protocol (e.g., whether or not to wear a face mask); gown protocol (e.g., whether or not to wear a hospital gown); gloves protocol (e.g., whether or not to wear latex rubber gloves); footwear protocol (e.g., whether or not to wear booties over the shoes); etc. For example, the hygiene protocol may be the same for a first hospital room and a second hospital room, or may be the same for a first section of the hospital and a second section of the hospital. As discussed further below, various HH protocols may be used, such as those issued by WHO. Alternatively, the hygiene protocol is different for different locations within a premises. For example, a first hospital room may have a first hygiene protocol and a second hospital room may have a second hygiene protocol, with the first hygiene protocol being different than the second hygiene protocol. In particular, the first hygiene protocol may be different from the second hygiene protocol in any one, any combination, or all of: hand hygiene protocol (e.g., whether to use hand sanitizer or use soap/water), mask protocol, gown protocol, or footwear protocol. As another example, a first section of the hospital, such as the ICU (or ICU-A), may have the first hygiene protocol whereas a second section of the hospital, such as the neonatal unit or ICU B, may have the second hygiene protocol (e.g., the ICU requires face masks whereas the neonatal unit requires gowns).

The hygiene protocol may be communicated to one or both of the stationary controller or the wristband in one of several ways. In one way, the stationary controller may have the specific protocol pre-programmed thereon (either upon installation or sent from the server). For example, responsive to a determination that a patient with pneumonia is staying in a particular room, the server may send a communication to the stationary controller (assigned to that particular room) to indicate the hygiene protocol for a patient with pneumonia. Similarly, the wristband may determine the specific protocol in one of several ways. In one way, the stationary controller in the specific location may send or push the protocol to the wristband. For example, a stationary controller in the first section of the hospital may send the first protocol (e.g., the correct hand movements or the requirement of a face mask) to the wristband in response to the stationary controller determining that the wristband is in proximity (see 638 of FIG. 6C). In another way, the wristband may, itself, determine its location, transmit the location to a server, with the server in response sending the specific protocol to the wristband.

In practice, the stationary controller and/or the wristband may generate an output indicating the protocol (e.g., the deviation in the protocol, such as wearing a face mask). For example, responsive to the stationary controller determining that the wristband is in proximity, the stationary controller may generate an output (e.g., an audio output stating: "please put on a face mask"; "please use soap and water to wash hands"; "please use hand sanitizer to wash hands"; "please first use soap and water to wash hands, then put on a gown, finally put on gloves, and then enter the room"; "please first use hand sanitizer, then put on mask, and then enter the room"; "please first remove your gloves, then your gown, and then use soap and water to wash your hands"). In this way, the output may provide a reminder as to the protocol(s) to be followed (e.g., a specific protocol that is assigned to a patient room or a general protocol that is assigned to an entire hospital). As another example, the wristband may generate the output, such as the audio output.

Further, the determination whether to generate the output may be dependent on one or more factors, such as any one, any combination, or all of: the status of the person; the type of protocol (e.g., whether the protocol is changeable); whether the protocol has changed; etc. For example, status may be defined in one of several ways, such as: a trainee (e.g., a new employee); an existing employee; a visitor; etc. In this regard, the output, either from the stationary controller and/or from the wristband, may be dependent on the status of the person (e.g., for a trainee, generate one or more outputs such as: generating a reminder to wash with soap and water; generating a reminder as to the correct sequence for performing the PPE protocol; generating a reminder as to the correct HH protocol and/or the correct PPE protocol; generating a reminder as to the correct sequence for the HH protocol and the PPE protocol when entering and/or exiting the patient area). As one example, the status of the person may be an employee. The status may be stored, for example, on the wristband. In the example of the stationary controller generating the output, the stationary controller may first receive the status of the person (e.g., the wristband transmitting the status of "trainee" to the stationary controller upon the wristband coming into proximity with the stationary controller). The stationary controller may determine whether to generate the output (e.g., generating a reminder to wear a mask) dependent on whether the person is designated as a trainee. If so, the stationary controller may generate the output. Conversely, in the event that the person is an "employee" (meaning more experienced than a trainee in the protocols of the hospital), responsive to the stationary controller determining the status of the person as "employee", the stationary controller may determine not to generate the output (e.g., not generate a reminder to wear a mask). Similarly, in the context of the wristband generating the output, the wristband may determine whether to generate the output based on the status of the person. As discussed above, the wristband may determine, either based on a communication from the stationary controller or from another external device, to output a particular protocol for a specific room or section of a hospital. The wristband may condition the output of the particular protocol on the status of the person. Specifically, the wristband may indicate that the wearer is a trainee. Responsive to the wristband determining that the wearer is a trainee, the wristband may determine to output the special protocol (e.g., generate a vibration, generate an audio and/or display output). Conversely, responsive to the wristband determining that the wearer is an "employee", the wristband may determine to output the special protocol (e.g., generate a vibration, generate an audio and/or display output).

As another example, determination whether to output the reminder may be based on the type of protocol. For example, the protocol may comprise a hygiene protocol that may be changed. In one particular example, a patient area may have an associated hand hygiene protocol selected from either hand sanitizer or soap/water based on the patient assigned to the patient area. Responsive to identifying that the hand hygiene protocol associated with the patient area may be changeable, an output may be generated in order to remind a healthcare worker interacting with the patient in the patient area (such as reminding the healthcare worker upon exit from the patient area to comply with the hand hygiene protocol currently associated with the patient area).

As still another example, determination whether to output the reminder may be based on whether the protocol has changed. In particular, responsive to identifying that the protocol has changed, such as having been changed within a period of X days since the present time at which the output is to be generated, it may be determined to generate the output.

Thus, in one implementation, the wristband may comprise an ultra-low-power device. Optionally, the wristband may be any one, any combination, or all of the following: waterproof; easy to clean; provide output to the healthcare provider (e.g., a warning vibrating alert if no or incomplete hand hygiene detected). To minimize the change on healthcare providers' workflow, the wristband may be configured such that power consumption may be reduced so that battery life is extended (e.g., approximately 12 months), as discussed in more detail below.

Since the sensors may be worn on different parts of the body, such as at the wrist, the sensors are not in direct contact with patients most of the time and are less likely to be contaminated. Nevertheless, the wristbands may be designed such that they can be easily cleaned with UV lights or sanitizer when needed.

Alternatively, or in addition, the wristband may include a simple and robust algorithm for hand rubbing detection. Rubbing hands with an alcohol-based formulation is one manner for routine hygienic hand antisepsis. Alternatively, soap and water may be used mostly for cleaning soiled hands. When using an alcohol-based formulation, healthcare providers can walk while rubbing hands. Therefore, a robust motion algorithm may be used to detect the hand rubbing motions, separate from noise factors such as walking and arm swing. Since the wristband tracks and stores the hand hygiene information and provide real-time intervening, the embedded algorithm may be straightforward in order to minimize the computing power and thus increase battery life of the wristband. In a first specific implementation, the wristband's sole focus is directed to hand hygiene compliance. In a second specific implementation, the wristband has multiple purposes, including any one, any combination, or all of: hand hygiene compliance; PPE compliance; access control (e.g., RFID tag); or activity tracking (e.g., pedometer, movement tracker, or the like). In this regard, the wristband may include algorithms to track different types of movements, such any one, any combination, or all of: hand hygiene movements; PPE movements; arm swinging movements; step movements, and the like. The wristband may thus analyze movements against multiple algorithms in order to determine the mostly likely type of movement. For example, the wristband may analyze the sensor output to determine whether the sensor output is more indicative of hand hygiene movements or arm swinging movements. Therefore, including algorithms directed to identifying different types of movements may improve operation of the hand hygiene compliance.

In still another implementation, the wristband may generate sensor data that may be analyzed by HH and/or PPE analytics. In particular, the sensor data may be stored in a HH and/or PPE database, which provides a variety of data to hospital management team and individual healthcare providers. Detailed HH and/or PPE compliance reports generated by date, location (floor, unit or room), or department are available to hospital administrators and can be used to set up incentive/penalty programs to motivate healthcare providers. Infection control professionals also have access to the information to differentiate between staff groups and identify trends based on time of shift, protocols, or other desired metrics. Further, a mobile app may be used, whereby healthcare providers can compare their performance to their colleagues' and be motivated through peer pressure and team competition. Thus, in one implementation, only HH compliance is stored and/or analyzed. In another implementation, only PPE compliance is stored and/or analyzed. In still another implementation, both HH and PPE compliance are stored and/or analyzed.

FIG. 1C is a third example block diagram of a HH and/or PPE system 160, with an application server 162, a database 172, one or more wristbands (wristband #1 (176) to wristband #N (178)), one or more stationary controllers (stationary controller #1 (180) to stationary controller #M (182)), and one or more notification electronic devices (electronic device #1 (184) to electronic device #L (186)). FIG. 1C shows N wristbands, M stationary controllers and L electronic devices. Any numbers of wristbands, stationary controllers, and electronic devices are contemplated.

The application server 162 is configured to include the hardware, software, firmware, and/or middleware for operating the HH and/or PPE analytical and monitoring application 168. In a first implementation, the application server 162 is configured for analysis and/or monitoring of HH compliance. In a second implementation, the application server 162 is configured for analysis and/or monitoring of PPE compliance. In a third implementation, the application server 162 is configured for analysis and/or monitoring of both HH and PPE compliance. In the third implementation, the application server 162 may analyze and/or monitor the HH compliance and PPE compliance independent of one another. Alternatively, the application server 162 may analyze and/or monitor the HH compliance and PPE compliance dependent on one another. Application server 162 is shown to include a processor 164, a memory 166, and a communication interface 170. The HH and/or PPE analytical and monitoring application 168 is described in terms of functionality to manage various stages of managing the HH and/or PPE data as generated by one or more wristbands (wristband #1 (176) to wristband #N (178)) and/or one or more stationary controllers (stationary controller #1 (180) to stationary controller #M (182)), and for notification via electronic device #1 (184) to electronic device #L (186).

HH and/or PPE analytical and monitoring application 168 (and HH and/or PPE analytics 306 and access control 374, 482 resident in wristband, HH and/or PPE control 432, and access control 434 in stationary controller, discussed further below), may be a representation of software, hardware, firmware, and/or middleware configured to implement the management of any one, any combination, or all of the stages of hand hygiene compliance.

The HH and/or PPE system 160 may further include a database 172 for storing data for use by the HH and/or PPE analytical and monitoring application 168. For example, data generated by one or both of wristbands 176, 178 and stationary controllers 180, 182 may be stored in database 172.

The application server 162 may communicate with the database 172 directly to access the data. Alternatively, the application server 162 may also communicate with the database 172 via network 174 (e.g., the Internet). Though FIG. 1C illustrates direct and indirect communication, in one implementation, only direct communication is used, in an alternate implementation, only indirect communication is used, and still in an alternate implementation, both direct and indirect communication is used.

The application server 162 may communicate with any number and type of communication devices via network 174. As illustrated in FIG. 1C, application server 162 may communicate with electronic devices associated with one or more users. For example, FIG. 1C depicts N wristbands 176, 178, M stationary controllers 180, 182, and L electronic devices 184, 186. The wristbands 176, 178 may communicate directly with application server 162 or may communicate via stationary controllers 180, 182 (not shown). The depiction in FIG. 1C is merely for illustration purposes. Fewer or greater numbers of wristbands, stationary controllers, and electronic devices are contemplated.

Electronic device #1 (184) to electronic device #L (186) shown in FIG. 1C may be used to notify one or more individuals, such as the healthcare provider associated with one of wristbands 176, 178, or another healthcare provider not associated with one of wristbands 176, 178. Further, electronic device #1 (184) to electronic device #L (186) may comprise smartphones, tablet computers, personal computers (PCs), server computers, handheld or laptop devices, multiprocessor systems, microprocessor-based systems, network PCs, or devices, and the like.

Figure 1D:
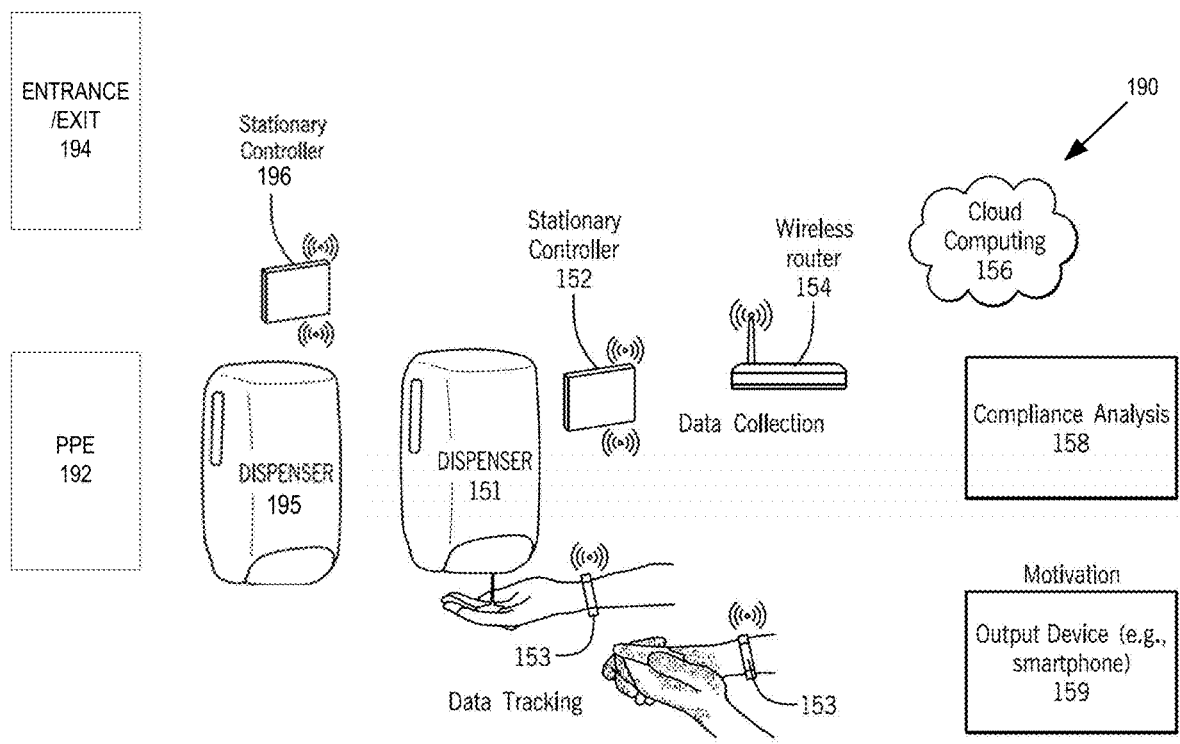
FIG. 1D is an example block diagram of a hand hygiene and personal protective equipment system, with a mobile wristband device, personal protective equipment, an entrance/exit, a dispenser, a local stationary controller, compliance analysis, one or more output devices, and cloud computing.
Figure 1C:
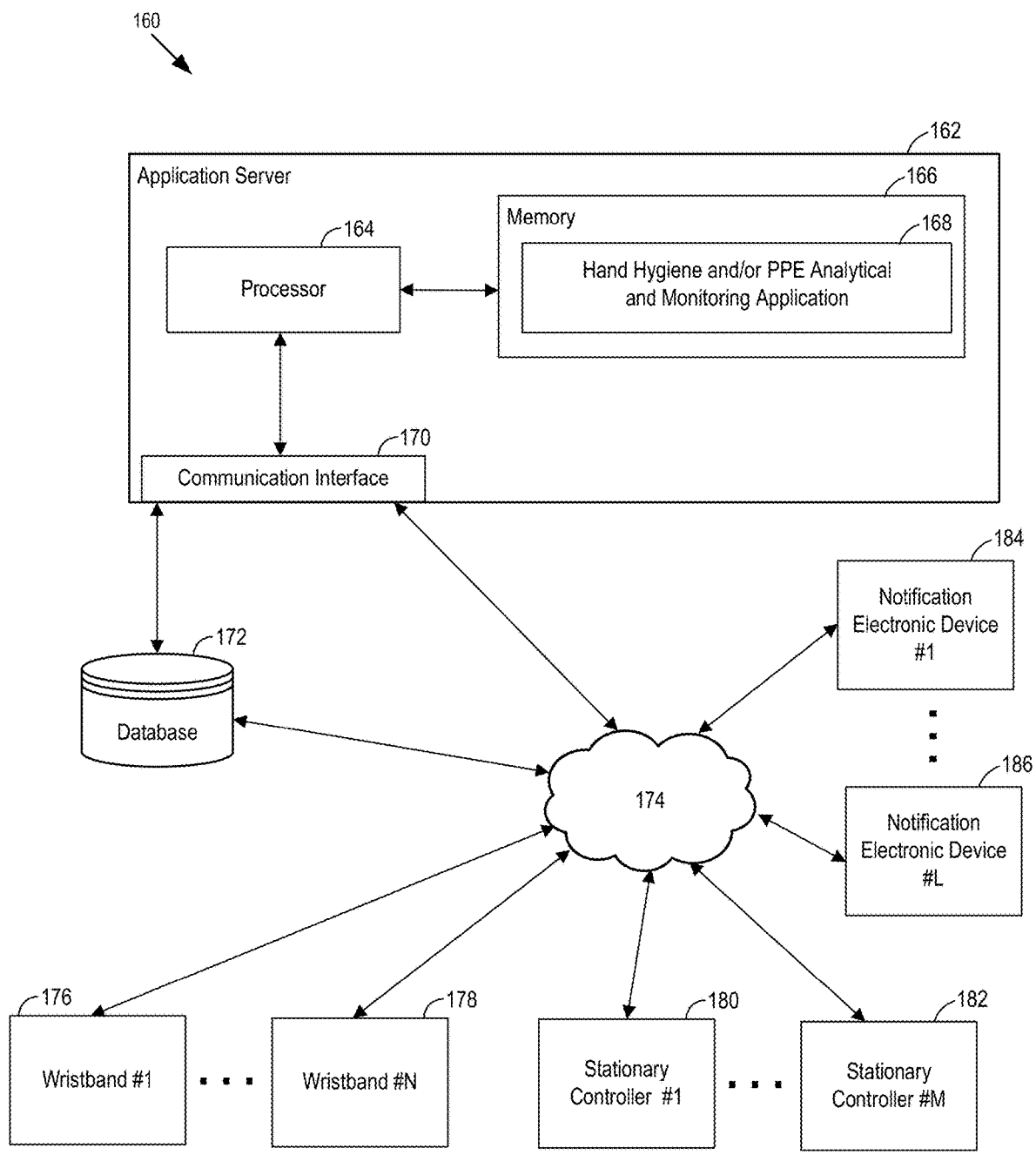
FIG. 1C is a third example block diagram of a hand hygiene and/or PPE system, with an application server, a database, one or more wristbands, one or more stationary controllers, and one or more notification electronic devices.

FIG. 1D is an example block diagram 190 of a HH and PPE system, with a mobile wristband device 153, personal protective equipment 192, an entrance/exit 194, one or more dispensers 151, 195, one or more stationary controllers, 152, 196, compliance analysis 158, one or more output devices 159, and cloud computing 156. As discussed further below, the stationary controller may be associated (such as proximate to) entrance/exit 194, which is the entrance and/or exit to a patient area (e.g., a patient room). In one implementation, two dispensers are used, with one dispenser located outside of the room near or proximate to the entrance/exit 194 (e.g., dispenser 151 in FIG. 1D) and a second dispenser located inside the room near or proximate to the entrance/exit 194 (e.g., dispenser 195 in FIG. 1D). For example, one typical clinical setting has a sanitizer dispenser (and/or a washing station) and PPE station positioned at the entrance to a patient room and another sanitizer dispenser (and/or a washing station) inside the patient room.

In practice, when the wristband 153 is proximate to dispenser 151 (as the healthcare provider is outside the room and moving toward the entrance), stationary controller 152 may communicate with wristband 153 in order to identify the HH and/or PPE opportunity upon entrance. As discussed above, identifying the HH opportunity and the PPE opportunity may be dependent on one another; alternatively, identifying the HH opportunity and the PPE opportunity may be independent of one another. Likewise, when the wristband 153 is proximate to dispenser 195 (as the healthcare provider is inside the room and moving toward the exit to leave), stationary controller 196 may communicate with wristband 153 in order to identify the HH and/or PPE opportunity upon exit. Again, identifying the HH opportunity and the PPE opportunity upon exit may be dependent on one another; alternatively, identifying the HH opportunity and the PPE opportunity upon exit may be independent of one another. Alternatively, instead of having two stationary controllers, a single stationary controller (such as stationary controller 152 outside of the room) may be used with an electronic device inside of the room that communicates with stationary controller 152.

Various types of communication between the different electronic devices depicted in FIG. 1D are contemplated. In one implementation, each electronic device depicted in FIG. 1D include Wi-Fi and/or cellular communication functionality in order to communicate, via cloud computing 156, with other devices. For example, stationary controller 152 may communicate with stationary controller 196 via the cloud, and vice-versa. In an alternate implementation, a wireless mesh network may be used. For example, stationary controllers 152, 196 may be organized in a mesh topology with each stationary controller 152, 196 performing different functions. Thus, the wireless mesh network may include an infrastructure of nodes in a mesh topology that are wirelessly connected to each other, with certain nodes piggybacking off each other to extend a radio signal to route, relay, and proxy traffic to/from clients. In one implementation, stationary controller 196 may comprises a node that communicates with stationary controller 152. Specifically, stationary controller 196, which is positioned inside a patient room, may act as an endpoint, thereby not routing messages for other devices, whereas stationary controller 152, positioned outside the patient room, is responsible for forwarding messages between the endpoints and connecting to the Wi-Fi gateway. The endpoints need not have networking tasks and may enter sleep mode. In this way, the endpoint devices enables a more flexible implementation (e.g., allowing the endpoint devices to be battery-powered), thereby being more conducive for scaling. Further, various electronic devices, such as stationary controller 152 and stationary controller 196, may have unique IDs (e.g., MAC address) within the network.

In this way, a mesh network may be formed, with the stationary controller acting as the access point (communicating with the back-end server via Wi-Fi) and in which the electronic device communicates via near-field communication with the stationary controller.

The personal protective equipment (PPE) 192 may comprise any type of equipment for protecting the person from transmitting a disease to and/or receiving a disease from the patient in the patent area. PPE 192 may include, for example, gloves, mask, goggles, gowns, or the like. As discussed in more detail below, as a person, such as a healthcare provider, enters and/or exits the patient area, one or both of HH protocols or PPE protocols may be monitored.

As discussed above, one or more electronic devices, such as depicted in FIGS. 1B and 1D, may determine whether a person is entering or exiting the patient area (e.g., patient room) in one of several ways. In one way, one or both of the stationary controllers 152, 196 may determine interaction (and in turn whether the person is entering or exiting the room) based on timing of the interaction. As one example, it may be assumed that the wristband worn by the person who is entering/exiting the room communicates (e.g., via Bluetooth) for a longer period of time than a person who is merely walking past the entrance to the room. In particular, the healthcare provider will remain at the proximity of the entrance for several seconds (to wash hands, don/doff PPE, open door, etc.), unlike someone simply walking by the patient room. Thus, in one implementation, the wristband signal, as detected by stationary controller (e.g., stationary controller 152 positioned at or outside of the entrance to patient room) will be strong (greater than a predetermined threshold) for a longer period of time when entering/exiting the room (as compared to walking by). In this way, the stationary controller may count the amount of time this pattern occurs (e.g., greater than the predetermined threshold) and responsive to determining that the amount of time is greater than the predetermined threshold, thereby detect a hygiene opportunity, such as if a healthcare provider is entering or exiting the room.

Thus, one or both of the wristband or the stationary controller may determine a period of time that the wristband (with its unique ID) and the stationary controller (also with its unique ID) interact. The wristband and/or the stationary controller may determine an entrance/exit opportunity responsive to determining that the interaction is greater than a predetermined time period. More specifically, the wristband and/or the stationary controller may determine whether the opportunity is an entrance or exit opportunity based on timing. For example, responsive to determining that this interaction is less than a predetermined time (such as 30 seconds), the interaction may be determined to be an entrance. Responsive determining that this interaction is greater than a predetermined time (such as 30 seconds), the interaction may be determined to be an exit.

Alternatively, multiple controllers, such as depicted in FIG. 1D, may be used to determine whether a person is entering or exiting the patient area. In particular, one stationary controller, such as stationary controller 152 is positioned outside of the patient room and a second stationary controller, such as stationary controller 196, is positioned inside the patient room. In this way, stationary controller 152 may be tasked with monitoring wristband interaction in order to identify a person entering the room and stationary controller 196 may be tasked with monitoring wristband interaction in order to identify a person exiting the room. Further, the stationary controller network (e.g., such as a stationary controller positioned at respective patient rooms, or multiple stationary controllers positioned at respective patient rooms) may perform multiple tasks, such as monitoring a healthcare provider entering/exiting room, and also monitoring the trace of each provider.

In still an alternate implementation, one or more movements associated with entering or exiting the patient area may be detected. As discussed herein, such as with respect to FIG. 18A, one or more motion sensors may detect movement of a movable item, such as a door opening and/or a door closing. The door may move in one of several ways, such as swinging open/closed or sliding open/closed. In one implementation, the wristband may sense movements (such as using the accelerometer and/or gyroscope housed therein) in order for the wristband to analyze the sensed movement in order to determine whether a door has been opened or a door has been closed (e.g., swing open or swung closed; slid open or slid closed). In an alternate implementation, an electronic device, separate from the wristband and the stationary controller, may sense the movements and may determine whether the door has opened or closed. An example of this is illustrated in FIG. 16D (e.g., see proximity sensing and output generating device 1680 on the front door). In this regard, responsive to the one or more motion sensors sensing a door opening, the one or more motion sensors may transmit a communication (such as a near-field Bluetooth communication) indicative that a door opening has been sensed, which may be received by one or both of the wristband and the stationary controller. Responsive to receipt of the communication indicative that a door opening has been sensed, the wristband and/or the stationary controller may determine that the healthcare provider is entering the room. Conversely, responsive to the one or more motion sensors sensing a door closing, the one or more motion sensors may transmit a communication (such as a near-field Bluetooth communication) indicative that a door closing has been sensed, which may be received by one or both of the wristband and the stationary controller. Responsive to receipt of the communication indicative that a door closing has been sensed, the wristband and/or the stationary controller may determine that the healthcare provider is exiting the room. Alternatively, the separate electronic device may transmit the sensed movements in order for the wristband and/or stationary controller to make the determination.

Alternatively, in the instance where the door is on a spring (and automatically closes after opening), the one or more motion sensors (such as illustrated in FIG. 16D) may still output indications of door openings/closings (e.g., sensor outputs indicative of door opening closing in quick succession).

In the instance where a separate sensor (such as illustrated in FIG. 16D) detects the door opening/closing and transmits the indication of the door opening/closing, responsive to receipt of the communication indicative that a door has opened or closed, the wristband and/or the stationary controller may determine whether the indication is for an entrance or an exit. For example, responsive to the wristband determining that the indication of entrance/exit has not been received within 1 minute (meaning that the wristband has not received an indication within 1 minute of any opening/closing of a door), the wristband may determine that the healthcare provider is entering the room. Conversely, responsive to the wristband determining that the indication of entrance/exit has been received within 1 minute, the wristband may determine that the healthcare provider is exiting the room.

FIG. 2 is a fourth example block diagram of a HH and/or PPE system 200, with a mobile wristband device 210 and a local stationary controller 230 communicating wirelessly 120 with one another. As shown, HH and/or PPE system 200 does not include a back-end server. Instead, all analytics discussed herein may be performed by one or both of the mobile wristband device 210 and the local stationary controller 230. Further, in one implementation, the mobile wristband device 210 and the local stationary controller 230 may communicate via near-field communication (e.g., Bluetooth, RFID, ZigBee, etc.), as discussed above.

Figure 3A:
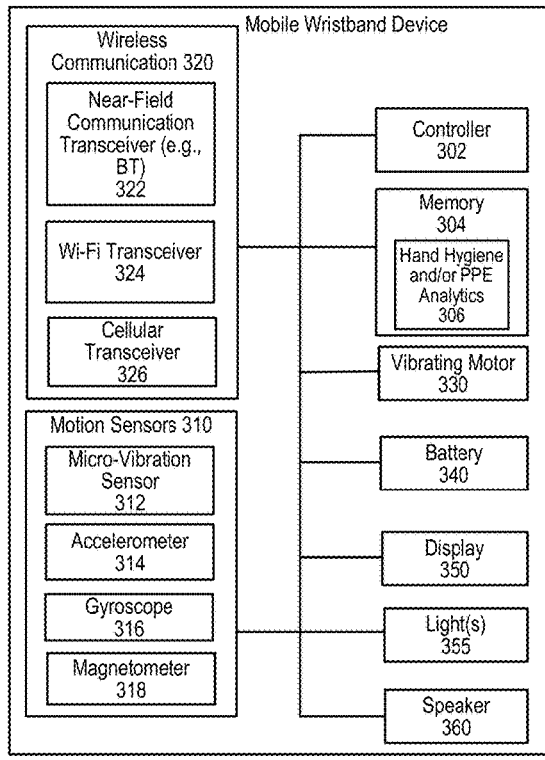
FIG. 3A is a first example block diagram of the mobile wristband device.

FIG. 3A is a first example block diagram of the mobile wristband device 300. As illustrated, the mobile wristband device 300 may include a controller 302, a memory 304, motion sensor(s) 310, wireless communication 320, vibrating motor 330, battery 340, display 350, light(s) 355, and speaker 360. The components illustrated in FIG. 3A may be housed in a mechanical structure that is configured to be attached to a wrist. For example, the mechanical structure may be in the form of a bangle or the like. In one implementation, all of the elements depicted in FIG. 3A are incorporated into the wristband. Alternatively, fewer than all of the elements depicted in FIG. 3A are incorporated into the wristband. For example, vibrating motor 330, display 350, light(s) 355, speaker 360, fewer than all of the motion sensors 310 and fewer than all of the wireless communication 320 need be included in the wristband.

Mobile wristband device 300 may be used in any one of FIG. 1A-D or 2. The controller 302 may comprise a microprocessor, a microcontroller/DSP, PLA, or the like. Further, the memory 304 may include software, such as hand hygiene and/or PPE analytics 306, and may include storage for storing data from motion sensor(s) 310. Thus, memory 304 may be configured for: (1) HH analytics; (2) PPE analytics; or (3) both HH and PPE analytics. FIG. 3A illustrates multiple motion sensors. In one implementation, a single motion sensor is used. Thus, in one implementation, mobile wristband device 300 includes only a single motion sensor, such as only accelerometer 314 or only gyroscope 316. Alternatively, multiple motion sensors may be used include any two, any three, or any four of the following: microvibration sensor 312, accelerometer 314, gyroscope 316, or magnetometer 318. In an alternative implementation, mobile wristband device 300 includes multiple sensors, such as both accelerometer 314 and gyroscope 316.

In addition, wristband device 300 includes wireless communication 320. In one implementation, a single wireless communication protocol is used. Alternatively, multiple wireless communication protocols may be used include any two, any three, or any four of the following: One or more near-field communication transceiver 308 may comprise functionality to communicate in any one, any combination, or all of the following: near field communication transceiver 322 (e.g., Bluetooth, RFID, and ZigBee); Wi-Fi transceiver 324; cellular transceiver 326; or other far-field communication.

In one implementation, mobile wristband device 300 is configured for low power consumption. Power dissipation of the mobile wristband device 300 may be dominated by one or more components: wireless communication 320; controller 302; motion sensor(s) 310 (including accelerometer 314 and gyroscope 316); vibrating motor 330; display 350; light(s) 355; or speaker 360. In order to reduce power consumption, low-power wireless protocols, such as Bluetooth Low Energy (BLE), RFID (HF/UHF) and ZigBee, may be used. Further, for minimum form factor and low power consumption in mobile applications, mobile wristband device 300 may comprise a system-on-chip (SOC) solution that integrates wireless transceiver and microcontrollers. For instance, DA14580 (Dialog Semiconductor) may be used as a BLE SOC chip developed for beacon, proximity, health and fitness (such as pedometer) applications, and may include a fully integrated BLE radio transceiver and baseband processor (ARM Cortex-M0). Further, the motion sensors may be operated in ultralow power mode and may be triggered into wake-up mode in one of several ways (e.g., by data generated from micro-vibration sensor 312 detecting movement of the mobile wristband device 300 and/or by receiving a communication from local stationary controller, discussed further below). In this regard, motion sensors 310 may include a 6-axis accelerometer/gyroscope combination device that features a configurable 200 μA operating current in normal mode with wake up and back to sleep functions.

Figure 3B:
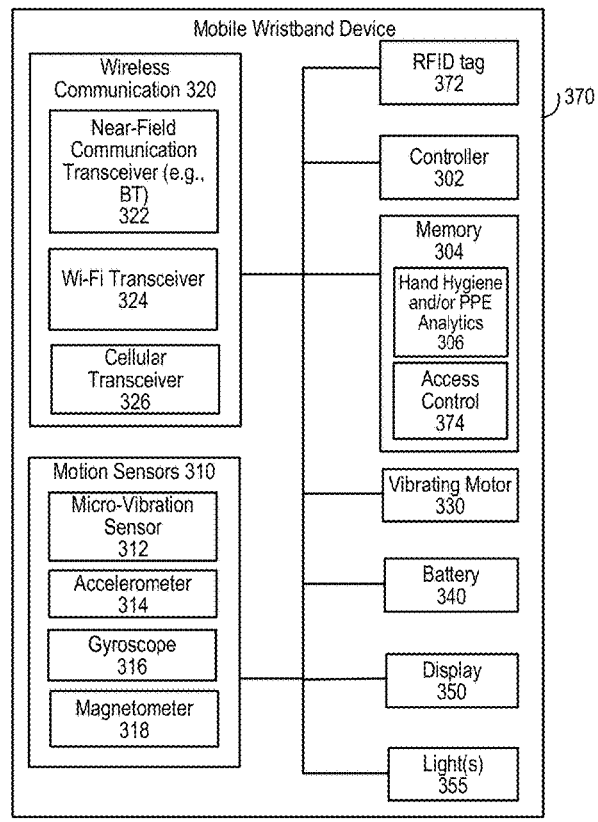
FIG. 3B is a second example block diagram of the mobile wristband device.

FIG. 3B is a second example block diagram of the mobile wristband device 370. Wristband device 370 has functionality similar to wristband device 300, with the additional functionality of access control. In particular, wristband device 370 may be used in combination with an RFID access control system and includes RFID tag 372. Further, wristband device 370 includes access control 374, which may be used to provide additional access control functionality to wristband device 370, as discussed further below.

Figure 3C:
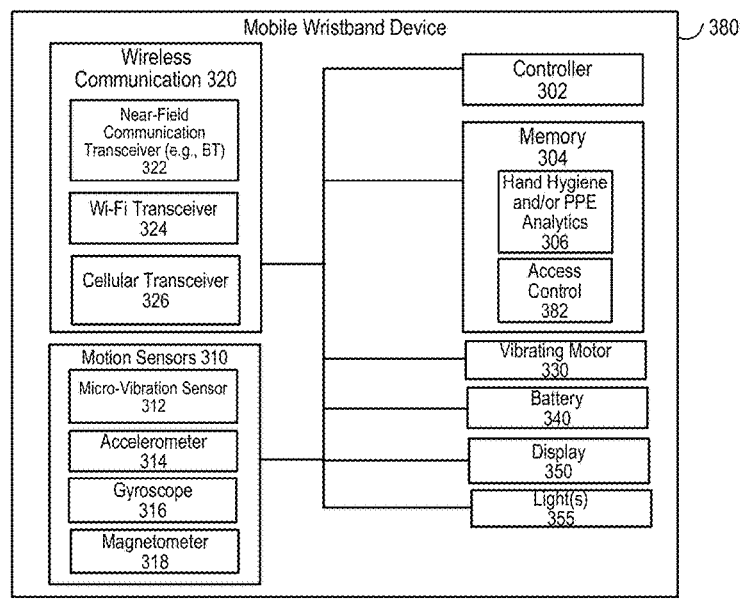
FIG. 3C is a third example block diagram of the mobile wristband device.

FIG. 3C is a third example block diagram of the mobile wristband device 380. Wristband device 380 has functionality similar to wristband device 300, with the additional functionality of access control. In particular, wristband device 380 may be used in combination with an access control system that uses a communication method included in wireless communication 320 (such as using near-field communication transceiver 322). In this regard, the identification code associated with the user of wristband 380 need not be stored in RFID tag 372, but may be stored in access control 382 (or other memory resident in wristband device 380). Further, wristband device 380 includes access control 382, which may be used to provide additional access control functionality to wristband device 380, as discussed further below.

FIG. 4A is a first example block diagram of local stationary controller 400. As illustrated, local stationary controller 400 may include a controller 402, a memory 404, one or more communication protocols, such as near-field communication transceiver 308, and a far-field communication transceiver (such as Wi-Fi transceiver 408 or cellular transceiver (not shown), proximity sensor 410, sound sensor 412, speaker 414, light(s) 416, and display 418. In one implementation, all of the elements depicted in FIG. 4A are incorporated into the stationary controller. Alternatively, fewer than all of the elements depicted in FIG. 4A are incorporated into the wristband. For example, proximity sensor 410, sound sensor 412, speaker 414, light(s) 416, display 418 need be included in the stationary controller.

Local stationary controller 400 may be used in any one of FIG. 1A-D or 2. The controller 402 may comprise a microprocessor, a microcontroller/DSP, PLA, or the like. Further, the memory 404 may include software, such as analytics 406 (e.g., HH analytics, PPE analytics, or HH and PPE analytics). As discussed above, analytics of the motion sensor data may be performed by the mobile wristband device and/or by the local stationary controller. Further, near-field communication transceiver 308 may be used to communicate via one or more near-field protocols with mobile wristband device. As discussed above, examples of near-field communication protocols include, but are not limited to Bluetooth, RFID, and ZigBee. Other near-field communication protocols are contemplated. Further, local stationary controller 400 may communicate with a back-end server, such as back-end server 130 or cloud computing E.

As discussed further below, in one implementation, stationary controller 400 may sense the proximity of the user (such as the healthcare provider). In a specific implementation, stationary controller 400 may sense the proximity of the wristband worn by the user. Proximity sensor 410 is a representation of the functionality to sense the proximity of the wristband worn by the user. As discussed herein, stationary controller 400 may sense a communication signal, such as a received signal strength indicator (RSSI) signal, which is an example of sensing the proximity of an electronic device. The stationary controller 400, via proximity sensor 410 or the like, may sense the RSSI signal of the wristband at being greater than a predetermined amount or strength (e.g., indicating that the wristband is within 1 meter, within 2 meters, within 3 meters, etc.) for at least a predetermined amount of time (e.g., at least 1 second, at least 2 seconds, at least 3 seconds, etc.) in order to determine whether the wristband is proximate to the stationary controller 400.

Further, as discussed below, sound sensor 412 may be used in order to sense sounds, such as sounds generated by dispenser 151 or sounds generated by user. Speaker 414, light(s) 416, and display 418 may be used as means for output of information to the user.

FIG. 4B is a second example block diagram of the local stationary controller 430. Stationary controller 430 is similar to stationary controller 400, with the addition of access control 434. As discussed further below, access control may comprise additional functionality that may be performed by stationary controller 430, such as illustrated in FIGS. 5A-J.

Further, as discussed above, the wristband and stationary controller may interact with one another during various times of a HH and/or PPE event and/or a HH and/or PPE opportunity. As discussed further below with regard to the flow charts, the following may comprise a sequence of interaction that includes any one, any combination, or all of: (1) proximity sensing of the stationary controller relative to and wristband or vice-versa in order to identify a HH and/or PPE opportunity; (2) generation of output on one or both of the stationary controller or the wristband to indicate the HH and/or PPE opportunity; (3) sensing whether hand cleaning agent has been dispensed (e.g., the stationary controller reviewing audio sensor data to determine whether the motor on the dispenser has dispensed the hand cleaning agent); (4) waking up part of the wristband responsive to determining that the hand cleaning agent has been dispensed (e.g., stationary controller sends a signal to wake-up the microcontroller and/or the accelerometer and/or gyroscope); (5) the awakened motion sensors generate sensor data; (6) the sensor data is analyzed to determine whether certain hand motions, indicative of sufficient hand hygiene, are detected in order to determine whether there is compliance with hand hygiene protocols; and (7) the sensor data is analyzed to determine whether certain hand motions, indicative of putting on or removing PPE garment(s), are detected in order to determine whether there is compliance with PPE protocols.

Figure 6A:
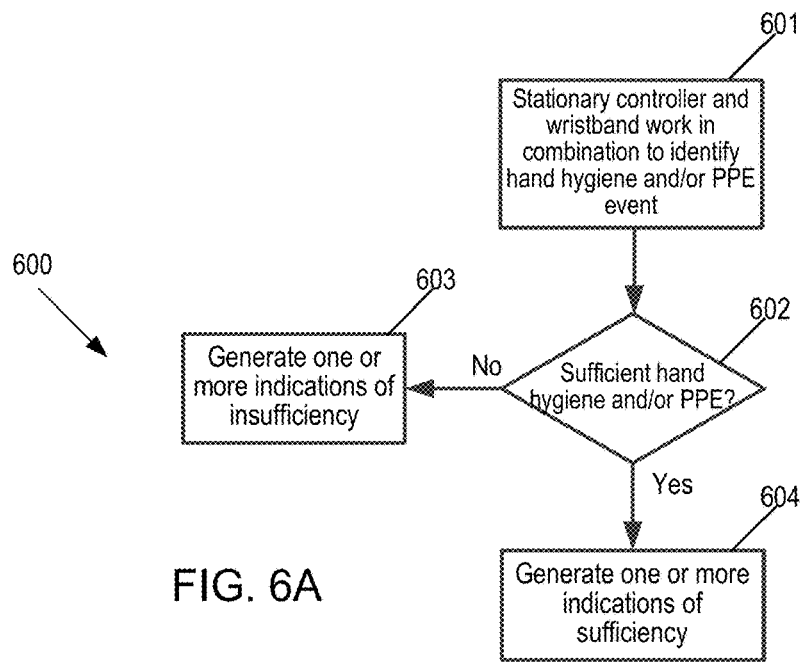
FIG. 6A illustrates a first flow chart of operation of the hand hygiene and/or PPE system.

FIG. 6A illustrates a first flow chart 600 of operation of the HH and/or PPE system. At 601, the stationary controller and the wristband work in combination in order to identify a HH and/or PPE event. As discussed above, the stationary controller and the wristband may work in combination in one of several ways. In one way, the stationary controller may sense the presence of the wristband (e.g., via the RSSI signal). In another way, the wristband may sense the presence of the stationary controller. Responsive to identifying the hand hygiene and/or PPE opportunity, one or both of the wristband or the stationary controller may determine whether sufficient hand hygiene was performed and/or sufficient PPE movement(s) were performed. As discussed above, there may be various metrics to determine whether there has been sufficient hand hygiene, such as whether hand cleaning agent has been dispensed, whether the user has performed hand rubbing motions, whether the user has performed hand rubbing motions for a predetermined amount of time, whether the user has performed a plurality of predetermined hand rubbing motions, whether the user has performed a plurality of predetermined hand rubbing motions each for a respective predetermined period of time, etc. Alternatively, or in addition, there may be various metrics to determine whether PPE protocols has been sufficient complied with. Responsive to determining that there was sufficient hand hygiene and/or sufficient PPE compliance, at 604, one or both of the stationary controller or the wristband may generate one or more indications of sufficiency. Responsive to determining that there was insufficient HH and/or PPE compliance, at 603, one or both of the stationary controller or the wristband may generate one or more indications of insufficiency. In one implementation, responsive to determining that there is sufficient HH and/or PPE compliance, no output is generated, but responsive to determining that there is insufficient HH and/or PPE compliance, an output is generated. Conversely, in another implementation, responsive to determining that there is insufficient HH and/or PPE compliance, no output is generated, but responsive to determining that there is sufficient hand hygiene and/or PPE compliance, an output is generated. In still another implementation, responsive to both sufficient and insufficient HH and/or PPE determination, outputs are generated, as shown in FIG. 6A.

Figure 6B:
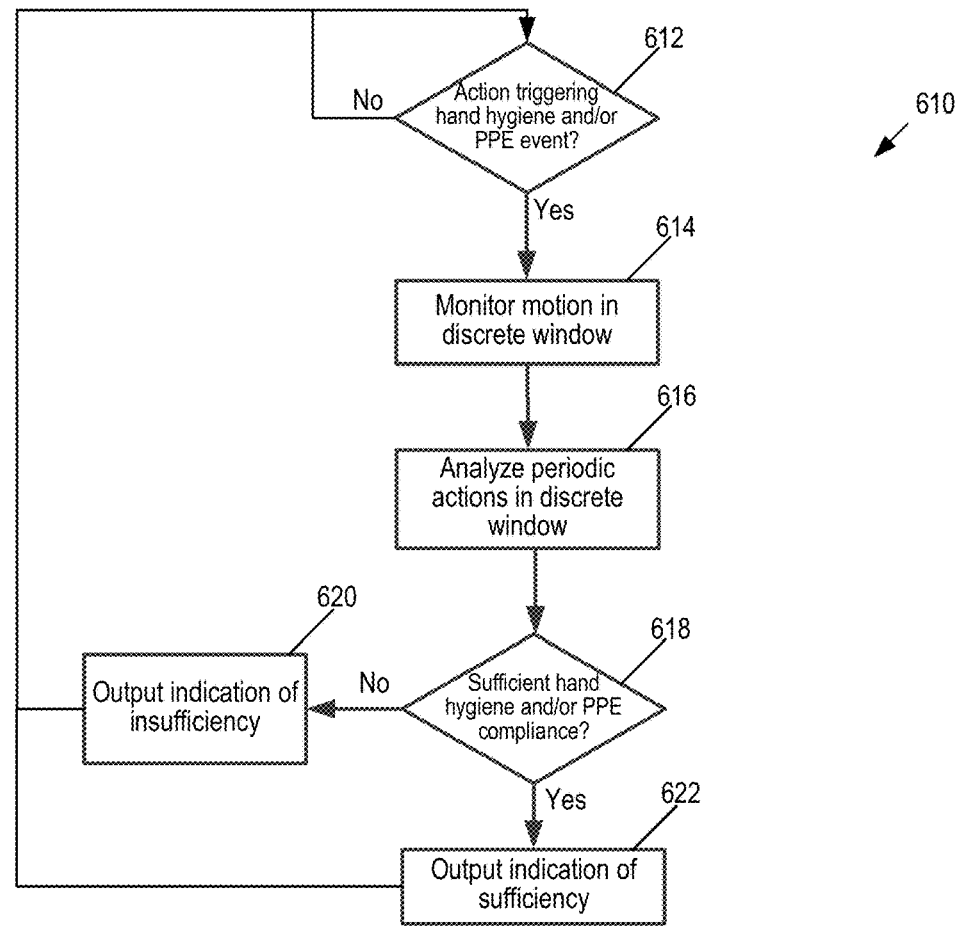
FIG. 6B illustrates a second flow chart of operation of the hand hygiene and/or PPE system.

FIG. 6B illustrates a second flow chart 610 of operation of the HH and/or PPE system. At 612, it is determined whether an action has occurred which triggered the HH and/or PPE event. As discussed above, in one or some embodiments, one or more actions may trigger the HH and/or PPE event, such as proximity to a dispenser, entrance into a room, or the like. Alternatively, other actions, such as an action as part of the HH and/or PPE event, may trigger the event, such as the dispensing of hand cleaning agent. In such embodiments, other actions, such as entrance into the room or the like, may be identified as opportunities to interact with the patient.

Regardless, if so, at 614, motion is monitored within a discrete window. As discussed above, in one implementation, the motion may be monitored responsive to an indication of a HH and/or PPE event. In this implementation, the monitoring may take place only responsive to the indication of the HH and/or PPE event. At 616, periodic actions are analyzed in the discrete window. Again, as discussed above, there may be periodic actions, within the discrete window, that are directed to HH and/or PPE and other periodic actions (such as arm swinging). In this regard, the analysis may differentiate between the different periodic actions in order to focus on HH periodic actions and/or PPE periodic actions.

At 618, it is determined whether, based on the analysis of the periodic action, there is sufficient HH or sufficient compliance with PPE. If so, at 622, an output may be generated that is indicative of sufficiency of HH and/or PPE. If not, at 620, an output may be generated that is indicative of insufficiency of HH and/or PPE.

Figure 6C:
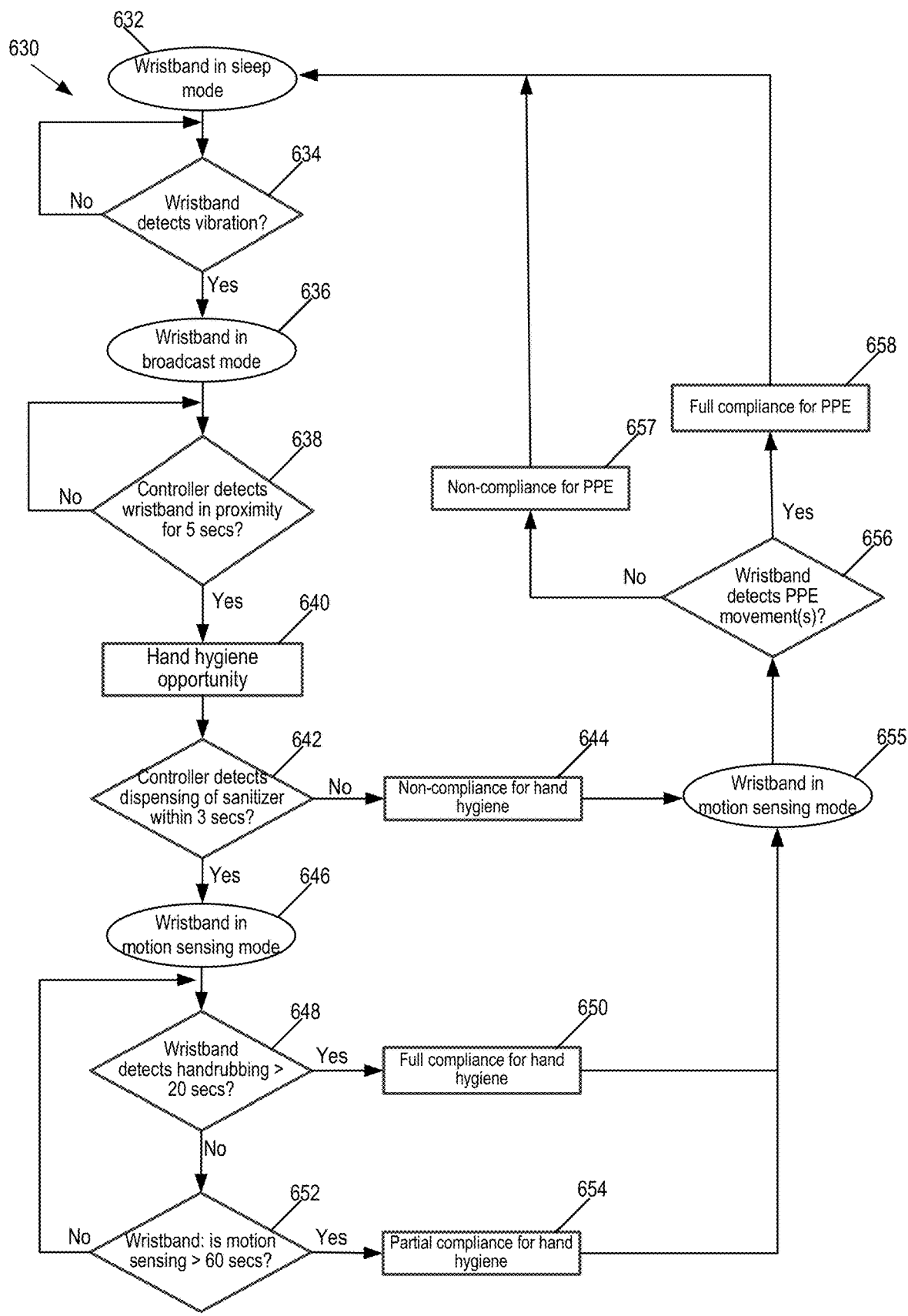
FIG. 6C illustrates a third flow chart of operation of the hand hygiene and PPE system.

FIG. 6C illustrates a third flow chart 630 of operation of the HH and PPE system upon entry of a patient area. At 632, the wristband is in sleep mode. As discussed above, various circuits within the wristband may be turned off or in low power mode when the wristband is in sleep mode. At 634, the wristband may detect a vibration, such as via the micro-vibration sensor. In one implementation, even in sleep mode, the micro-vibration sensor remains active. If vibration is detected, at 636, the wristband may transition to broadcast mode. As one example, the wristband may activate one or more of the wireless communication transceivers, such as near-field communication transceiver 322.

For example, when the micro-vibration sensor detects a small movement, the wristband enters broadcast mode and sends Bluetooth low energy beacon continuously until the wristband connects to a stationary controller. The stationary controller may beep to remind the healthcare worker wearing the wristband of HH (and/or PPE) when its received signal strength indicator (RSSI) from the wristband is over the preset threshold over a preset amount of time. After the stationary controller detects a dispensing sound, the wristband enters motion sensing mode. Motion detection may be active for only 1 minute to reduce power consumption and false detections caused by interfering motions. If no dispensing event is detected by the stationary controller, there will be real-time intervention on the wristband (e.g., vibration) and controller (e.g., voice prompt) with notification "non-compliance" sent to the server.

In this way, at 638, the stationary controller may determine, such as via the RSSI signal, whether the wristband is in proximity for a certain amount of time (e.g., 5 seconds). If so, at 640, it is determined that there is a hand hygiene opportunity.

At 642, the controller determines whether it has detected dispensing of sanitizer within a predetermined amount of time (e.g., 3 seconds) since the HH opportunity determination. As discussed above, the stationary controller may determine whether sanitizer has been dispensed in one of several ways, such as via a sound sensor, via integration with the motor on the stationary controller, or the like. Alternatively, the wristband may determine whether the sanitizer has been dispensed, such as via a sound sensor resident on the wristband. If it is determined that no sanitizer has been dispensed, at 644, it is determined that there is non-compliance for hand hygiene. This determination may be made by the stationary controller and/or the wristband. For example, in response to the wristband making the non-compliance determination, the wristband may send a communication to another electronic device, such as the stationary controller, with the communication indicating the non-compliance (e.g., a field in the communication=0 for non-compliance). Further, in one implementation, non-compliance may be indicative that no sanitizer was even used during the hand hygiene opportunity.

If it is determined that sanitizer has been dispensed, at 646, the wristband may be changed to motion sensing mode. In one implementation, the stationary controller may determine that the sanitizer has been dispensed and then send a signal to the wristband to change its mode to motion sensing mode (e.g., to activate the accelerometer and/or gyroscope and/or magnetometer). In another implementation, the wristband may determine that the sanitizer has been dispensed and then change its mode to motion sensing mode.

At 648, the wristband determines whether it has detected hand rubbing for at least 20 seconds. As discussed above, various analytics on the wristband or on the stationary controller may be used to determine whether there is hand hygiene compliance, one of which is duration of the hand rubbing. If the wristband detects hand rubbing for at least 20 seconds, at 650, the wristband determines that there is full compliance of hand hygiene. In response to this determination, the wristband may send a communication to another electronic device, such as the stationary controller and/or the back end server, with the communication indicating the hand hygiene compliance (e.g., X=1 for compliance). If the wristband does not detect hand rubbing for at least 20 seconds, at 652, the wristband determines whether 60 seconds has elapsed since the wristband is in motion sensing mode. If not, flow chart 630 loops back to 648. If so, at 654, the wristband determines that there is partial compliance of hand hygiene (e.g., sanitizer was taken but the hand rubbing motion was insufficient, such as the hand rubbing motion was not for a long enough time or was not according to the predetermined hand movements). In this regard, the user has a 60 second window in which to be compliant with the hand hygiene guidelines.

After which, at 655, the wristband is in motion sensing mode for PPE analysis. In one implementation, the wristband stays in the motion sensing mode as in 646. Alternatively, the wristband changes its motion sensing mode to sense PPE movements. At 656, the wristband determines whether it detects the PPE movement(s). As discussed above, one or more PPE garment(s) may be required to be worn upon entry into a patient area. In this regard, multiple PPE movements may be detected indicative of putting on a single PPE garment or indicative of putting on multiple PPE garments. Regardless, the wristband may determine whether the requisite PPE movement(s) are detected to determine whether there is PPE compliance. If the wristband does not detect hand rubbing indicative of the PPE movement(s), at 657, the wristband determines that there is non-compliance with PPE. In response to this determination, the wristband may send a communication to another electronic device, such as the stationary controller and/or the back end server, with the communication indicating the PPE non-compliance. Conversely, if the wristband does detect hand rubbing indicative of the PPE movement(s), at 658, the wristband determines that there is compliance with PPE. In response to this determination, the wristband may send a communication to another electronic device, such as the stationary controller and/or the back end server, with the communication indicating the PPE compliance. In the instance that there are multiple PPE garments to put on and in the instance that the wristband determines that the movements comply with putting on one of the PPE garments but not putting on a remainder of the PPE garments, the wristband may determine that there is partial compliance for PPE.

Figure 6D:
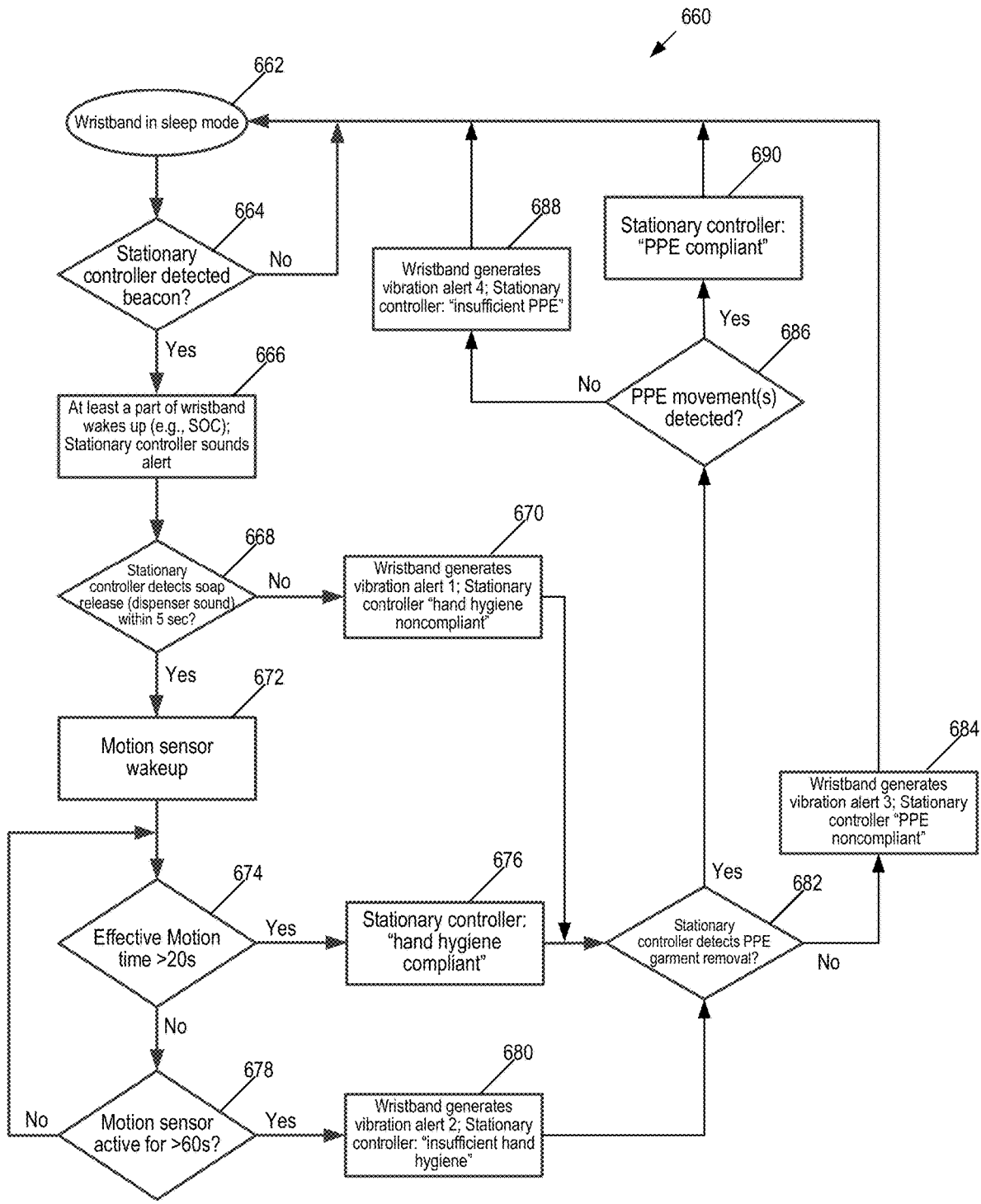
FIG. 6D illustrates a fourth flow chart of operation of the hand hygiene and PPE system.
Figure 6E:
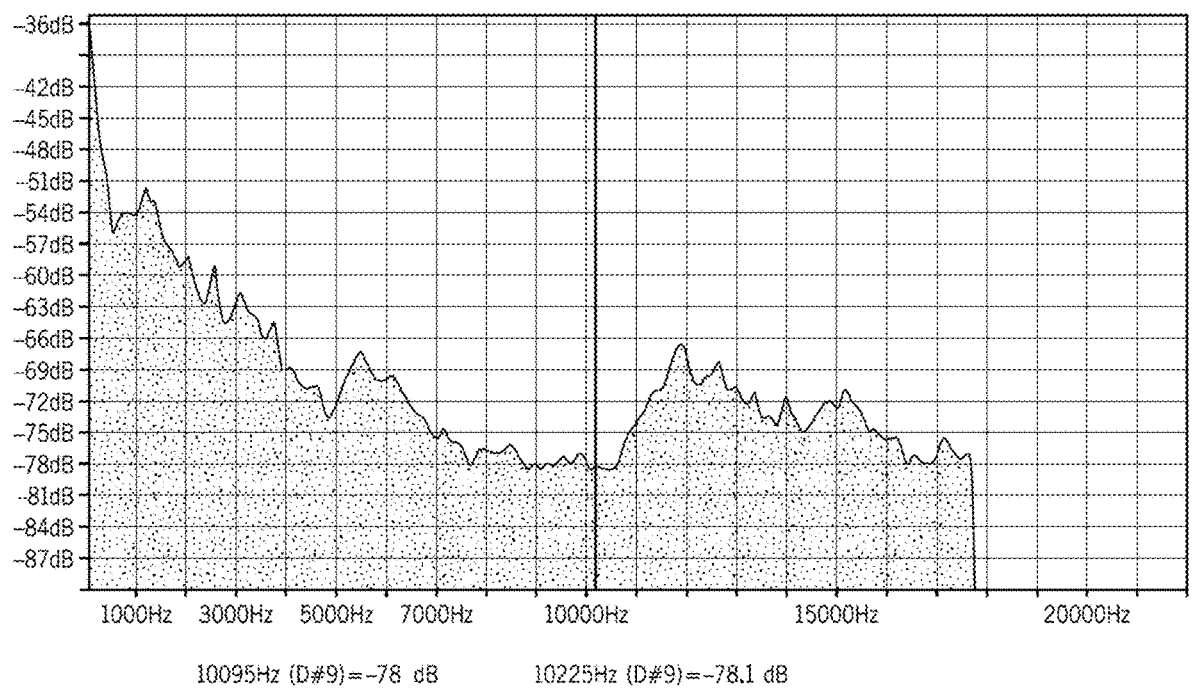
FIG. 6E is a graph of the background sound without dispensing in frequency domain analysis.
Figure 6F:
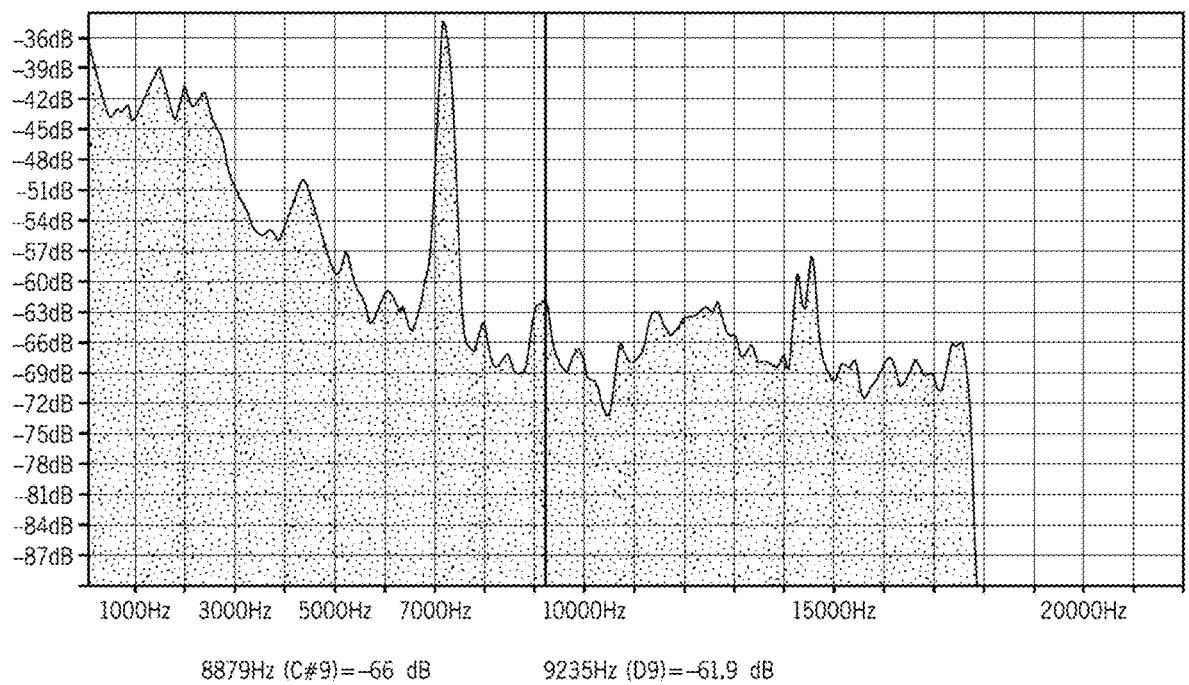
FIG. 6F is a graph of the dispensing sound in frequency domain analysis.

FIG. 6D illustrates a fourth flow chart 660 of operation of the hand hygiene and PPE system. At 662, the wristband is in sleep mode. At 664, the stationary controller determines whether it has detected a beacon from the wristband. As discussed above, one of the stationary controller or the wristband may generate a beacon. The other of the stationary controller or the wristband may sense the beacon to identify a hand hygiene opportunity. As shown in FIG. 6D, the stationary controller detects a beacon generated by the wristband to identify a hand hygiene opportunity. At 666, at least a part of the wristband is woken up, such as the system-on-a-chip. Further, the stationary controller may generate an output (e.g., sound an alert) indicative to the healthcare provider to obtain hand cleaning solution from the dispenser (e.g., output an audio message: "take sanitizer from the dispenser").

At 668, the stationary controller determines whether it has detected the release of the hand cleaning solution (e.g., soap) within a period of time (e.g., 5 seconds). As discussed above, the stationary controller may monitor one or more operations associated with the dispenser, such as the sound associated with the dispensing of the hand cleaning solution. In that regard, the stationary controller may include a sound sensor in order to monitor the sounds generated by the dispenser to determine whether the dispenser has dispensed the hand cleaning solution within the allotted time. If not, at 670, the stationary controller may send a command to the wristband to generate an output, such as a vibration output and/or an aural output (e.g., "please take sanitizer from the dispenser") on the wristband. Alternatively, the stationary controller may generate an output itself. Thus, in one implementation as illustrated in FIG. 6D, a hand hygiene event/opportunity only starts when the stationary controller detects the following two events in sequence: 1) a healthcare provider is approaching the stationary controller (indicating a HH opportunity) which may be installed next to the dispenser located at ICU/ward entrance or the like; and 2) a dispensing event indicating the healthcare provider has taken sanitizer (indicating a HH event). These two functions may be achieved by Bluetooth proximity sensing and detection/analysis of dispenser sound respectively.

If so, at 672, the wristband may wakeup the motion sensor(s) and record motion sensor(s) data. At 674, it is determined, based on analysis of the sensor(s) data, whether the effective motion time for hand movement is greater than 20 seconds. This determination may be performed either by the wristband or by the stationary controller. As discussed above, the user may start/stop the hand rubbing motion. In that regard, the wristband may use a counter in order to determine whether the effective total time of the hand rubbing motion is at least 20 seconds. If so, at 676, the stationary controller may determine that the hand hygiene is compliant. Alternatively, the wristband may determine compliance and transmit that determination to the stationary controller. If not, at 678, the wristband may determine whether the motion sensor, which was awakened at 672, has been active for 60 seconds. If not, the flow chart 660 loops back to 674. If so, at 680, the wristband generates vibration alert 2 (indicating that the user has not complied with hand hygiene). Further, the stationary controller may determine that the hand rubbing was insufficient for hand hygiene. Alternatively, the wristband may determine hand hygiene insufficiency and transmit that determination to the stationary controller. In one implementation, vibration alert 1 may be different from vibration alert 2. For example, vibration alert 1 may be louder or more forceful than vibration alert 2. Alternatively, vibration alert 1 may be the same as vibration alert 2.

As shown in FIG. 6D, there may be multiple alerts issued to the healthcare provider, such as the start of hand hygiene event and a conclusion of the hand hygiene event (e.g., the output of an indication of sufficiency and/or insufficiency of the hand hygiene. Further, the system may monitor the hand hygiene for compliance according to WHO guideline.

After which, at 680, the stationary controller (or other device associated with the PPE container(s)) may detect whether the PPE garment(s) have been removed. As discussed above, various PPE garments are contemplated, including masks, gowns, gloves, etc. One or more sensors may be proximate to the various containers of the PPE garments, such as a first sensor associated with the glove container (containing the gloves), a second sensor associated with the mask container (containing the masks), etc. Similar to determining whether the hand cleaning agent has been dispensed, the sensor(s) and electronics to process the sensor data may determine whether the PPE garment(s) have been dispensed (thereby detecting a PPE event). If not, at 684, the stationary controller may send a command to the wristband to generate an output, such as a vibration alert 3 and/or an aural output (e.g., "please take the mask"; "please take the gown"; etc.; which may be tailored to the PPE requirements for the specific patient area) on the wristband. Alternatively, the stationary controller may generate an output itself.

If so, at 686, it is determined, based on analysis of the sensor(s) data, whether the PPE movement(s) indicative of putting on the PPE garment(s) have been detected. This determination may be performed either by the wristband or by the stationary controller. If so, at 690, the stationary controller may determine that the PPE is compliant. Alternatively, the wristband may determine compliance and transmit that determination to the stationary controller. If not, the wristband may determine whether the motion sensor, which was awakened at 672, has been active for a certain period of time (e.g., 60 seconds). If not, the flow chart may loop back to 686 (not shown). If so, at 688, the wristband generates vibration alert 4 (indicating that the user has not complied with PPE and optionally outputting an aural output based on the PPE movement(s) not detected: e.g., "please put on your mask" (in the instance that the PPE protocol is to put on a mask and it is determined that the movement associated with putting on the mask is not detected). Further, the stationary controller may determine that the movement(s) were insufficient for PPE. Alternatively, the wristband may determine PPE insufficiency and transmit that determination to the stationary controller.

In addition, as shown in FIGS. 6C-D, the wristband may re-enter sleep mode responsive to one (or both) of a timeout or a determination of sufficiency and/or insufficiency of the hand motions complying with a standard.

Thus, in one design, the SOC may stay in extended sleep mode unless being woken up into "near field" active mode. For example, in the Bluetooth Low Energy (BLE) protocol, 3 ms is used for data transmission. Assuming 3 milliseconds for ARM computing, then during a 60-second hand hygiene event, the current consumption of the wristband SOC is only 3 mA-second and less than 12 mA-second for a KXG07 motion sensor. Assuming 100 hand hygiene events per healthcare provider per day, the total power consumption of the wristband is merely 0.42 mAh per day. Therefore, the wristband can last more than one year on a 200 mAh CR2032 coin battery. The calculation shows that with careful selection of low-power components and optimized power management, the wristband may have a longer battery life.

As discussed above, hand rubbing motions and/or putting on/taking off PPE garment motions may be difficult to differentiate from other types of motions or other noise factors. In this regard, it may be difficult to detect subtle hand rubbing motions and/or putting on/taking off PPE garment motions among interfering motions. In practice, when using an alcohol-based formulation, the healthcare provider may walk away from the dispenser and controller while rubbing hands. Therefore, walking and arm swinging are possible noise factors. Further, while putting on or taking off PPE garments, the healthcare provider may be walking to or away from the patient room. Likewise, door knocking may cause interference in determining hand rubbing motions.

As discussed herein, one or more sensors may be used to monitor the movement of the wristband. For example, one or both of a miniaturized accelerometer or a gyroscope may be used. The accelerometer may provide information on linear acceleration. The gyroscope may measure the angular velocity rate. In one specific implementation, a 3-axis accelerometer and a 3-axis gyroscope may be used. The accelerometer and gyroscope may sense a variety of movements, such as the hand rubbing movements and various interference movements (e.g., walking, arm swinging and door knocking).

Figure 7:
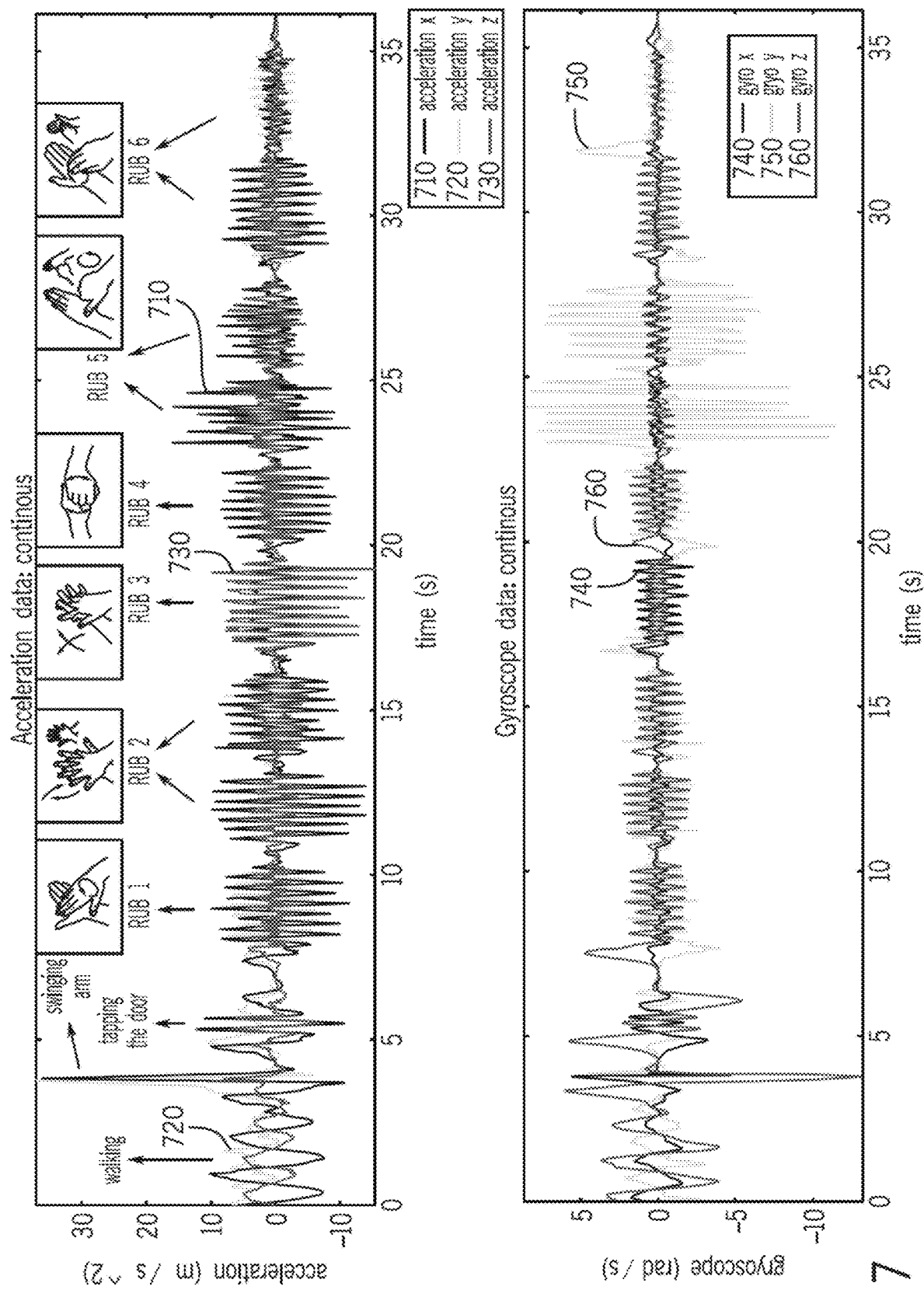
FIG. 7 illustrates graphs of accelerometer data (time versus linear acceleration) and gyroscope data (time versus angular acceleration).
Figure 21A:
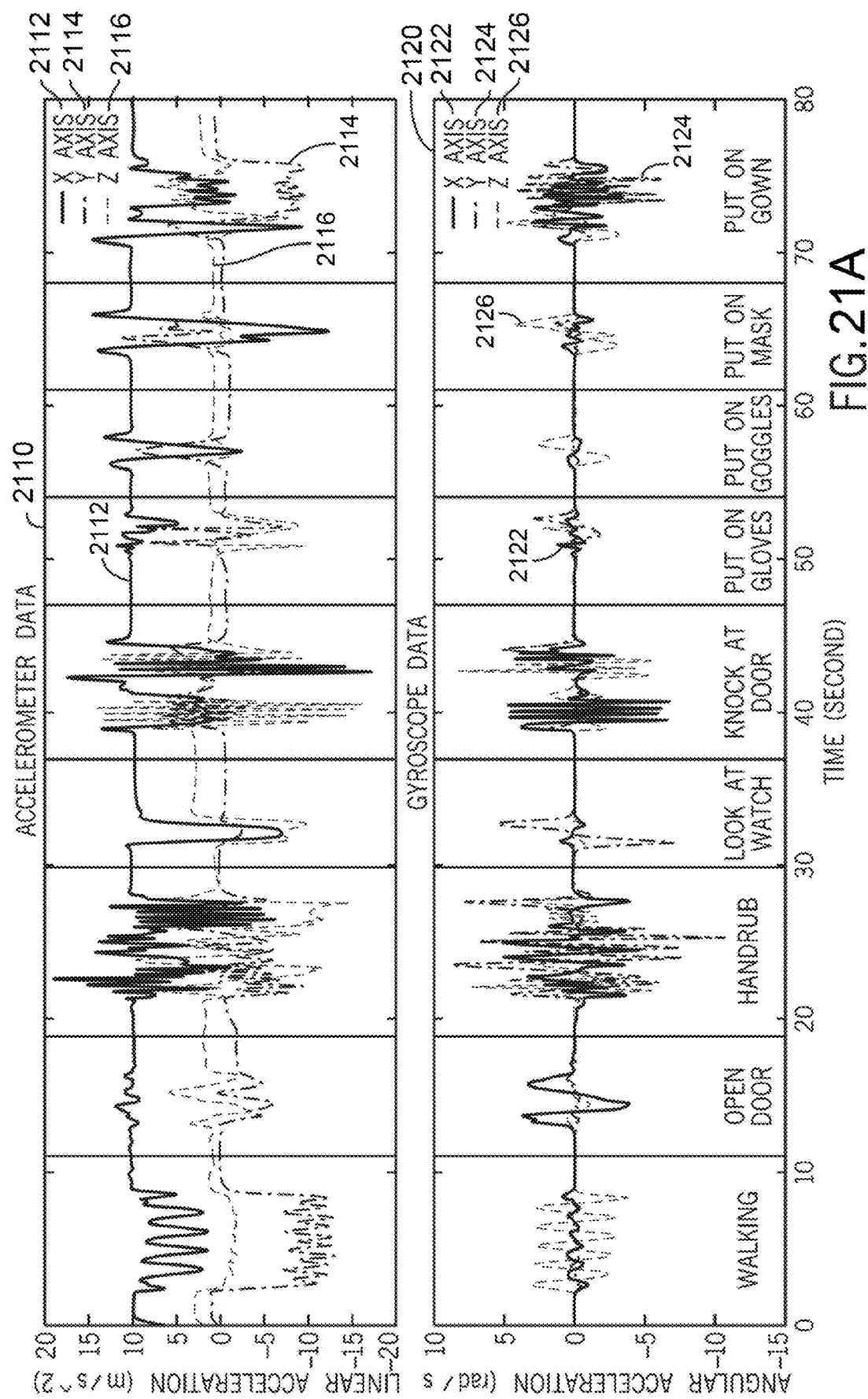
FIG. 21A are graphs of outputs of motion sensors, including an accelerometer and a gyroscope, for donning PPE motions and interfering motions measured by accelerometer (upper) and gyroscope (lower).

FIG. 7 illustrates graphs of accelerometer data (time versus linear acceleration) and gyroscope data (time versus angular acceleration). Motions tested include three possible interferences during a hand hygiene event and/or PPE event (walking, arm swinging and door knocking), followed by the six hand rub motions described in FIG. 10A. See also FIG. 21A, illustrating interfering motions and hand hygiene motions and PPE motions, as discussed further below. Each sensor has outputs on x (710 for accelerometer and 740 for gyroscope), y (720 for accelerometer and 750 for gyroscope) and z (730 for accelerometer and 760 for gyroscope) axis.

As illustrated in FIG. 7, the waveforms indicate: (1) the accelerometer responses to most of the rubbing motions are reasonably large. In many cases, their magnitude is larger or comparable to that of interferences; (2) most hand rubbing motions show large linear acceleration mainly on x- and y-axis. This is because when a person wears a wrist sensor, the x- and y-axis of the accelerometer are parallel to the wrist. Most hand rubbing motions in fact occurs parallel to the wrist; (3) while it is very challenging to distinguish all 6 hand rubbing motions from each other, several hand rubbing motions show their unique characteristics. For instance, rotational rubbing (Rub 5) is the only motion with large rotation rate along y-axis (pitch); rubbing palm to palm with finger interlaced (Rub 3) can be distinguished by its large acceleration along z axis; rubbing hands palm to palm (Rub 1) is a circle motion and therefore shows large acceleration in both x- and y-axis; (4) Hand rub motions in general have shorter periods than periodic noises such as walking and swinging arm. This may be an important property to differentiate the hand rub motions. In this way, the output from one motion sensor may be more indicative of one type of motion whereas another motion sensor may be indicative of another type of motion. Specifically, as illustrated above, the gyroscope output is much more indicative for the motion corresponding to Rub 5 than the accelerometer. For rub 3, the converse is true in that the accelerometer output is more indicative than the gyroscope output. In this regard, in one implementation, the wristband may examine both accelerometer data and gyroscope data in order to determine whether a rubbing motion is being performed. In an alternate implementation, for one or more of the hand rubbing motions, the wristband my use only the output from one motion sensor (and may alternate using the output from different motion sensors depending on the hand rubbing motion).

Figure 8:
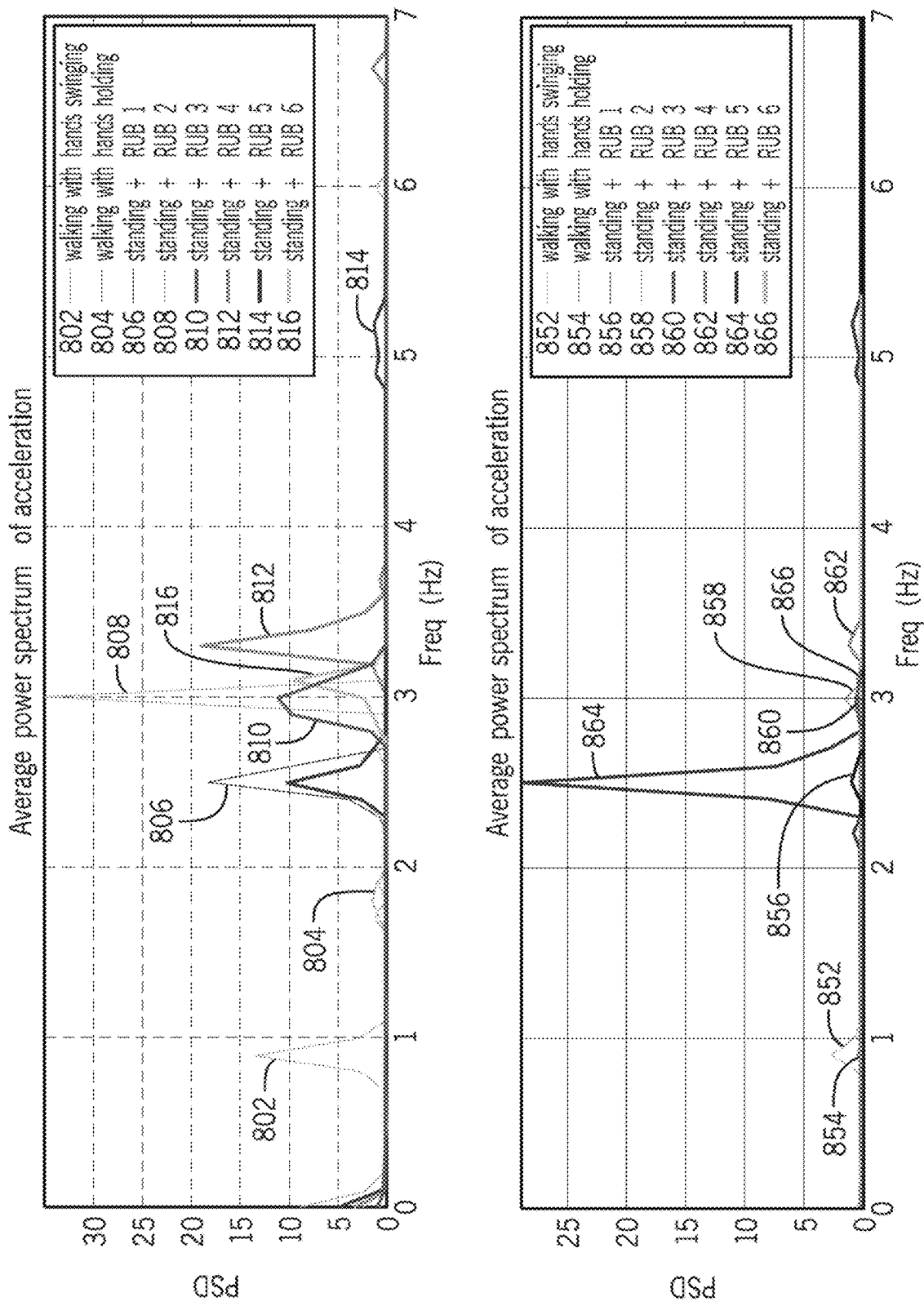
FIG. 8 illustrates graphs of average power spectrum of acceleration (frequency versus power spectrum density) and average power spectrum of rotation (frequency versus power spectrum density).

FIG. 8 illustrates graphs of average power spectrum of acceleration (frequency versus power spectrum density) and average power spectrum of rotation (frequency versus power spectrum density). Analysis of the PSD plot indicates that hand rubbing motions and walking have significantly different peak frequencies. In particular, all hand rubbing motions illustrated have their peak power occurring in the frequency range of 2.5-3.5 Hz, whereas the peak power for normal walking is less than 1 Hz. In this regard, a filter, such as a digital high-pass filter, may be used to attenuate the noise from walking and arm swinging.

As discussed above, the wristband may be configured for a low power mode. Thus, in one implementation, the wristband may have multiple operation modes, such as four operation modes including: sleep (e.g., only micro-vibration sensor 312 active); broadcast (e.g., near-field wireless communication transceiver 322 and controller 302 active); motion sensing (e.g., near-field wireless communication transceiver 322, controller 302, motion sensors (e.g., accelerometer 314 and/or gyroscope 316 and/or magnetometer 318 active); and motor vibration. In one implementation, an ultra-low-power micro-vibration sensor on the wristband is configured to detect if the wristband is static and, responsive to that detection, for the wristband to enter sleep mode. This power-saving mode applies when the wristband is not worn by providers. When the micro-vibration sensor detects micro-vibration, the wristband device may enter broadcast mode and may send Bluetooth-Low-Energy beacon every second until the wristband connects to a stationary controller. After a hand hygiene opportunity and/or PPE opportunity is detected, the wristband enters motion sensing mode and operates for 1 minute before going back to broadcast mode. During a non-compliant hand hygiene event, the wristband may generate a vibration alert that lasts for 1 second.

In one implementation, the average current dissipation is 2.4 µA (sleep), 11.8 µA (broadcast), 613 µA (motion sensing) and 25,400 µA (vibration), respectively. It is estimated that the regular usage time and calculated the power dissipation is assumed to be: (1) an average of 30 hand hygiene opportunities per healthcare provider during an 8-hour shift; and (2) 10 of the 30 hand hygiene opportunities are non-compliant so the motor vibration mode will take no more than 10 seconds per day. Therefore, average daily power consumption of the wristband is ~1800 mAs. A CR2032 coin battery has a capacity of 220 mAh or 792,000 mAs and will last more than one year on the wristband.

Figure 9:
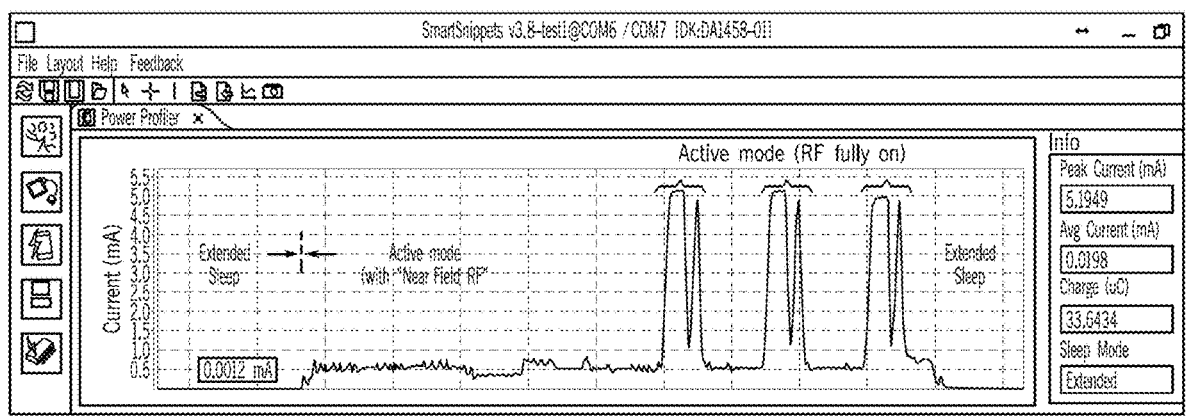
FIG. 9 illustrates a graph of time versus current, including showing in extended sleep mode, the system-on-a-chip (SOC) consumes 1.2 uA, while in full-speed active mode, the SOC current dissipation rises to about 0.45-0.7 mA ("near field RF mode") and 5.2 mA (RF fully on) respectively, with each grid on the x-axis (time) representing 1 milli-second.

FIG. 9 illustrates a graph of time versus current, including showing in extended sleep mode, the system-on-a-chip (SOC) consumes 1.2 µA, while in full-speed active mode, the SOC current dissipation rises to about 0.45-0.7 mA ("near field RF mode") and 5.2 mA (RF fully on) respectively, with each grid on the x-axis (time) representing 1 milli-second.

FIG. 10A illustrates a series of pictures which highlights the recommended hand hygiene techniques with alcohol-based formulation in World Health Organization (WHO) guidelines on hand hygiene in healthcare, with the duration of the hand hygiene motions (picture #2-7) recommended to last 20-30 seconds.

Figure 11:
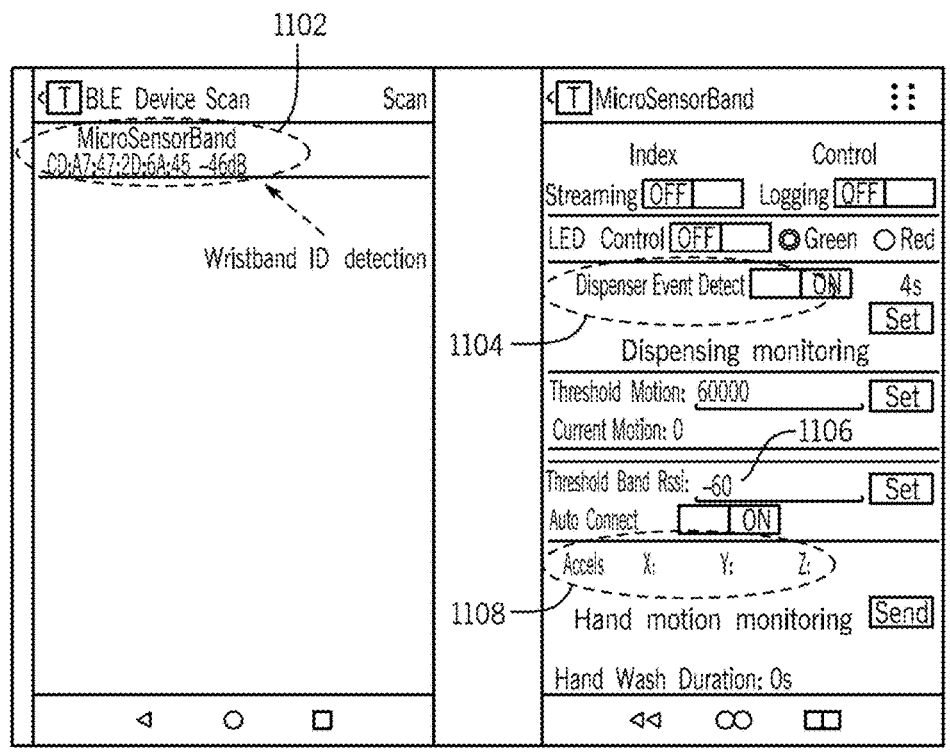
FIG. 11 illustrates a graphical user interface (GUI) for illustration of hand washing event monitoring shown on a stationary controller.

FIG. 11 illustrates a graphical user interface (GUI) for illustration of hand washing event monitoring on a stationary controller. Alternatively, or in addition, a similar GUI may be generated for illustrating PPE event monitoring. The controller detects a wristband device (MicroSensorBand in the example illustrated in FIG. 11) at its proximity by Bluetooth low-energy (BLE) scan (1102) with signal strength of −46 dB, which is higher than the detection threshold of −60 dB set by 1106. The stationary controller may be configurable to detect how long to wait for the dispensing of sanitizer (1104). As discussed above, at 642 or at 668, the stationary controller waits for 3 or 5 seconds, respectively, to determine whether sanitizer has been dispensed. The threshold RSSI signal (1106) may likewise be set at −60 dB. Finally, if a dispensing event is detected, the controller will start to collect hand motion data from the wristband (1108). All data may then be transmitted to a back-end server for analytics.

As discussed above, various analytics may be generated for various uses. In one use, the analytics may be used for notification of one or more parties, such as the healthcare worker who is the subject of the analytics, an infectious disease specialist, a hospital administrator (e.g., an administrator of nurses or doctors), or the like. In another use, the analytics may be used to track, such as in real time, transmission of pathogens or diseases amongst patients, from healthcare workers to patients, or the like.

In still another use, the analytics may be used to generate one or more graphical user interfaces (GUIs). With regard to GUIs, three components may be used, including a web interface, the background database (such as database 172), and the analytical and computational system (such as application server 162). The web interface allows the user to input the query information and displays the search results, the database stores the data collected by the data collection hardware, and the analytical and computational system implements data analysis and computation, and produces results to be shown on the web interface.

Figure 12A:
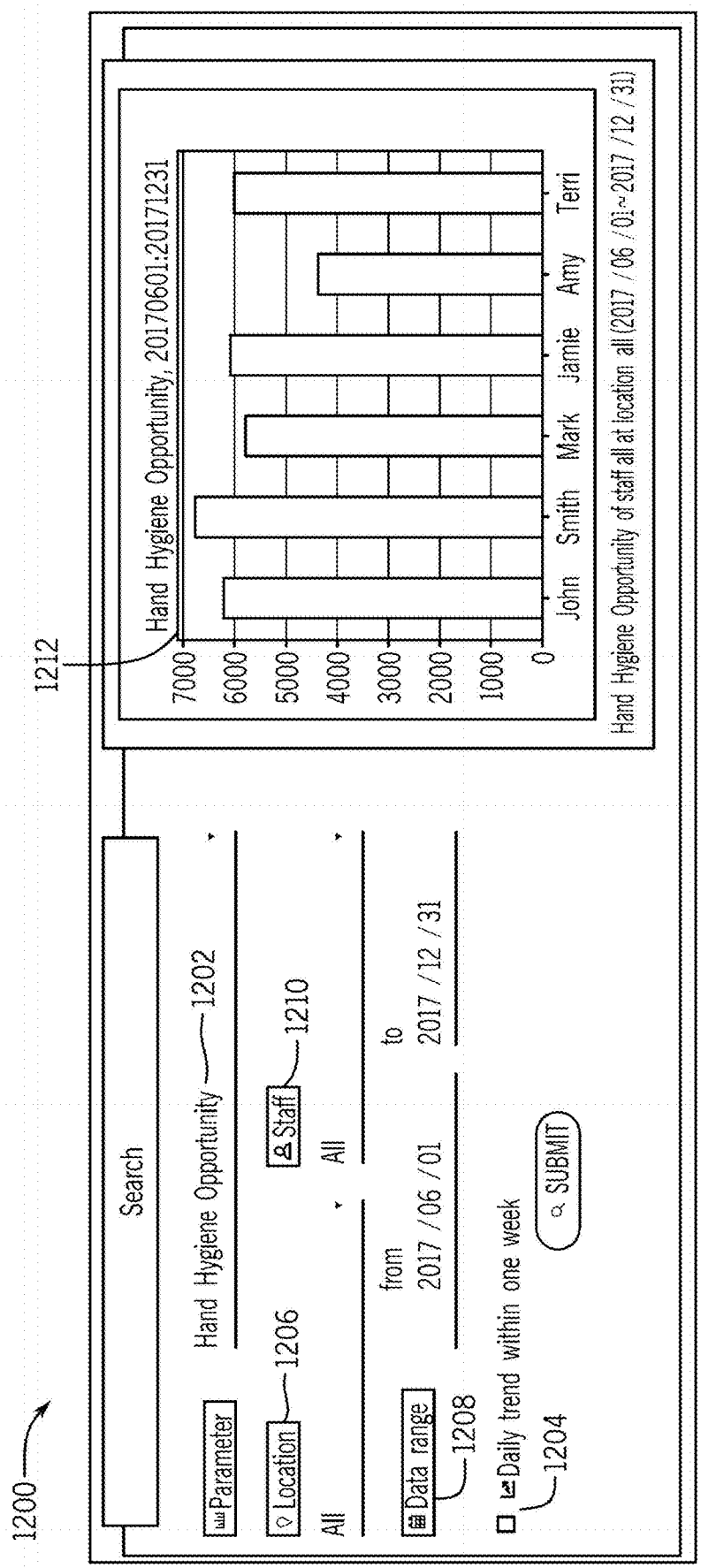
FIG. 12A illustrates a first GUI of a web interface for an electronic device to access the hand hygiene and/or PPE analytical and computational system in which one or more of the following may be selected: hand hygiene opportunity (and/or PPE opportunity); locations; staff; date range; and/or trend analyses.

FIG. 12A illustrates a first GUI 1200 of a web interface for an electronic device to access the hand hygiene and/or PPE analytical and computational system in which one or more of the following may be selected: hand hygiene opportunity 1202; locations 1206; staff 1210; date range 1208; and/or trend analyses 1204. Though FIGS. 12A-E do not illustrate PPE information, in one implementation, the hand hygiene information may be replaced with PPE information. Alternatively, the PPE information may be illustrated in conjunction with the hand hygiene information, such as illustrated in FIGS. 12A-E.

As one example, various types of hand hygiene opportunities may be listed including: non-compliant hand hygiene (e.g., instances of a non-compliant hand hygiene event); partial compliant hand hygiene; full compliant hand hygiene; non-compliant hand hygiene rate; partial compliant hand hygiene rate; and full compliant hand hygiene rate. Alternatively, or in addition, non-compliant PPE (e.g., instances of a non-compliant PPE event); partial compliant PPE; full compliant PPE; non-compliant PPE rate; partial compliant PPE rate; and full compliant PPE rate may be illustrated.

Various locations 1206 may be entered, such as all locations, ICU-A, ICU-B, or ICU-C (e.g., different intensive care units in a hospital). The listing of locations is merely for illustration purposes; other types of locations are contemplated. Likewise, various date ranges 1208 may be entered. Further, staff 1210 may be selected, such as various staff groupings including all staff, all nurses, or all doctors, or such as different individuals. A graph 1212 showing the output may be generated based on the input of hand hygiene opportunity 1202, locations 1206, staff 1210, date range 1208, and/or trend analyses 1204. Alternatively, or in addition, graphs may be generated based on the input of PPE opportunity, locations 1206, staff 1210, date range 1208, and/or trend analyses 1204.

In this regard, the back-end server may enable a search function that allows managers (e.g., ICU managers, department manager, infection control team) to analyze the compliance data and obtain detailed infection control compliance reports based on the selection of date, location (e.g., floor, unit and room), role (e.g. nurse, doctor, PSA, etc.) and individual provider. Such reports may be used by the hospital administrators to configure an incentive program to motivate trainees or provide feedback.

Figure 12B:
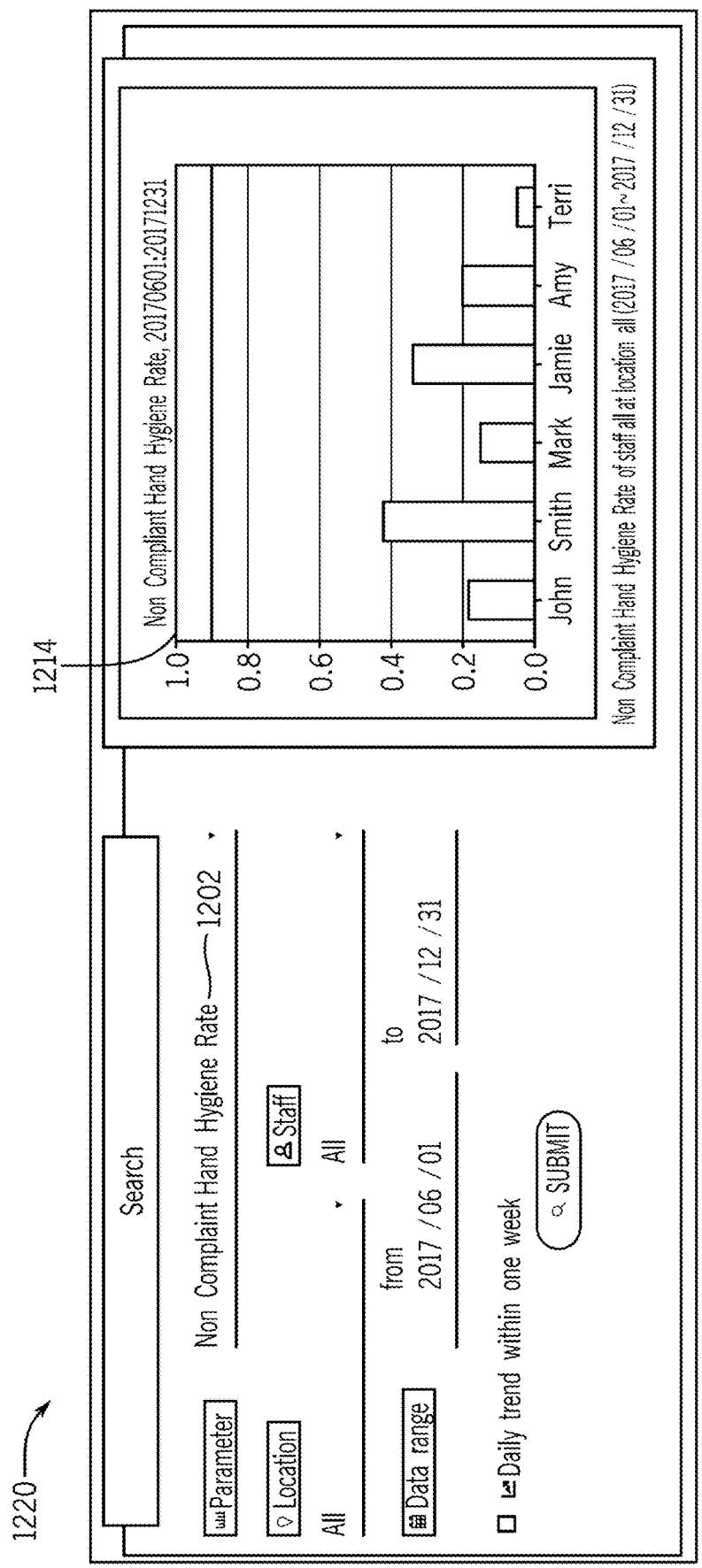
FIG. 12B illustrates a second GUI of a web interface for an electronic device to access the hand hygiene and/or PPE analytical and computational system in which the hand hygiene opportunity (and/or PPE opportunity) selected is non-compliant hand hygiene rate (and/or non-compliant PPE rate).

FIG. 12B illustrates a second GUI 1220 of a web interface for an electronic device to access the hand hygiene and/or PPE analytical and computational system in which the hand hygiene opportunity 1202 (and/or PPE opportunity) selected is non-compliant hand hygiene rate (and/or non-compliant PPE rate), with the associated graph 1214.

Figure 12C:
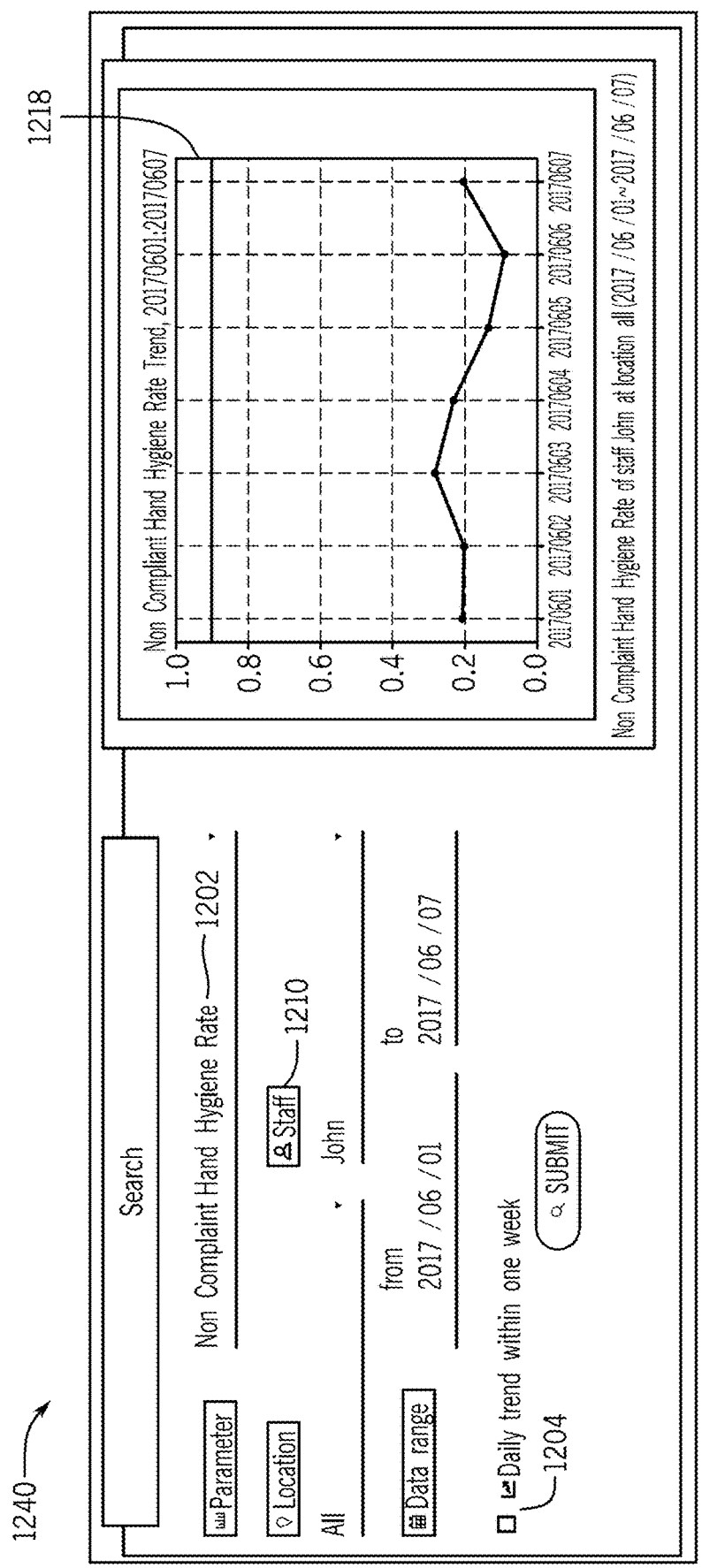
FIG. 12C illustrates a third GUI of a web interface for an electronic device to access the hand hygiene and/or PPE analytical and computational system in which the hand hygiene opportunity (and/or PPE opportunity) selected is non-compliant hand hygiene rate (and/or non-compliant PPE rate), the staff selected is John, and in which a daily trend is illustrated in an associated graph.

FIG. 12C illustrates a third GUI 1240 of a web interface for an electronic device to access the hand hygiene and/or PPE analytical and computational system in which the hand hygiene opportunity 1202 (and/or PPE opportunity) selected is non-compliant hand hygiene rate (and/or non-compliant PPE rate), the staff 1210 selected is John, and in which a daily trend 1204 is illustrated in associated graph 1218.

Figure 12D:
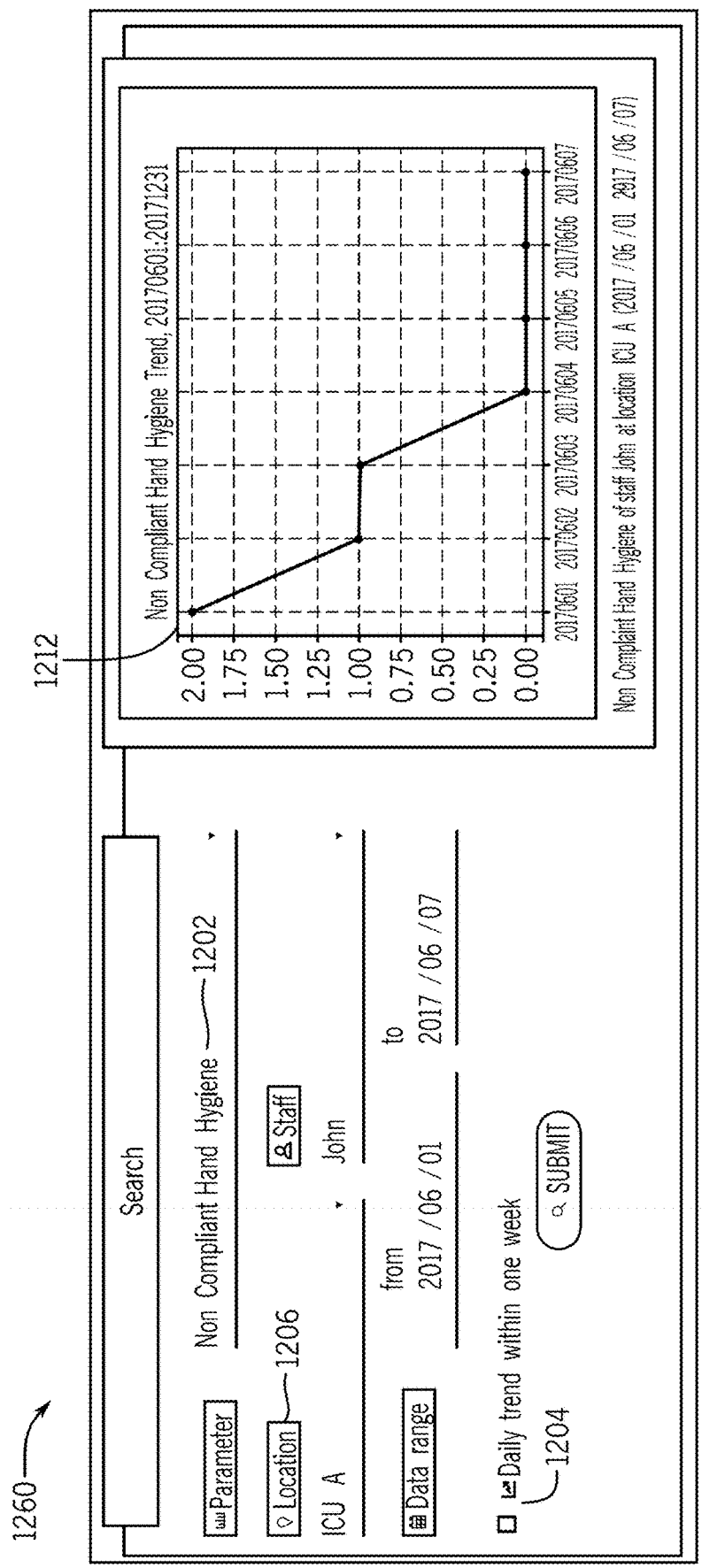
FIG. 12D illustrates a fourth GUI of a web interface for an electronic device to access the hand hygiene and/or PPE analytical and computational system in which the hand hygiene opportunity (and/or PPE opportunity) selected is non-compliant hand hygiene (and/or non-compliant PPE), the staff selected is John, the location is ICU-A, and in which a daily trend is illustrated in an associated graph.

FIG. 12D illustrates a fourth GUI 1260 of a web interface for an electronic device to access the hand hygiene and/or PPE analytical and computational system in which the hand hygiene opportunity 1202 (and/or PPE opportunity) selected is non-compliant hand hygiene (and/or non-compliant PPE), the staff 1210 selected is John, the location 1206 is ICU-A, and in which a daily trend 1204 in associated graph 1222.

As discussed above, responsive to partial compliance or non-compliance, one or more aspects of the system may change. For example, responsive to a single instance of partial compliance or non-compliance, the one or more aspects of the system may change. Alternatively, or in addition, responsive to identifying a pattern of partial compliance or non-compliance (e.g., for an individual or a group of people), the one or more aspects of the system may change. For example, dependent on the analysis of the hand hygiene data (e.g., whether the healthcare provider's non-compliance rate is below a predetermined rate; whether the healthcare provider's number of non-compliant hygiene events is above a predetermined number; whether the healthcare provider's partial-compliance rate is below a predetermined rate; whether the healthcare provider's number of partial-compliant hygiene events is above a predetermined number), the system may modify its operation in one or more aspects. In particular, if the system identifies that a healthcare provider is consistently not washing hands or using sanitizer or consistently not performing the proper hand movements, the system may modify its operation in the one or more aspects. Alternatively, or in addition, dependent on the analysis of the PPE data (e.g., whether the healthcare provider's non-compliance rate is below a predetermined rate; whether the healthcare provider's number of non-compliant PPE events is above a predetermined number; whether the healthcare provider's partial-compliance rate is below a predetermined rate; whether the healthcare provider's number of partial-compliant PPE events is above a predetermined number), the system may modify its operation in one or more aspects. In particular, if the system identifies that a healthcare provider is consistently not taking the PPE garment(s) or consistently not performing the proper hand movements to put on or take off the PPE garment(s) (e.g., not performing the movements in the proper sequence), the system may modify its operation in the one or more aspects. In still an alternate implementation, dependent on the analysis of the hand hygiene data and PPE data in combination, the system may modify its operation in one or more aspects. In particular, if based on the analysis of the data that the healthcare provider is not cleaning hands prior to putting on the PPE garment(s) and/or the healthcare provider is not cleaning hands after removing the PPE garment(s), the system may provide special notifications.

Example aspects include, but are not limited to: notification; analytics; and alerts. As discussed above, the healthcare provider may be notified of a hand hygiene event and/or a PPE event, such as via the wristband and/or the stationary controller. As another example, the healthcare provider may be notified of a failure to perform one aspect of the hygiene event (e.g., failure to take hand cleaning agent; failure to perform the proper hand motions; failure to perform the proper hand motions for a long enough time; etc.) and/or the PPE event (e.g., failure to take one or more PPE garments; failure to put on and/or remove the one or more PPE garments; failure to put on or take off the PPE garments in the proper sequence). Responsive to partial compliance or non-compliance, at least one aspect of the notification may be modified. In one implementation, the modification of notification may be the same responsive to a determination as to partial compliance and as to non-compliance. In an alternate implementation, the modification of notification may be different responsive to a determination as to partial compliance than to a determination as to non-compliance (e.g., non-compliance may comprise additional notifications or louder notifications than partial compliance). In one implementation, the type of notification may remain the same (e.g., a buzzing sound from the stationary controller; a vibration from the wristband); however, the intensity of the notification may change (e.g., a louder buzzing sound in response to a determination of previous partial compliance or non-compliance; a stronger vibration from the wristband in response to a determination of previous partial compliance or non-compliance). In another implementation, a different type of notification may be output. In a first specific implementation, the type of notification responsive to partial compliance or non-compliance may replace the previous notification (e.g., instead of a buzzing sound from the stationary controller, a light is output; instead of vibration from the wristband, an audible output is generated). For example, one metric for hand hygiene compliance is proper hand motions for 20 seconds. Responsive to determining partial compliance or non-compliance, a display on the wristband may display a 20 second countdown, indicating how much proper hand motions the healthcare provider needs to perform. As another example, one metric for PPE compliance is the proper sequence for putting on and taking off the PPE garments. Responsive to determining partial compliance or non-compliance (e.g., failure to put on or take off the PPE garments in the proper sequence), a display on the wristband may display the proper sequence of putting on or taking off the PPE garments. Alternatively, this mode (of displaying the 20 second countdown, which may account for stopping and restarting the proper hand motions or of displaying the proper sequence of putting on or taking off the PPE garments) may further be used when a healthcare provider is identified as a trainee (e.g., the wristband is programmed so that the user is identified as a "trainee"). In a second specific implementation, a new type of notification in addition to the standard notification is generated (e.g., a buzzing sound and a light are output from the stationary controller; a vibration and an audible output are generated by the wristband). Thus, in one implementation, the output may be personalized to the healthcare provider based on any one, any combination, or all of: status; hand hygiene performance; or PPE performance.

Another aspect comprises the analytics of hand hygiene and/or PPE compliance. In one implementation, responsive to partial compliance or non-compliance, the analytics performed on the wristband, the stationary controller, and/or the server may be modified (e.g., more stringent than typical hand hygiene and/or PPE compliance analysis). Still another aspect comprises alerts. As discussed above, various parties may be alerted as to partial compliance and/or non-compliance. As one example, the healthcare provider, subject to the partial compliance and/or non-compliance, may be notified. Alternatively, or in addition, a separate entity or person may be notified. For example, a hospital administrator tasked with overseeing hygiene and/or PPE compliance may be notified, such as responsive to any one, any combination or all of: a hand hygiene event with partial compliance or non-compliance; a non-compliance rate that is below a predetermined rate; a healthcare provider's number of non-compliant hygiene events being above a predetermined number; a healthcare provider's partial-compliance rate being below a predetermined rate; a healthcare provider's number of partial-compliant hygiene events being above a predetermined number; a PPE event with partial compliance or non-compliance; a PPE non-compliance rate that is below a predetermined rate; a healthcare provider's number of non-compliant PPE events being above a predetermined number; a healthcare provider's PPE partial-compliance rate being below a predetermined rate; a healthcare provider's number of partial-compliant PPE events being above a predetermined number.

In this way, detailed hand hygiene and/or PPE compliance reports (such as illustrated in FIGS. 12A-D) may be generated based on the selection of date, location (e.g., floor, unit and/or room), department and individual staff members. They may be available to hospital administrators and may be used to set up an incentive program to motivate healthcare providers. Infection control professionals and unit managers can use this information to identify issues and trends in terms of frequent compliance violators and time of shift variations so that policies and protocols may be revised accordingly. In this way, the analytics is designed to assist and encourage healthcare providers to improve their hand hygiene and/or PPE practices, thus reducing HAIs and costs to the healthcare system. Healthcare providers may login to their own account and compare their performance to colleagues' and be motivated through peer pressure and team competition. The analytics may track the infection source to help hospitals to contain further infections and evaluate the efficacy of any infection control initiatives.

Figure 12E:
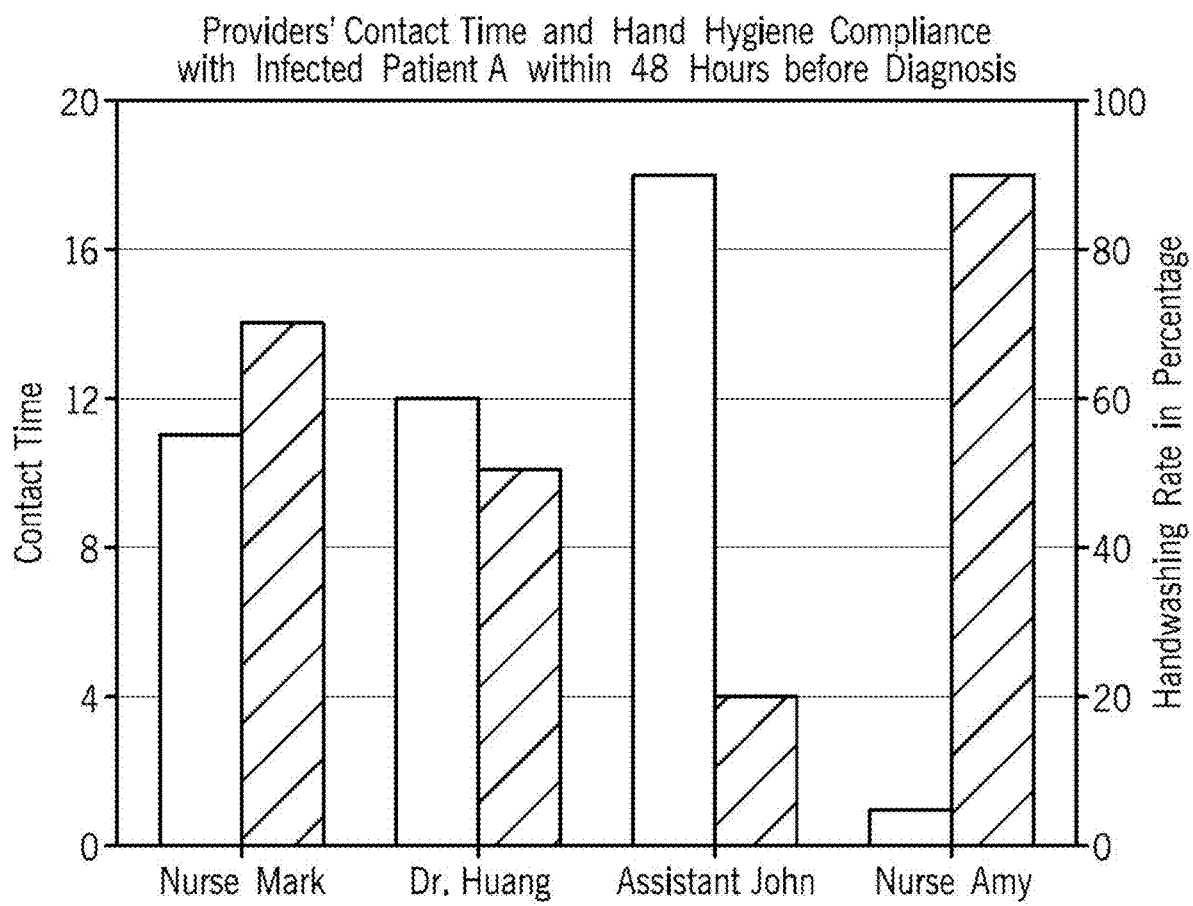
FIG. 12E is a graph of providers' contact time and hand hygiene compliance (and/or PPE compliance) with infected patient A within 48 hours before diagnosis.

As discussed above, one feature of the analytics may be configured to track infection associated hand hygiene information and/or PPE information. Thus, based on mining of data stored in the hand hygiene and/or PPE database and combining with other databases such as infection control data from the hospital, the analytics may be used by the hospital management team to formulate effective strategies against infections. In clinical care, it is very challenging, yet critical, to identify the source of infections in the hospital. Thus, in one implementation, the analytics is configured to track all information associated with a specific infection case. For instance, users may be able to specify the time window and infected patient's room location when searching from the enormous amount of hand hygiene and/or PPE data. This assists in identifying the provider that had the most contact with the infected patient and relatively low hand hygiene compliance rate and/or PPE compliance rate during the interested time period before diagnosis. Then, potential carriers for this infection may be identified by various statistical inference methods (such as illustrated in FIG. 12E). Furthermore, in the situation of spiked infections of common bacteria in the hospital, the analytics may be configured to instantaneously perform conjoint analysis of all infection events and hand hygiene performance and/or PPE performance of healthcare providers who have touched these patients, hence tracking bacteria origin down to specific locations and providers.

Specifically, FIG. 12E is a graph of providers' contact time and hand hygiene compliance with infected patient A within 48 hours before diagnosis. In this regard, the graph illustrated in FIG. 12E is an example of tracking information associated with an infected patient. By searching the patient's room location and a predetermined time before diagnosis (e.g., a 48-hr window), the analytics may display the names of all the providers that were in contact with the patient during the time frame, their contact time with the patient and their hand hygiene compliance rate. In this example, Assistant John has the longest contact time and lowest hand hygiene compliance for this soon-to-be infected patient. Thus, the analytics may track the source of infection down to Assistant John for education and isolation strategies. Alternatively, or in addition, providers' contact time and PPE compliance with an infected patient may be tracked as well.

Figure 12F:
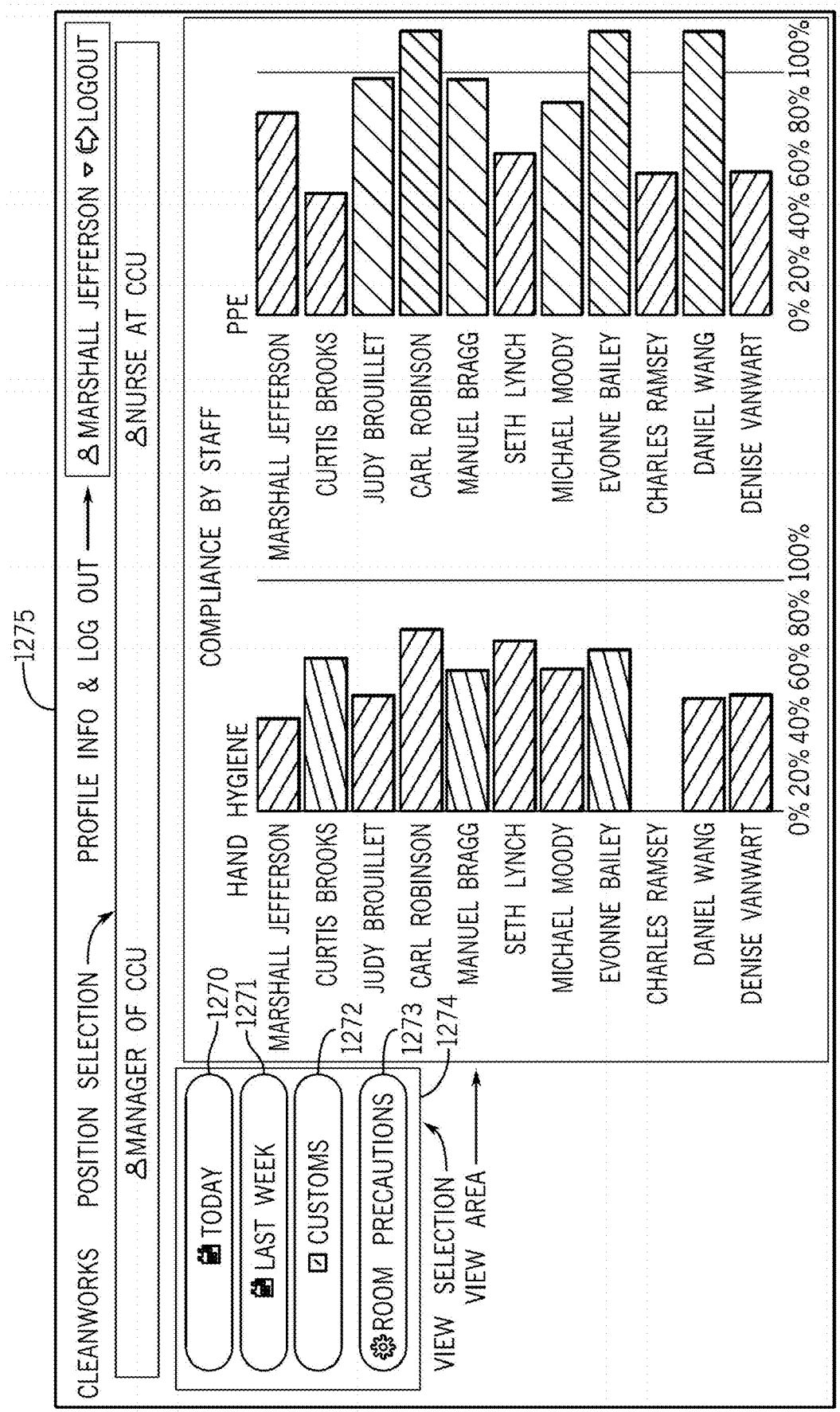

FIGS. 12F-I illustrate various screens of a hand hygiene/PPE compliance system, which may use cloud-based compliance analytic software. Users may login, optionally select his/her assigned positions, and access the hygiene data through automatically generated reports and/or custom reports. An example of the custom report is illustrated in FIG. 12F.

Automatically generated reports may be tailored to a specific user's role, which may provide an easy way in which to access the most relevant information. For instance, ICU managers may view providers' compliance in their ICUs in real time, as well as the compliance by ICU rooms and the daily trend over last week. As an example, FIG. 12F shows a screen 1275 coronary care unit (CCU) Manager Marshall Jefferson receiving real-time update on the compliance rate of healthcare providers in the CCU. Automatic reports may be viewed by selecting "Today" 1270 or "Last Week" 1271 from the View Selection area 1274.

The custom reports function 1272, which may also be selectable in the View Selection area 1274, allows ICU managers, department managers and the infection control team to filter compliance data by date, location (e.g., floor, unit, room), role, and individual provider.

In addition to reports, managers of an ICU may select Room Precautions 1273 in the View Selection 1274 and tell the system what precautions each room of the ICU requires (see screen 1280 in FIG. 12G). With precautions configured, the system may verify whether a provider donned all the appropriate PPE.

Figure 12H:
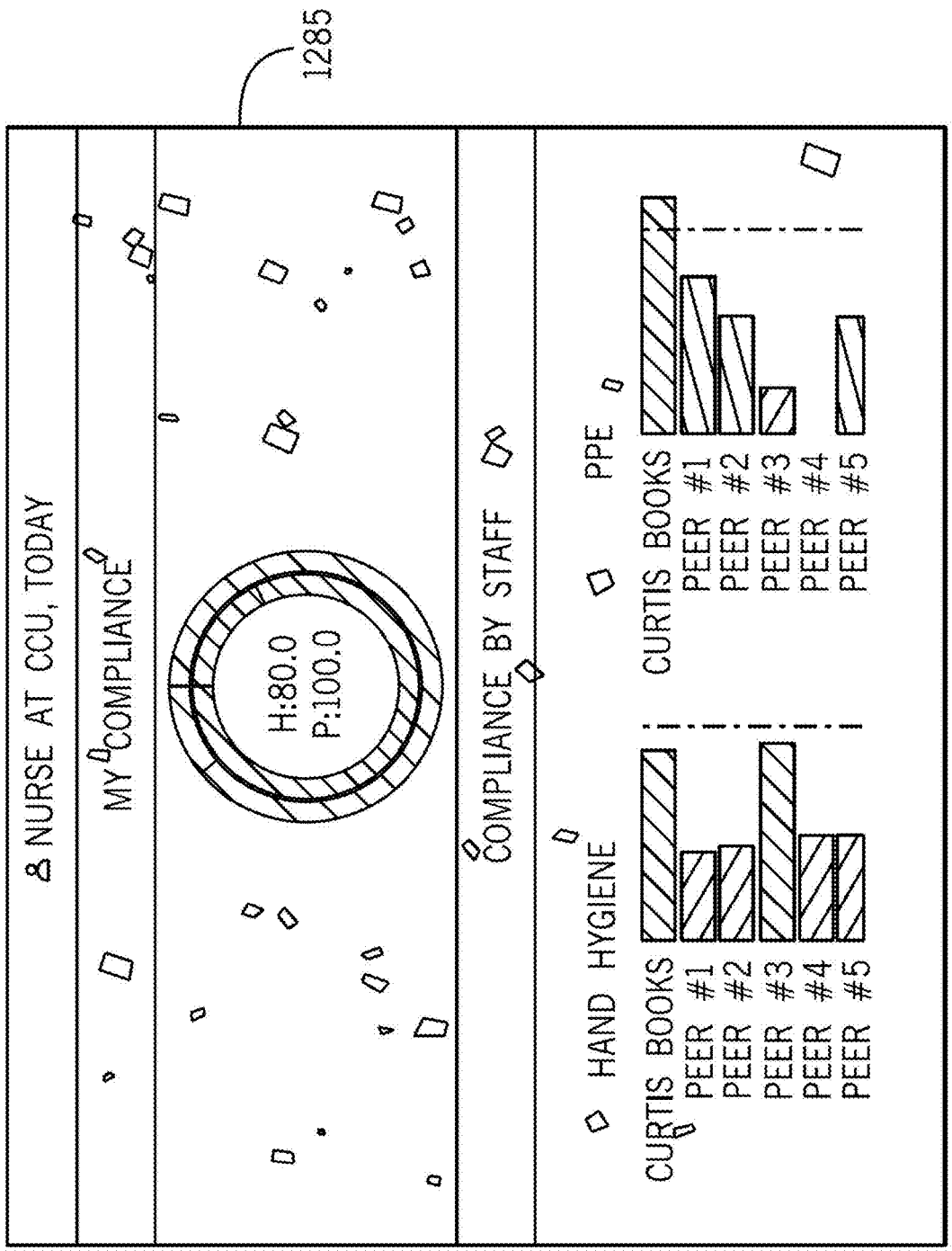
Figure 12I:

Finally, views for individual providers (see FIGS. 12H-I) may be designed to provide positive reinforcement for good habits by following well-established gamification practices inspired by fitness tracking platforms, such as Fitbit® and Apple Watch®. FIG. 12H illustrates a screen 1285 that shows as Nurse Curtis nears his hospital-set handwash or PPE compliance goal, his ring turns greenish as it closes. Reaching the compliance goal triggers a confetti animation. Each user's progress towards the goal may be placed next to their peers' progress to provide competition (e.g., per focus group's request, peers' names are hidden to avoid embarrassment). Users may also strive to reach achievements, like passing a goal multiple days in a row, which can result in physical rewards, like a cafeteria coupon (see screen 1290 in FIG. 12I). In this way, hand hygiene and/or PPE compliance may be game-ified for better learning and/or compliance.

Further, in one implementation, the analytics may illustrate the correlation between any one, any combination, or all of: hand hygiene compliance rate; PPE compliance rate; and infection rate. With infection data input from hospitals, the analytics may generate detailed analysis and generate visualized reports. For instance, hospital users or researchers from relevant fields may use the software to analyze the correlation between a specific category of infection (e.g., Central Line Infection) and hand hygiene compliance and/or PPE compliance of all providers associated with these patients in that category.

Figure 13A:
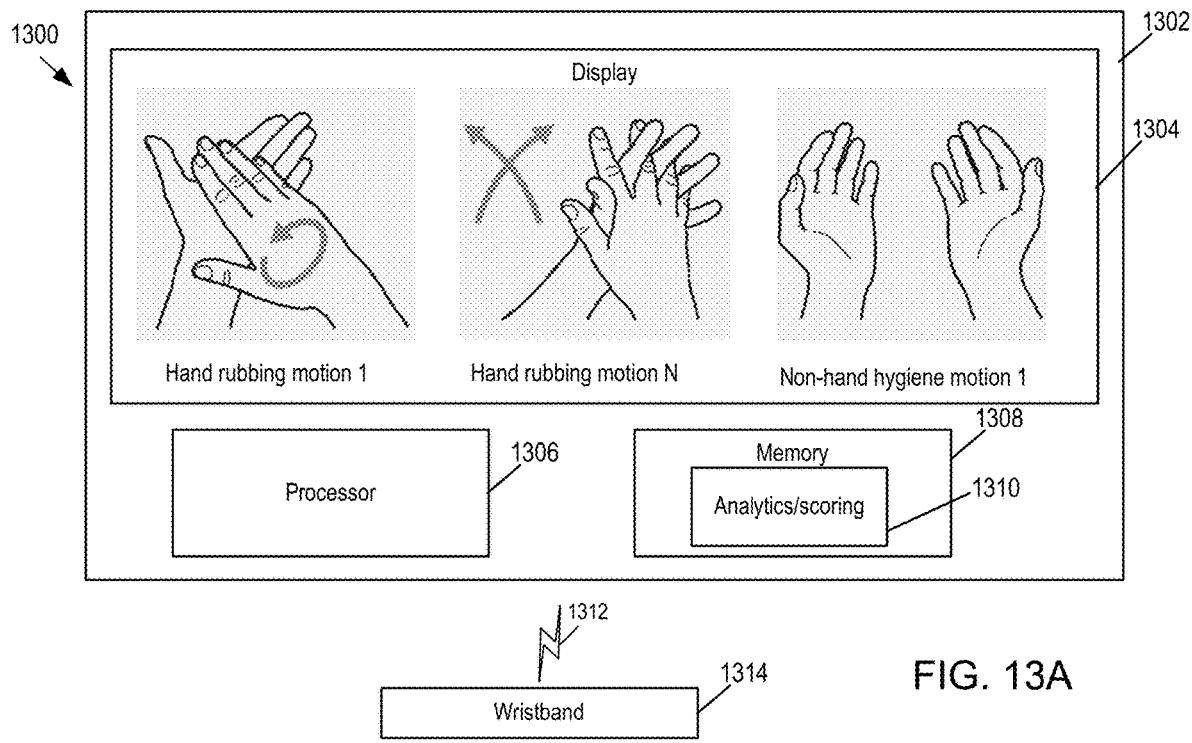
FIG. 13A is a block diagram of a system for instructing and/or scoring a user in hand hygiene compliance (and/or PPE compliance).

Users may be instructed in a variety of ways for WHO hand hygiene training and/or PPE training. In one way, the users may wear the wristband, and may receive feedback from the wristband and/or the stationary controller. In another way, an electronic device may work in combination with the wristband, such as illustrated in FIG. 13A, and discussed further below. Alternatively, or in addition, electronic device may work in combination with the wristband to provide PPE training Various types of users may be instructed, including healthcare providers, children, and the elderly. With regard to healthcare providers, the system may train for different hygiene protocols, such as hand hygiene protocols (e.g., WHO hand hygiene guidelines), PPE protocols, infectious hygiene protocols (e.g., for treatment of patients with infectious diseases or immuno-compromised diseases), etc. In this regard, the training may learn general hygiene protocols or specific hygiene protocols. Further, the system disclosed herein may be integrated with a virtual reality or augmented reality system in which the trainee healthcare provider enters different "rooms" and practices different hygiene protocols, such as hand hygiene protocols, infectious hygiene protocols, etc. For example, the trainee may "walk" from one "room" in ICU #1 with pneumonia with one set of hygiene protocols (and optionally output to the trainee healthcare provider an indication of one or both of the HH protocol or the PPE protocol associated with ICU #1) to another "room" in ICU #2 with a different set of hygiene protocols (and optionally output to the trainee healthcare provider an indication of one or both of the HH protocol or the PPE protocol associated with ICU #2). As another example, the trainee may "walk" into a room to perform the hand hygiene protocols first, then perform the PPE protocols (to put on the garment(s) in the proper sequence), and thereafter "walk" out of the room to perform the PPE protocols first (to remove the garment(s) in the proper sequence) and then perform the hand hygiene protocols. In addition, the feedback given to the healthcare provider may be given in one of several ways. In one way, the feedback may be solely based on the current training session. For example, the system may: determine the plurality of hand motions; determine a respective time period for each of the plurality of hand motions; cause the plurality of hand motions to be displayed on the display for the respective times; receive the sensor data, the sensor data indicative of user hand motions and associated respective times for the user hand motions; analyze the sensor data in order to determine a difference between the plurality of hand motions and the user hand motions, and a difference between the respective times and the associated respective times for the user hand motions; and output via the display an indication of the difference between the plurality of hand motions and the user hand motions, and a difference between the respective times and the associated respective times for the user hand motions. In another way, the feedback may compare the difference between the plurality of hand motions and the user hand motions with results from a previous training session, such as a previous difference between previous plurality of hand motions and previous user hand motions in a previous training session, and output the comparison via the display. Alternatively, or in addition, the system may: determine the plurality of PPE motions; determine a respective sequence for each of the plurality of PPE motions; cause the plurality of PPE motions to be displayed on the display in the respective sequence; receive the sensor data, the sensor data indicative of user PPE motions and associated respective sequences for the user PPE motions; analyze the sensor data in order to determine a difference between the plurality of PPE motions and the user PPE motions, and a difference between the respective sequence and the associated respective sequence for the user PPE motions; and output via the display an indication of the difference between the plurality of PPE motions and the user PPE motions, and a difference between the respective sequence and the associated respective sequences for the user PPE motions. In another way, the feedback may compare the difference between the plurality of PPE motions and the user PPE motions with results from a previous training session, such as a previous difference between previous plurality of PPE motions and previous user PPE motions in a previous training session, and output the comparison via the display.

Similarly, with regard to children, a wristband in combination with an electronic device may be used to educate, motivate and improve children's hand hygiene. The video game console-like game may make the seemingly boring hand hygiene fun and entertaining. In this regard, the goal of the system is to train the young children with correct hand hygiene behaviors and ultimately reduce infections and absenteeism in daycare centers, schools and pediatric long-term care centers.

FIG. 13A is a block diagram of a system 1300 for instructing and/or scoring a user in hand hygiene compliance. Alternatively, or in addition, the system 1300 may be configured for instructing and/or scoring the user in PPE compliance. The system 1300 includes a wristband 1314 and an electronic device 1302, which may comprise a mobile electronic device (e.g., tablet or cell phone) installed with a hand hygiene mobile app and includes a display 1304. In this regard, electronic device 1302 may include a processor 1306 and a memory 1308, with analytics/scoring 1310, which may comprise the hand hygiene mobile app. In practice, display 1304 may illustrate various rubbing motions, such as hand rubbing motions and/or non-hand rubbing motions. As shown in FIG. 13A, display 1304 displays two hand rubbing motions (hand rubbing motion 1 and hand rubbing motion N) and a non-hand rubbing motion (non-hand hygiene motion 1). In this regard, display 1304 may display a sequence of the motions. Alternatively, or in addition, display 1304 may display PPE motions for putting on or taking off the PPE garment(s) in the proper sequence. Finally, display 1304 may display hand rubbing motions and PPE motions in the proper sequence when entering and/or when exiting a patient area.

Though not illustrated in FIG. 13A, electronic device may be in communication with a server, such as back-end server 130. For example, in adult education, a server-based instructional system may be used. In that regard, the server may send motion instructions to a local computer, such as electronic device 1302, for interaction with the person and for central monitoring. Alternatively, the electronic device 1302 is locally operated without server guidance. For example, in child education, central monitoring may not be necessary. In this instance, the electronic device may be a smartphone executing an app for use with wristband 1314.

In either an office setting or a daycare setting, the electronic device 1302 may comprise a tablet or other mobile electronic device, which may be installed in front of the washing station. Further, to avoid the wristband 1314 becoming a fomite, all electronic components may be sealed in the wristband 1314 with silicone, which may make the wristband 1314 easier to clean or sanitize. In one implementation, the wristband 1314 for an office setting (e.g., for adult use) may have the same functionality as the wristband 1314 for a daycare/school setting (e.g., for child use). Alternatively, the wristband 1314 for child use may have less functionality, such as the removal of the vibrating motor.

When the user, such as the healthcare provider or the child, puts on the wristband 1314, the hand hygiene app on the tablet or mobile electronic device may be activated. As one example, the wristband may have built-in motion sensors and Bluetooth chip, such as discussed above. Responsive to the user putting on the wristband, the micro-vibration sensor resident on the wristband may wake-up the wristband. Further, upon wake-up, the wristband 1314 may send a wireless communication via 1312 to electronic device 1302 in order to activate the hand hygiene app. In this way, the battery of the wristband 1314 may last longer and require less recharging or fewer replacements.

With regard to healthcare providers, a series of motions, such as those identical or similar to the motions in the WHO guidelines in FIGS. 10A-C, or those different from the motions in FIGS. 10A-C. Further, the duration for the various motions may be predetermined (e.g., 1 second, 2 seconds, etc.), or may be selected randomly.

With regard to children, the hand hygiene app may comprise a game whose theme is to fight germs. Cartoon monsters, which may represent bacteria on the child's hands, may appear in the game. The game may provide step-by-step video- and/or audio-based instructions to guide the children through all the hand hygiene steps recommended by WHO: wet hands, apply soap, rub hands, clean fingernails, rinse soap and dry hands (see FIGS. 10A-B). Each step of the child's hand hygiene behavior may be detected by the wristband 1314 and sent to the mobile app for evaluation. Alternatively, the wristband 1314 may detect and evaluate the hand hygiene behavior, and transmit the evaluation to the mobile app. The child may be rewarded prizes, such as stars and scores, based on how well the child follows the guidance. If required motions are not completed, the game will provide real-time feedback and remind the child to correct his/her behaviors to be compliant. After each of the required hand hygiene steps is completed, a portion of the monsters may be eliminated to give children an indication of their progress. When adequate hand washing has been achieved, all monsters on the display 1304 will be removed and compliments such as "Good Job!" will be output to encourage children in the correct behavior. Thus, the monsters may represent a plurality of indicia for display. Based on the difference between the plurality of hand hygiene motions and the user hand motions, more or less of the indicia (e.g., the monsters) may be removed from the display, with a greater difference between the plurality of hand hygiene motions and the user hand motions (e.g., the child was further away from the correct hand hygiene motions) resulting in less removal of the number of the monsters on the screen for display and with a lesser difference between the plurality of hand motions and the user hand motions (e.g., the child was closer to the correct hand hygiene motions) resulting in a greater removal of the number of monsters on the screen for display. Alternatively, or in addition, the mobile app may provide a score based on hand hygiene compliance and behavior improvement.

In practice, the wristband may detect the hand hygiene motion and/or PPE motion of the user by the embedded motion sensor (e.g., an accelerometer and/or gyroscope and/or magnetometer, as discussed above) and transmitted to the mobile app through Bluetooth or other wireless protocol. Various types of hand rubbing motions and/or PPE motions may be detected. For example, with regard to a healthcare provider, the motions may be detected as described above. For a child, the detection may take into account more gentle rubbing motions that are common in children. In addition, children may move their body dramatically during handwashing or hand rubbing. Therefore, the analytics (present either on the wristband 1314 or on the electronic device 1302) may comprise a robust motion algorithm to detect the hand rubbing motions from interferences such as body movement. Since the wristband 1314 tracks and sends the hand hygiene information to the electronic device (e.g., the smartphone) and receives feedback, the embedded algorithm may be simple to minimize the computing power and thus increase battery life of the wristband 1314. In this way, the system 1300 may provide an entertaining, engaging, and enhancing real-time hand hygiene training for user, such as children, with the goal of helping children to form solid hand-hygiene habits and to develop proper hand hygiene techniques.

Figure 13B:
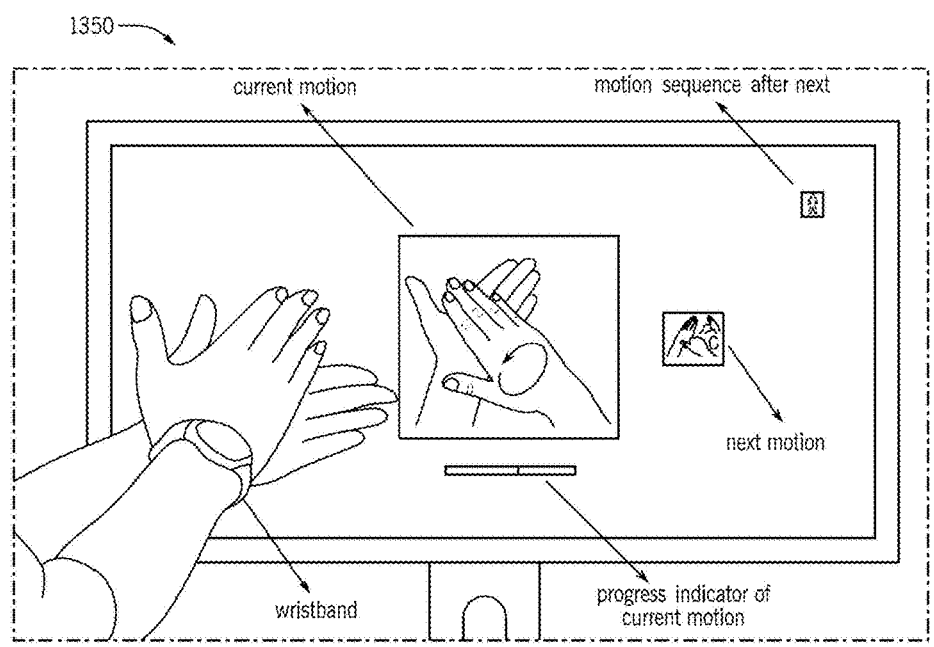
FIG. 13B is an illustration of a GUI illustrated in the system of FIG. 13A.

FIG. 13B is an illustration of a GUI illustrated in the system of FIG. 13A. Each trainee may wear the wristband and perform the motion following the displayed motion image on the display. The image of the current motion is enlarged and located at the center of the screen with a progress bar underneath showing its progress (shown as "progress indicator of current motion"). A small image of the next motion (shown in FIG. 13B as "next motion") is also displayed next to the image of the current motion. This user-friendly interface facilitates the trainee on the transition from one motion to the next. Though FIG. 13B illustrates hand hygiene motions, PPE motions may be displayed instead of, or in addition to, hand hygiene motions.

Specifically, the computer-guided test program may generate a sequence of random motion images, including the 6 hand rubbing motions in WHO guideline (positive motions) and non-hand-hygiene interfering motions (negative motions such as walking, swinging arm, knocking a door, opening a door, etc.). To mimic an actual hand hygiene event, the duration of each motion may be set as a random value, such as between 2 s and 4.5 s. Further, in one implementation, each trial may begin and end with a "rest" action, indicating the trainee to keep hands motionless.

Each trainee may first become familiar with all the possible motions and images displayed on the computer screen. During the tutorial, the computer-guided test program may calculate the sum of the durations of all the positive motions (e.g., the 6 hand rubbing motions in WHO guideline), which may be denoted as TP. The motion duration detected by the sensor algorithm on the wristband may be denoted as TS. For each user, the range of TP and TS may be listed. Further, the duration error $\Delta T$ may be calculated as the absolute value of the difference between sensor measurement and the positive hand hygiene duration generated by the program (e.g., $|TS-TP|$). The error rate may thus be calculated as the ratio of the duration error $\Delta T$ to the sum of program generated positive durations TP. For both the duration error and duration error rate, the mean values and standard deviations over all trials may be given.

Further, similar to the computer-guided test program for healthcare providers, the mismatch between the sensor-measured duration and mobile app-generated duration may be used as the basis for scoring for each step. In this way, the game may assist children in developing the correct hand hygiene behavior in their early age.

Figure 14:
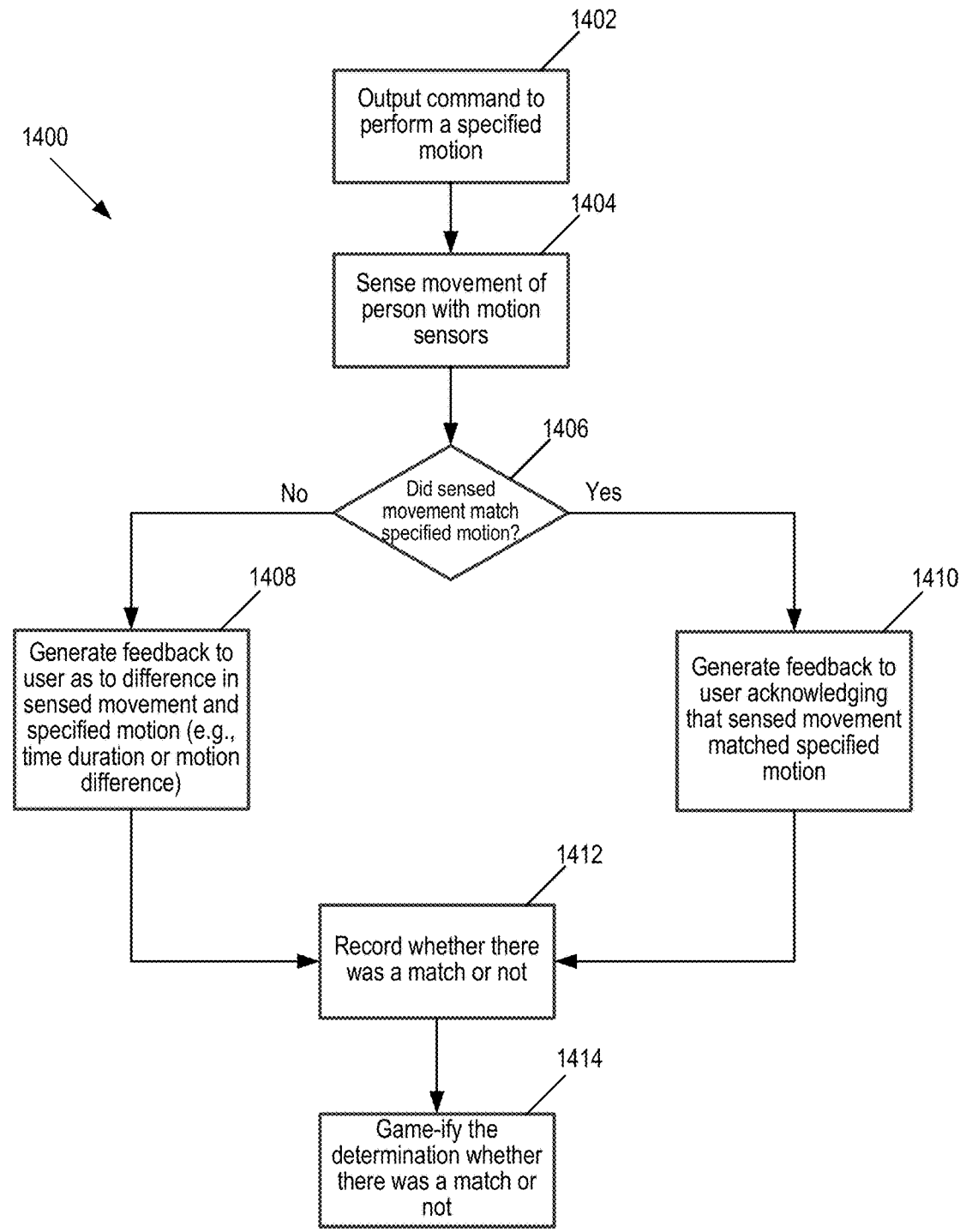
FIG. 14 is flow chart of operation of the system of FIGS. 13A-B.

FIG. 14 is flow chart 1400 of operation of the system of FIGS. 13A-B. At 1402, a command is output to perform a specified motion. In one implementation, the specified motion is a hand hygiene motion. In another implementation, the specified motion is a PPE motion. In still another implementation, the specified motions comprise both a hand hygiene motion and a PPE motion. At 1404, the movement of the person is sensed with one or more motion sensors. At 1406, it is determined whether the sensed movement matched the specified motion. If yes, at 1410, feedback may be generated acknowledging to the user that the sensed movement matched the specified motion. If no, at 1408, feedback may be generated for output to the user indicating the difference between the sensed movement matched the specified motion. At 1412, it is recorded whether there was a match or not. Finally, at 1414, the determination may be game-ified as to whether there was a match or not.

As discussed above, the hand hygiene and/or PPE monitoring may be integrated with access control. The integration of hand hygiene monitoring and access control may be on one or more levels, including at the mobile electronic device level (e.g., at the wristband), at the local level (e.g., the stationary controller and/or at the local access control reader), and/or at the central level (e.g., the central access control system and/or the hand hygiene monitoring central system).

Hand hygiene and/or PPE monitoring may be integrated with various types of access control systems. One type of access control system is based on RFID technology. In one implementation, a passive RFID tag, which includes an identification code associated with a user, may be included in the mobile electronic device, such as the mobile wristband device. The RFID local access control reader may read the identification code in the RFID tag in order to determine whether the user is to be granted access. One example RFID system comprises HID® Global's multiCLASS reader, which supports a variety of RFID standards including high frequency 13.56 MHz ISO 15693, ISO 14443A/B and low frequency 125 kHz technologies. Another type of access control system is based on a different wireless technology, such as near field (e.g., Bluetooth) wireless communication of the identification code associated with the user.

Figure 5A:
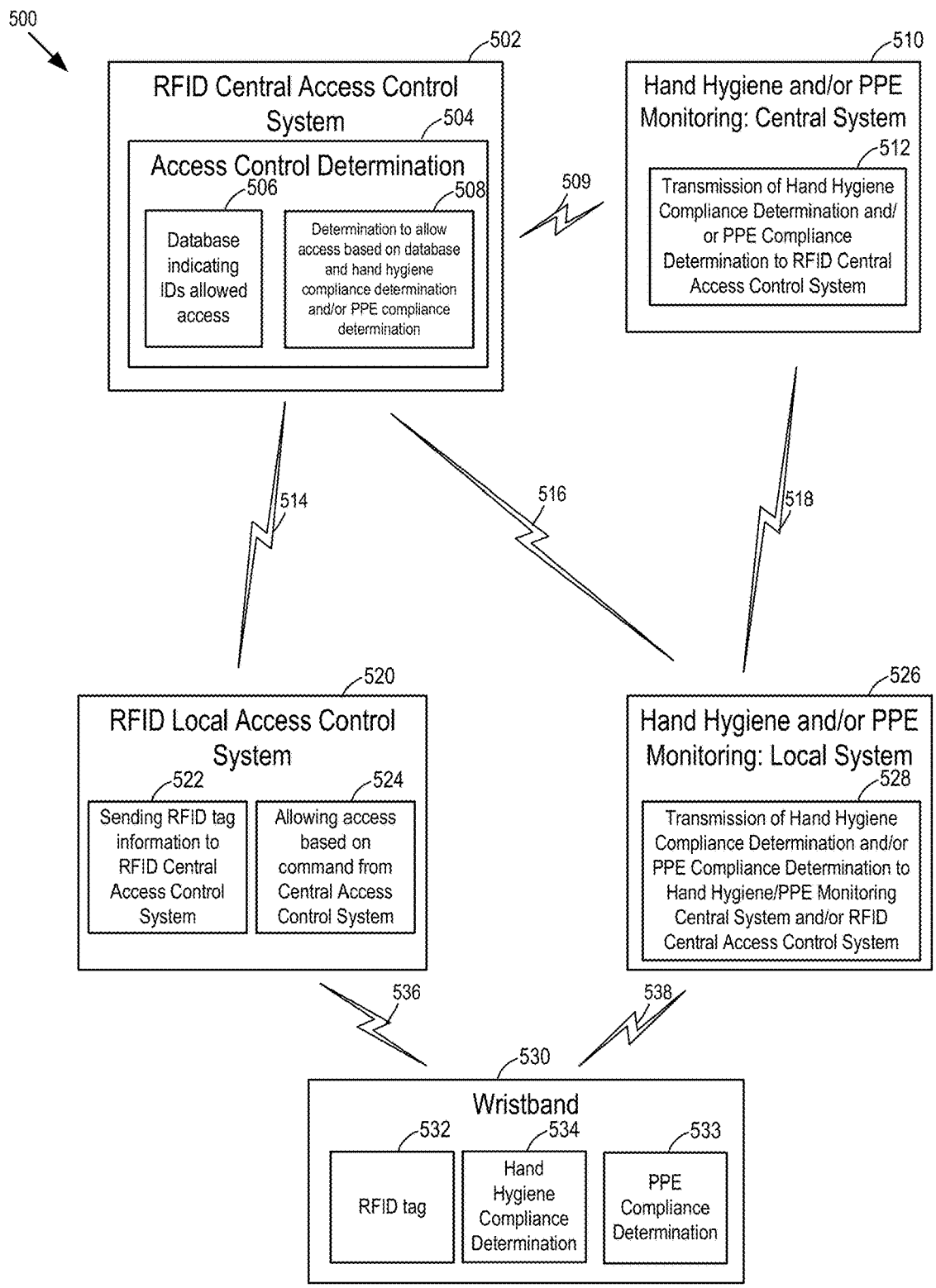
FIG. 5A is a first example block diagram of an access control system (using RFID) and a hand hygiene and/or PPE monitoring system, whereby the access control is centrally determined and whereby the hand hygiene and/or PPE compliance determination is performed at the wristband.

FIG. 5A is a first example block diagram 500 of an access control system (using RFID) and a hand hygiene and/or PPE monitoring system, whereby the access control is centrally determined and whereby the hand hygiene and/or PPE compliance determination is performed at the wristband. In one implementation, the access control determination is independent of hand hygiene and/or PPE compliance. For example, regardless of whether a user has complied with hand hygiene and/or PPE protocols, the user will be granted access if the ID associated with the user is indicative of access. In another implementation, the access control determination is dependent, at least in part, on hand hygiene compliance and/or PPE compliance. For example, the access control determination includes two determinations in order to grant access: (1) compliant hand hygiene and/or PPE determination for a user; and (2) identification of the user indicating allowed access. One example for (1) comprises determination of hand hygiene compliance for the user. Another example for (1) comprises determination of PPE compliance for the user. Still example for (1) comprises determination of both hand hygiene and PPE compliance for the user. Thus, any discussion regarding (1) may include any one, any combination, or all of these three examples. As discussed above, (1) and (2) may be determined in any order.

FIG. 5A illustrates that RFID central access control system 502 includes access control determination 504, which includes a database 506, whose contents indicate IDs that are allowed access, and determination to allow access based on the database and hand hygiene compliance and/or PPE compliance determination 508 (e.g., determining to allow access based on the database and hygiene compliance determination, determining to allow access based on the database and PPE determination, or determining to allow access based on the database, the hygiene compliance determination and the PPE compliance determination). FIG. 5A further illustrates hand hygiene and/or PPE monitoring: central system 510 (which may be the central monitoring system for determining one or both of hand hygiene compliance determination or PPE compliance determination), which includes transmission of one or both of hand hygiene compliance determination or PPE compliance determination to RFID central access control system 512. As such, FIG. 5A illustrates that the access control determination is dependent, at least in part, on: (i) hand hygiene compliance; (ii) PPE compliance; or (iii) hand hygiene compliance and PPE compliance. Alternatively, access control determination may be independent of hand hygiene compliance and/or PPE compliance, in which instance RFID central access control system determines to allow access based on the database (and not based on the hand hygiene compliance determination and/or the PPE compliance determination). Further, FIGS. 5A-H illustrate separate access control and hand hygiene/PPE monitoring systems. Alternatively, a single access control system may be used for both access and hand hygiene monitoring and/or PPE monitoring. In an implementation with separate systems, the hand hygiene compliance determination and/or the PPE compliance determination may be sent to both systems (either directly from the determining device or via an intermediary device), or may be sent to only one system (such as the hand hygiene/PPE monitoring system). Thus, though FIGS. 5A-H illustrate that the hand hygiene compliance determination and/or the PPE compliance determination is sent to at least a part of both the access control system and the hand hygiene/PPE monitoring system, alternatively, the hand hygiene compliance determination and/or the PPE compliance determination may only be transmitted within the hand hygiene/PPE monitoring system without transmission to the access control system. As discussed here, any hand hygiene and/or PPE monitoring system may comprise a monitoring system only to hand hygiene, a monitoring system only to PPE, or a monitoring system to both hand hygiene and PPE.

Wristband 530, which includes RFID tag 532 (such as a passive RFID tag), hand hygiene compliance determination 534, and PPE compliance determination 533, is configured to determine whether the hand motions of the user is compliant with hand hygiene standards and/or with PPE protocols. Thus, in one implementation, the RFID feature in wristband 530 is independent of other wristband functions, such as the hand hygiene compliance determination and/or PPE compliance determination. RFID local access control system 520, which may include an RFID reader, may read information from RFID tag 532. In this way, the information from RFID tag 532 may be sent to an electronic device external to wristband 530. Further, in one implementation, the information as to hand hygiene compliance and/or PPE compliance may be transmitted from wristband 530 in a communication that is separate from the information from RFID tag 532 (and potentially may be sent to different external electronic devices). Alternatively, as discussed below, the information as hand hygiene compliance and/or PPE compliance, and the identification information of the healthcare provider may be sent in a single communication to an external electronic device (such as to a local access control system).

The wristband 530 may transmit the hand hygiene compliance determination and/or PPE compliance determination to an external electronic device via near-field wireless transmission 538 to hand hygiene and/or PPE monitoring: local system 526, one example of which is the stationary controller discussed above. The hand hygiene compliance determination and/or PPE compliance determination may comprise one or more fields in a communication indicating that hand hygiene and/or PPE was complied with (e.g., a field in the communication=1 for compliance with hand hygiene or PPE; a field in the communication=11 for compliance with both hand hygiene and PPE) or that hand hygiene was not complied with (e.g., a field in the communication=0 for non-compliance with hand hygiene or PPE; a field in the communication=00 for non-compliance with both hand hygiene and PPE). In the implementation in which access control is dependent on hand hygiene compliance and/or PPE compliance, RFID central access control system 502 may receive the hand hygiene compliance determination and/or the PPE compliance determination in one of several ways including: (1) directly from wristband 530; (2) indirectly from hand hygiene and/or PPE monitoring: local system 526 (using transmission of hand hygiene compliance determination and/or PPE compliance determination to hand hygiene and/or PPE monitoring: central system 510 and/or RFID central access control system 528); or indirectly from hand hygiene and/or PPE monitoring: central system 510 (using transmission of hand hygiene compliance determination and/or PPE compliance determination to RFID central access control system 502). In the implementation in which access control is independent of hand hygiene compliance and/or PPE compliance, RFID central access control system 502 need not receive the hand hygiene compliance determination and/or the PPE compliance determination.

Communications may be sent wirelessly, such as via 509, 514, 516, 518, 536, 536. Of note, 536 may be a wireless communication via RF for RFID whereas 538 may be a wireless communication via Bluetooth or Wi-Fi. The frequency bands may be different for the RFID transmission versus the Bluetooth or WIFI transmission. RFID transmission may be in the 125 or 134 kHz areas of the spectrum for low-frequency RFID systems, and 13.56 MHz for high-frequency RFID systems. Bluetooth may operate at frequencies between 2402 and 2480 MHz, or 2400 and 2483.5 MHz including guard bands 2 MHz wide at the bottom end and 3.5 MHz wide at the top. Wi-Fi may use five distinct frequency ranges including: 2.4 GHz, 3.6 GHz, 4.9 GHz, 5 GHz, and 5.9 GHz bands.

Because of the central access determination, RFID local access control system 520 transmits the RFID tag information using sending RFID tag information to RFID central access control system 522, and allows access (e.g., unlocks an electronic lock) responsive to a command from the RFID central access control system 502 using allowing access based on command from central access control system 524.

Figure 5B:
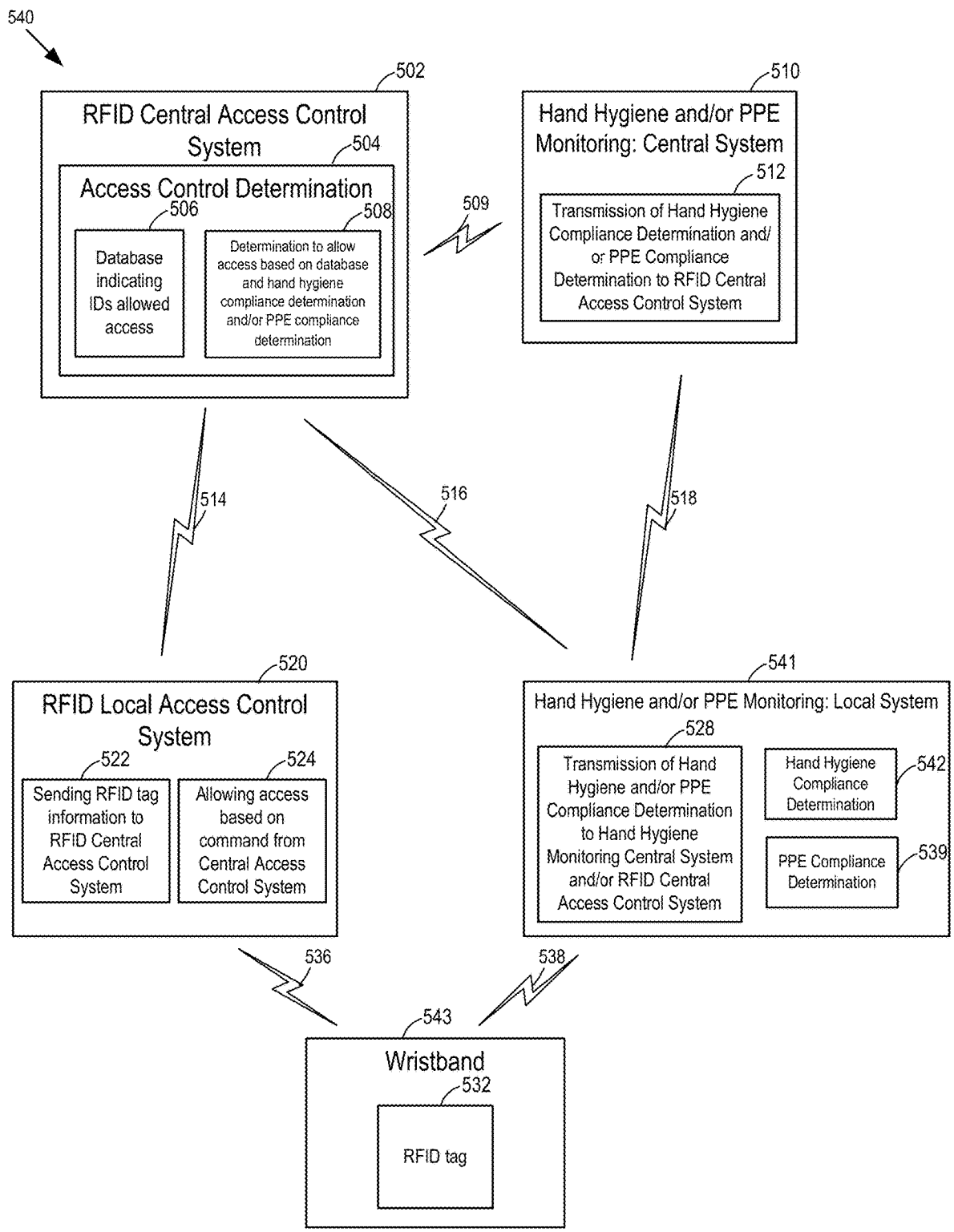
FIG. 5B is a second example block diagram of an access control system (using RFID) and a hand hygiene and/or PPE monitoring system, whereby the access control is centrally determined and whereby the hand hygiene and/or PPE compliance determination is performed at the stationary controller.

FIG. 5B is a second example block diagram 540 of an access control system (using RFID) and a hand hygiene and/or PPE monitoring system, whereby the access control is centrally determined and whereby the hand hygiene compliance determination and/or the PPE compliance determination is performed at the stationary controller. Thus, in contrast to FIG. 5A, hand hygiene and/or PPE monitoring: local system 541 includes one or both of hand hygiene compliance determination 542 and PPE compliance determination 539, and not on wristband 543.

Figure 5C:
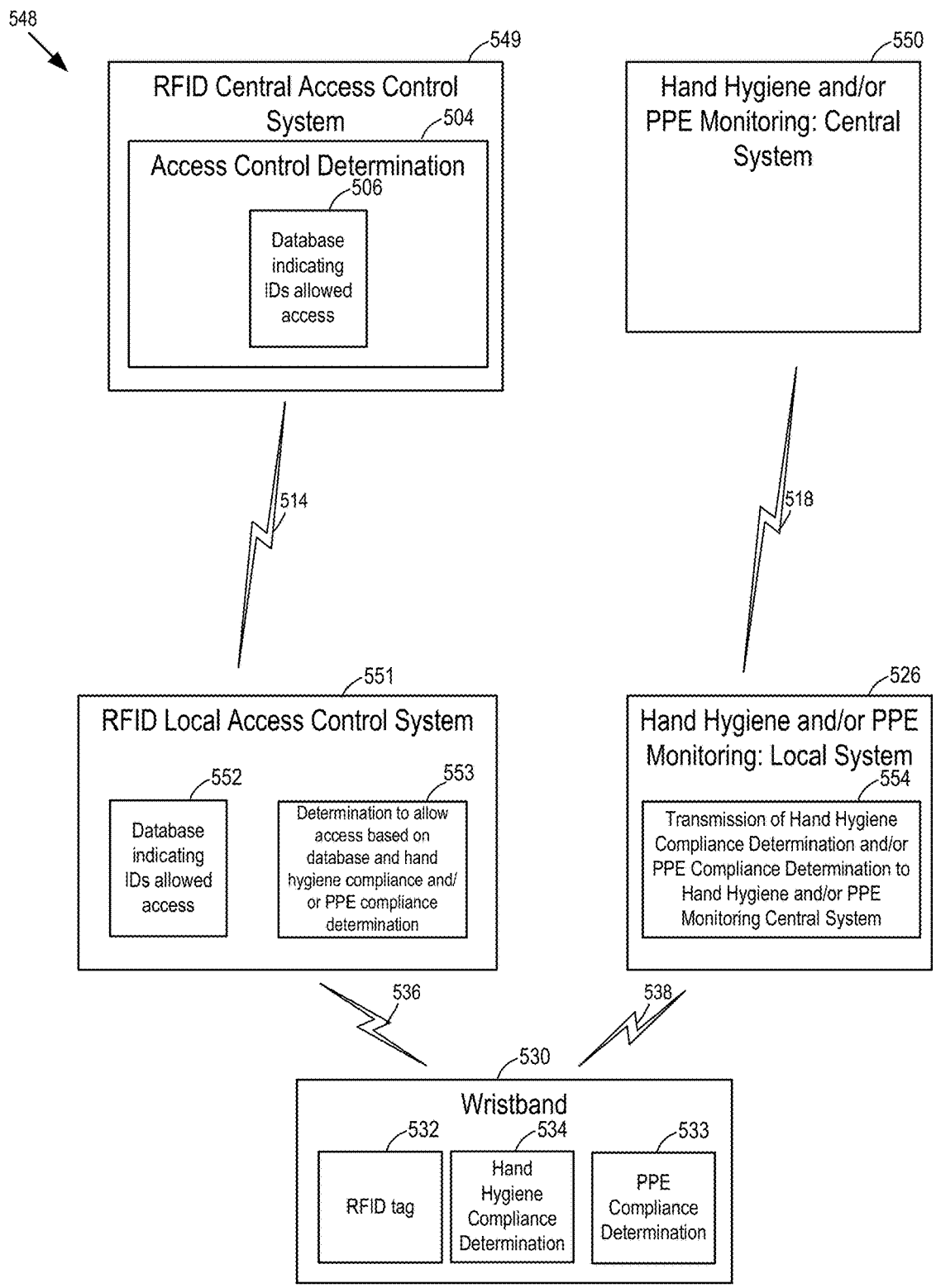
FIG. 5C is a third example block diagram of an access control system (using RFID) and a hand hygiene and/or PPE monitoring system, whereby the access control is locally determined and whereby the hand hygiene and/or PPE compliance determination is performed at the wristband.

FIG. 5C is a third example block diagram 548 of an access control system (using RFID) and a hand hygiene and/or PPE monitoring system, whereby the access control is locally determined and whereby the hand hygiene compliance determination 534 and/or the PPE compliance determination 533 is performed at the wristband 530. FIG. 5C illustrates that RFID local access control system 551 includes database indicating IDs allowed access 552, whose contents indicate IDs that are allowed access, and determination to allow access based on the database and hand hygiene compliance determination and/or the PPE compliance determination 553 (e.g., based on the database and the hand hygiene compliance determination; based on the database and the PPE compliance determination; or based on the database and the hand hygiene compliance determination and the PPE compliance determination). As such, FIG. 5C illustrates that the access control determination is dependent, at least in part, on hand hygiene compliance and/or PPE compliance. Alternatively, access control determination may be independent of hand hygiene compliance and/or PPE compliance, in which instance RFID local access control system determines to allow access based on the database (and not based on the hand hygiene compliance determination and/or the PPE compliance determination). Further, hand hygiene and/or PPE monitoring: local system 526 may use transmission of hand hygiene compliance determination and/or PPE compliance determination to hand hygiene and/or PPE monitoring central system 554 in order to transmit the hand hygiene compliance determination and/or PPE compliance determination to hand hygiene and/or PPE monitoring: central system 550.

Figure 5D:
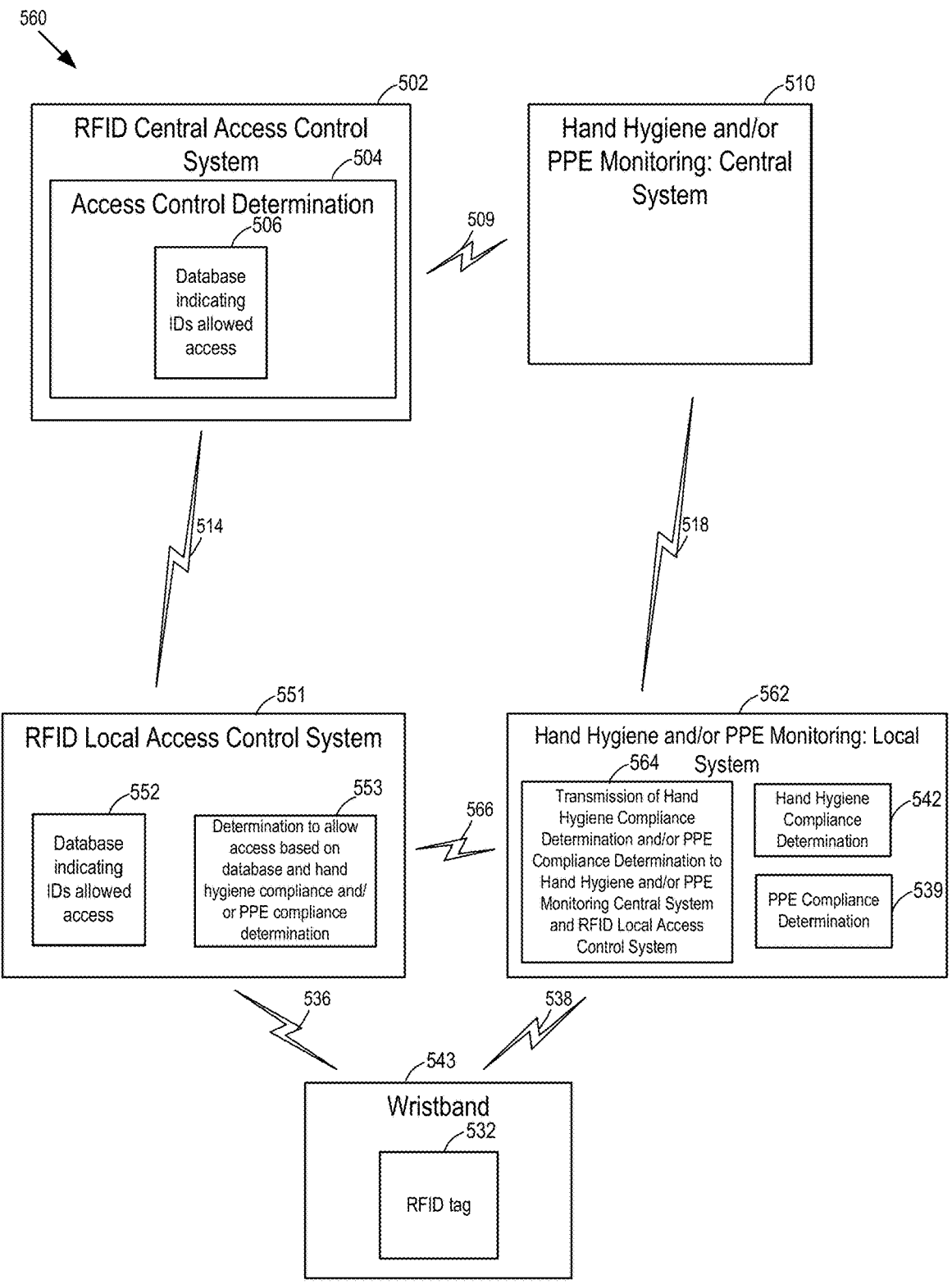
FIG. 5D is a fourth example block diagram of an access control system (using RFID) and a hand hygiene and/or PPE monitoring system, whereby the access control is locally determined and whereby the hand hygiene and/or PPE compliance determination is performed at the stationary controller.

FIG. 5D is a fourth example block diagram 560 of an access control system (using RFID) and a hand hygiene and/or PPE monitoring system, whereby the access control is locally determined and whereby the hand hygiene compliance determination and/or the PPE compliance determination is performed at the stationary controller. Thus, in contrast to FIG. 5C, hand hygiene and/or PPE monitoring: local system 562 includes hand hygiene compliance determination 542 and/or PPE compliance determination 539, and not on wristband 543. Further, hand hygiene and/or PPE monitoring: local system 562 includes transmission of hand hygiene compliance determination and/or PPE compliance determination to hand hygiene and/or PPE monitoring central system and RFID local access control system 564. Thus, FIG. 5D illustrates that access control is dependent on hand hygiene compliance and/or PPE compliance. In the instance of independence of access control from hand hygiene compliance and/or PPE compliance, the hand hygiene compliance determination and/or the PPE compliance determination need not be transmitted to RFID local access control system 551.

Figure 5E:
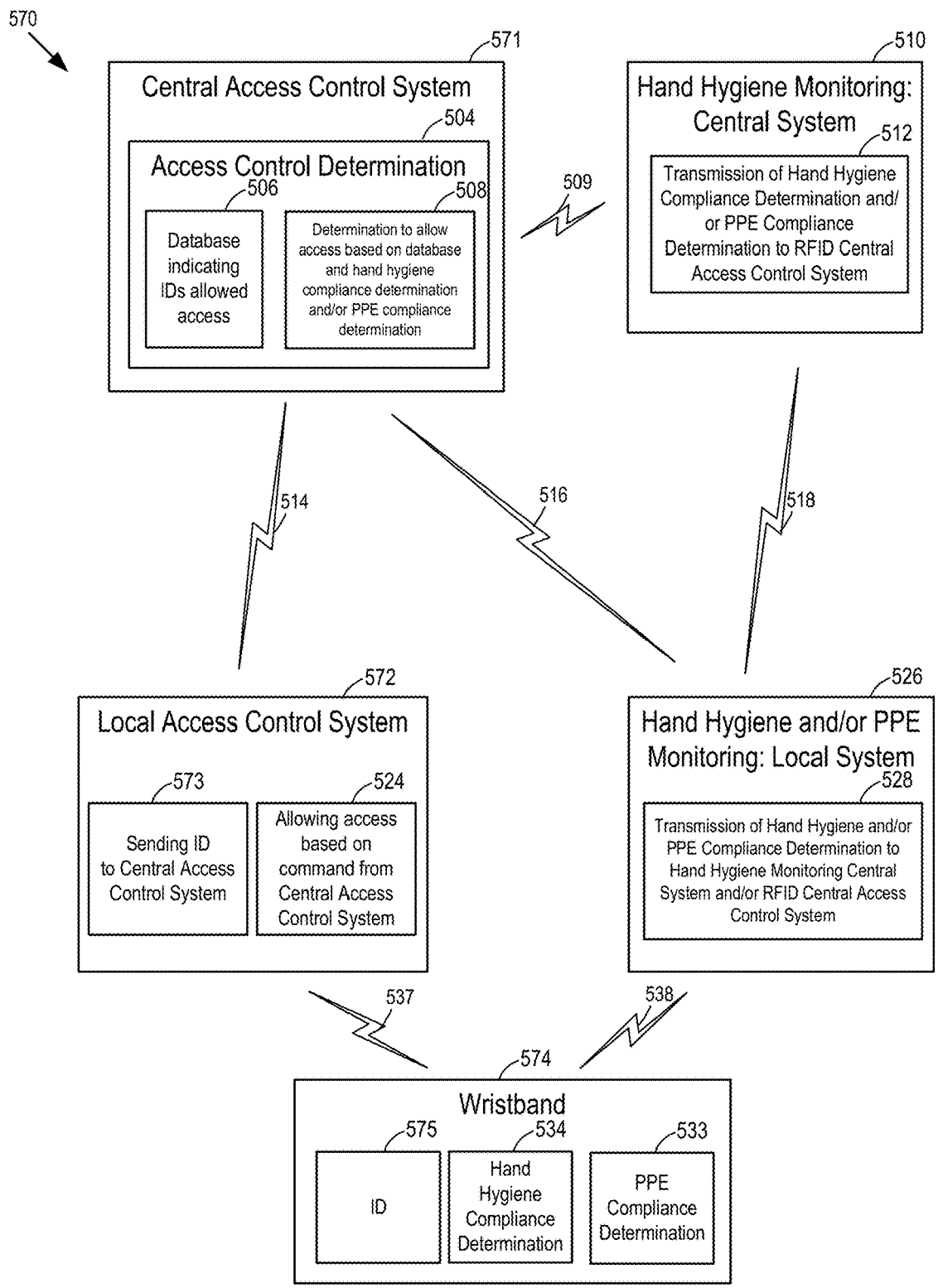
FIG. 5E is a fifth example block diagram of an access control system and a hand hygiene and/or PPE monitoring system, whereby the access control and hand hygiene and/or PPE communication communicate via the same wireless protocol, whereby access control is centrally determined and whereby the hand hygiene and/or PPE compliance determination is performed at the wristband.

As discussed above, access control in one implementation may be based on RFID technology and may be based on non-RFID technology. FIG. 5E is a fifth example block diagram 570 of an access control system which is based on non-RFID technology and a hand hygiene and/or PPE monitoring system, whereby the access control and hand hygiene communication and/or PPE communication communicate via the same wireless protocol, whereby access control is centrally determined and whereby the hand hygiene compliance determination and/or the PPE compliance determination is performed at the wristband. Specifically, central access control system 571 is similar to that in FIG. 5A. However, wristband 574 includes ID 575, which is not an RFID tag, but instead may be an identification in stored memory. Wireless communication 537 may comprise a non-RFID frequency band, such as Bluetooth or Wi-Fi, thereby communicating the ID 575 to local access control system 572. Local access control system 572 uses sending ID to central access control system 573. Similar to FIG. 5A, FIG. 5E illustrates that the access control determination is dependent on the hand hygiene compliance determination and/or the PPE compliance determination. Alternatively, in the implementation in which access control is independent of hand hygiene compliance and/or the PPE compliance, central access control system 571 need not receive the hand hygiene compliance determination and/or the PPE compliance determination, and the determination to grant access need not be dependent on the hand hygiene compliance determination and/or the PPE compliance determination.

Figure 5F:
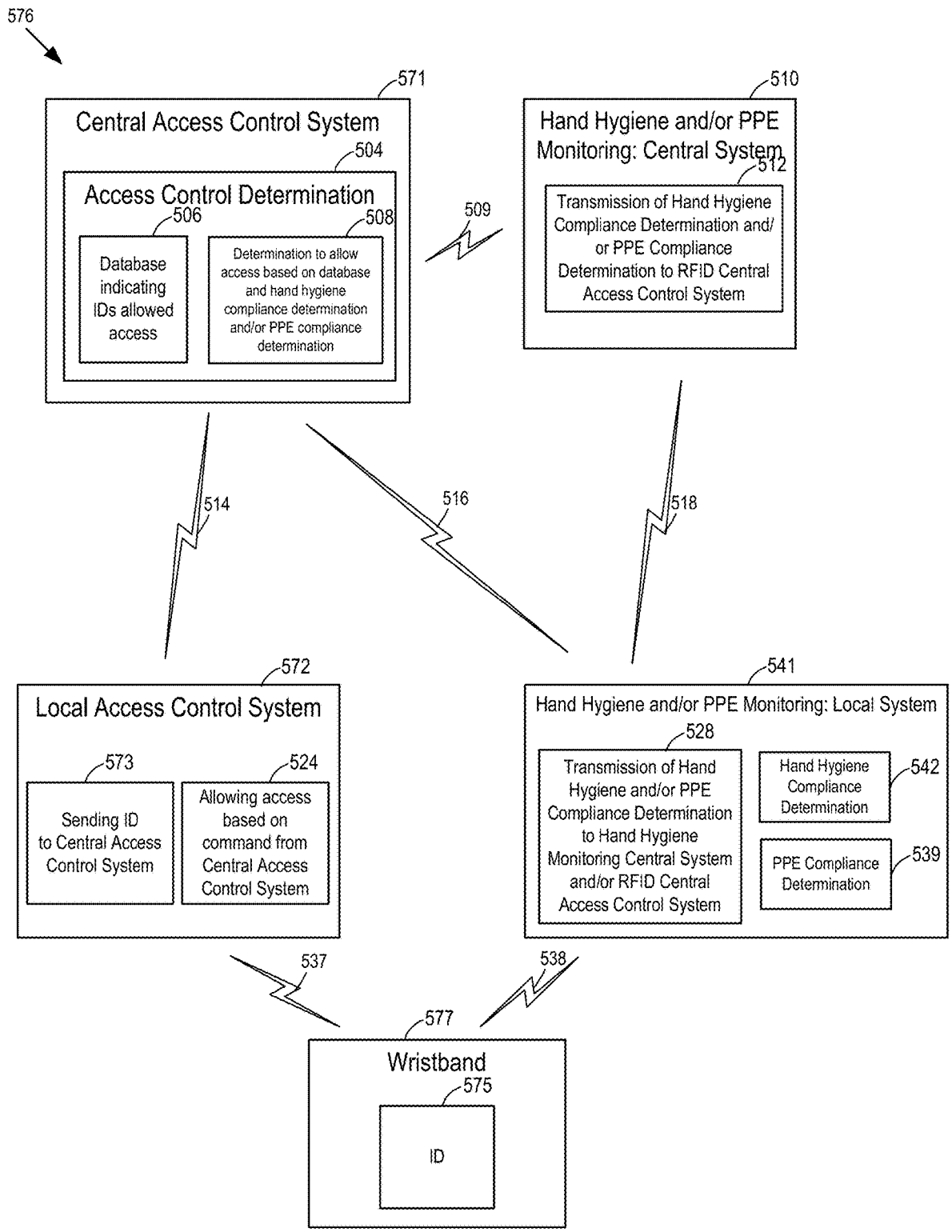
FIG. 5F is a sixth example block diagram of an access control system and a hand hygiene and/or PPE monitoring system, whereby the access control and hand hygiene and/or PPE communication communicate via the same wireless protocol, whereby access control is centrally determined and whereby the hand hygiene and/or PPE compliance determination is performed at the stationary controller.

FIG. 5F is a sixth example block diagram 576 of an access control system and a hand hygiene and/or PPE monitoring system, whereby the access control and hand hygiene communication and/or PPE communication communicate via the same wireless protocol, whereby access control is centrally determined and whereby the hand hygiene compliance determination and/or PPE compliance determination is performed at the hand hygiene and/or PPE monitoring: local system 541 (e.g., the stationary controller). FIG. 5F is similar to FIG. 5B except that the wristband 577 includes ID 575, and the central access control system 571 and local access control system 572 (with sending ID to central access control system 573) are not RFID based.

Figure 5G:
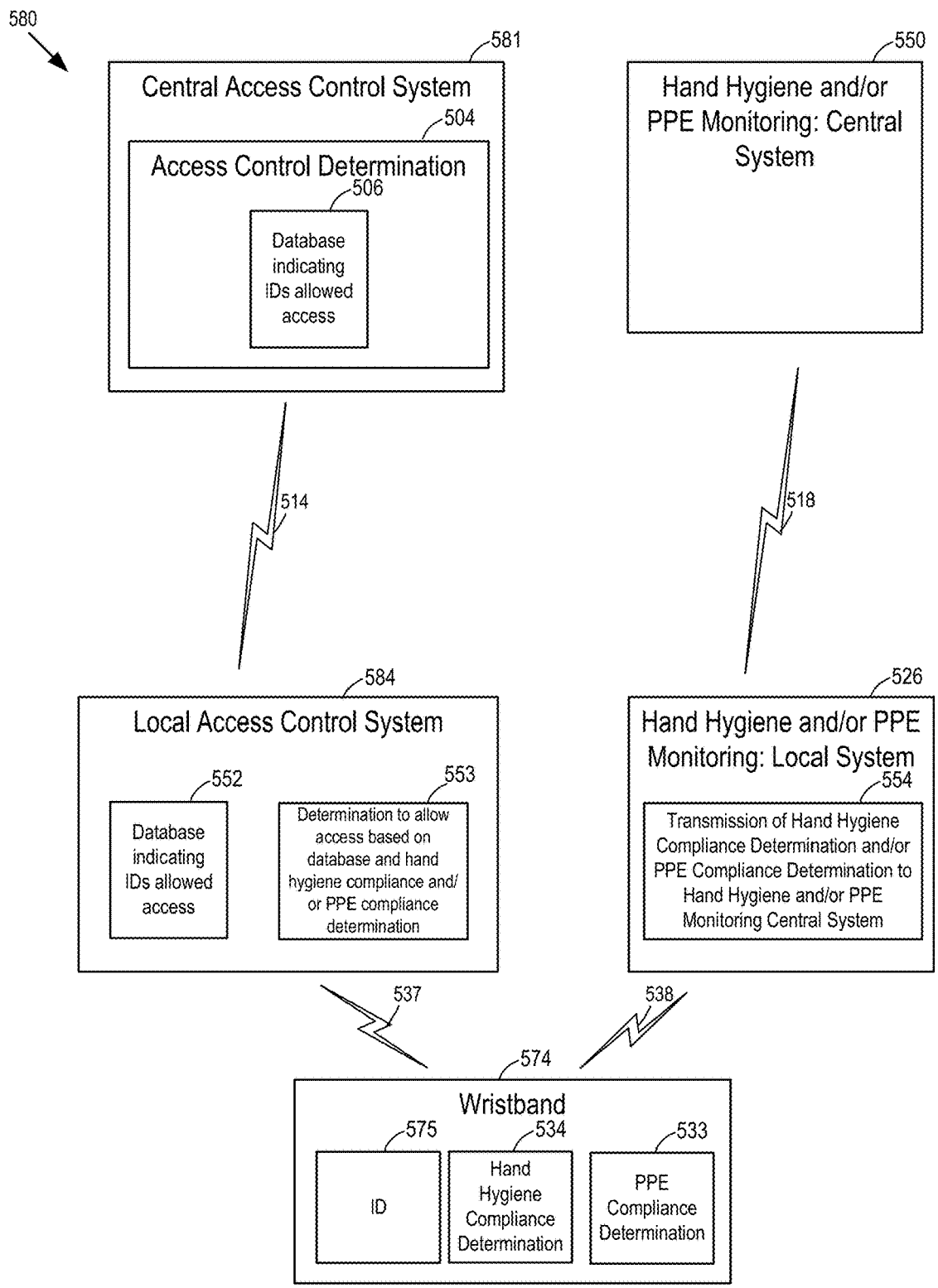
FIG. 5G is a seventh example block diagram of an access control system and a hand hygiene and/or PPE monitoring system, whereby the access control and hand hygiene and/or PPE communication communicate via the same wireless protocol, whereby access control is locally determined and whereby the hand hygiene and/or PPE compliance determination is performed at the wristband.

FIG. 5G is a seventh example block diagram 580 of an access control system and a hand hygiene and/or PPE monitoring system, whereby the access control and hand hygiene communication and/or PPE communication communicate via the same wireless protocol, whereby access control is locally determined and whereby the hand hygiene compliance determination and/or PPE compliance determination is performed at the wristband 574. FIG. 5G is similar to FIG. 5C except that the wristband 577 includes ID 575, and the central access control system 581 and local access control system 584 are not RFID based.

Figure 5H:
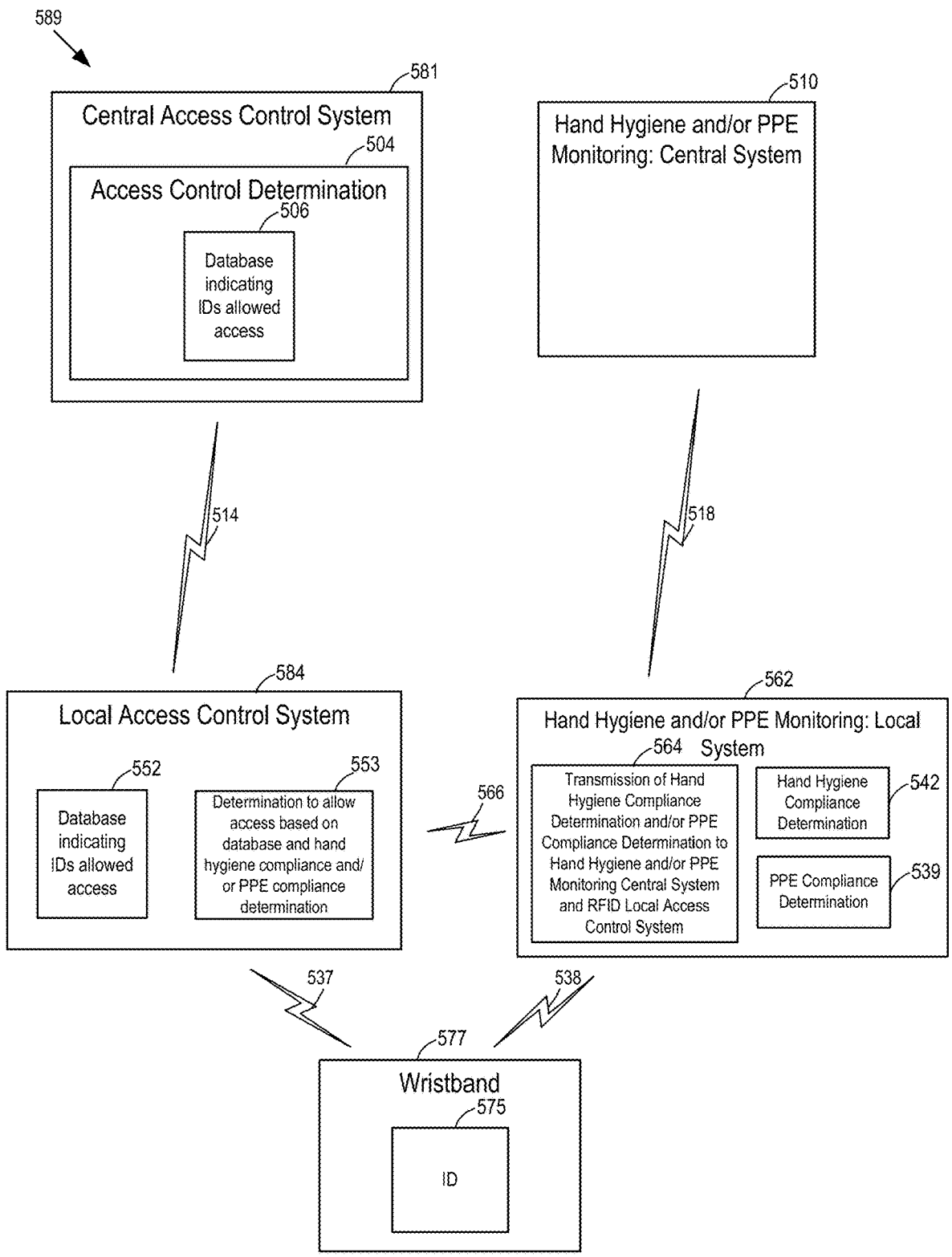
FIG. 5H is an eighth example block diagram of an access control system and a hand hygiene and/or PPE monitoring system, whereby the access control and hand hygiene and/or PPE communication communicate via the same wireless protocol, whereby access control is locally determined and whereby the hand hygiene and/or PPE compliance determination is performed at the stationary controller.

FIG. 5H is an eighth example block diagram 589 of an access control system and a hand hygiene and/or PPE monitoring system, whereby the access control and hand hygiene communication and/or PPE communication communicate via the same wireless protocol, whereby access control is locally determined and whereby the hand hygiene compliance determination and/or the PPE compliance determination is performed at the stationary controller.

Figure 5I:
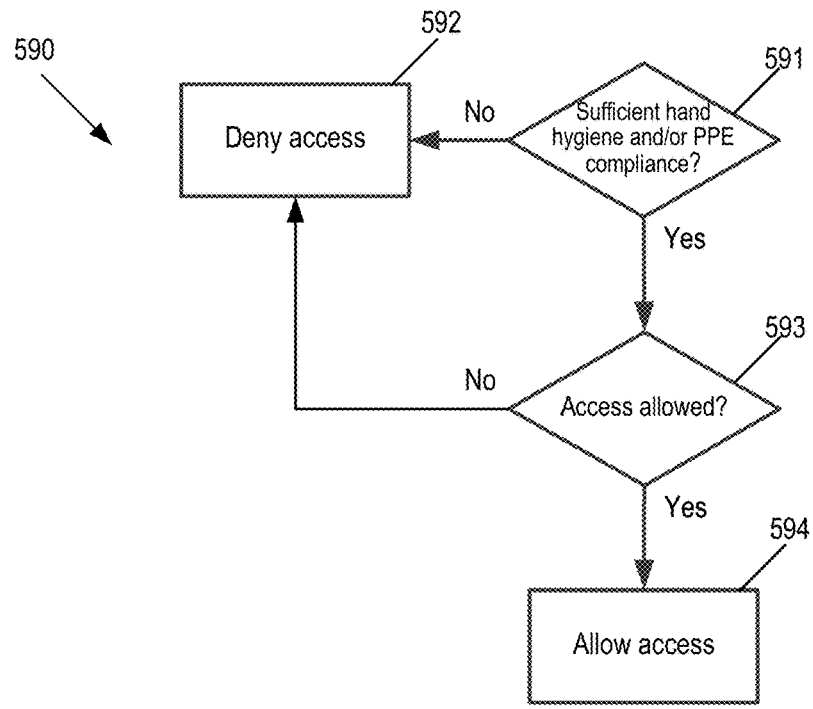
FIG. 5I illustrates a first flow chart of operation to determine access control, such as resident at the central or local RFID access control system.

FIG. 5I illustrates a first flow chart 590 of operation to determine access control, such as resident at the central or local RFID access control system. At 591, it is determined (either at the central or at the local access control system) whether there is sufficient or compliant hand hygiene and/or PPE compliance (e.g., whether there is sufficient hand hygiene; whether there is sufficient PPE compliance; or whether there is sufficient hand hygiene and PPE compliance). If not, at 592, access is denied. If so, it is determined (either at the central or at the local access control system) whether access should be allowed (e.g., the ID of the user indicates access is to be granted). If not, flow chart 590 loops back to 592 and access is denied. If so, at 594, access is granted (e.g., an electronic lock is unlocked).

Figure 5J:
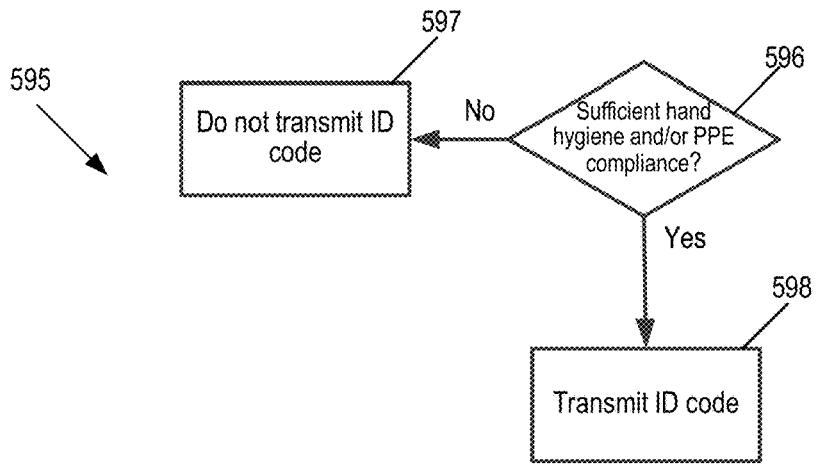
FIG. 5J illustrates a first flow chart of operation for the wristband to determine whether to send an ID to an access control system, such as a local access control system.

FIG. 5J illustrates a first flow chart 595 of operation for the wristband to determine whether to send an ID to an access control system, such as a local access control system. At 596, the wristband determines whether there is sufficient hand hygiene and/or PPE compliance (e.g., whether there is sufficient hand hygiene; whether there is sufficient PPE compliance; or whether there is sufficient hand hygiene and PPE compliance). If not, at 597, the wristband determines not to transmit the ID code to the local access control system (with the wristband effectively denying access to the user based on a failure to comply with hand hygiene). If so, at 598, the wristband determines to transmit the ID code to the local access control system (with the local access control system making the access determination).

As discussed above, dementia is a syndrome associated with a decline in memory or thinking skills that is severe enough to interfere with daily life, with Alzheimer's disease (AD) being the most common type of dementia. Dementia is not only devastating for the person with it, but also is overwhelming for their caregivers and families with substantial physical, emotional and financial pressures. Therefore, in one implementation, a proximity sensing and output generating device is disclosed that is cost-effective and includes user-friendly technology with accessible interventions that reduces the burden of dementia care.

In particular, the proximity sensing and output generating device comprises a smart voice-cueing device that reminds and guides dementia individuals to perform everyday tasks in real time. The tasks may comprise any type of human task, including various tasks related to hygiene and safety (e.g., toileting, cooking, and going outdoors). The proximity sensing and output generating device may be small (e.g., the size of a US quarter or smaller) and ultra-low-power.

The proximity sensing and output generating device may be placed in a variety of places for a variety of tasks, such as illustrated in FIG. 16D. As illustrated, the proximity sensing and output generating device may be placed in the bathroom (see proximity sensing and output generating device 1670 on door of bathroom for toileting), the kitchen (see proximity sensing and output generating device 1660 on drawer for preparing food), and the main entrance (see proximity sensing and output generating device 1680 on front door for going outdoors). As discussed further below, the proximity sensing and output generating device may include a housing or other type of mechanical structure that has a fastener configured to fasten the proximity sensing and output generating device to a part of the premises. The fastener may comprise an adhesive on the housing (e.g., glue) so that the proximity sensing and output generating device may be attached to a part of the premises. Alternatively, the fastener may comprise a connector, such as a screw with the housing including a hole through which the screw may traverse and connect to the part of the premises.

As discussed further below, various parts of the premises are contemplated at which the proximity sensing and output generating device may be attached. For example, doors (such as front doors, interior doors, cabinet doors, electrical appliance doors (e.g., refrigerator door), and the like), drawers, etc. may be parts of the premises to which the proximity sensing and output generating device may be attached. In this regard, doors and drawers are examples of movable portions of the premises. Other movable portions of the premises are contemplated.

In one implementation, the proximity sensing and output generating device includes various functionalities, such as motion sensing and sound detection. For example, the proximity sensing and output generating device, using the data from motion sensing and/or sound detection, determine a task (e.g., toileting, preparing food, going outdoors) is occurring, responsive thereto, generate an output. As one example, responsive to the motion sensor sensing movement of the front door, the controller of the proximity sensing and output generating device may determine that the person is going outdoors. As another example, responsive to the motion sensor sensing movement of an interior door, the controller of the proximity sensing and output generating device may determine that the person is going into a certain room of the premises (such as the bathroom). As still another example, responsive to the motion sensor sensing movement of the kitchen drawer, the controller of the proximity sensing and output generating device may determine that the person is preparing food. As another example, responsive to the motion sensor sensing movement in the kitchen, the proximity sensing and output generating device may access a heat sensor (e.g., an IR sensor) in order to determine whether the person has turned on the stove. If so, the proximity sensing and output generating device may generate an output to remind the person to turn off the stove after use. As yet another example, responsive to the sound sensor sensing the toilet flushing or running water from the faucet, the controller of the proximity sensing and output generating device may determine that the person is using the bathroom. Further, responsive to the proximity sensing and output generating device determining a task, the proximity sensing and output generating device may generate an output (e.g., a pre-recorded voice message to remind the person to perform an act related to the task). For example, responsive to determining that the person is going outdoors, the pre-recorded message may remind the person to carry cellular phones or location-monitoring devices before going outside. As another example, responsive to determining that the person is preparing food, the pre-recorded message may remind the person to wash hands prior to preparing food. As still another example, responsive to determining that the person is using the toilet, the pre-recorded message may remind the person to remember to flush the toilet, remember to wash hands after using the toilet, and/or remember to turn off the faucet after washing hands. Further, the analytics in the proximity sensing and output generating device recording daily activities of the dementia persons may also be used for health evaluation, as discussed further below. In this way, the proximity sensing and output generating device may provide interventions and prevent accidents, such as wandering outside or a water leak.

In one implementation, family members or caregivers may pre-record their personal messages for storage within the proximity sensing-output generating device. In one implementation, a button (not shown) on the housing of the proximity sensing-output generating device may be pressed, activating a microphone on the proximity sensing-output generating device in order to record the personal message. Alternatively, the message may be recorded onto another electronic device, such as a smartphone, and transferred to the proximity sensing-output generating device (such as via Bluetooth) and stored in the memory of the proximity sensing-output generating device (e.g., in microcontroller memory).

Figure 15A:
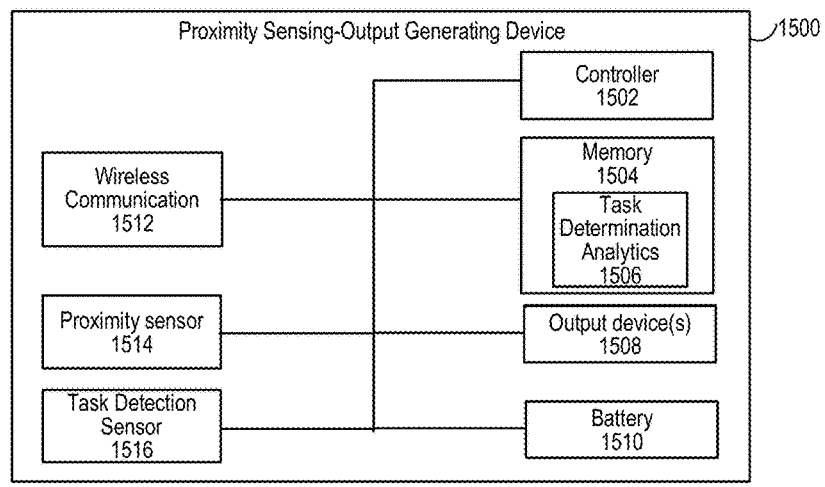
FIG. 15A is a first example block diagram of a proximity sensing-output generating device.

FIG. 15A is a first example block diagram of a proximity sensing-output generating device 1500. The proximity sensing-output generating device 1500 includes a controller 1502, a memory 1504, output device(s) 1508, a battery 1510, wireless communication 1512, proximity sensor 1514, and task detection sensor 1516. Though FIG. 15A depicts separate blocks for various elements, the blocks may be combined. For example, the controller 1502, memory 1504 and wireless communication 1512 may be combined, such as discussed below.

As discussed further below, proximity sensing-output generating device 1500 performs multiple functions, including sensing, using proximity sensor 1514, the proximity of a person to the proximity sensing-output generating device 1500; determining, using task detection sensor 1516 and task determination analytics 1506, whether a specific task is occurring; and outputting, using output device(s) 1508, an output in response to determining that the specific task is occurring. Proximity sensor 1514, which may generate proximity sensor output indicative of a person proximate to the proximity sensing-output generating device 1500, may take one of several forms. In one form, proximity sensor 1514 may comprise a micro vibration sensor, discussed further below. In another form, proximity sensor 1514 may comprise a sound sensor, such as a microphone. Further, various task detection sensors 1516 may be used, such as one or more motion sensors, one or more sound sensors, or the like. Further, the task determination analytics 1506 may determine whether a specific task (e.g., toileting, preparing food, going outdoors) is occurring.

Thus, in one implementation, the following components may be used: wireless transceiver, microcontroller, sensors (microphone, accelerometer & gyroscope) and speaker. Various low-power wireless protocols may be used, such as Bluetooth Low Energy (BLE), RFID and ZigBee. For small form factor and low power consumption, a system-on-chip (SOC) solution may be used that integrates wireless transceiver and microcontrollers. For instance, DA14580 (Dialog Semiconductor) is a BLE SOC chip configured for wearable applications. It has a fully integrated BLE radio transceiver and baseband processor (ARM Cortex-M0) and dissipates 4.9 mA in typical working condition with transceiver fully on, 0.5 mA with RF in "Near Field Mode" and 1.2 uA in extended sleep mode (ARM idle, RAM retention, RF off).

One motion sensor may comprise an ultralow power, 3-axis MEMS accelerometer that consumes less than 2 μA at a 100 Hz output data rate, and 270 nA when in motion triggered wake-up mode. Another motion sensor may comprise KXG07 (Kionix), which is a 6-axis accelerometer/gyroscope combination device that features a configurable 200 μA operating current in normal mode with wake up and back to sleep functions.

For the sound sensor, a microphone may be used. One type of microphone is ICS-40310 from InvenSense, which is a MEMS microphone with a combination of very low power consumption (~16 μA), high SNR, and a tiny package. With such a low power consumption, the microphone may always remain on.

For the speaker circuit, Texas Instrument TLV320AIC3 from and Cirrus Logic CS42L52 each integrate low-power stereo codec and mono class-D speaker amplifier. Since the voice cueing device is for use in small space, such as a bathroom, kitchen and front entrance, a speaker that delivers 80 dB (or ~10 mW) power may be satisfactory.

Figure 15B:
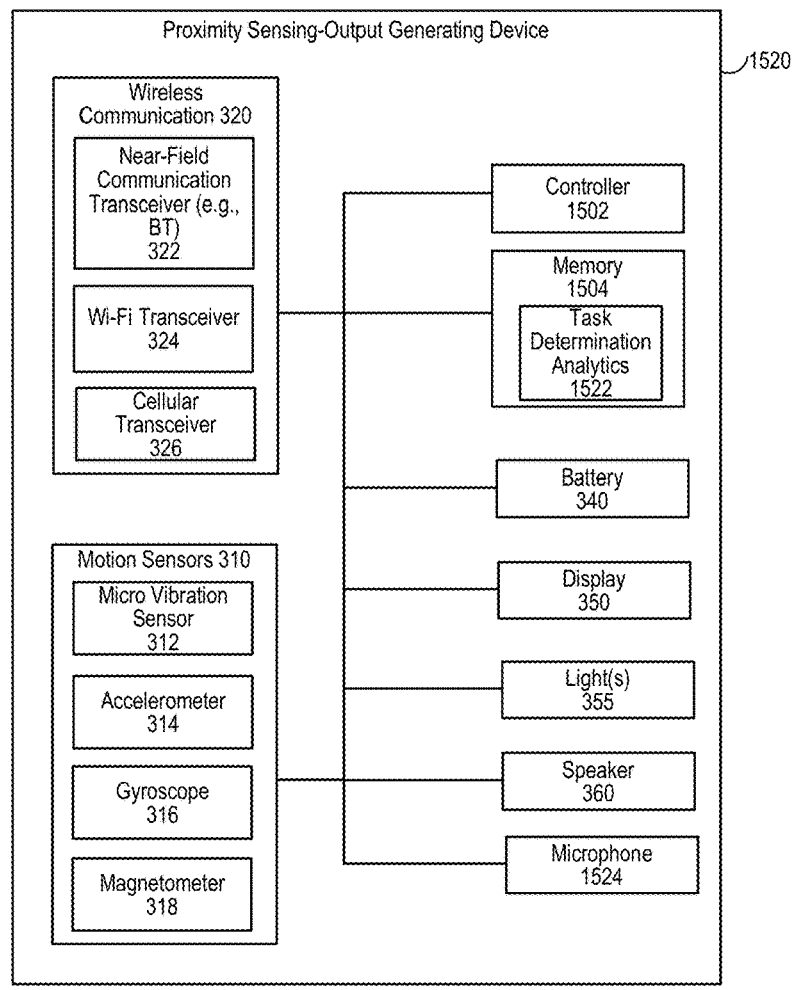
FIG. 15B is a second example block diagram of a proximity sensing-output generating device.

FIG. 15B is a second example block diagram of a proximity sensing-output generating device 1520. As illustrated, various type of wireless communication 320 may be used, as discussed above. Though three types of wireless communication 320 are illustrated, fewer or greater numbers of wireless communication protocols may be used. Further, one or more motion sensors 310 may be used. Though three types of motion sensors 310 are illustrated, fewer or greater numbers of motion sensors may be used. As discussed above, for power management purposes, micro-vibration sensor 312 may be always on and/or microphone 1524 may be always on, with its output used to awaken various other parts of the proximity sensing-output generating device 1520, such as wireless communication 320 and/or other motion sensors (such as accelerometer 313 and gyroscope 316). Finally, task determination analytics 1522 may be used to determine, based on sensor input, whether a specific task is being performed, as discussed above.

In one implementation, the speaker and microcontroller, both of which may consume mWs of power, will only work when the low-power sensor(s) (such as micro-vibration sensor 312, which operates on the order of μWs) detect a signal over the threshold level. For instance, for sound monitoring, since most of the time the output of the microphone 1524 is just background noise, instead of activating the microcontroller and analyze the sound all the time, proximity sensing-output generating device 1520 may include a hardware comparator to check the sound level, awakening the microcontroller only when the detected sound level is over a threshold.

Figure 15C:
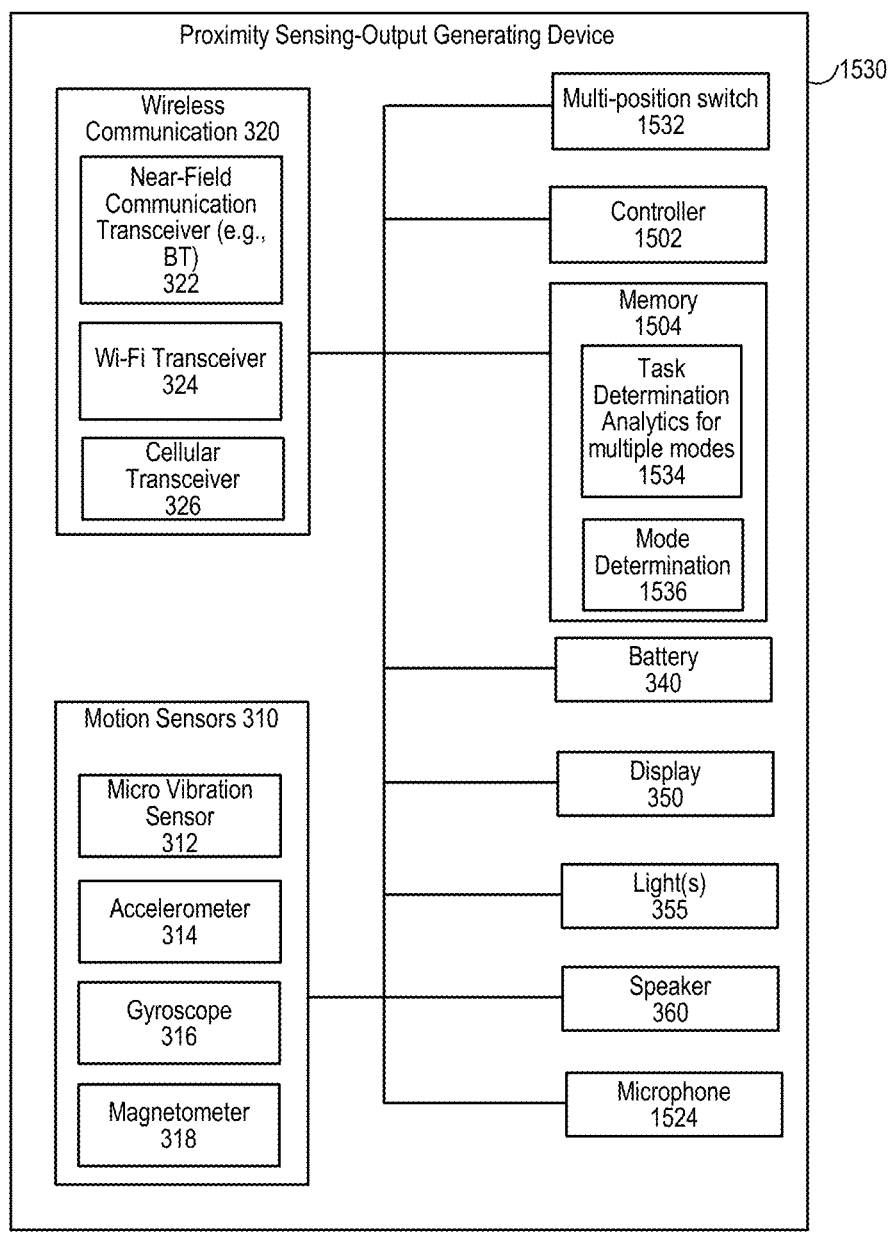
FIG. 15C is a third example block diagram of a proximity sensing-output generating device.

FIG. 15C is a third example block diagram of a proximity sensing-output generating device 1530. As discussed above, the proximity sensing-output generating device may be placed in different parts of the premises, such as the kitchen, the bathroom, the front door, etc. The tasks monitored and/or the output generated may be different depending on the placement, such as toileting for the bathroom, food preparation for the kitchen, and going outdoors for the front door. For example, with regard to the placement in the bathroom, the controller 1502, using the task determination analytics for multiple modes 1534, may determine that the placement is in the bathroom and whether a task specific to the bathroom (toilet flushing or faucet running water) is being performed based on comparing the sound generated by the microphone with pre-recorded sound(s). Further, responsive to determination that a specific task is occurring (e.g., using the toilet in the bathroom), the proximity sensing-output generating device 1530 may generate an output specific to the specific task (e.g., "remember to flush the toilet after use").

The proximity sensing-output generating device 1530 may determine the placement of the proximity sensing-output generating device 1530 in one of several ways. In one way, the proximity sensing-output generating device 1530 may include a multi-position switch 1532. The multi-position switch 1532 may be placed on an external housing of proximity sensing-output generating device 1530. The multi-position switch 1532 may have two positions, three positions, or more. The different positions of the multi-position switch 1532 may be correlated to different placements. For example, when the multi-position switch 1532 is set to the first position, this is indicative to controller 1502, using mode determination 1536, that the proximity sensing-output generating device 1530 is positioned in the kitchen. Responsive to determining that the proximity sensing-output generating device 1530 is positioned in the kitchen, the controller 1502 may determine the task(s) for monitoring and the output(s) to generate. When the multi-position switch 1532 is set to the second position, this is indicative to controller 1502, using mode determination 1536, that the proximity sensing-output generating device 1530 is positioned in the bathroom. When the multi-position switch 1532 is set to the third position, this is indicative to controller 1502, using mode determination 1536, that the proximity sensing-output generating device 1530 is positioned on the front door. The example positions of the multi-position switch 1532 are merely for illustration purposes. In another way, the proximity sensing-output generating device 1530 may receive a communication via wireless communication 320 indicative of the placement of the proximity sensing-output generating device 1530. The communication may be sent via the Internet, such as via electronic device 1630, discussed further below.

Figure 16A:
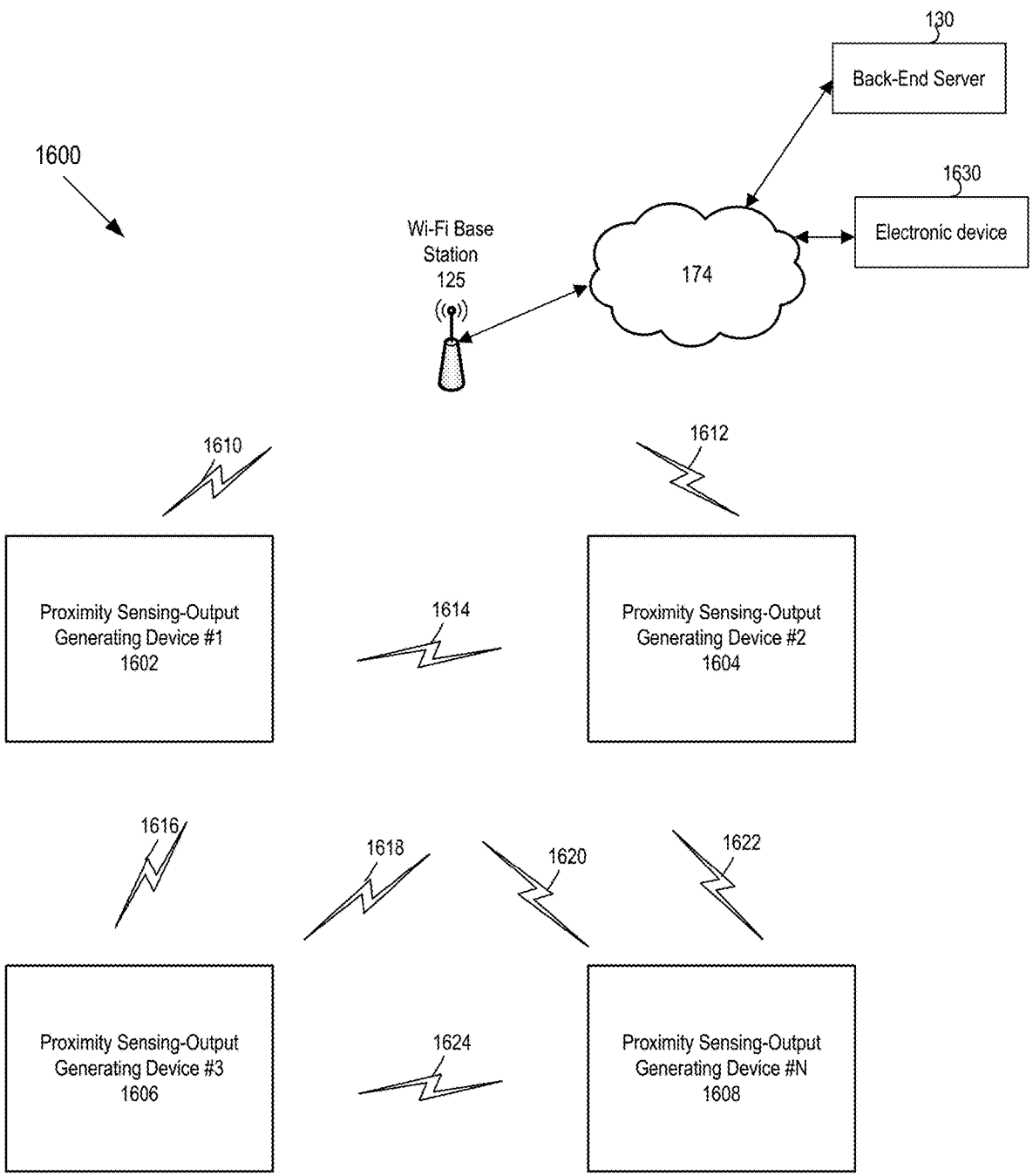
FIG. 16A is a first example block diagram of a system that uses a plurality of a proximity sensing-output generating devices.

FIG. 16A is a first example block diagram of a system 1600 that uses a plurality of a proximity sensing-output generating devices, including proximity sensing-output generating device #1 (1602), proximity sensing-output generating device #2 (1604), proximity sensing-output generating device #3 (1606), and proximity sensing-output generating device #N (1608). Any number of proximity sensing-output generating devices may be used and may be placed in various parts of the premises. As discussed above, the proximity sensing-output generating device may include wireless communication functionality. In that regard, the proximity sensing-output generating devices may communicate wirelessly amongst themselves or with base station 125. For example, proximity sensing-output generating device #1 (1602) may communicate wirelessly via 1610 with base station 125, via 1614 with proximity sensing-output generating device #2 (1604), via 1616 with proximity sensing-output generating device #3 (1606), and via 1620 with proximity sensing-output generating device #4 (1608). Similarly, proximity sensing-output generating device #2 (1604) may communication wirelessly via 1612 with base station 125, via 1618 with proximity sensing-output generating device #3 (1606) and via 1622 with proximity sensing-output generating device #4 (1608). The wireless communications illustrated in FIGS. 16A-B are merely for illustration purposes.

As discussed above, the proximity sensing-output generating device that monitors the task may be the same proximity sensing-output generating device that generates the output (e.g., the vocal reminder). Alternatively, or in addition, the proximity sensing-output generating device may send a communication to an external device (such as another proximity sensing-output generating device located in the same premises and/or an electronic device remote from the premises). As one example, responsive to determining that the person has likely left the part of the premises where the task is being monitoring (e.g., the water in the faucet is continuing to run, likely meaning that the person left the bathroom and is in another part of the premises), the proximity sensing-output generating device may send a communication, such as a wireless communication, to another proximity sensing-output generating device in order for the another proximity sensing-output generating device to generate an output (e.g., "please return to the bathroom to turn off the water in the faucet). As another example, the proximity sensing-output generating device may monitor the front door of the premises. Responsive to determining that a person has exited the premises, the proximity sensing-output generating device may send (e.g., via the Internet or a cellular communication) an alert to an electronic device (e.g., a smartphone) external to the premises, with the alert indicating: "the resident has left the premises". In this way, the smart voice reminder device sends real-time notification to mobile electronic devices and can be easily integrated into smart home network through Bluetooth low energy (BLE) wireless communication.

Figure 16B:
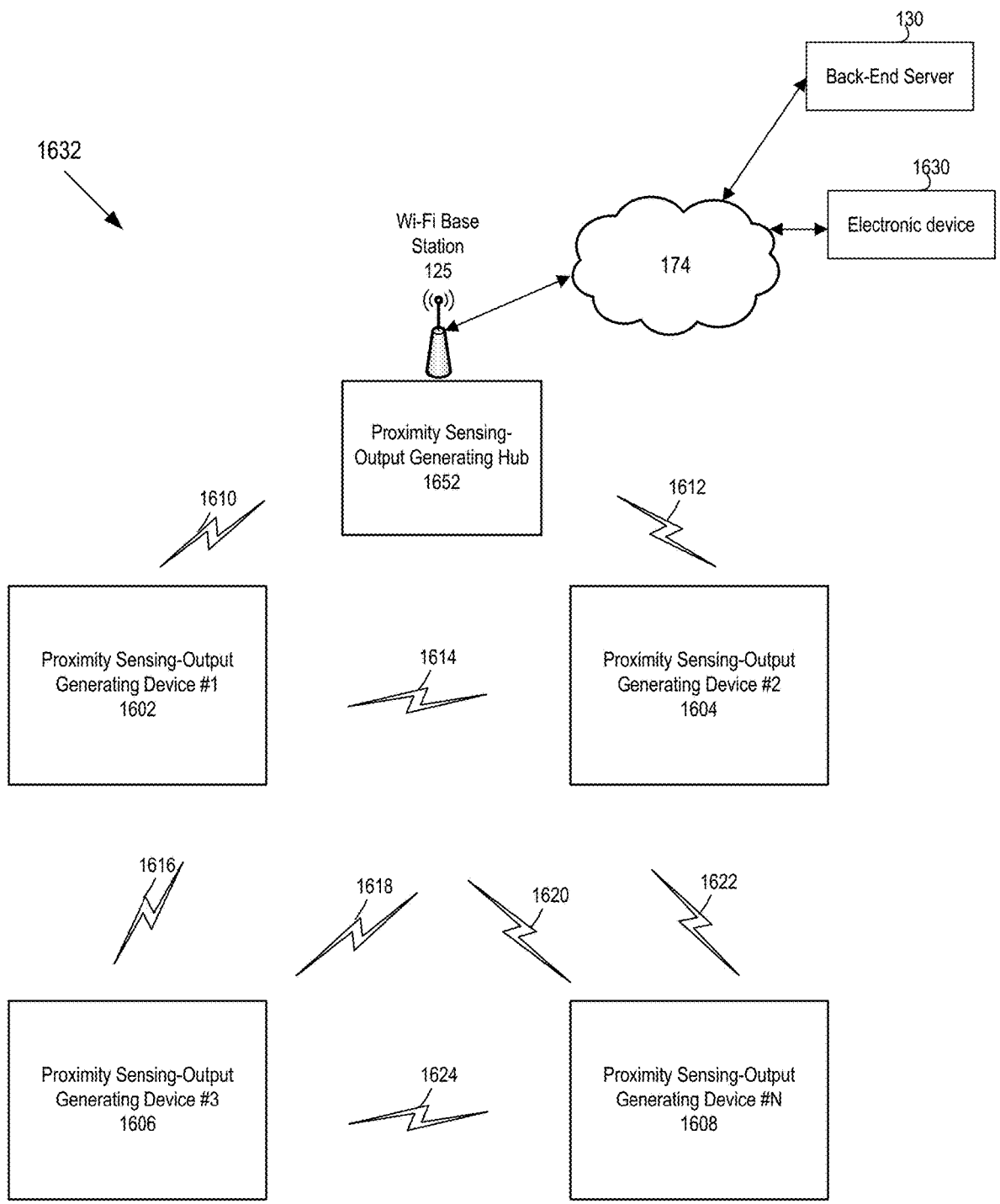
FIG. 16B is a second example block diagram of a system that uses a plurality of a proximity sensing-output generating devices.

FIG. 16B is a second example block diagram of a system 1632 that uses a plurality of a proximity sensing-output generating devices. FIG. 16B is similar to FIG. 16A, except with the addition of proximity sensing-output generating hub 1652, which may coordinate communications amongst the different proximity sensing-output generating devices on the premises. For example, the proximity sensing-output generating hub 1652 may route communications received from one proximity sensing-output generating device to another proximity sensing-output generating device on the premises. Alternatively, or in addition, the proximity sensing-output generating hub 1652 may route communications received from one proximity sensing-output generating device to electronic device 1630, which is external to the premises (e.g., a smartphone of a family member of the person living on the premises), or to back-end server 130, which may record various tasks performed. For example, one proximity sensing-output generating device may be positioned in the bathroom (e.g., the door into the bathroom) and may record bathroom habits. This information may be sent to back-end server 130 for recording and potential subsequent analysis. As another example, one proximity sensing-output generating device may be positioned in the kitchen (e.g., the drawer for the cutlery, the cabinet door for the dishes, the refrigerator door) and may record eating habits. Similarly, this information may be sent to back-end server 130 for recording and potential subsequent analysis.

Figure 16C:
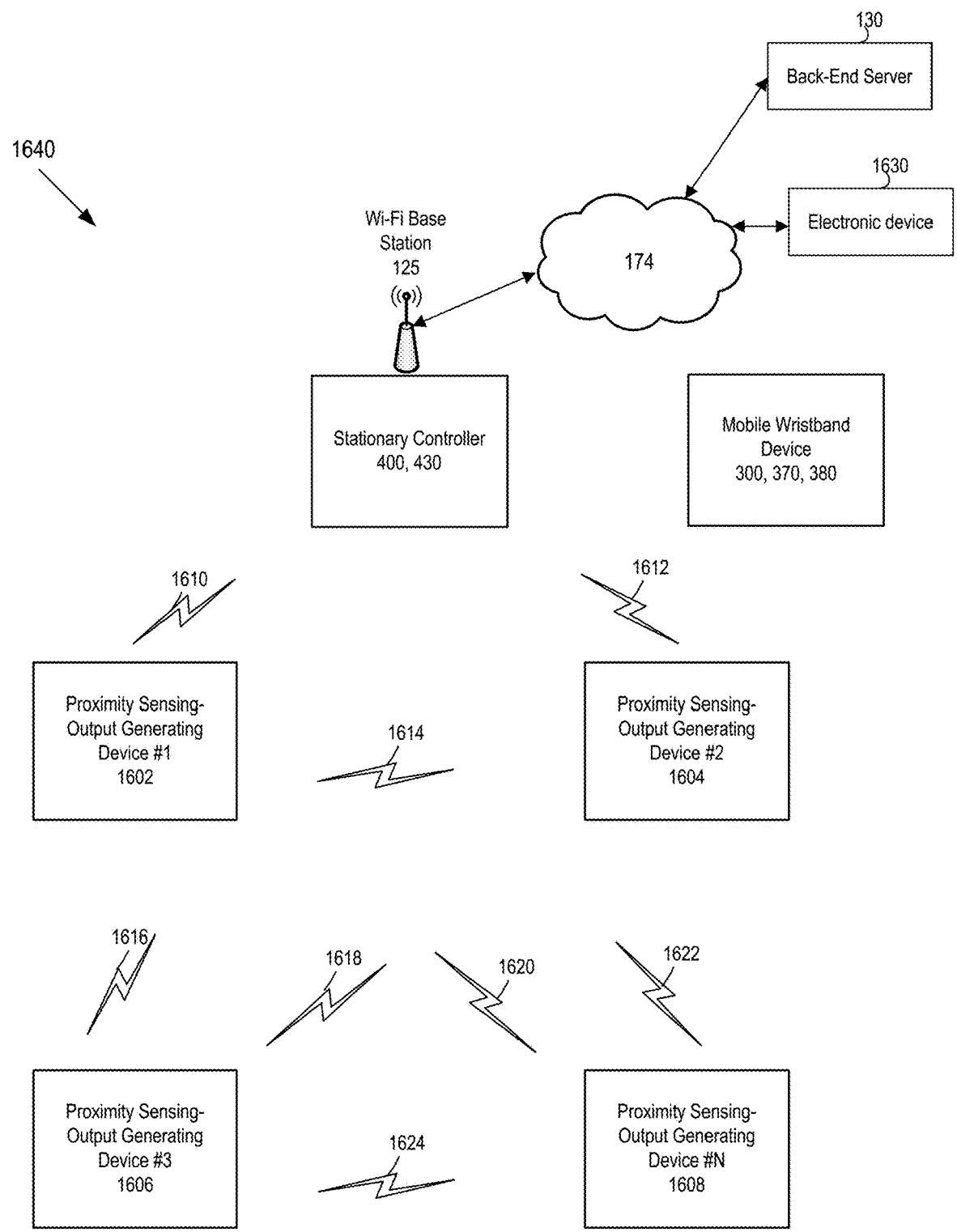
FIG. 16C is a third example block diagram of a system that uses a plurality of a proximity sensing-output generating devices, a stationary controller and a mobile wristband device.
Figure 16D:
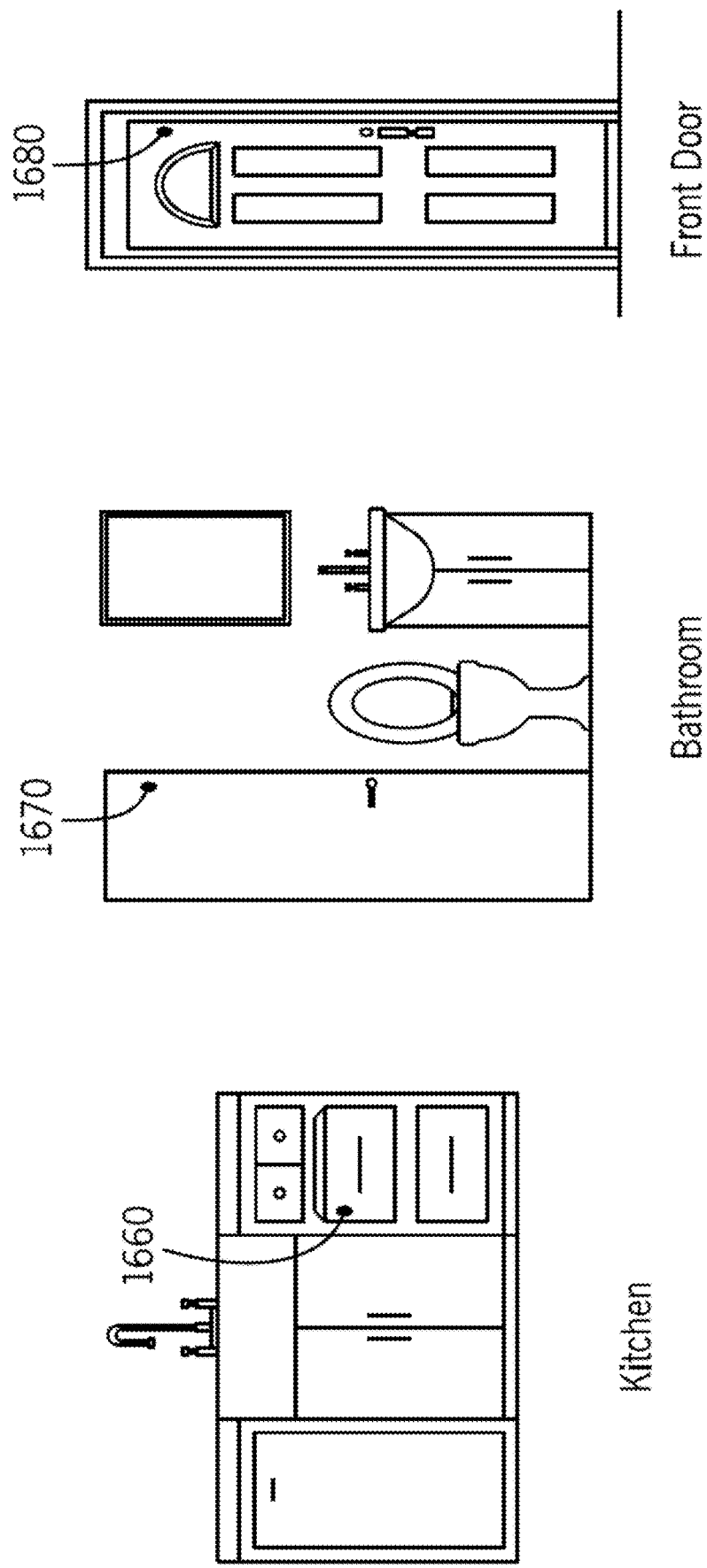
FIG. 16D are illustrations of locations in a premises where the proximity sensing-output generating device may be placed.

FIG. 16C is a third example block diagram of a system 1640 that uses a plurality of a proximity sensing-output generating devices 1602, 1604, 1606, 1608, a stationary controller 400, 430 and a mobile wristband device 300, 370, 380. For background, a healthcare provider may have 5 moments, phases or opportunities with a patient: (1) before touching a patient; (2) before clean/aseptic procedure; (3) after body fluid exposure risk; (4) after touching the patient; and (5) after touching the patient surrounds. As discussed above, the stationary controller 400, 430 may identify when the healthcare provider has entered the room (such as when the RSSI signal is greater than a predetermined amount for a certain period of time). Similarly, the stationary controller 400, 430 may determine when the healthcare provider is exiting the room (e.g., after the initial identification of the healthcare provider, the stationary controller may continue to monitor the RSSI signal. When the RSSI signal increases again (presumably when the healthcare provider has finished with the patient and moves toward the door), the stationary controller may determine that the healthcare provider is exiting the room. In this way, the stationary controller may determine moments (1), (4) and (5).

Alternatively, or in addition, the proximity sensing-output generating devices 1602, 1604, 1606, 1608 may be installed at the door, thereby indicating whether the door is first being opened (so that the entrance of the healthcare provider may be identified) or whether the door is being opened again (so that the exit of the healthcare provider may be identified). In one implementation, the proximity sensing-output generating devices 1602, 1604, 1606, 1608 may be placed in a hospital room in order to determine moments (2) and/or (3). For example, the proximity sensing-output generating devices 1602, 1604, 1606, 1608 may be positioned on a drawer or a cabinet, such as a central line cart, a drawer containing medical supplies, and/or a medicine cabinet. Responsive to the proximity sensing-output generating devices 1602, 1604, 1606, 1608 sensing the drawer opening, it may be presumed that the healthcare provider is performing a procedure, such as performing a clean/aseptic procedure. In this regard, the proximity sensing-output generating devices 1602, 1604, 1606, 1608 may identify moment (2), and may generate an output (e.g., "remember to wash hands before the aseptic procedure").

Alternatively, or in addition, the proximity sensing-output generating devices 1602, 1604, 1606, 1608 may send a communication to one or both of the stationary controller 400, 430 or the wristband 300, 370, 380, with the communication indicative that the proximity sensing-output generating devices 1602, 1604, 1606, 1608 identified a drawer opening. Responsive to the communication, one or both of the stationary controller 400, 430 or wristband 300, 370, 380 may generate an output. In a first implementation, the output generated by one or both of the stationary controller 400, 430 or wristband 300, 370, 380 may be independent of the status of the person and may remind the healthcare provider to wash hands before the aseptic procedure. In a second implementation, the output generated by one or both of the stationary controller 400, 430 or wristband 300, 370, 380 may be dependent on the status of the person. As one example, if the healthcare worker is designated as a "trainee" (e.g., based on an indicator that is stored in the memory in the wristband 300, 370, 380), the output reminds the healthcare provider to wash hands before the aseptic procedure. In particular, the controller 302 may access memory 304 for an indication of the status of the healthcare worker. Responsive to the controller determining that the indication of the status is that of a trainee, the controller 302 may cause an output from the wristband 300, 370, 380. The output may be indicative to the healthcare worker as part of training for the HH opportunity (e.g., aural output: "take soap from the dispenser") and/or for the PPE opportunity (e.g., aural output responsive to detecting entry into a patient area: "first put on mask and then put on gloves"). In this regard, responsive to the communication between the wristband and the stationary controller identifying the HH opportunity and/or the PPE opportunity (and potentially before a determination as to whether there is compliance with the HH opportunity and/or the PPE opportunity), the wristband may generate the output. As another example, if the healthcare worker is designated as an "employee" (e.g., not a "trainee"), the stationary controller 400, 430 or wristband 300, 370, 380 may determine not to output the reminder. In this way, the stationary controller 400, 430 and/or the mobile wristband 300, 370, 380 may work in combination with the proximity sensing-output generating devices 1602, 1604, 1606, 1608 to remind the healthcare worker about hygiene protocols.

In this way, the proximity sensing-output generating devices 1602, 1604, 1606, 1608 may be installed in various parts of the patient's room, such as at the door into the patient's room, at the medicine cabinet, and/or the drawers inside a patient's room. For instance, when healthcare providers open the medicine cabinet, or a drawer of a central line cart (e.g. before an aseptic task), they will be reminded for hand hygiene. In this way, one may capture 4 out of 5 moments/opportunities for hand hygiene. In addition, a reminder device installed on the door of the patient's room will also allow one to know better if someone is leaving the room or entering the room (being alternative or complementary to RSSI detection).

Figure 17A:
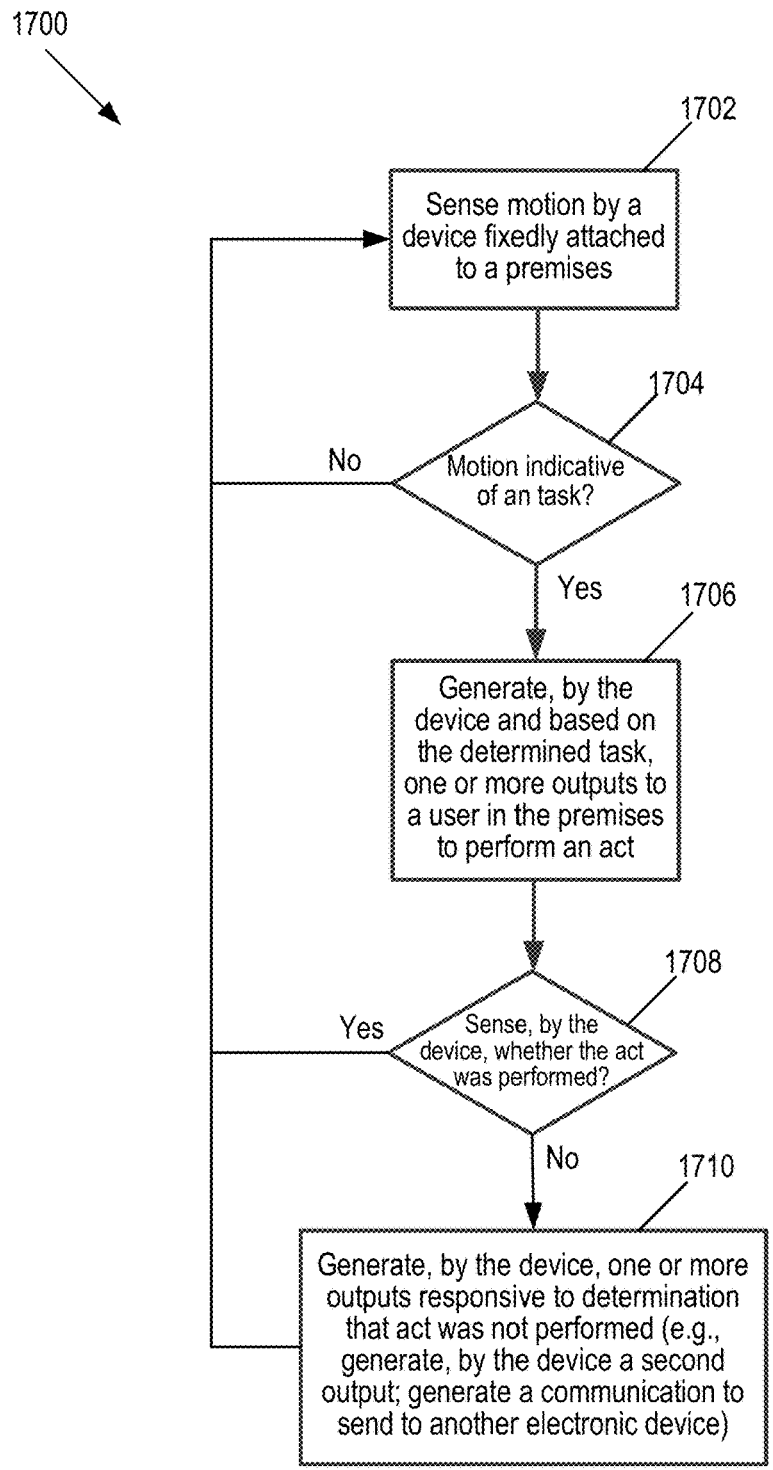
FIG. 17A is a first flow chart of operation of the proximity sensing-output generating device.

FIG. 17A is a first flow chart 1700 of operation of the proximity sensing-output generating device. At 1702, the proximity sensing-output generating device, fixedly attached to a part of the premises, may sense motion. In this way, motion sensing may begin the process of determining whether a task is being performed. Alternatively, the proximity sensing-output generating device may begin the process of determining whether a task is being performed by analyzing sound. For example, the proximity sensing-output generating device may use a microphone to generate sound data to determine whether the sound data is indicative of a person entering the bathroom (which may indicate that the person is preparing to use the toilet and should be reminded to flush the toilet and/or wash hands). As another example, the proximity sensing-output generating device may use a microphone to generate sound data to determine whether the sound data is indicative of a toilet flushing (which may indicate that the person has already used the toilet and should be reminded to wash hands). In particular, in the instance of the proximity sensing-output generating device determining, based on the sound data, that the toilet has flushed, an output may be generated, such as by the proximity sensing-output generating device and/or by another electronic device, such as a wristband (such as wristband 300, 370, 380) which may output the reminder as well. At 1704, the proximity sensing-output generating device may determine whether the sensed motion is indicative of a task, such as going to the toilet, preparing food, going outdoors, or the like. If so, at 1706, the proximity sensing-output generating device may generate an output based on the determined task, with the output indicative of performing an act (e.g., "remember to flush the toilet"; "remember to wash your hands"; "remember to turn off the water in the faucet"; "remember to take your cellphone and ID"). At 1708, the proximity sensing-output generating device may sense whether the act was performed. For example, responsive to outputting a reminder to flush the toilet, the proximity sensing-output generating device, analyzing sound data generated by a sound sensor, may determine whether the toilet was flushed. As another example, responsive to outputting a reminder to wash hands and turn off the faucet, the proximity sensing-output generating device, analyzing sound data generated by a sound sensor, may determine first whether the faucet was turned on and subsequently whether the faucet was turned off. At 1710, responsive to sensing that the act was not performed, generating one or more outputs. For example, responsive to determining that the faucet was not turned off, the proximity sensing-output generating device located in the bathroom may generate an output reminding the person to turn off the faucet. Alternatively, or in addition, the proximity sensing-output generating device may send a communication so that another proximity sensing-output generating device, such as located in the kitchen or in the main entranceway, may output the reminder to the person to turn off the faucet.

Figure 17B:
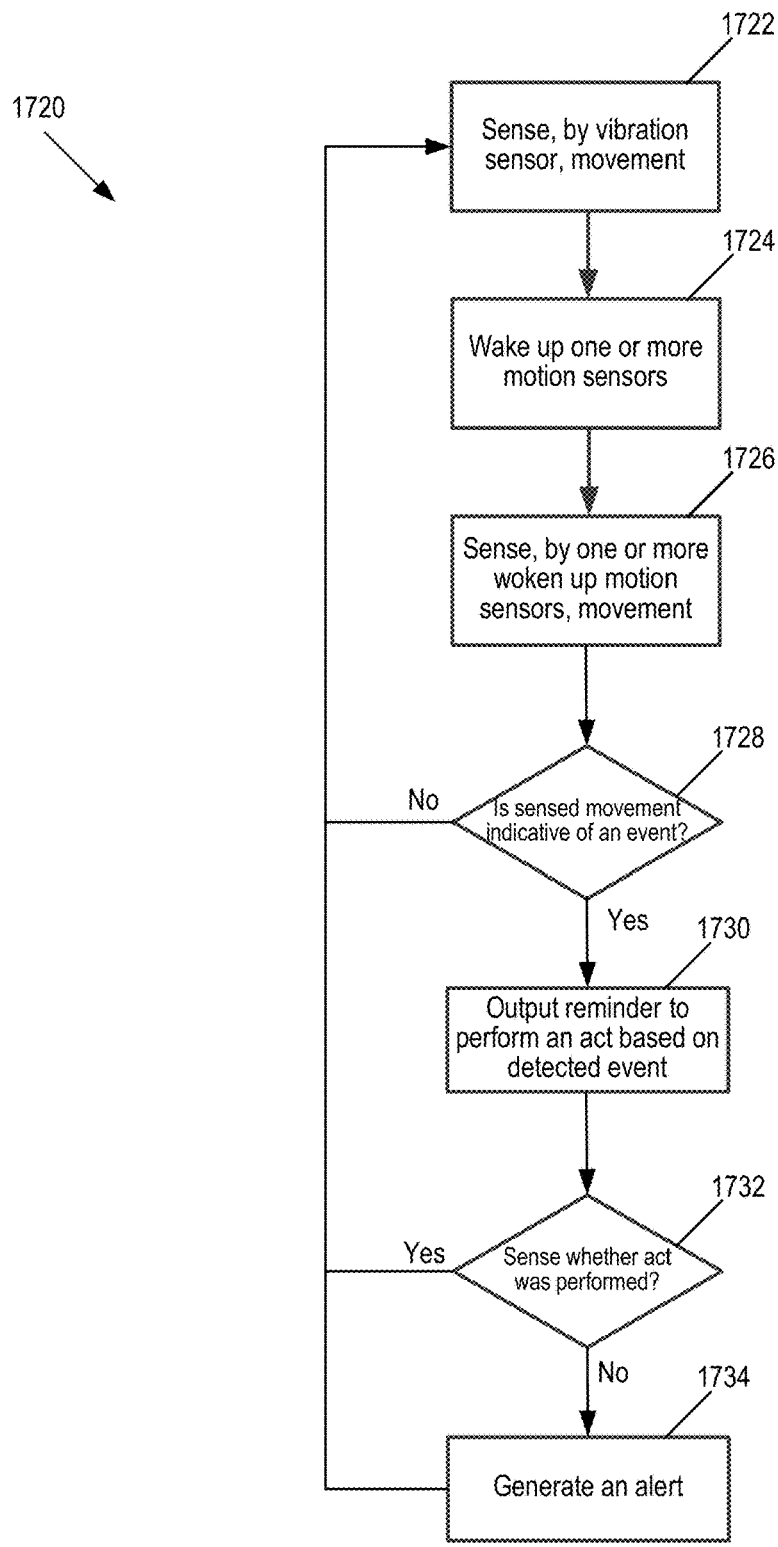
FIG. 17B is a second flow chart of operation of the proximity sensing-output generating device.

FIG. 17B is a second flow chart 1710 of operation of the proximity sensing-output generating device. At 1722, a vibration sensor of the proximity sensing-output generating device may sense movement. Responsive to sensing the vibration, at 1724, one or more of the motion sensors in the proximity sensing-output generating device may be activated (e.g., transitioned from sleep mode to normal mode). At 1726, the activated one or more motion sensors may sense movement. At 1728, the proximity sensing-output generating device may determine whether the sensed movement is indicative of a task. If so, at 1730, the proximity sensing-output generating device may output a reminder to perform an act based on the detected task. At 1732, the proximity sensing-output generating device may determine whether the act was performed. If not, at 1734, the proximity sensing-output generating device (and/or another electronic device) may generate an alert.

Figure 18A:
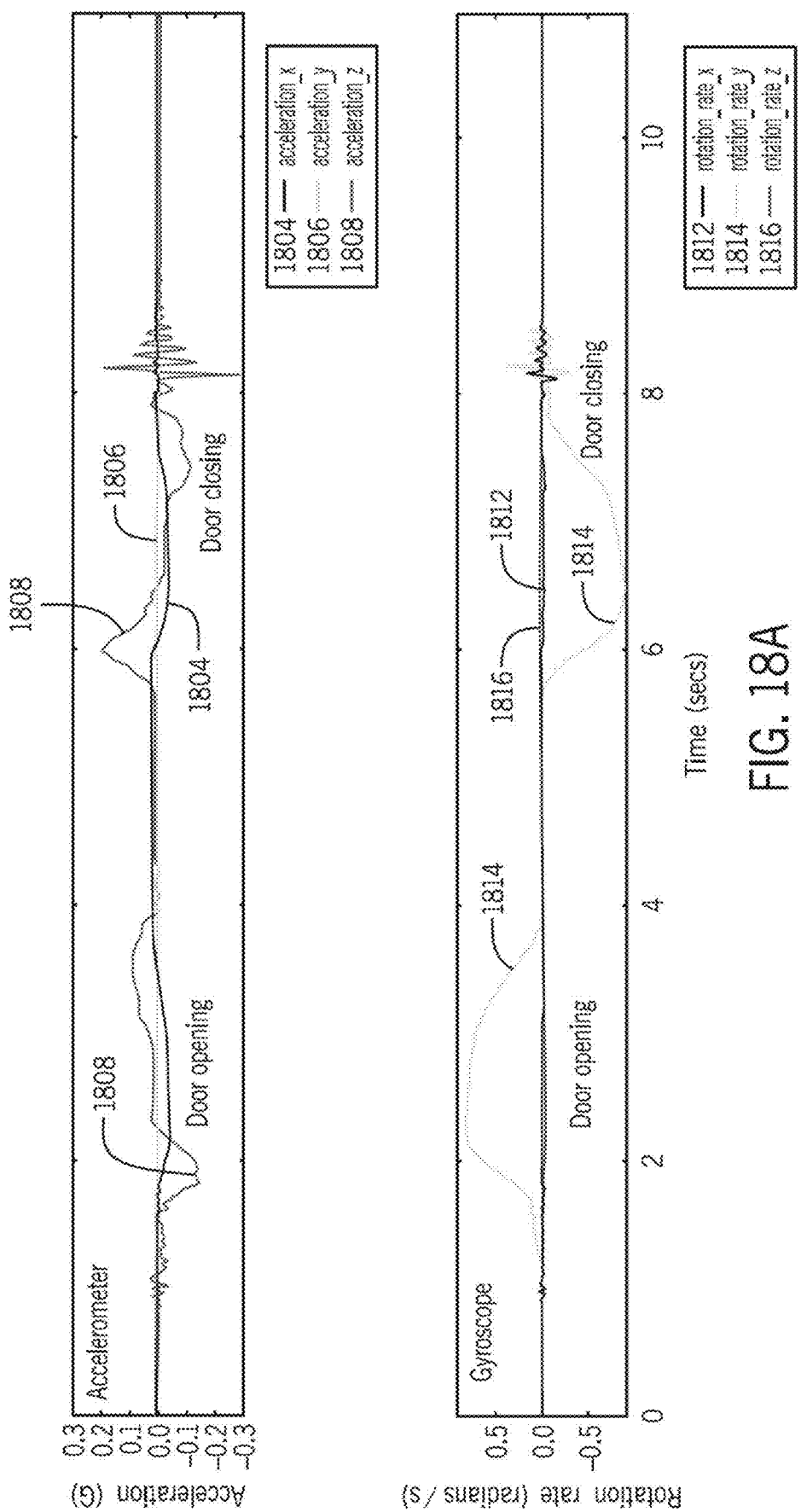
FIG. 18A are graphs of outputs of motion sensors, including an accelerometer and a gyroscope, for a door opening and a door closing.
Figure 18B:
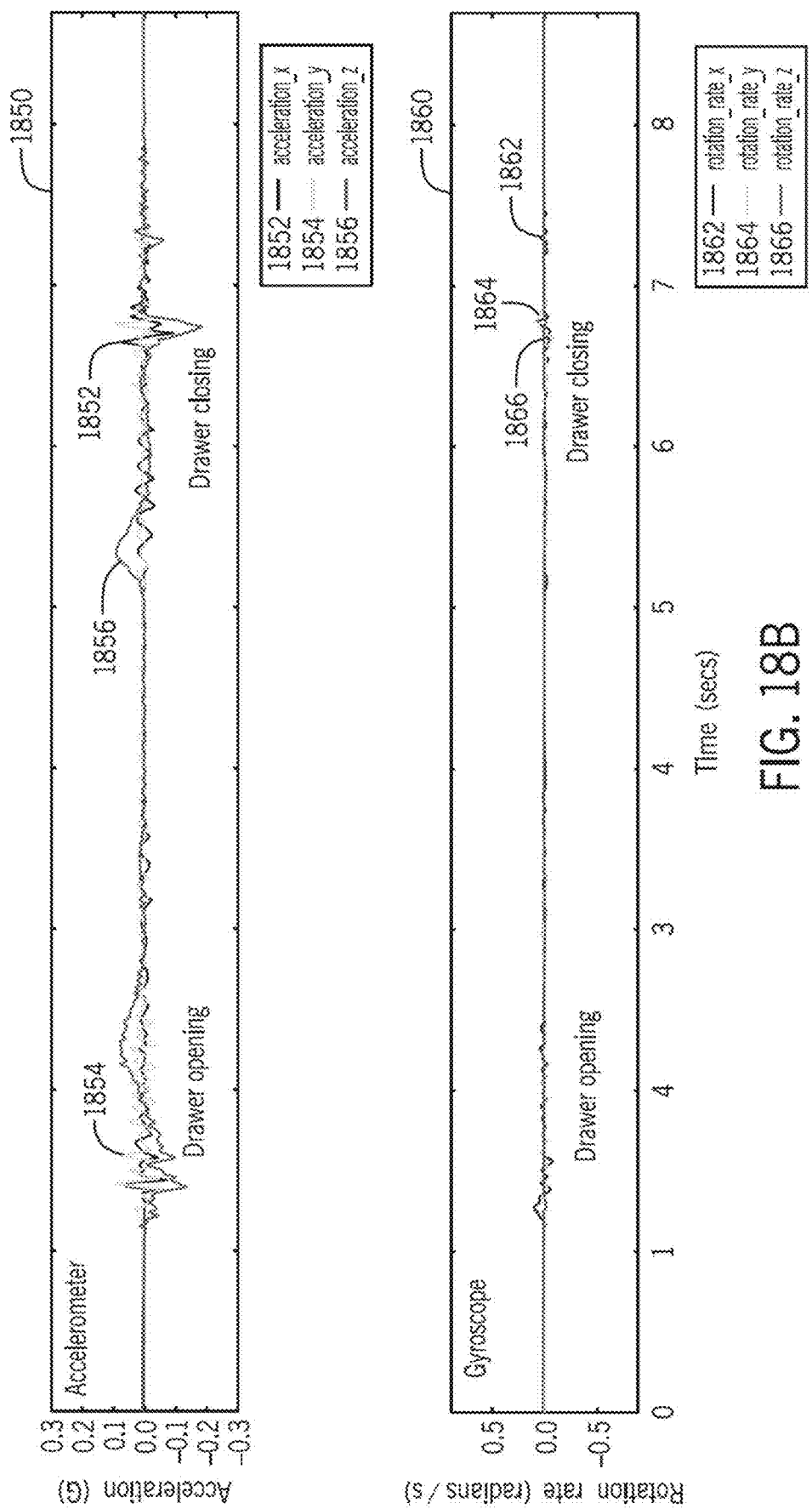
FIG. 18B are graphs of outputs of motion sensors, including an accelerometer and a gyroscope, for a drawer opening and a drawer closing.

FIG. 18A are graphs 1802, 1810 of outputs of motion sensors, including an accelerometer and a gyroscope, for a door opening and a door closing. Specifically, 1804 illustrates acceleration in the x direction, 1806 illustrates acceleration in the y direction, and 1808 illustrates acceleration in the z direction. Further, 1812 illustrates rotation rate in the x direction, 1814 illustrates rotation rate in the y direction, and 1816 illustrates rotation rate in the z direction. FIG. 18B are graphs 1850, 1860 of outputs of motion sensors, including an accelerometer and a gyroscope, for a drawer opening and a drawer closing. Specifically, 1852 illustrates acceleration in the x direction, 1854 illustrates acceleration in the y direction, and 1856 illustrates acceleration in the z direction. Further, 1862 illustrates rotation rate in the x direction, 1864 illustrates rotation rate in the y direction, and 1866 illustrates rotation rate in the z direction. For the device to send the correct voice reminder, the corresponding events may be detected. In one implementation, one or more motion sensors and/or one or more sound sensors may detect the following events: front door opening, drawer opening, running water and toilet flushing. Detection of other events is contemplated.

For example, analysis of motion sensor data may be used to determine whether a door or drawer has been opened. For example, opening a front door is an indication of going outside. As another example, opening a kitchen drawer (e.g., to get flatware) may indicate that the person has finished cooking and is preparing to eat a meal. Therefore, monitoring the events of door/drawer opening may be used to trigger outputs, such as voice messages including as "carrying your cell phone" or "wash your hand before meal and shut off fire/water". As discussed above, one or more motion sensors may be used. For example, an accelerometer may provide information on linear acceleration whereas gyroscope may measure the angular velocity rate (e.g., the rotational rate). The linear and angular motion recorded by the accelerometer and gyroscope along x-, y- and z-axis are illustrated in FIG. 18A. The waveforms indicate several aspects. For example, FIG. 18A indicates that the door opening and closing have clear acceleration on the two axes (e.g., x and z) on the rotation plane (detected by accelerometer) and angular velocity along 1 axis (detected by the gyroscope). FIG. 18B indicates that drawer movement causes linear acceleration mainly in one axis (z) and no detectable rotation. Further, FIGS. 18A-B indicate that opening and closing causes different acceleration and rotation directions. Thus, as illustrated in FIGS. 18A-B, the movement data for the door and the drawer have unique characteristics, are distinguishable, and what may be used by the proximity sensing-output generating device to identify a direction of movement (e.g., opening or closing).

Figure 19:
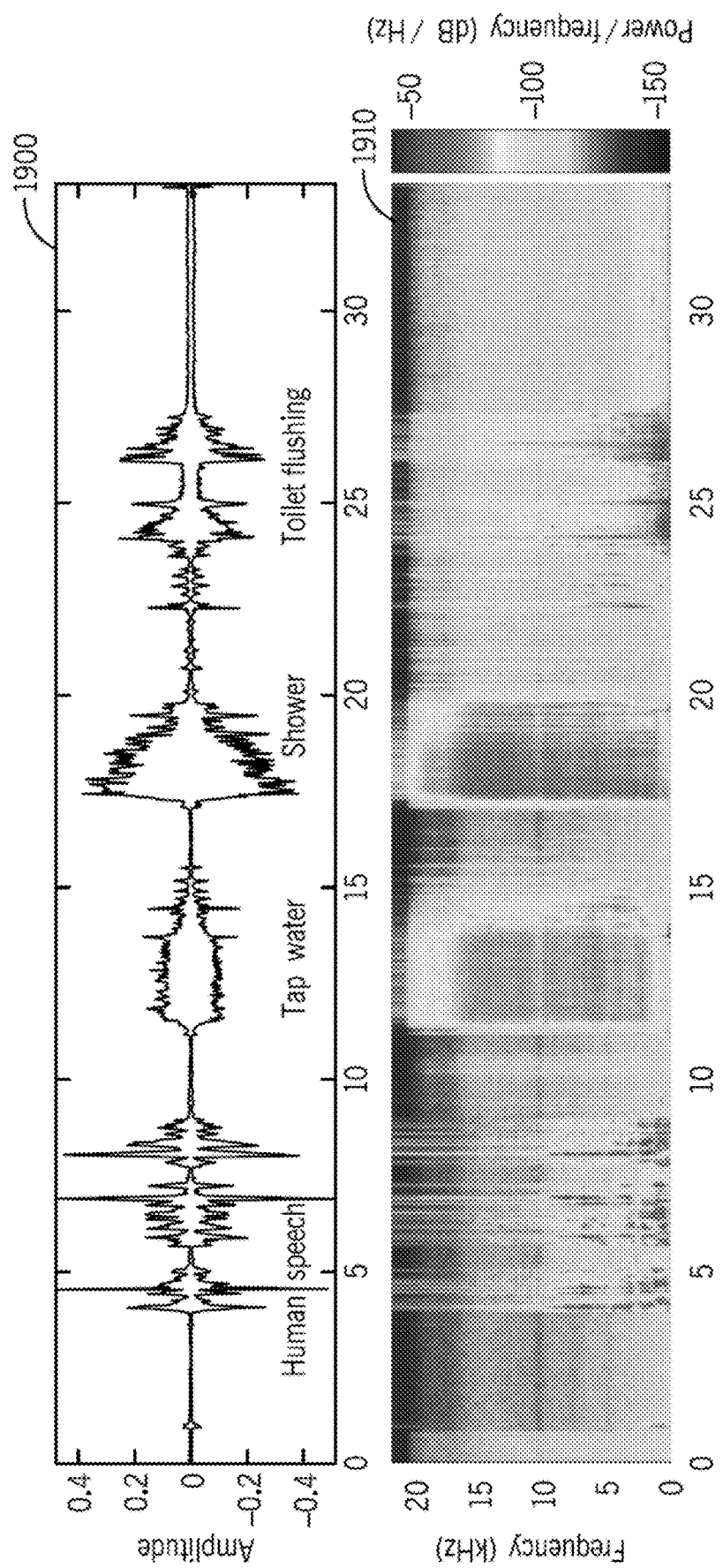
FIG. 19 are graphs of recorded waveforms of a sequence of typical sounds in a bathroom (such as human speech, tap water, shower and toilet flushing) and the corresponding spectrograms.

FIG. 19 are graphs 1900, 1910 of recorded waveforms of a sequence of typical sounds in a bathroom (such as human speech, tap water, shower and toilet flushing) and the corresponding spectrograms.

The spectrogram illustrated in FIG. 19 shows how the frequency spectrum and magnitude of a sound vary with time. The fundamental frequency of a typical voiced speech usually varies from 80 to 250 Hz (male: 80-180 Hz and female 160 to 250 Hz) with the formant frequencies usually lower than 8 KHz; running water has white-noise characteristics, where the power is almost uniformly distributed in a wide range of frequency bands. For toilet flushing measurement, the toilet tank lever was turned at 22.5 seconds in FIG. 19. The amplitude reaches to the first peak level at 24 seconds at the flushing and its second peak level around 26 seconds when the toilet valve is closed, followed by multiple seconds of water tank refilling. Thus, FIG. 19 illustrates the unique sound measurements that may be used to identify whether a specific task, such as toileting, using the shower, running the water in the faucet, is being performed.

Figure 20A:
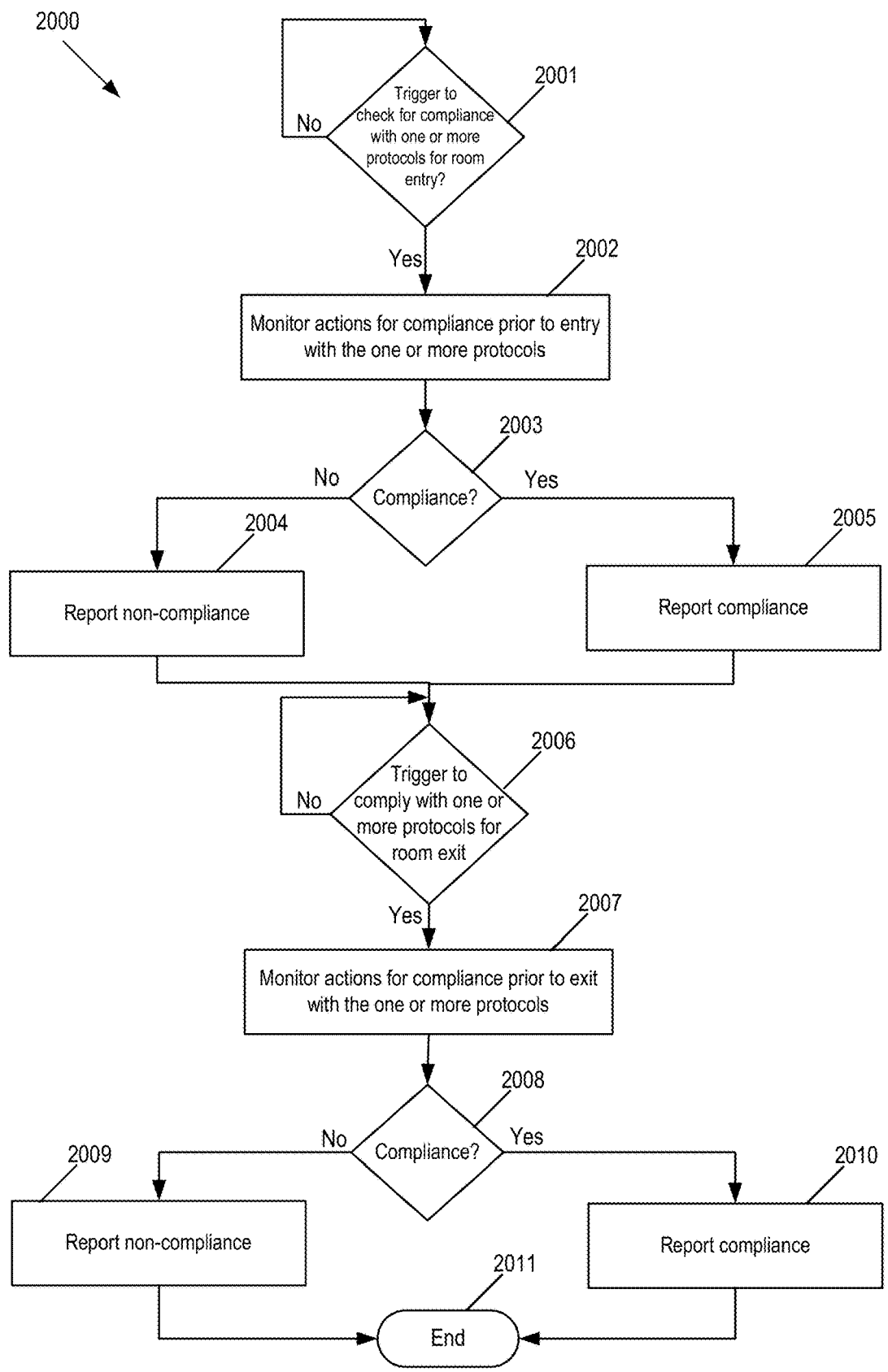
FIG. 20A is a flow chart of one example of monitoring compliance with one or more protocols when entering and exiting a patient area.

FIG. 20A is a flow chart 2000 of one example of monitoring compliance with one or more protocols when entering and exiting a patient area. As discussed above, one or more protocols may be monitored for compliance, such as one or more opportunities, which may be dependent on entering and/or exiting a patient area. At 2001, it is determined whether there is a trigger to check for compliance with one or more protocols for room entry. Examples of protocols include, but are not limited to, HH protocol(s) and/or PPE protocol(s). As discussed above, the stationary controller and/or the wristband may make the determination as to whether there has been a trigger to check for compliance with the one or more protocols for room entry.

At 2002, one or more actions are monitored for compliance with the one or more protocols prior to or attendant to entry. As discussed above, one or more types of actions may be monitored, such as movements of the body and/or actions taken with regard to a device (such as receiving alcohol-based formulation, turning on the faucet, or receiving soap).

At 2003, it is determined whether there is compliance with the one or more protocols for entry. If so, at 2005, the compliance is reported. There are a multitude of ways in which to report compliance, such as to output (via the wristband and/or via the stationary controller of an indication of compliance), and/or reporting the compliance to a separate electronic device (e.g., a back-end server and/or a separate mobile electronic device). If non-compliance is determined, at 2003, the non-compliance is reported. Again, there are a multitude of ways in which to report non-compliance, such as to output (via the wristband and/or via the stationary controller of an indication of compliance), and/or reporting the compliance to a separate electronic device (e.g., a back-end server and/or a separate mobile electronic device, such as the chief of the nurses station).

At 2006, it is determined whether there is a trigger to comply with one or more protocols for room exit. Again, examples of protocols include, but are not limited to, HH protocol or PPE protocol. As discussed above, the stationary controller and/or the wristband may make the determination as to whether there has been a trigger to comply with the one or more protocols for room exit.

At 2007, one or more actions are monitored for compliance with the one or more protocols prior to or shortly after exit. As discussed above, one or more types of actions may be monitored, such as movements of the body and/or actions taken with regard to a device (such as receiving alcohol-based formulation, turning on the faucet, or receiving soap).

At 2008, it is determined whether there is compliance with the one or more protocols for exit. If so, at 2010, the compliance is reported. Again, there are a multitude of ways in which to report compliance, such as to output (via the wristband and/or via the stationary controller of an indication of compliance), and/or reporting the compliance to a separate electronic device (e.g., a back-end server and/or a separate mobile electronic device). If non-compliance is determined, at 2009, the non-compliance is reported. Again, there are a multitude of ways in which to report non-compliance, such as to output (via the wristband and/or via the stationary controller of an indication of compliance), and/or reporting the compliance to a separate electronic device (e.g., a back-end server and/or a separate mobile electronic device, such as the chief of the nurses station). FIG. 20A illustrates that protocol(s) are examined both upon entry to and exit from the patient area. Alternatively, protocol(s) are examined only upon entry to the patient area. In still an alternate implementation, protocol(s) are examined only upon exit from the patient area.

Figure 20B:
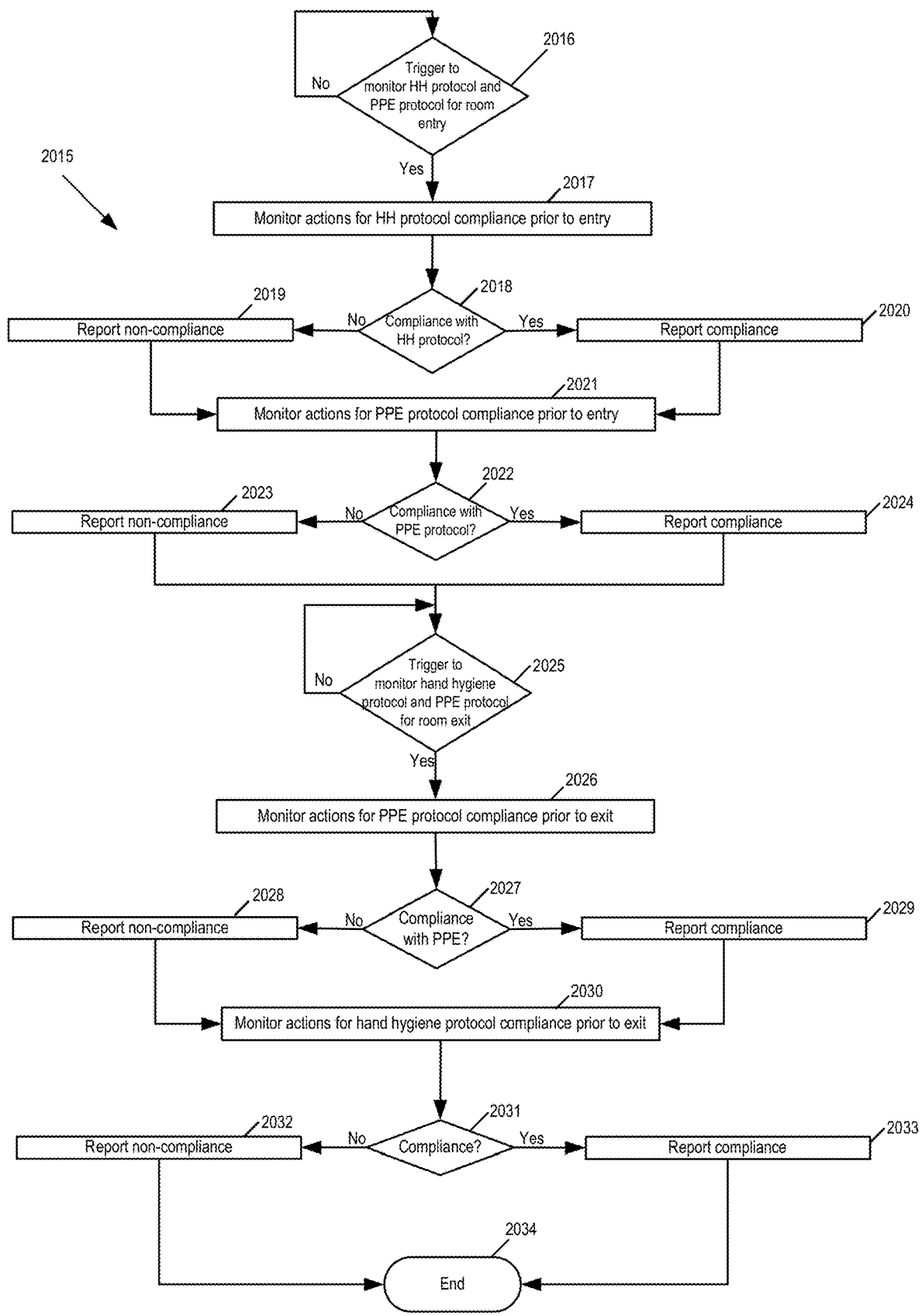
FIG. 20B is a flow chart of one example of monitoring compliance for hand hygiene (HH) and personal protective equipment (PPE) protocols for entry and exit from a patient area.

FIG. 20B is a flow chart 2015 of one example of monitoring compliance for hand hygiene (HH) and personal protective equipment (PPE) protocols for entry and exit from a patient area. At 2016, it is determined whether there has been a trigger to monitor the HH protocol and the PPE protocol for room entry. As discussed above, in one implementation, a single interaction may identify a hygiene opportunity and may thus serve as a trigger to monitor both the HH protocol and the PPE protocol. Alternatively, separate interactions may server as respective triggers to monitor both the HH protocol and the PPE protocol.

At 2017, actions are monitored for the HH protocol compliance prior to entry. As discussed above, in certain instances, the different protocols may have a specific sequence in which to perform. For example, upon or prior to entry of the patient room, the HH protocol is to be performed prior to the PPE protocol. In this regard, FIG. 20B illustrates that movements after identifying the HH and PPE opportunities are examined for HH protocol compliance. Movements thereafter are monitored for PPE protocol compliance.

At 2018, it is determined whether there is compliance with the HH protocol for entry. As discussed above, compliance with the HH protocol may comprise any one, any combination, or all of: determining whether hand cleaning solution has been dispensed; determining whether the proper type of hand cleaning solution has been dispensed (e.g., as discussed below, multiple types of hand cleaning solutions (such as an alcohol-based cleaning solution or soap-based cleaning solution) may be dispensed; certain HH protocols require that a specific type of handing cleaning solution be dispensed); determining whether the hand movements have been for at least a certain time period; determining whether a set of movements have been performed; or determining whether a certain sequence of movements have been performed. If not, at 2019, the non-compliance is reported. If so, at 2020, the compliance is reported. In one implementation, the reporting of compliance with the HH protocol may be silent to the healthcare provider; rather, the back-end server may receive the report of compliance for record-keeping purposes. Alternatively, the reporting of compliance with the HH protocol may be evident to the healthcare provider. For example, for a HH protocol requiring 20 seconds of rubbing, and responsive to the system determining compliance with the required 20 seconds of rubbing, an output (such as a light output and/or a sound output (aural output stating "you can now proceed to putting on your gloves") on the wristband and/or by the stationary controller) may be generated indicative of compliance with the HH protocol. In this way, the healthcare provider may receive feedback in order to proceed to the next protocol in the sequence, such as the PPE protocol. Alternatively, or in addition, responsive to determination of compliance with the HH protocol, one or more actions with regard to the PPE may be generated. As one example, responsive to determination of compliance with the HH protocol, a command may be sent to unlock a lock that houses a container for the PPE, thereby allowing the healthcare provider to access the PPE.

Thus, as one example, one or more electronic devices (such as the stationary controller, the wristband, the stationary controller/wristband in combination) may monitor whether the specific type of hand cleaning solution, dictated by the HH protocol, has been dispensed. The one or more electronic devices may analyze the sound to determine whether the sound is indicative of a dispensing from an alcohol-based solution dispenser (which may have a certain sound) or indicative of a dispensing from a soap-based solution dispenser (which may have a different sound). Alternatively, or in addition, the one or more electronic devices may analyze the sound to determine whether the sound is indicative of running water, which may indicate that the healthcare provider is using water to clean his or her hands. In a specific implementation, the one or more electronic devices may analyze whether the dispensing sound and the sound indicative of running water are contemporaneous with one another (e.g., the dispensing sound is within a predetermined time (such as 2 seconds) from the beginning of the water sound; and/or the dispensing sound is within the time that the water sound is registered). Responsive to determining that the dispensing sound and the sound indicative of running water are contemporaneous with one another, the one or more electronic devices may determine compliance with that part of the HH protocol.

At 2021, actions are monitored for the PPE protocol compliance prior to entry. At 2022, it is determined whether there is compliance with the PPE protocol for entry. If not, at 2023, the non-compliance is reported. If so, at 2024, the compliance is reported. In one implementation, the reporting of compliance with the PPE protocol may be silent to the healthcare provider; rather, the back-end server may receive the report of compliance for record-keeping purposes. Alternatively, the reporting of compliance with the PPE protocol may be evident to the healthcare provider. For example, for a PPE protocol requiring removal of gloves, and responsive to the system determining compliance with the removal of gloves, an output (such as a light output and/or a sound output (aural output stating "you can now proceed to washing your hands") on the wristband and/or by the stationary controller) may be generated indicative of compliance with the PPE protocol. In this way, the healthcare provider may receive feedback in order to proceed to the next protocol in the sequence, such as the HH protocol.

At 2025, it is determined whether there has been a trigger to monitor the HH protocol and the PPE protocol for room exit. Similar to entering, for exiting, there may be a sequence for following the multiple protocols. As one example, in one implementation, upon exiting, the PPE protocol are to be followed prior to the HH protocol. In particular, when the healthcare provider is wearing latex rubber gloves, the first movement at exit is removal of the gloves. In this regard, the sequence of monitoring the protocols upon exit is the reverse as the sequence upon entry.

At 2026, actions are monitored for the PPE protocol compliance prior to exit. At 2027, it is determined whether there is compliance with the PPE protocol for exit. If not, at 2028, the non-compliance is reported. If so, at 2029, the compliance is reported.

At 2030, actions are monitored for the HH protocol compliance prior to exit. At 2031, it is determined whether there is compliance with the HH protocol for exit. If not, at 2032, the non-compliance is reported. If so, at 2033, the compliance is reported. After which, flow chart 2015 ends at 2034.

Thus, in one implementation, the stationary controller is programmable, based on a specific patient in the patient area, for a specific PPE action and/or a specific HH action. Responsive to interaction of the wristband with the stationary controller, the wristband receives from the stationary controller, the specific PPE action and/or the specific HH action responsive to identifying the PPE event and/or responsive to identifying the HH event. The mobile electronic device may determine, based on the specific PPE action and/or the specific HH action received from the stationary controller and the stored motion data (motion data generated by and stored in the wristband), one or both of compliance or non-compliance with regard to the PPE event and/or the HH event.

In one implementation, the stationary controller that is associated with the specific patient in the patient area, may be programmed with one or more specific PPE indicators and/or one or more specific HH indicators. For example, the specific PPE indicators may be indicative of specific PPE, such as one or both of specific PPE movements (such as illustrated in FIG. 21) or specific PPE (e.g., putting on a gown is coded with a "0001"; taking off a gown is coded with a "0010"; putting on gloves is coded with "0011", etc.). As another example, the specific HH indicators may be indicative of specific HH, such as one or both of specific HH movements (such as illustrated in FIG. 7) or specific HH (e.g., using ABHR is coded with a "1000"; using soap/water is coded with a "1001"; etc.).

In practice, the wristband may store in its memory a table that correlates a plurality of PPE indicators with respective movement markers. Each of the plurality of PPE indicators correlates to one or both of a respective PPE movement or a respective PPE. The respective movement markers indicative of the one or both of the respective PPE movement or the respective PPE (e.g., the code "0001" may be correlated to one or more movement markers indicative of putting on a gown). Thus, using the table, glove movements may be associated with the glove indicator, mask movements may be associated with the mask indicator, gown movements may be associated with the gown indicator, and protective eyewear movements may be associated with the protective eyewear indicator. The wristband may receive the specific PPE indicators programmed for the specific patient room. For example, the healthcare provider must use gloves and a gown; hence, the stationary controller is programmed to send codes "0001" and "0011" to the wristband (which is a subset of the all of the correlated movements (i.e., the mask code and the protective eyewear codes are not sent). Responsive to receipt of the codes "0001" and "0011", the wristband uses the table to access the respective movement markers (e.g., the movement markers for putting on the gown and the movement markers for putting on gloves), and determines, using the movement data that was generated and stored in the wristband, whether there is compliance with the PPE protocol. In a specific implementation, the stationary controller may arrange the codes in a specific sequence in order to indicate to the wristband a specific sequence that the movements should be performed. In the example given above, the stationary controller may arrange the codes as "0001" and thereafter "0011" to indicate to the wristband that the wristband should check whether movements associated with putting on the gown were performed prior to the movements associated with putting on the gloves.

Thus, in one implementation, the wristband, in its determination of compliance or non-compliance with PPE protocols, may be dependent on the stationary controller. In one implementation, the wristband may determine compliance or non-compliance with regard to the HH event based on its stored sensor data and without reliance on any indication from the stationary controller of sequence of HH movement or the HH movement. Specifically, the wristband may be programmed to perform the HH compliance determination responsive to identifying the HH event, without anything further from the stationary controller.

Figure 20C:
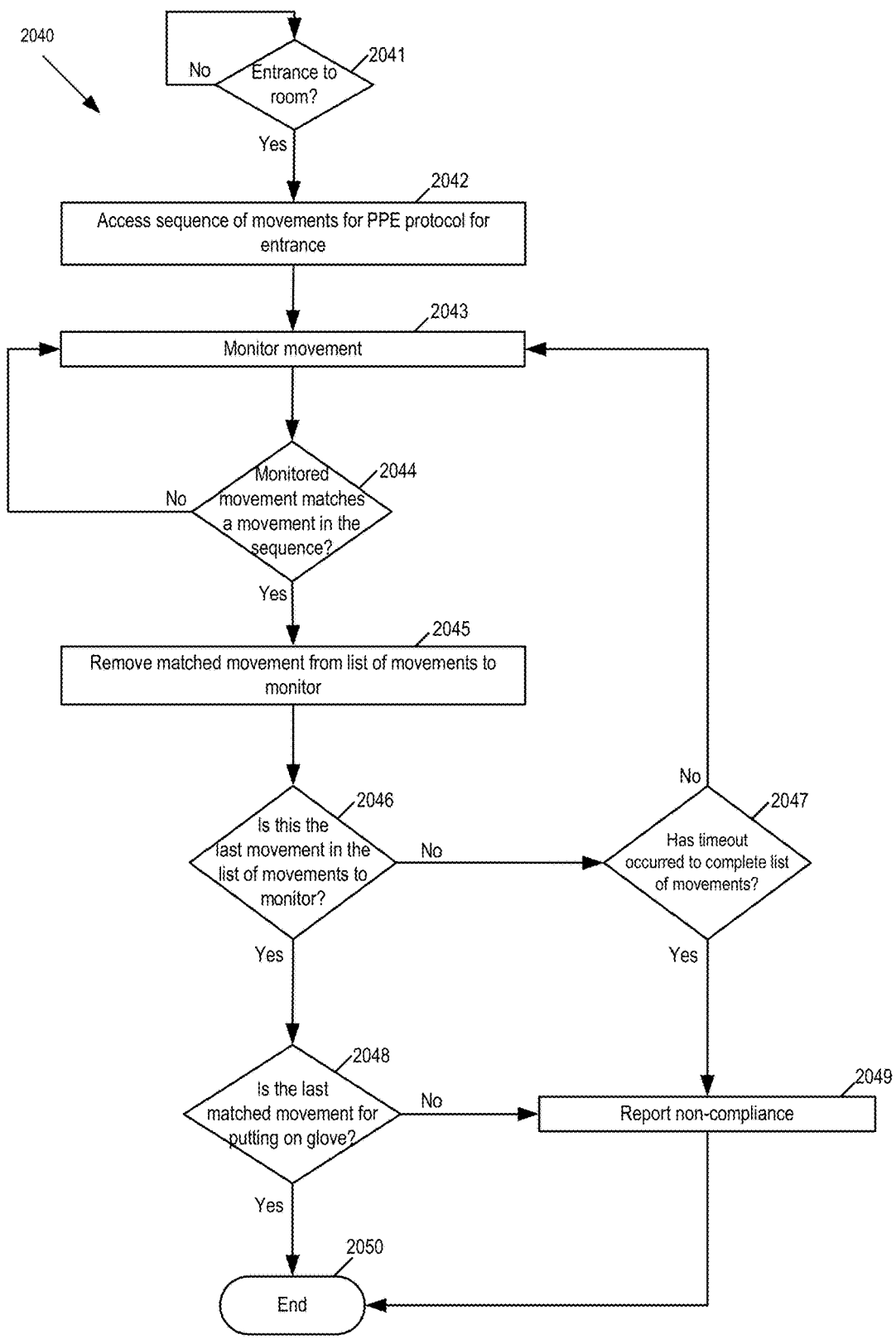
FIG. 20C is a flow chart of one example of monitoring PPE protocols for entry into a patient area.

FIG. 20C is a flow chart 2040 of one example of monitoring PPE protocols for entry into a patient area. At 2041, it is determined whether the healthcare provider has approached the entrance or entered a room, such as a particular patient's room. If so, at 2042, the sequence of movements for the PPE protocol at entrance are accessed. As discussed above, different patients (and different patient areas) may have different PPE protocols. An example table of the different protocols are shown below:

| Scenario | Isolation Precaution | ABHR or Soap/Water | PPE |
| --- | --- | --- | --- |
| Patient with Methicillin-resistant *Staphylococcus aureus* (MRSA) in a first patient situation (e.g., would to particular body part necessitating certain precautions and dressings) | Standard Precautions; Contact Precautions | ABHR | Glove Gown Face Shield or mask and goggles |
| Patient with pneumonia caused by a certain drug resistant bacteria | Standard Precautions; Contact Precautions | ABHR | Glove Gown |
| Patient with urinary tract infection caused by a first bacterium exhibiting certain symptoms | Standard Precautions; Contact Precautions | ABHR | Glove Gown |
| Patient with active diarrhea (>3 loose stools in 24 hours) with positive stool culture for a second bacterium | Standard Precautions; Contact Precautions | Soap and water | Glove Gown |
| Patient with influenza Type A with heavy cough and requiring particular treatments | Standard Precautions; Droplet Precautions | ABHR | Glove Gown Surgical Mask |
| Pediatric Patient with adenovirus with certain symptoms and having a particular bacterial infection | Standard Precautions; Contact Precautions; Droplet Precautions | ABHR | Glove Gown Surgical Mask |
| Patient arriving at Emergency Department with vomiting and diarrhea. A certain virus is suspected due to outbreak in community. | Standard Precautions; Contact Precautions; Droplet Precautions | Soap and Water | Glove Gown Surgical Mask |

As shown above, patients with different illnesses may require different precautions, such as standard precautions, contact precautions, and/or droplet precautions. Further, the different illnesses may necessitate different types of hand hygiene, such as in certain instances using ABHR or soap/water for hand hygiene. In addition, the different illnesses may necessitate different types of personal protective equipment (e.g., gloves, gown, surgical mask, face shield, goggles, etc.).

The determination as to the type of HH protocol (e.g., ABHR or soap/water) and/or the PPE protocol may be performed in one of several ways. In one way, a specific area (such as a room) may be assigned a particular patient (e.g., patient #3357). The HH protocol and/or the PPE protocol may be correlated to the specific area (which is in turn correlated to the particular patient). Alternatively, the HH protocol and/or the PPE protocol may be correlated directly to the particular patient. Thus, responsive to a healthcare provider entering and/or exiting the specific area (thereby identifying a hygiene opportunity), the HH protocol and/or PPE protocol may be accessed.

In either implementation, the HH protocol and/or the PPE protocol for the particular patient may be manifested by using particular patient HH indicators and/or particular patient PPE indicators. Merely by way of example, and not to be interpreted as limiting, ABHR may be assigned indicator="0" and soap/water may be assigned indicator="1". The stationary controller for the room of the particular patient may be programmed, such as by back-end server 130, with the particular patient HH indicator (either "0" for ABHR or "1" for soap/water) based on the needs of the particular patient.

In practice, when the wristband communicates with the stationary controller, the stationary controller may send the particular patient HH indicator. Responsive to receipt, the wristband may access a table (or other type of memory construct that correlates HH indicators with corresponding movements. In the given example, the memory in the wristband may store a correlation of "0" for ABHR with one or more movement markers associated with the movements for ABHR. Likewise, the memory in the wristband may store a correlation of "1" for soap/water with one or more movement markers associated with the movements for using soap/water for cleaning the hands of the healthcare provider. Thus, responsive to receipt of a "0" (indicative of ABHR), the wristband may access the one or more movement markers associated with the movements for ABHR in order for the wristband to check whether the movements registered by the sensors on the wristband match with the movement markers associated with the movements for ABHR. Alternatively, or in addition, responsive to receipt of a "0" (indicative of ABHR), the wristband may output an indication that ABHR is the hand hygiene protocol. Conversely, responsive to receipt of a "1" (indicative of soap/water), the wristband may access the one or more movement markers associated with the movements for soap/water in order for the wristband to check whether the movements registered by the sensors on the wristband match with the movement markers associated with the movements for soap/water. Alternatively, or in addition, responsive to receipt of a "1" (indicative of soap/water), the wristband may output an indication that soap/water is the hand hygiene protocol.

Again, merely by way of example, and not to be interpreted as limiting, PPE may include: gloves; mask; gown; and goggles. Gloves may be assigned indicator="2"; mask may be assigned indicator="3"; gown may be assigned indicator="4"; and goggles may be assigned indicator="5". The stationary controller for the room of the particular patient may be programmed, such as by back-end server 130, with the particular patient PPE indicator (any one, any combination or all of: "2" for gloves; "3" for mask; "4" for gown; or "5" for goggles) based on the needs of the particular patient.

In practice, when the wristband communicates with the stationary controller, the stationary controller may send the particular patient PPE indicator(s). Responsive to receipt, the wristband may access a table or other type of memory construct that correlates PPE indicators with corresponding movements. In the given example, the memory in the wristband may store: a correlation of "2" for gloves with one or more movement markers associated with the movements for putting on and/or removing gloves; a correlation of "3" for mask with one or more movement markers associated with the movements for putting on and/or removing a mask; a correlation of "4" for gown with one or more movement markers associated with the movements for putting on and/or removing a gown; and a correlation of "5" for goggles with one or more movement markers associated with the movements for putting on and/or removing goggles. Thus, responsive to receipt of a "2" (indicative of gloves), the wristband may access the one or more movement markers associated with the movements for gloves in order for the wristband to check whether the movements registered by the sensors on the wristband match with the movement markers associated with the movements for gloves. Responsive to receipt of a "2" and a "3" (indicative of gloves and mask), the wristband may access the one or more movement markers associated with the movements for gloves and for a mask in order for the wristband to check whether the movements registered by the sensors on the wristband match with the movement markers associated with the movements for gloves and with the movements for mask. In one implementation, the sequence of the indicators (with "2" included after "3") is indicative that the movement for gloves should be checked after checking for the movements for the mask. Further, the receipt of fewer than all of the PPE indicators (such as "2" and "3") results in the wristband checking for fewer than all of the PPE movements stored in the wristband (e.g., checking for movements for gloves and mask, but not checking for movements for gown and goggles). As discussed above, in one or some embodiments, one or both of the wristband or the stationary controller may output (e.g., via sound and/or via a display) the instructions regarding PPE, such as the sequence of putting on PPE (such as when entering a patient area) and/or taking off PPE (such as when exiting a patient area). The output generated may be triggered in one of several ways including any one, any combination, or all of: responsive to determining a PPE event (e.g., identifying a PPE entrance event and/or a PPE exit event); and/or responsive to identifying a predicate PPE movement. As one example, responsive to determining the PPE event, the wristband and/or the stationary controller may generate an indication of the entire HH and/or PPE protocol (e.g., "prior to entering the patient's room, first wash hands with soap and water, then put on mask, then gown, and then gloves"; "first use hand sanitizer, then put on a mask and then gloves"). As another example, as the healthcare provider is putting on the PPE, the wristband and/or stationary controller may generate an output indicating the next item to put on or take off. In particular, for a PPE sequence of mask, gown, and gloves, the wristband may monitor movements to determine that the mask has been put on. Responsive to this determination, the wristband may then output: "after the mask, please put on the gown". Responsive to the wristband determining that the gown has been put on, the wristband may then output: "after the gown, please put on the gloves". In this way, the wristband and/or the stationary controller may dynamically determine in real time the actions and provide feedback to the healthcare provider accordingly.

Alternatively, different PPE indicators may be received based on entrance into and/or exit from the patient area. As one example, putting on gloves may be assigned indicator="2"; putting on mask may be assigned indicator="3"; putting on gown may be assigned indicator="4"; putting on goggles may be assigned indicator="5"; removing gloves may be assigned indicator="6"; removing mask may be assigned indicator="7"; removing gown may be assigned indicator="8"; and removing goggles may be assigned indicator="9". Responsive to receipt of the specific PPE indicator(s), the wristband may check whether the respective PPE movements have been detected.

Further, the device which performs the determination as to whether the protocol has been followed may receive an indication as to the protocol in one of several ways. In one implementation, the wristband performs the determination as to whether the protocol has been followed. In a first specific implementation, the wristband may receive from the stationary controller the indication as to what protocols to monitor.

In particular, multiple HH protocols and/or multiple PPE protocols may be resident in the wristband. For example, the ABHR protocol and the soap/water protocol (including associated movements indicating compliance with the ABHR protocol and the soap/water protocol) may be resident within the wristband. As another example, different PPE protocols may be resident within the wristband. In particular, the wristband may include a putting on glove protocol (such as movements indicative of putting on a glove); removing a glove protocol (such as movements indicative of removing a glove); a putting on a gown protocol (such as movements indicative of putting on a gown); a removing a gown protocol (such as movements indicative of removing a gown); a putting on face shield protocol (such as movements indicative of putting on a face shield); a removing a face shield protocol (such as movements indicative of removing a face shield); a putting on mask protocol (such as movements indicative of putting on a mask); a removing mask protocol (such as movements indicative of removing a mask); a putting on goggles protocol (such as movements indicative of putting on goggles); a removing goggles protocol (such as movements indicative of removing goggles).

In practice, the stationary controller may receive an indication from a separate electronic device (such as back-end server 130) as to the protocols to follow for a specific patient area (such as a specific room in a hospital). For example, a first specific patient area may be subject to ABHR protocol and subject to mask protocol and gloves protocol, and a second patient area may be subject to soap/water protocol and subject to gown protocol and gloves protocol. The back-end server 130 may transmit the protocols to the respective stationary controllers (e.g., transmit to the first stationary controller, associated with the first specific patient area, an indication that the ABHR protocol, the mask protocol and the gloves protocol are to be followed; transmit to the second stationary controller, associated with the second specific patient area, an indication that the soap/water protocol, the gown protocol and the gloves protocol are to be followed).

Responsive to the interaction of the wristband with the stationary controller, the stationary controller may send the specific HH protocol and/or specific PPE protocol to the wristband (such as whether ABHR or soap/water is used or whether all or a subset of the PPE are used). Thus, in the example given above, the first stationary controller may transmit to the wristband an indication that the ABHR protocol, the mask protocol and the gloves protocol to be followed. Alternatively, responsive to interaction with the stationary controller, the wristband may communicate directly with the back-end server in order to receive the indication of the protocols to follow (e.g., responsive to interacting with the first stationary controller, the wristband communicates with the back-end server 130 (with the communication having a field indicating the stationary controller) requesting the protocols associated with the room for the first stationary controller). Thus, the wristband may have stored therein a set of HH protocols and/or a set of PPE protocols. Responsive to interaction with another device (such as the stationary controller and/or the back-end server), the wristband may access a subset of the set of HH protocols (e.g., less than all of the HH protocols stored in the wristband) and/or access a subset of the set of PPE protocols (e.g., less than all of the PPE protocols stored in the wristband).

In one implementation, both the movements and a sequence of the movements are monitored. As one example with regard to PPE upon entrance, the gloves are put on last. If there are other PPE to be used, such as putting on gowns, mask, etc., movements associated with those other PPE may be performed in any sequence prior to the last step of putting on the gloves. Optionally, movements other than for PPE (such as hand sanitizing) may be monitored as well. For example, taking an alcohol-based sanitizer or soap, and performing hand movements consistent with hand washing may be monitored prior to monitoring for any PPE movements.

As discussed above, in one implementation, upon entry to a patient room, the healthcare provider is to perform hand hygiene (either using ABHR or soap/water) and thereafter perform one or more PPE movements. In this regard, after identifying the entry of the healthcare provider into the room, sensor data from the one or more sensors configured to indicate movement may be stored. The stored sensor data may thereafter be examined by comparing the stored sensor data with predetermined movements, such as predetermined hand hygiene movements and/or predetermined PPE movements. Alternatively, upon entry to a patient room, the healthcare provider is to perform one or more PPE movements. In this regard, after identifying the entry of the healthcare provider into the room, sensor data from the one or more sensors configured to indicate movement may be stored. The sensor data may thereafter be examined for comparison with predetermined movements, such as predetermined PPE movements.

Referring back to FIG. 20C, at 2043, the movement is monitored. At 2044, it is determined whether the monitored movement matches the movement in the designated sequence. In this regard, the monitored movement may be matched with one or both of predetermined hand movements or predetermined PPE movements. At 2045, the matched movement is removed from the list of movements. For example, responsive to the identifying a match with the putting on a gown movement, that matched movement is removed from the list of movements to be tracked.

At 2046, it is determined whether all of the movements in the list of movements for tracking have been matched. If not, at 2047, it is determined whether a timeout has occurred. The timeout may be a predetermined time period, such as 30 seconds or 1 minute after identifying the entrance of the healthcare provider. If the timeout has occurred, at 2049, the non-compliance is reported. In this instance, the non-compliance may be reported in one of several ways. In one way, a general indication of non-compliance may be reported along with the identification of the healthcare provider who is entering the room. In another way, an indication of what movements the healthcare provider performed and/or did not perform in the time allotted along with the identification of the healthcare provider who is entering the room may be reported. If the timeout has not occurred, flow chart 2040 loops back to 2043 in order to continue monitoring for movement of the healthcare provider.

If all of the movements subject to tracking have been matched, at 2048, it is determined whether the last matched movement is for putting on the gloves. As discussed above, separate from identifying movements, a sequence of movements may be tracked. In one instance, the last tracked PPE movement upon entrance is the putting on of gloves. If the last matched movement upon entrance is not putting on of gloves, at 2049, this non-compliance may be reported. Again, the report of non-compliance may comprise a general indication of non-compliance and the identification of the healthcare provider, or may comprise an indication of non-compliance of putting on the gloves as the last step and the identification of the healthcare provider. After which, at 2050, flow chart 2040 ends.

Figure 20D:
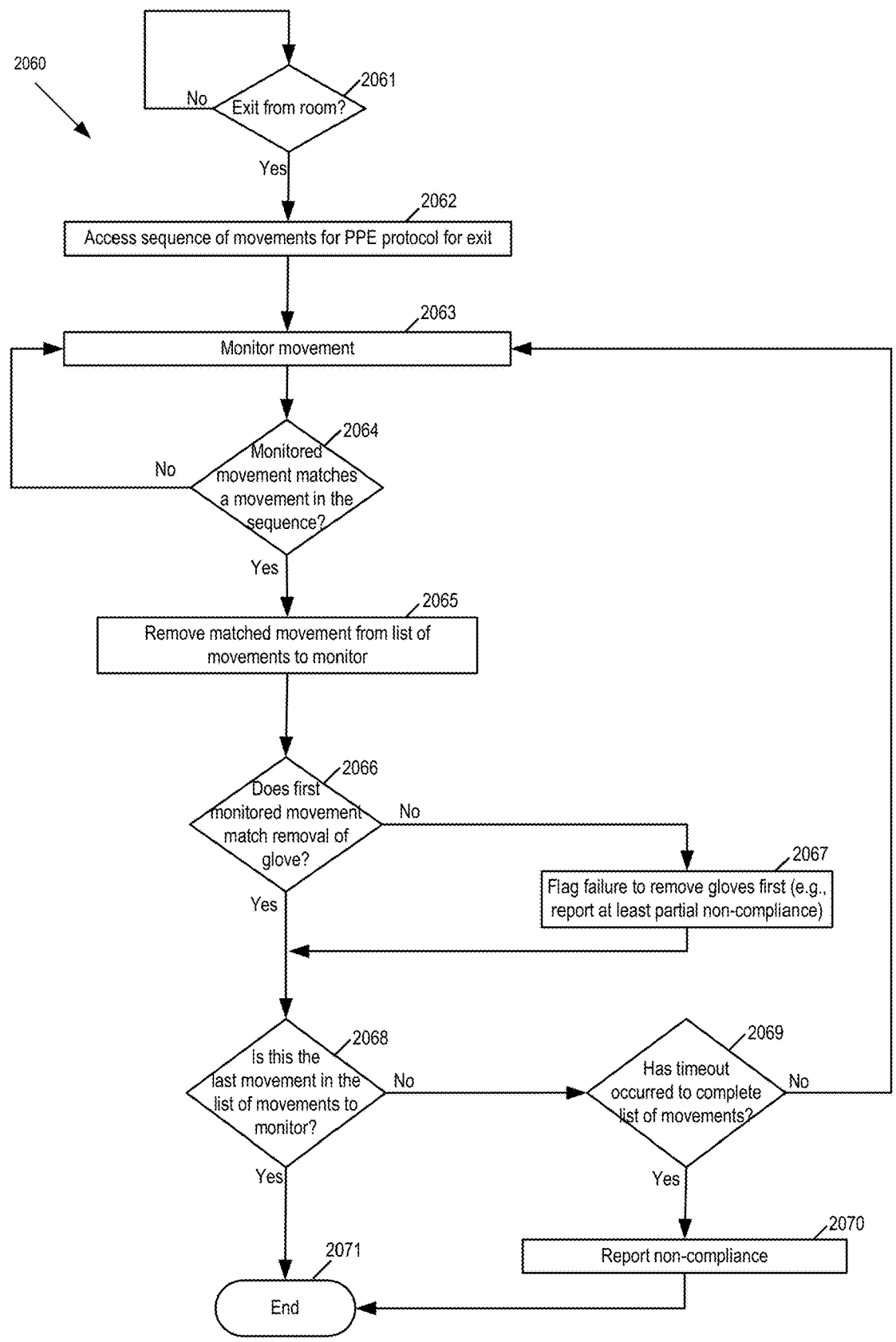
FIG. 20D is a flow chart of one example of monitoring PPE protocols for exit from a patient area.

FIG. 20D is a flow chart 2060 of one example of monitoring PPE protocols for exit from a patient area. Similar to entering the patient area, exiting the patient area may comprise monitoring a set of tracked movements and/or a sequence of the set of tracked movements. At 2061, it is determined whether the healthcare provider has approached the exit or exited a room, such as a particular patient's room. If so, at 2062, the sequence of movements for the PPE protocol at exit are accessed. As discussed above, there are several ways to determine what protocols to access for monitoring.

At 2063, the movement is monitored. At 2064, it is determined whether the monitored movement matches the movement in the designated sequence. In this regard, the monitored movement may be matched with one or both of predetermined hand movements or predetermined PPE movements associated with exiting the patient area. At 2065, the matched movement is removed from the list of movements. For example, responsive to the identifying a match with the removing a gown movement, that matched movement is removed from the list of movements to be tracked.

At 2066, it is determined whether the first matched movement is for removing the gloves. As discussed above, separate from identifying movements, a sequence of movements may be tracked. In one instance, the first tracked PPE movement upon or at exit is the removal of gloves. If the first matched movement upon or at exit is not removing the gloves, at 2067, this non-compliance may be reported (e.g., flagging failure to remove gloves first, indicating at least partial non-compliance). Again, the report of non-compliance may comprise a general indication of non-compliance and the identification of the healthcare provider, or may comprise an indication of non-compliance of removing the gloves as the first step and the identification of the healthcare provider. Alternatively, or in addition, the non-compliance may be generated for notification of the particular healthcare provider that failed to comply with protocols (e.g., aural or light output indicative of non-compliance).

At 2068, it is determined whether all of the movements in the list of movements for tracking have been matched. If not, at 2069, it is determined whether a timeout has occurred. The timeout may be a predetermined time period, such as 30 seconds or 1 minute after identifying the entrance of the healthcare provider. If the timeout has occurred, at 2070, the non-compliance is reported. In this instance, the non-compliance may be reported in one of ways. In one way, a general indication of non-compliance may be reported along with the identification of the healthcare provider who is exiting the room. In another way, an indication of what movements the healthcare provider performed and/or did not perform in the time allotted along with the identification of the healthcare provider who is exiting the room may be reported. Alternatively, or in addition, the non-compliance may be generated for notification of the particular healthcare provider that failed to comply with protocols (e.g., aural or light output indicative of non-compliance). If the timeout has not occurred, flow chart 2060 loops back to 2063 in order to continue monitoring for movement of the healthcare provider. If all of the movements subject to tracking have been matched, at 2071, flow chart 2060 ends.

Figure 20E:
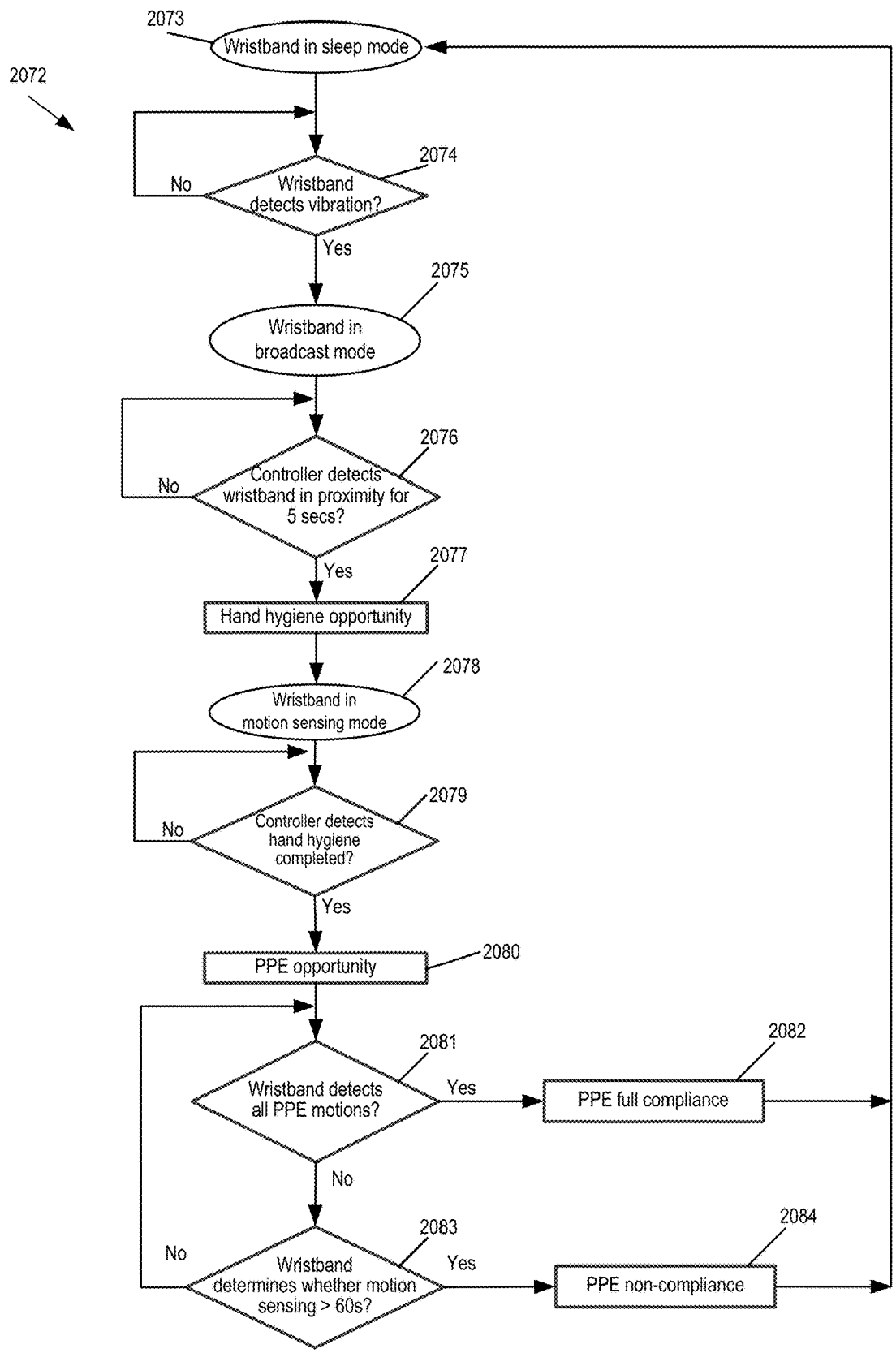
FIG. 20E is a flow chart of another example of monitoring HH and PPE protocols for entry to a patient area.

FIG. 20E is a flow chart 2072 of another example of PPE compliance monitoring when entering a patient area. At 2073, the wristband is in sleep mode. As discussed above, various circuits within the wristband may be turned off or in low power mode when the wristband is in sleep mode. At 2074, the wristband may detect a vibration, such as via the micro-vibration sensor. In one implementation, even in sleep mode, the micro-vibration sensor remains active. If vibration is detected, at 2075, the wristband may transition to broadcast mode. As one example, the wristband may activate one or more of the wireless communication transceivers, such as near-field communication transceiver 322.

In this way, at 2076, the stationary controller may determine, such as via the RSSI signal, whether the wristband is in proximity for a certain amount of time (e.g., 5 seconds). If so, at 2077, it is determined that there is a hand hygiene opportunity (and in turn whether there is compliance with the hand hygiene opportunity).

At 2078, the wristband may be changed to motion sensing mode. At 2079, the controller (and/or the wristband) may detect that hand hygiene has been completed. In one implementation, the stationary controller may determine whether the hand cleaning agent (e.g., sanitizer) has been dispensed. If not, non-compliance may be noted and/or a notification may be output. If it is detected that hand hygiene has been completed, at 2080, it is determined that there is a PPE opportunity (e.g., an entrance PPE opportunity), and in turn whether there is compliance with the PPE opportunity. At 2081, the wristband detects whether all PPE motions have been detected. If so, at 2082, PPE full compliance is determined (and notification of PPE compliance may be output via the wristband and/or the stationary controller, and/or a communication indicating PPE compliance may be send to the back-end server for recordal purposes).

If not, at 2083, the wristband detects whether the period for motion sensing is greater than 60 seconds. If so, at 2084, PPE non-compliance is determined (and notification of PPE non-compliance may be output via the wristband and/or the stationary controller, and/or a communication indicating PPE non-compliance may be send to the back-end server for recordal purposes). If the wristband has not performed motion sensing for 60 seconds, flow chart 2072 loops back to 2081.

Thus, the PPE opportunity may comprise an entrance PPE opportunity associated with entering the patient area and/or an exit PPE opportunity associated with exiting the patient area. As discussed above, an opportunity may have an associated event, which may comprise one or more actions associated with compliance with the opportunity. For example, the entrance event associated with the entrance PPE opportunity may include a first PPE putting-on movement associated with putting on the first PPE (e.g., one of a mask putting-on movement, a gown putting-on movement, etc.), a second PPE putting-on movement associated with putting on the second PPE (e.g., another of a mask putting-on movement, a gown putting-on movement, etc.), and a glove putting-on movement associated with putting on the gloves. As another example, the exit PPE event associated with the exit PPE opportunity may include a first PPE taking-off movement associated with taking off the first PPE, a second PPE taking-off movement associated with taking off the second PPE, and a glove taking-off movement associated with taking off the gloves. The glove putting-on movement and the glove taking-off movement are examples of glove movements. Likewise, the mask putting-on movement and the mask taking-off movement are examples of mask movements, the gown putting-on movement and the gown taking-off movement are examples of gown movements, and the protective eyewear putting-on movement and the protective eyewear taking-off movement are examples of protective eyewear movements. One or both of compliance or non-compliance determination with regard to the PPE opportunity may comprise: determining whether both of the first PPE putting-on movement and the second PPE putting-on movement, in any order, are performed prior to the glove putting-on movement; and determining whether both of the first PPE taking-off movement and the second PPE taking-off movement, in any order, are performed after the glove taking-off movement.

In one implementation, the stationary controller may be implemented with sound and light interventions whereas the wristband may be implemented with vibration reminders.

For instance, when the healthcare worker (e.g., trainee) is not compliant with the infection control measures, the wristband may vibrate while the stationary controller will flash in red light. Further, since the system tracks each trainee's performance, the system may also implement reminders that targets those trainees with poor behaviors (e.g., compliance rate less than a pre-determined percentage). For instance, if a trainee with a low compliance rate approaches the entrance of a patient room, the controller may beep to prompt the trainee for hand wash and/or PPE. By identifying the target trainees and sending personalized reminders, the system may improve the target trainee's performance while avoiding annoyance to other trainees.

Thus, in one implementation, the motion sensor inside the wristband may monitor whether the trainee performed the proper motions (e.g., hand rubbing for 20 seconds; donning or removing PPEs in the correct order) and sends real-time alert (to any one, any combination, or all of: the trainee; the back-end server; a supervisor) indicative of compliance and/or non-compliance. In a more specific implementation, in addition to the compliance and non-compliance data, the wristband may send related data, such as timestamps, stationary controller ID and wristband ID, to the back-end server in order to generate a compliance report. In one implementation, each trainee may compare his/her performance with peers from a web or mobile app login, thereby motivating trainees through peer pressure and team competition.

The training and/or monitoring methodology provides one or more benefits. As one example, the training and/or monitoring methodology provides just-in-time infection control training in practice settings. In particular, the training and/or monitoring methodology may educate and train students in both simulation and practice settings, and track their performance in practice to ensure they achieve a high infection-control compliance rate. For instance, the training and/or monitoring methodology may capture three out of five of the "critical moments" specified by WHO (e.g., before touching a patient, after touching a patient, and after touching patient surroundings) to ensure a significant impact on the reduction of HAIs.

In addition, the training and/or monitoring methodology may be tailored to trainees' and/or healthcare workers' practice setting and their roles. As one example, training may be tailored in one instance to a first site (surgical site infection (SSI) prevention specifically for operating room (OR) nurses) as opposed to another instance (general infection control overview). In this way, the training may be more effective. In addition, different infection control measures are required based on the patient infection and/or the nature of the patient contact. The training and/or monitoring methodology may be easily configured to accommodate different patient scenarios and healthcare settings (e.g., community, homecare, hospital).

Further, the training and/or monitoring methodology may provide real-time feedback and interventions for non-compliant incidences. In particular, the training and/or monitoring methodology may provide real-time intervention to poor performance through various types of alerts/reminders and immediate supervisor notification.

Also, the training and/or monitoring methodology may use electronic sensors to track each trainee's or healthcare worker's performance on hand hygiene and PPE use. Such information may be used by the infection control team or the supervisors to evaluate the progress of the trainees or healthcare workers, to identify issues, and to provide feedback. Detailed infection control compliance reports may also be available by any one, any combination, or all of: date; location (e.g., floor, unit and room); or group or individual trainee/healthcare worker.

In addition, the wristbands, which in one implementation include low power modes, may operate for a longer time (e.g., over 1 year) with a coin battery. The use of the wristband may result in little, if any, interruption in workflow for the person.

Figure 20F:
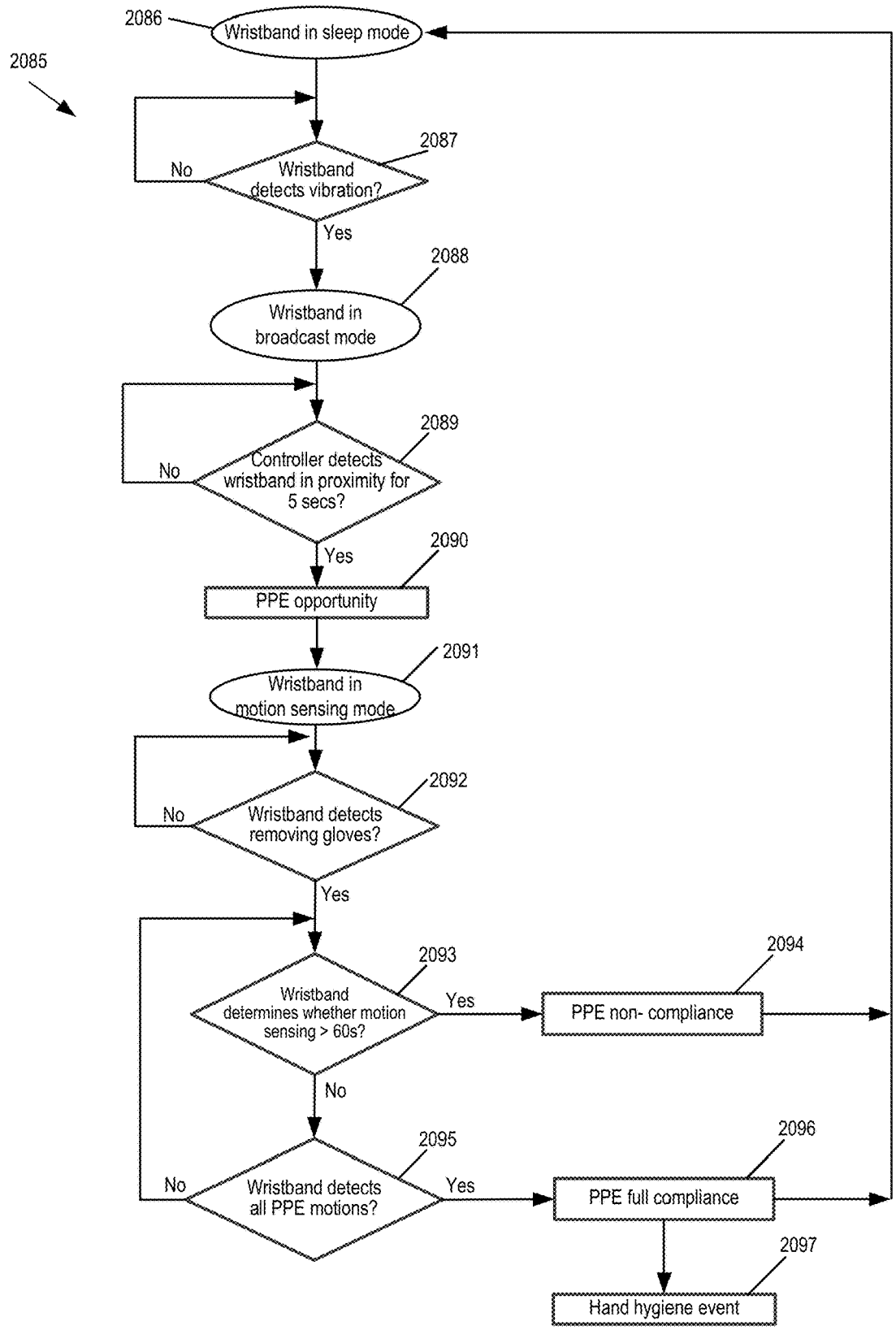
FIG. 20F is a flow chart of another example of monitoring HH and PPE protocols for exit from a patient area.

FIG. 20F is a flow chart 2085 of another example of PPE compliance monitoring when exiting a patient area. At 2086, the wristband is in sleep mode. At 2087, the wristband may detect a vibration, such as via the micro-vibration sensor. If vibration is detected, at 2088, the wristband may transition to broadcast mode. At 2089, the stationary controller may determine, such as via the RSSI signal, whether the wristband is in proximity for a certain amount of time (e.g., 5 seconds). If so, at 2090, it is determined that there is a PPE opportunity (e.g., an exit PPE opportunity).

Responsive to identifying the PPE opportunity, it may be determined whether there is a compliant PPE event. At 2091, the wristband may be changed to motion sensing mode. At 2092, the wristband detects whether the gloves have been removed. As discussed above, when exiting the patient room, the recommended first motion is the removal of the gloves. If glove removal is detected, at 2093, the wristband detects whether the period for motion sensing is greater than 60 seconds. If so, at 2094, PPE non-compliance is determined (and notification of PPE non-compliance may be output via the wristband and/or the stationary controller, and/or a communication indicating PPE non-compliance may be send to the back-end server for recordal purposes). If not, at 2095, the wristband detects whether all PPE motions have been detected. If so, at 2096, PPE full compliance is determined (and notification of PPE compliance may be output via the wristband and/or the stationary controller, and/or a communication indicating PPE compliance may be send to the back-end server for recordal purposes). After which, at 2097, it is determined that there is a hand hygiene event, with the attendant checking of compliance with one or more hand hygiene protocols. If not, flow chart 2085 loops back to 2093.

FIG. 21A are graphs of outputs of motion sensors, including a graph 2110 of accelerometer data (time versus linear acceleration) and a graph 2120 of gyroscope data (time versus angular acceleration), for donning PPE motions and interfering motions. Each sensor has outputs on x-axis (2112 in graph 2110 and 2122 in graph 2120), y-axis (2114 in graph 2110 and 2124 in graph 2120) and z-axis (2116 in graph 2110 and 2126 in graph 2120). Donning/doffing PPEs may cause very close responses. In this regard, only responses from donning PPE motions are illustrated in FIG. 21A. PPE-donning motions have unique characteristics and may be clearly distinguished from interfering motions. For instance, donning goggles cause a large response in accelerometer (x- and y-axis) and gyroscope (z-axis) (due to raising and lowering arms); donning a mask comprises (or consists) of the following motions in sequence (raise arm, tie the mask and lower arm) so that its response is similar to donning goggles but with a longer interval; donning gloves generates large and short pulses on the accelerometer due to sudden arm stretching; donning a gown comprises (or consists) of motions of raising arms, lowering arms then tying the gown behind waist, so its response is close to donning goggles followed by several seconds of large responses on accelerometer and gyroscope cause by tying the gown; opening door has a noticeable gyroscope response in x-axis; and both hand rubbing and walking are periodic motions with frequency of hand rubbing being much higher. Though FIG. 21A illustrates donning PPE, accelerometer and gyroscope data may be analyzed for doffing PPE in order to detect whether the doffing motions associated with PPE have been performed. Further, in one implementation, the detection of the movements, such as the hand washing and/or PPE movements, may be limited in time and responsive to a certain trigger event (e.g., communication with a stationary controller). In this way, limiting the time in which the movements are detected may reduce the possibility of false detections.

Figure 21B:
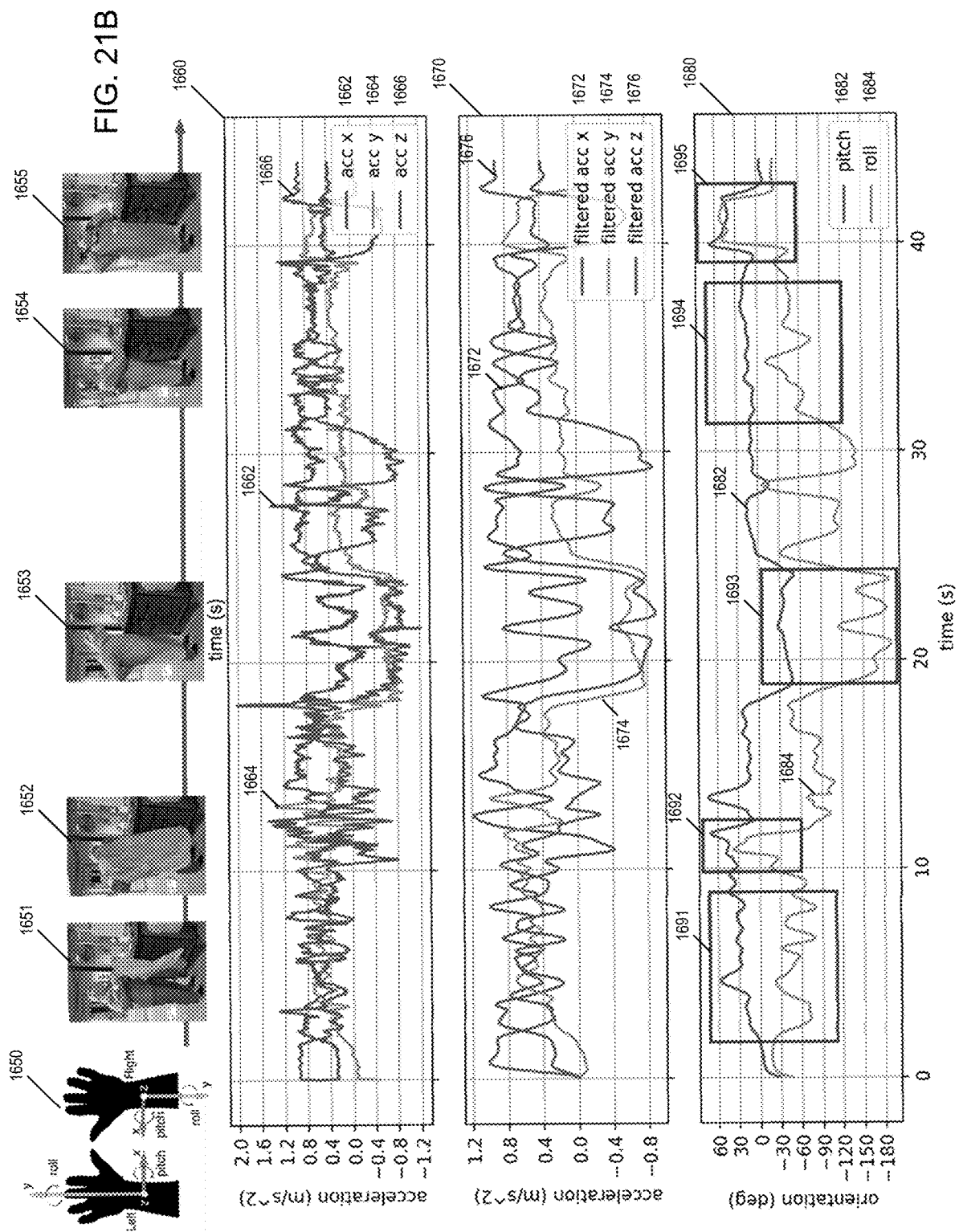
FIG. 21B illustrates another example of motions (e.g., donning gown, gloves, and mask) associated with PPE, such as by using an accelerometer in a wristband.

FIG. 21B illustrates another example of motions (e.g., donning gown, gloves, and mask) associated with PPE, such as by using an accelerometer in a wristband. 2150 illustrates the accelerometer's coordinate system, such as the x-, y- and z-axes of the sensor are lateral, longitudinal and perpendicular to the forearm respectively; pitch and roll are rotation angles around x and y axis. For example, the y axis of the sensor may be the longitudinal axis aligned with the forearm, the x axis may be lateral to the forearm, and the z axis may be perpendicular. Pitch and roll may be rotation angles around x and y axis (directions may be adjusted to output symmetrical values for two hands). Initial state of pitch and roll angles starting from initial orientation may be defined as the palm lying palm flat facing earth, pitch is the angle raising hand and roll is the angle rolling palm toward outside.

2151, 2152, 2153, 2154, and 2155 illustrate PPE donning motions in sequence including: i) opening the blue gown (2151); ii) putting gown over neck (2152); iii) wrapping around and fastening gown in the back (2153); iv) putting on gloves (2154); v) putting on mask (2155). 2160 is a graph of raw accelerometer signals on the 3-axes: x (2162), y (2164) and z (2166); 2170 is a graph of smoothed accelerometer signals after high-frequency noise is removed on the 3-axes: x (2172), y (2174) and z (2176). 2180 is a graph of pitch (2182) and roll (2184) angles derived from 2170. It is clearly shown that PPE donning motions in 2151, 2152, 2153, 2154, and 2155 can be recognized by the value and duration of pitch/roll angles at corresponding 2191, 2192, 2193, 2194, and 2195. For instance, fastening gown at the back (2153) generates large negative roll values for several seconds (see 2193), and raising hands to put on mask (2155) generates both positive pith and roll values (see 2195). In addition, PPE motions may be inferred from the sequence of these characteristic hand gestures.

As discussed above, the monitoring of the HH protocols and/or PPE protocols may be used in a variety of contexts. In one context, the monitoring of the HH protocols and/or PPE protocols may be used for overseeing healthcare providers' treatment of patients. This is illustrated, for example, in the reports in FIGS. 12A-E. In another context, the monitoring of the HH protocols and/or PPE protocols may be used for training healthcare providers. Thus, in one implementation, the status of the healthcare provider (e.g., trainee versus non-trainee; nurse versus doctor; etc.) may implicate whether the respective healthcare provider is subject to HH protocol and/or PPE protocol monitoring.

In one implementation, the status may be determined based on interaction with the wristband. For example, the wristband may include an identification of the person wearing the wristband. The identification may comprise an ID associated with the person (with the ID then being correlated to the status of the person) or may comprise the status of the person. In one implementation, a first device may identify the status of the person and a second device may determine, based on the identified status, whether to monitor HH protocols and/or PPE protocol. For example, the wristband may identify the status of the person and the stationary controller, having received the status from the wristband, may determine whether to monitor HH protocols and/or PPE protocol. In another implementation, a single device may identify the status of the person and determine, based on the identified status, whether to monitor HH protocols and/or PPE protocol. For example, the wristband may identify the status of the person (e.g., the status is stored in a memory resident in the wristband) and the wristband may determine, based on the stored status, whether to monitor HH protocols and/or PPE protocol. In particular, responsive to an electronic device identifying the particular status of the person (such as the wristband indicating a trainee) and to the particular status indicating that monitoring of HH protocols and/or PPE protocols are to be performed, the electronic device may monitor for the HH protocols and/or PPE protocols.

Responsive to determining compliance and/or non-compliance of one or both of the HH or the PPE protocols, a device (such as the wristband and/or the stationary controller and/or the back-end server) may generate an electronic message indicative of an intervention. The electronic message may be generated in any one, any combination, or all of: (1) prior to performing the respective protocol; (2) during the performance of one, some, or each of the act(s) to perform in order to comply the respective protocol; or (3) after the respective protocol should have been performed. As one example, responsive to stationary controller identifying a HH opportunity or a PPE opportunity and/or detecting a HH event or a PPE event, the stationary controller may output a message (e.g., a light and/or a sound) indicative of the HH event or the PPE event (e.g., "please wash your hands"). As another example, responsive to the wristband identifying a HH opportunity or a PPE opportunity and/or monitoring a HH event or a PPE event, the wristband may output a message (e.g., a light and/or a sound) indicative of the HH event or the PPE event (e.g., playing music for 20 seconds indicative to the healthcare worker to rub hands for 20 seconds during the HH event). As still another example, responsive to the determination that the HH event or the PPE event is over (either due to compliance or due to non-compliance), an electronic device (e.g., the stationary controller and/or the wristband) may generate an output indicative of at least one aspect of the event (e.g., indicative of compliance, indicative of non-compliance, or indicative that the event is completed).

In one implementation, the trigger for intervention may comprise the determination of non-compliance of a protocol. As one example, an electronic device may determine non-compliance with the HH protocol. As discussed above, one aspect of compliance with the HH protocol is the dispensing of hand-cleaning agent, such as ABHR or soap. An electronic device, such as the stationary controller which may be positioned within or proximate to the dispenser of the hand-cleaning agent, may sense whether the dispenser has dispensed the hand-cleaning agent. In particular, responsive to the stationary controller determining that the wristband has been within Bluetooth range of the stationary controller for at least a predetermined amount of time (e.g., 3-5 seconds, indicating that the person wearing the wristband is likely entering the room indicating an entrance opportunity), the stationary controller may wait a predetermined amount of time (e.g., 3-5 seconds) to determine whether the dispenser has dispensed the hand-cleaning agent. If the stationary controller determines that the dispenser has dispensed the hand-cleaning agent within the predetermined amount of time, the stationary controller may determine that this portion of the HH protocol has been satisfied. However, if the stationary controller determines that the dispenser has not dispensed the hand-cleaning agent within the predetermined amount of time (e.g., the stationary controller has not sensed the sound indicative that the dispenser has dispensed hand-cleaning agent) and/or that the healthcare worker has moved into the patient area (e.g., a first stationary controller exterior to the patient room senses the healthcare worker and thus triggers the HH opportunity; a second stationary controller interior to the patient room senses that the healthcare worker has moved into the room; the proximity sensing and output generating device has identified that the door into the patient room has been opened, indicating that the person has entered into the room), the stationary controller may determine that this portion of the HH protocol has not been satisfied, thereby triggering an intervention. Thus, based on a timeout (e.g., not taking the hand-cleaning agent within a predetermined amount of time) and/or based on a movement into the patient area without performing the requisite action, the intervention may be triggered.

Another aspect of compliance with the HH protocol may comprise the amount of time spent rubbing hands (e.g., 20 seconds). An electronic device, such as the wristband, may sense whether the healthcare worker has spent the requisite time rubbing hands. If the wristband determines that the healthcare worker has spent the requisite time rubbing hands, the wristband may determine that this portion of the HH protocol has been satisfied. However, if the wristband determines that the healthcare worker has not spent the requisite time rubbing hands (e.g., within a period of 60 seconds from trigger of the HH event (e.g., detecting dispensing of the hand cleaning agent), the healthcare worker has not rubbed for 20 total seconds), the wristband may determine that this portion of the HH protocol has not been satisfied, thereby triggering an intervention. In this regard, responsive to determining that the healthcare worker has taken hand-cleaning agent but has not rubbed hands for the requisite amount of time, the system may determine partial compliance. In one implementation, the intervention for partial compliance may be different from the intervention for non-compliance.

Still another aspect of compliance with the HH protocol may comprise the requisite motions, such as illustrated in FIGS. 10A-B. An electronic device, such as the wristband, may sense whether the healthcare worker has spent the requisite time rubbing hands. If the wristband determines that the healthcare worker has performed the requisite motions, the wristband may determine that this portion of the HH protocol has been satisfied. However, if the wristband determines that the healthcare worker has not performed the requisite motions (e.g., within a period of 60 seconds from trigger of the HH event, the healthcare worker has performed steps 2-7 in FIG. 10A), the wristband may determine that this portion of the HH protocol has not been satisfied, thereby triggering an intervention.

As another example, an electronic device may determine non-compliance with the PPE protocol. As discussed above, one aspect of compliance with the PPE protocol is the donning or doffing of certain PPE. Responsive to an electronic device (e.g., the wristband) determining that the requisite movements (e.g., indicating the donning or doffing of the certain PPE) have not been performed within a predetermined amount of time (e.g., 60 seconds) or were not performed in the proper order, the system may trigger an intervention. Alternatively, or in addition, responsive to determining that the healthcare worker has moved into the patient area without performing the requisite movements, the system may trigger an intervention.

In one implementation, the trigger for an intervention for a first protocol may be independent of the trigger for an intervention for a second protocol. For example, the trigger to intervene based on non-compliance with the HH protocol may be independent of the trigger to intervene based on non-compliance with the PPE protocol. In particular, prior to entry to a patient area and a failure to take hand-cleaning agent, the intervention may be performed regardless of whether the healthcare worker complied with the PPE protocol. In an alternative implementation, the trigger for an intervention for the first protocol may be dependent of the trigger for the intervention for the second protocol.

Responsive to triggers, various types of intervention may be performed including any one, any combination, or all of: light output (e.g., on the wristband and/or on the stationary controller); aural output (e.g., on the wristband and/or on the stationary controller); or electronic notification (e.g., to the back-end server and/or to a supervisor). For example, light and/or sound may be indicative that an action should be taken. For example, responsive to the stationary controller determining that the dispenser has not dispensed hand-cleaning agent, the stationary controller may output a beep and/or a sound stating: "please take hand-sanitizer from the dispenser". As another example, responsive to non-compliance, the supervisor may be notified in real-time. In particular, responsive to the stationary controller determining the non-compliance, the stationary controller may send a communication to the back-end server indicating the non-compliance of a certain individual (such as identified by the wristband worn by the individual) and/or of a certain part of the building (such as the neonatal intensive care unit). The back-end server may access a look-up table, correlating the identity of the individual and/or the certain part of the building in order to immediately notify a supervisor in real-time (e.g., send a text to the mobile phone number associated with the supervisor).

Further, in one implementation, the intervention may be based on any one, any combination, or all of the following: determination of compliance or non-compliance; determination of partial compliance; status of the person subject to the compliance, non-compliance, or partial compliance (e.g., whether the person is a trainee or a full-time employee); history of compliance of the person (e.g., whether trends indicate that the person has a history of compliance, non-compliance, or partial compliance); or location of the compliance, non-compliance, or partial compliance (e.g., whether the setting is a home, an intensive care unit, a long-term care facility, or a community care facility). As one example, in response to determining compliance, the healthcare worker may not be notified; however, the back-end server may be notified. in response to determining non-compliance, the healthcare worker, the supervisor, and the back-end server are notified. In response to determining that the status of the person is a trainee, the person is notified regardless of compliance, non-compliance, or partial compliance. In response to determining that the status of the person is a full-time employee, the person is notified only responsive to determination of non-compliance or partial compliance. As still another example, responsive to determining that the person has a history of non-compliance or partial-compliance (e.g., the percentage of non-compliance or partial compliance is greater than a predetermined percentage; certain number of times indicative of non-compliance or partial compliance), the system generate an output (e.g., light and/or aural) to the person. Conversely, responsive to determining that the person does not have a history of non-compliance or partial-compliance, the system does not generate an output to the person.

FIG. 22A is a flow diagram 2200 of detecting both the HH opportunity and the HH event and determining HH compliance based on a combination of the detected HH opportunity and the HH event. At 2201, the HH opportunity is detected. At 2202, the HH event is detected. As discussed above, the HH opportunity may be detected before detecting the HH event (e.g., entering the room and then taking sanitizer). Conversely, the HH opportunity may be detected after detecting the HH event (e.g., taking sanitizer in the hallway before entering the room; taking sanitizer in the hallway before exiting the room). Thus, while flow diagram 2200 depicts detecting the HH opportunity before detecting the HH event, the converse may be true.

Further, at 2203, HH compliance is determined based on a combination of the detected HH opportunity and the detected HH event. As discussed above, in one or some embodiments, the HH event (such as the detection of and/or determined compliance with the HH event) is sufficiently connected to the HH opportunity in order for the compliance with the HH event to be associated with or assigned to the HH opportunity. Discussed in more detail below in FIGS. 22B and 23, the determination of compliance may be based on whether there is sufficient connection (such as connection in time) between the detected HH event and the detected HH opportunity.

FIG. 22B is a flow diagram 2220 of one example of determining whether there is sufficient connection between the detected HH event and the detected HH opportunity. At 2222, it is determined whether there is a HH opportunity detected. As discussed above, various ways are contemplated to detect the HH opportunity, including based on tracking movement of the healthcare provider. Further, various devices are contemplated to detect the HH opportunity, including one or both of the wristband or the stationary controller.

Figure 22C:
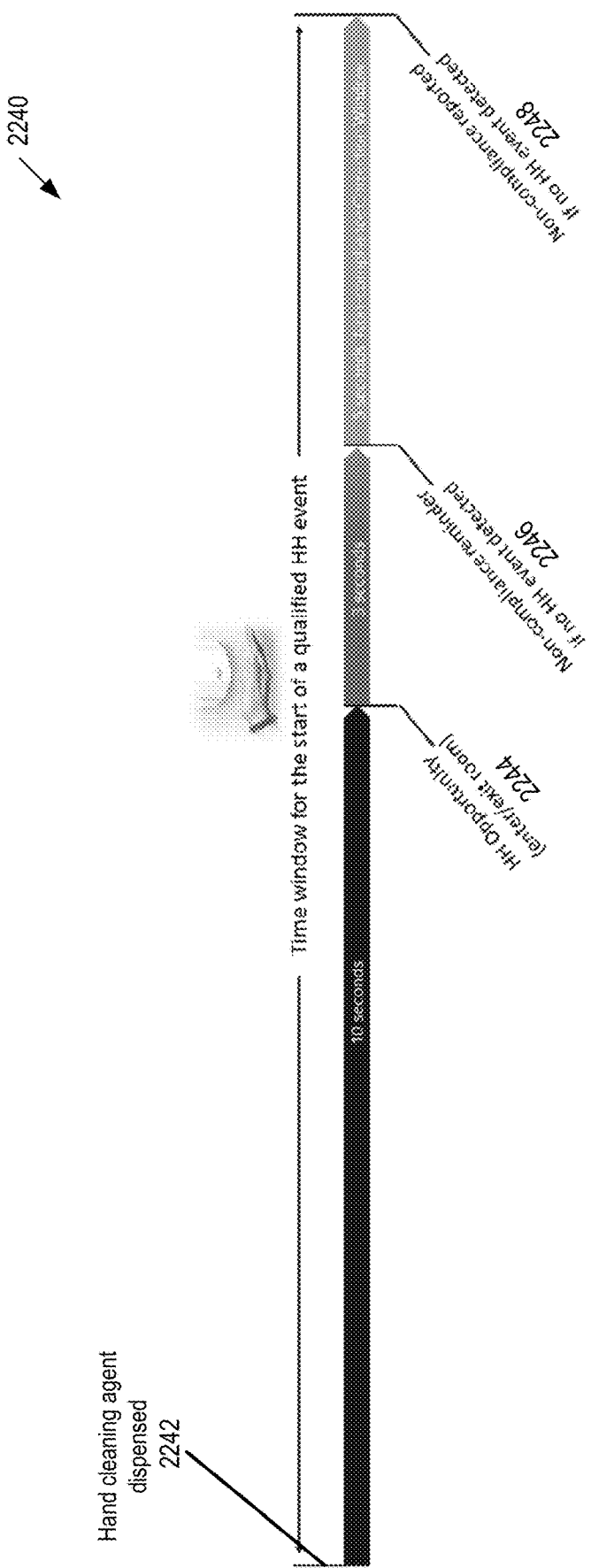
FIG. 22C is a timing diagram for determining whether there is sufficient connection between the detected HH event and the detected HH opportunity.

Responsive to detecting a HH opportunity, at 2223, it is determined whether a HH event has previously been detected within a certain time period. For example, this is illustrated in FIG. 22C, which shows a time window 2240 for the start of a qualified HH event. Specifically, 2242 is the furthest time of detecting dispensing hand cleaning agent from detecting the HH opportunity 2244 (e.g., 10 seconds) while still qualifying the HH event as being sufficiently tied to the HH opportunity. Otherwise, the detected HH opportunity 2244 is considered too remote (such as too remote in time) to be a qualifying HH event for purposes of determining compliance with a HH opportunity.

If at 2223 it is determined that the HH event was detected within a certain time, at 2224, the motion data (such as stored in the wristband) may be accessed based on time of detected HH event in order to determine compliance with hand movements. As discussed above, responsive to the stationary controller detecting the HH event (e.g., detecting dispensing of hand cleaning agent), the stationary controller may send a message to wristbands proximate to the stationary controller (e.g., in the dispensing messaging zone). Responsive thereto, the wristband may wake up and begin detecting and/or analyzing hand movements. Thus, prior to determination of a HH opportunity, the wristband already may have stored motion data based on when the HH event has been detected, with the trigger (such as the communication from the stationary controller) focusing the wristband's analysis of the stored motion data (e.g., the wristband selects the motion data for analysis based on its time stamp so that the motion data analyzed for compliance begins at, or approximately begins at, the time at which the communication is received from the stationary controller).

If at 2223 it is determined that the HH event was not detected within a certain time, at 2225, it is determined whether the HH event was or will be detected within a certain time of detecting the HH opportunity. For example, this is illustrated in FIG. 22C at 2246 as a certain period (e.g., 3 seconds). If the HH event has not been detected at 2225 (e.g., no dispensing of hand cleaning agent detected), at 2226, a reminder may be generated. For example, in one or some embodiments, if the stationary controller does not detect a dispensing of hand cleaning agent within the certain period (e.g., 3 seconds), the stationary controller may generate an output (such as an auditory output on a speaker associated with the stationary controller and/or visual output on a light associated with the stationary controller) reminding the healthcare provider to take hand cleaning agent. Alternatively, or in addition, the stationary controller may send a message to wristbands (such as in the dispensing messaging zone, discussed herein) indicating to the wristbands to generate the reminder output (such as an auditory output on a speaker resident on the wristband and/or visual output using a light resident on the wristband). Still alternatively, responsive to the wristband identifying the HH opportunity, and if in 3 seconds after identifying the HH opportunity, the wristband fails to receive a communication from a stationary controller, indicating dispensing of hand cleaning agent has occurred, the wristband may generate the reminder output. In one or some embodiments, responsive to receiving the message from the stationary controller, the wristband generates the reminder output regardless of the status of the healthcare provider. Alternatively, responsive to receiving the message from the stationary controller, the wristband determines whether to generate the reminder output dependent on the status of the healthcare provider (e.g., the status (e.g., trainee or non-trainee) of the healthcare provider may be stored in the wristband; responsive to receiving the reminder message from the stationary controller, the wristband determines to generate the reminder output responsive to identifying the healthcare provider wearing the wristband as a trainee and determines not to generate the reminder output responsive to identifying the healthcare provider wearing the wristband as a non-trainee). Still alternatively, no reminder (such as reminder 2246) need be issued.

At 2227, it is determined whether the HH event was detected within another time period after detecting the HH opportunity. For example, this is illustrated in FIG. 22C at 2248 as a certain period (e.g., 5 seconds from the reminder 2246). Thus, in one embodiment, the amount of time looking backward from detecting the HH opportunity is different from the amount of time looking forward from detecting the HH opportunity (e.g., 10 seconds versus 8 seconds). Alternatively, the amount of time looking forward and backward from detecting the HH opportunity may be the same. It is noted that the figures illustrate detecting the HH opportunity and then determining whether a HH event is proximate (such as in time or space). Alternatively, the HH event may first be detected and then it may be determined whether a HH opportunity is proximate.

In the event that the HH event has not been detected within the time period, at 2231, non-compliance is determined. For example, if it is determined that there has been no dispensing of hand cleaning agent within a certain time period of detecting the HH opportunity, it may then be determined that there is no compliance with the HH opportunity. In one or some embodiments, the stationary controller may determine this non-compliance. Alternatively, the wristband, in combination with receiving a communication from proximate stationary controller(s), may determine this non-compliance. Still alternatively, the wristband, identifying the HH opportunity and failing to receive a communication with the certain time period from the stationary controller indicating dispensing of hand cleaning agent, determines there is no compliance with the HH opportunity.

At 2228, compliance with hand motions (e.g., durations and/or specific movements) may then be determined. For example, as discussed above, one or both of duration and/or specific movements may be monitored by the wristband in order to determine compliance. If so, at 2229, full compliance is determined. For example, the wristband, responsive to reviewing the motion data stored thereon, may determine whether the motion data is indicative of compliance. If not, at 2230, partial compliance may be determined. As discussed above, partial compliance may be based on several criteria including: taking hand cleaning agent but not complying with hand motions; or taking hand cleaning agent and only partially complying with hand motions (e.g., complying with duration but not with specific hand motions; complying with duration and partially complying with specific hand motions).

At 2232, the compliance determination may be transmitted. As discussed above, HH events may be insufficiently tied to a HH opportunity. In that regard, merely focusing on determining compliance for HH events (without sufficient connection to an identified HH opportunity) may be misplaced. Rather, in one or some embodiments, one, some or all of transmission, recordal, or tagging of compliance with HH events may be dependent on sufficient connection to the identified HH opportunity. As one example, responsive to determining that the HH event is not sufficiently connected to the identified HH opportunity, no transmission of the compliance determination (e.g., compliance, partial-compliance or non-compliance) with the detected HH event is made. In particular, without the connection of the HH event to the identified HH opportunity, the compliance determination is not transmitted external to the wristband and/or the stationary controller so that the back-end servers have no knowledge thereof (e.g., no knowledge of a detected HH event or of compliance with the detected HH event). As another example, responsive to determining that the HH event is not sufficiently connected to the identified HH opportunity, the results of compliance, partial-compliance or non-compliance may be transmitted (with an indication that the HH event is not sufficiently connected to any identified HH opportunity), but that the back-end server may treat the results differently than if the results were tied to an identified HH opportunity (e.g., the back-end server may decide not to record the results or may decide to record the results but to tag the compliance determination to indicate that the results are not sufficiently connected to any identified HH opportunity). In this way, in one or some embodiments, hand hygiene results may be more focused on the identified HH opportunities, which are typically the focus, rather than more generally relating to compliance with detected HH events.

As shown, FIG. 22B begins by determining whether a HH opportunity has been detected, and thereafter checking either forward or backward in time whether the HH event has been detected. Conversely, the flow may comprise determining whether a HH event has been detected, and thereafter checking either forward or backward in time whether the HH opportunity has been detected, as discussed above.

Figure 23:
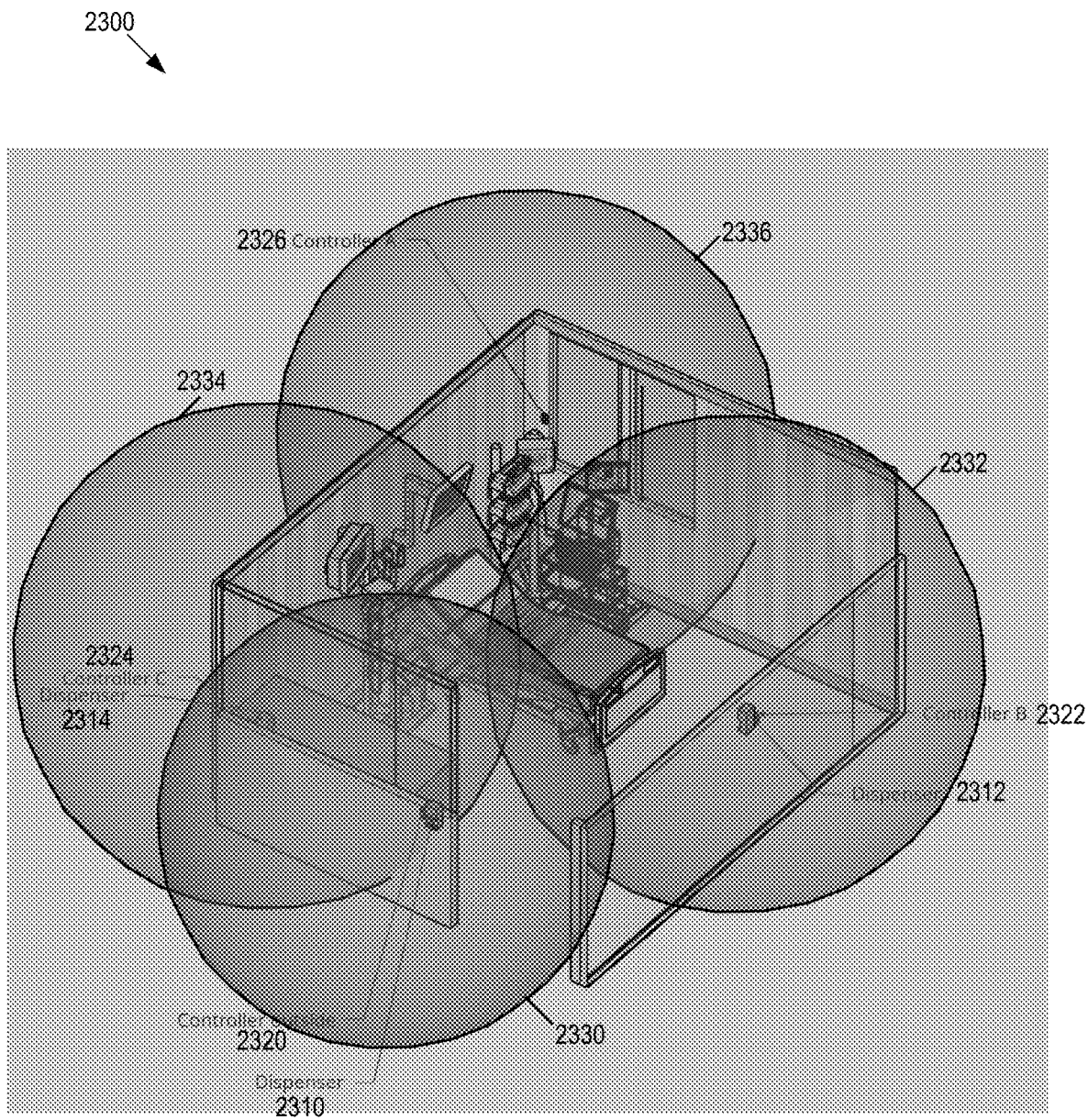
FIG. 23 illustrates a 3-D perspective view of a patient room with a plurality of communication zones.

As discussed above, tracking movement of the healthcare provider may be performed in one of several ways. As one example, communication(s) with the wristband of the healthcare provider may be used to track the movement of the healthcare provider, as illustrated in FIG. 23. In particular, FIG. 23 is a perspective view of one example of a patient area (e.g., a patient room), with a plurality of stationary controllers (controller outside of patient room 2320, controller A 2326, controller B 2322, controller C 2324) and associated communication zones 2330, 2336, 2332, 2334. As shown in FIG. 23, some of the controllers are associated with a respective dispenser, such as dispenser 2310 associated with controller outside 2320, dispenser 2312 associated with controller B 2322, and dispenser 2314 associated with controller C 2324. As one example of tracking, communication with a single controller (and more particularly communication with a single controller for at least a predetermined amount of time) may be indicative of tracking movement of the healthcare provider. In particular, communication of the mobile electronic device with controller outside 2320 for at least 1.5 seconds may be indicative that the healthcare worker is planning to enter the patient area. Alternatively, communication of the mobile electronic device with controller B 2322 for at least 1.5 seconds may be indicative that the healthcare worker has already entered the patient area. As another example of tracking, communication with multiple controllers (and more particularly communication with the multiple controllers for at least a predetermined amount of time) may be indicative of tracking movement of the healthcare provider. In either instance, the mobile electronic device, itself, may (using communication with stationary controller(s)) make the determination as to the tracking of movement of the healthcare provider the mobile electronic device is associated with. As discussed above, the controller may be associated with a respective dispenser in one of several ways, such as being integrated with or proximate to the respective dispenser. Further, a controller, such as controller A 2326, need not be associated with a respective dispenser.

Thus, it is noted that the time period between a previous HH event determination and a subsequent HH opportunity determination may vary depending on whether PPE is required for the patient room. For example, in compliance only with the HH protocol, FIG. 22B (at 2223) and FIG. 22C (between 2242 and 2244) have a span of 10 seconds between detecting the HH event and detecting the subsequent HH opportunity, discussed below. However, in the event that the patient room requires PPE, 10 seconds may not be sufficient to comply with the HH protocol, comply with the PPE protocol (e.g., by putting on PPE) and also enter the room. Thus, in one or some embodiments, the time period between the HH event determination and the subsequent HH opportunity may be dynamic, such as dependent on whether there is another protocol (separate from hand hygiene) to follow, such as to follow a PPE protocol.

Figure 22D:
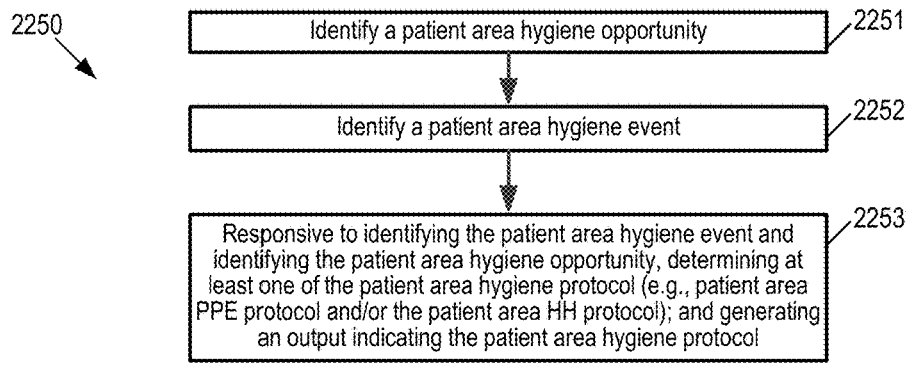
FIG. 22D is a flow diagram for identifying a patient area hygiene opportunity, identifying a patient area hygiene event, and determining whether and what to output regarding protocol(s) responsive to identifying the patient area hygiene opportunity and patient area hygiene event.

FIG. 22D is a flow diagram 2250 of identifying a patient area hygiene opportunity, identifying a patient area hygiene event, and determining whether and what to output regarding protocol(s) responsive to identifying the patient area hygiene opportunity and patient area hygiene event. As discussed above, the healthcare provider may be notified regarding one or more protocols associated with a patient area. This notification may be provided either in conjunction with monitoring compliance (e.g., monitoring HH compliance with HH protocol(s) and/or PPE compliance with PPE protocol(s)). Alternatively, the notification may be provided separate from any monitoring compliance. In this regard, any discussion herein regarding notification may be performed in conjunction with compliance determination or may not be performed in conjunction compliance determination. As discussed above, notification may be opportunity-based. Specifically, healthcare providers may be constantly inundated with notifications of compliance with various protocols. In order to minimize the number of notification while still providing notification when believed necessary, an opportunity-based notification is provided in which notification occurs responsive to identifying an opportunity for patient interaction (such as the 5 WHO opportunities discussed above). Thus, at 2251, a patient area hygiene opportunity (such as one or both of a HH opportunity or a PPE opportunity) is identified. As discussed above, various ways to identify a patient area hygiene opportunity are contemplated. At 2252, a patient area hygiene event (such as one or both of a HH event or a PPE event) is identified. As discussed above, various ways to identify a patient area hygiene event are contemplated (e.g., detecting dispensing of hand cleaning agent; detecting removing of PPE; etc.). At 2253, responsive to identifying the patient area hygiene event and identifying the patient area hygiene opportunity: determining at least a part of the patient area hygiene protocol (e.g., the patient area hygiene protocol includes one or both of the patient area PPE protocol or the patient area HH protocol); and generating an output indicating at least a part of the patient area hygiene protocol (e.g., at least one of the patient area PPE protocol or the patient area HH protocol). As discussed above, one or more protocols, such as one or both of a HH protocol or a PPE protocol may be associated with a patient area, such as a patient room. As such, responsive to identifying the patient area hygiene event and identifying the patient area hygiene opportunity, the protocol(s) associated with the patient area may be determined (e.g., using the stationary controller associated with the patient area, which has stored therein the protocol(s) and/or communicating with a backend server, which includes a database correlating patient areas with corresponding protocol(s)). Further, at least one aspect of the protocol(s) may be output. As one example with regard to HH, the type of hand cleaning agent to use, such as either soap or hand sanitizer, may be output. As another example with regard to PPE, the type of PPE garments (e.g., only gloves; only a mask and gloves; etc.) may be output. Alternatively, the sequence of PPE to put on, such as first the mask and then the gloves, may be output. Still alternatively, in combination with monitoring the movements of the healthcare provider, the outputs may track the sequence (e.g., in the example of putting on a mask and gloves, the wristband may monitor the movements for putting on a mask; after confirmation that the healthcare providers has performed the movements for putting on the mask, the wristband may generate an output to put on the gloves). Yet alternatively, the sequence of HH and PPE may be output (e.g., when entering the patient area, the wristband may output: "first wash hands with soap, and then put on a mask and gloves"; when exiting the patient area, the wristband may output: "first remove gloves and then mask, and then wash hands with soap"). Or, the output may be dynamic based on the tracked movements (e.g., when entering the room, the wristband may monitor hand movements for hand washing; after confirmation that the healthcare provider has performed the movements for washing hands, the wristband may generate an output indicative of "now put on the mask and then the gloves"). Though FIG. 22D illustrates identifying the patient area hygiene opportunity prior to identifying the patient area hygiene event, the converse may be true.

Figure 22E:
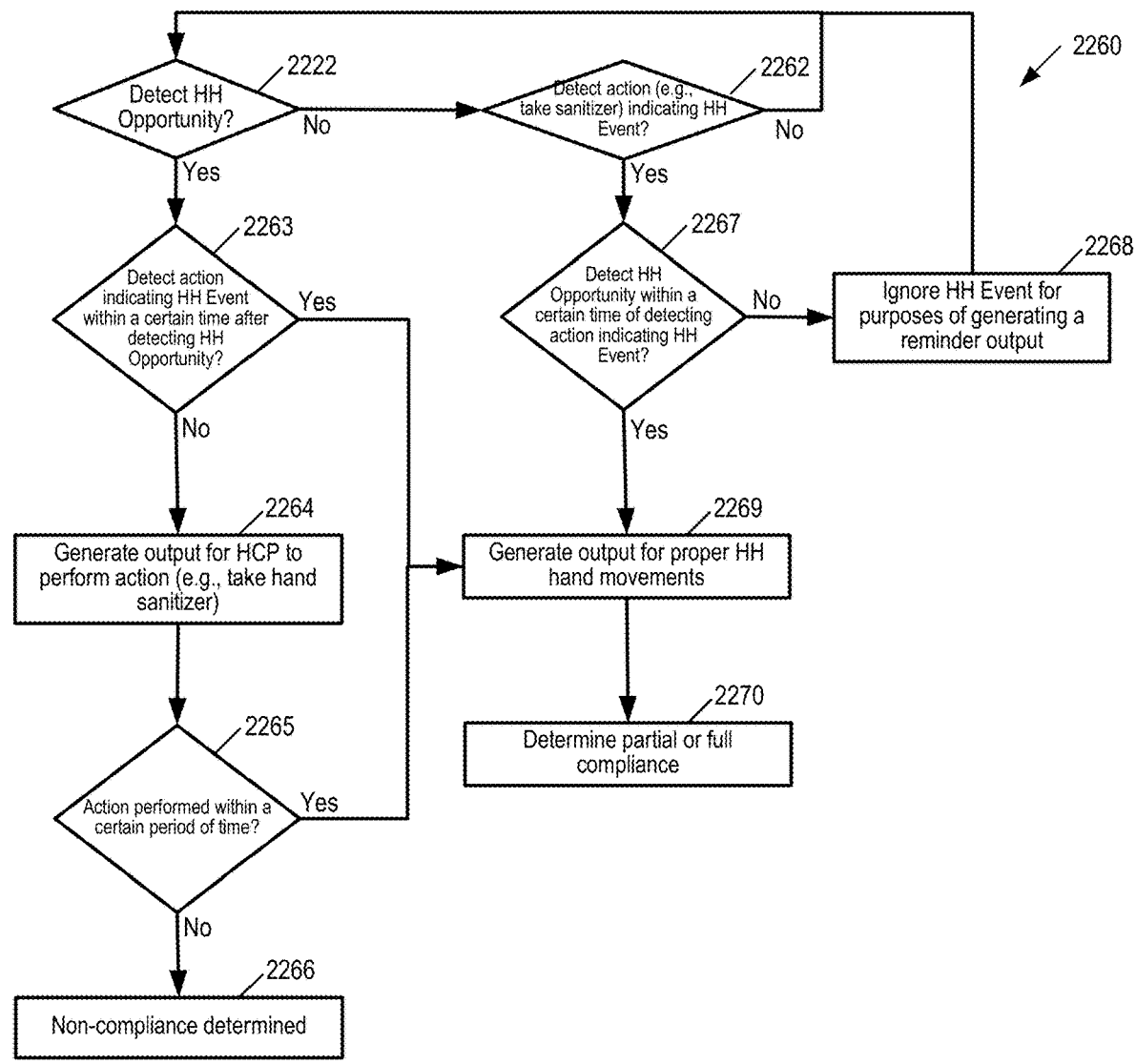
FIG. 22E is a flow diagram for determining whether to generate reminder outputs for HH protocol(s) and what outputs to generate for the HH protocols when detecting a HH opportunity.

FIG. 22E is a flow diagram 2260 of determining whether to generate reminder outputs for HH protocol(s) and what outputs to generate for the HH protocols when detecting a HH opportunity. At 2222, it is determined whether the HH opportunity is detected. For example, the wristband may determine whether there is movement either into or out of the patient area. If yes, at 2263, it is determined whether an action indicating the HH event has occurred within a certain time after detecting the HH opportunity (e.g., the time period between 2244 and 2246 in FIG. 22C). As one example, an action may comprise the healthcare provider taking hand cleaning agent from a dispenser. If not, at 2264, an output may be generated for the healthcare provider (HCP) to perform the action (e.g., take hand sanitizer). This output is illustrated at 2246 in FIG. 22C. If so, flow diagram 2260 moves to 2269.

At 2265, it is determined whether the action (e.g., taking hand sanitizer) has been performed with a certain time period (such as the time period between 2246 and 2248 of 5 seconds). If not, at 2266, one or both of the wristband or the stationary controller may determine non-compliance. If so, flow diagram 2260 moves to 2269.

If at 2222 no HH opportunity is detected, the system (such as the stationary controller) may determine whether an action has been detecting indicating a HH Event (such as taking hand sanitizer). If not, flow diagram loops back to 2222. If so, at 2267, the system determines whether a HH opportunity has been detected or identified within a certain time of detecting the action indicating the HH event. If not, at 2268, the HH event is ignored for purposes of generating a reminder output. If so, at 2269, an output, such as via one or both of the wristband or the stationary controller, may be generated for proper HH movements (e.g., one or both of an indication of the amount of time, such as 20 seconds of rubbing, or the proper sequence of hand movements). After which, at 2270, partial or full compliance with the HH opportunity is determined.

Figure 22F:
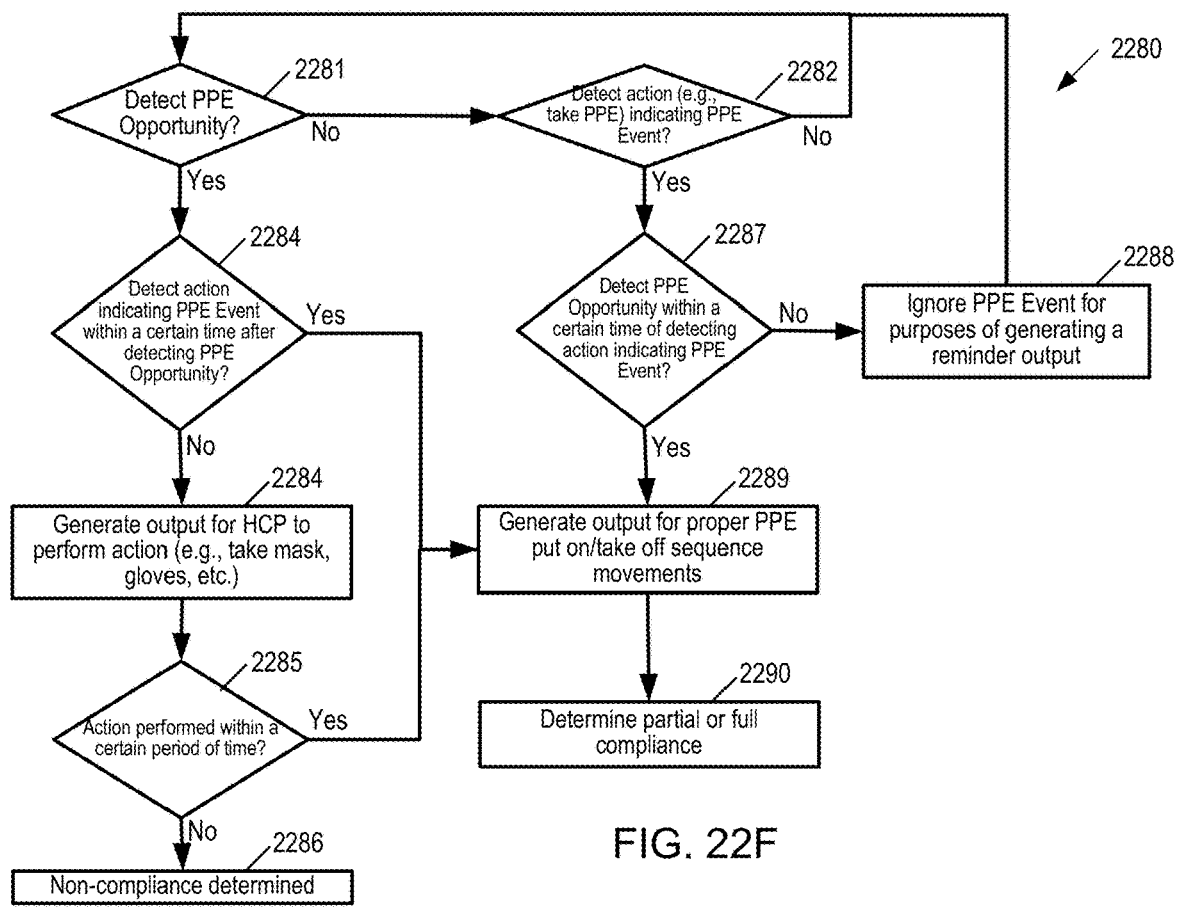
FIG. 22F is a flow diagram for determining whether to generate reminder outputs for PPE protocol(s) and what outputs to generate for the PPE protocols when detecting a PPE opportunity.

FIG. 22F is a flow diagram 2280 of determining whether to generate reminder outputs for PPE protocol(s) and what outputs to generate for the PPE protocols when detecting a PPE opportunity. At 2281, it is determined whether a PPE opportunity has been detected. For example, the wristband may determine whether there is movement either into or out of the patient area. If yes, at 2284, it is determined whether an action indicating the PPE event has occurred within a certain time after detecting the HH opportunity. As one example, an action may comprise the healthcare provider taking PPE from a PPE container. If not, at 2284, an output may be generated for the healthcare provider (HCP) to perform the action (e.g., take PPE). If so, flow diagram 2280 moves to 2289.

At 2285, it is determined whether the action (e.g., taking PPE) has been performed with a certain time period. If not, at 2286, one or both of the wristband or the stationary controller may determine non-compliance. If so, flow diagram 2280 moves to 2289.

If at 2281 no PPE opportunity is detected, the system (such as the stationary controller) may determine whether an action has been detecting indicating a PPE Event (such as taking PPE). If not, flow diagram 2280 loops back to 2281. If so, at 2287, the system determines whether a PPE opportunity has been detected or identified within a certain time of detecting the action indicating the PPE event. If not, at 2288, the PPE event is ignored for purposes of generating a reminder output. If so, at 2289, an output, such as via one or both of the wristband or the stationary controller, may be generated for proper PPE movements (e.g., proper sequence of PPE to put on or take off). After which, at 2290, partial or full compliance with the PPE opportunity is determined.

As discussed herein, a patient area may have associated therewith a patient area protocol, such as a HH protocol and/or a PPE protocol. The patient area protocol may be dynamically assigned, such as based on a diagnosis associated with the patient. For example, the patient, upon admittance to a specific hospital room, may already have been diagnosed with a MRSA infection. As such, the specific hospital room may be assigned the HH protocol and/or a PPE protocol for treating a MRSA infection. Alternatively, after the patient was admitted to the specific hospital room, the patient may thereafter have been infected, such as having been infected with a MRSA infection. Thus, the specific hospital room may have its associated protocol be dynamically changed from a first patient area protocol to a second patient area protocol, with the second patient area protocol being different from the first patient area protocol (e.g., prior to being diagnosed with a MRSA infection, the specific hospital room has assigned a non-MRSA infection protocol; after being diagnosed with the MRSA infection, the specific hospital room has assigned a MRSA infection protocol). In this way, the various patient areas in a hospital, nursing home, or other healthcare environment may dynamically change its protocols based on changed circumstances.

In order to assist the healthcare providers in awareness of the changing patient area protocols, the system may identify a patient area hygiene opportunity, and responsive to identifying the patient area hygiene opportunity, intelligently determine whether to generate an output to remind the healthcare provider. In this way, reminders may be kept to a minimum, thereby being less intrusive to the healthcare provider, while still being used when a patient area hygiene opportunity is identified.

Figure 22G:
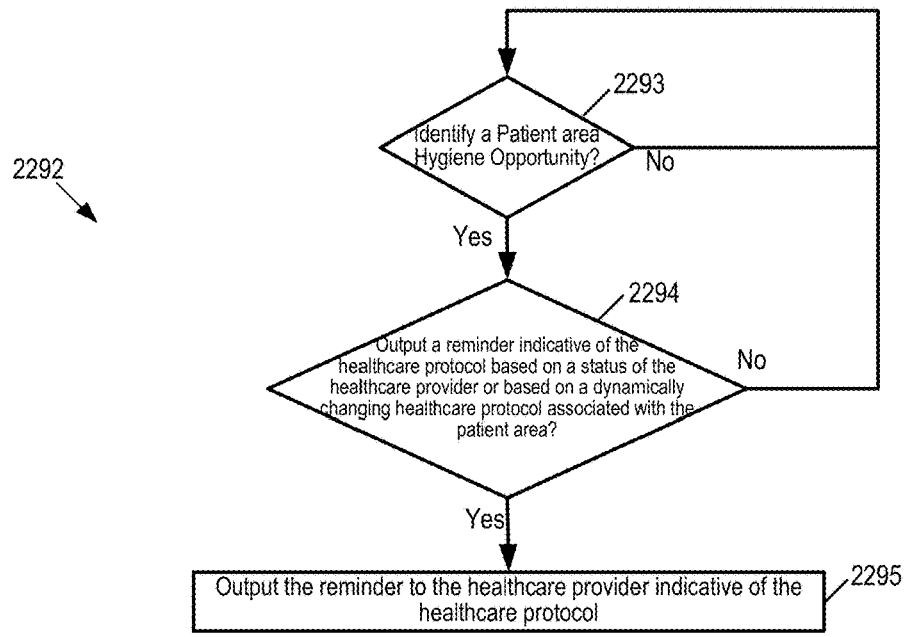
FIG. 22G is a flow diagram for identifying a patient area hygiene opportunity associated with a patient area and determining whether to generate a reminder indicative of the healthcare protocol associated with the patient area.

One example of the intelligent reminder system is illustrated in the flow diagram 2292 in FIG. 22G for identifying a patient area hygiene opportunity associated with a patient area and determining whether to generate a reminder indicative of the healthcare protocol associated with the patient area. At 2293, it is determined whether a patient area hygiene opportunity is present, such as an opportunity associated with a specific patient room. As discussed above, the patient area hygiene opportunity may be indicative of interaction of the healthcare provider with a patient in the patient area. Further, various hygiene opportunities are contemplated, such as one or both of a HH opportunity or a PPE opportunity.

Responsive to not identifying the patient area hygiene opportunity, flow diagram 2292 loops back to 2293. Responsive to identifying the patient area hygiene opportunity, at 2294, it is determined whether to output a reminder indicative of the healthcare protocol associated with the patient area. As discussed above, several ways are contemplated to associate a healthcare protocol with a patient area. The association may be performed at the server level, and may be dynamically accessed at the server level (e.g., one or both of a mobile electronic device or a local stationary controller (positioned in or about the patient area) may dynamically access the healthcare protocol on a server). The association may be performed at the server level, and may be dynamically accessed at the patient area level (e.g., the healthcare protocol may be sent (e.g., pushed or pulled) from the server to a local stationary controller positioned in or about the patient area; a mobile electronic device, when proximate to the local stationary controller, may communicate with the local stationary controller to determine the healthcare protocol). Still alternatively, the association may be performed at the patient area level, and may be dynamically accessed at the patient area level (e.g., the local stationary controller may be programmed with the healthcare protocol and may dynamically access the healthcare protocol (and/or send the healthcare protocol to a proximate mobile electronic device). Yet alternatively, the association and the access may be at the mobile electronic device level (e.g., the mobile electronic device locally stores patient area rooms (with associated location coordinates and associated healthcare protocols); the mobile electronic device, using its GPS receiver, determines its current location determines the patient area closest to its current location, and accesses the associated healthcare protocol for the determined patient area).

Further, various bases to determine whether to output the reminder are contemplated. One manner to determine whether to output the reminder is based on a status of the healthcare provider (e.g., responsive to determining that the healthcare provider is a trainee, output the reminder; responsive to determining that the healthcare provider is not a trainee, decide not to output the reminder). Another manner to determine whether to output the reminder is based on a dynamically changing healthcare protocol associated with the patient area based on a diagnosis of the patient in the patient area. For example, a protocol associated with the patient area may dynamically change based on the diagnosis of the patient associated with the patient area (e.g., the patient is diagnosed with a MRSA infection). In one particular manner, in deciding whether the protocol has dynamically changed, the healthcare provider may interact with the patient area at a current time, it may be determined whether one or both of the PPE protocol or the HH protocol associated with the patient area has changed within a predetermined time period prior to the current time, and if so, the reminder indicative of the healthcare protocol may be output. In this regard, responsive to identifying that the patient area has a dynamically changing protocol and/or that the protocol has been changed within in a certain time period (e.g., the protocol has changed within the past week), it is determined to output the reminder.

Responsive to determining to output the reminder, at 2295, the reminder is output to the healthcare provider indicative of the healthcare protocol. Responsive to determining not to output the reminder, flow diagram 2292 loops back to 2293. Further, in order to avoid an excessive number of reminders, even though the patient area has a dynamically changing protocol and/or that the protocol has been changed within a certain time period, the system, under certain circumstances, may determine not to output the reminder. As one example, responsive to outputting the reminder a certain set number of times, such as a certain number of times for a specific healthcare provider, for a group of healthcare providers, etc., no further reminders are given.

The identification of the patient area hygiene opportunity and/or the determination as to whether to output the reminder indicative of the patient area healthcare protocol may be performed by the same device or, alternatively, may be performed by different devices. In one embodiment, the mobile electronic device may identify the patient area hygiene opportunity and determine whether to output the reminder indicative of the patient area healthcare protocol. For example, the mobile electronic device may communicate with an external device, such as the stationary controller and/or the backend server in order to determine whether the patient area healthcare protocol associated with the patient area is dynamically changeable (e.g., determine whether the protocol associated with the area indicates a dynamically changing protocol; determine whether the protocol has changed within a certain time period; etc.). Alternatively, separate devices may identify the patient area hygiene opportunity and determine whether to output the reminder indicative of the patient area healthcare protocol. For example, the mobile electronic device may identify the healthcare opportunity and a backend server determines whether to cause an output of the reminder. Specifically, the backend server may: responsive to identifying a healthcare opportunity for a healthcare worker to interact with the patient associated with the patient area, access a database storing the patient area healthcare protocol associated with the patient area that is dynamically changeable; and cause an output to be generated, the output indicative to the healthcare worker of the patient area healthcare protocol (e.g., send a command so that one or both of the mobile electronic device or the stationary controller outputs the indication of the patient area healthcare protocol). Still alternatively, the stationary controller may be programmed with the protocol (which may be changed) and also may be programmed with a time window in which to output reminders. Responsive to interaction with a wristband in near-field communication range of the stationary controller and responsive to the stationary controller determining that a current time is within the time window, the stationary controller may output the reminder and/or may send a command to the wristband to output the reminder.

FIG. 23 illustrates communication zones 2330, 2336, 2332, 2334, with some communication zones 2330, 2336, 2332, 2334 in one embodiment at least partially overlapping one another. Alternatively, the communication zones do not overlap one another at all. Thus, each sphere in FIG. 23 represents a communication zone 2330, 2336, 2332, 2334 for a respective controller (controller outside 2320, controller A 2326, controller B 2322, controller C 2324). In one or some embodiments, the size (e.g., distance from an electronic device to the stationary controller) of each zone may be programmed by setting a threshold for the Received Signal Strength Indicator (RSSI) values obtained from the wristbands. Thus, the wristband may receive a signal from an external electronic device, such as a respective stationary controller, and determine a zone relative to the external electronic device.

In one or some embodiments, multiple zones, such as three zones, may be programmed for each controller. However, fewer or greater numbers of zones are contemplated. As one example, the following three zones comprise: (1) connection zone; (2) a dispensing messaging zone; and (3) a proximity zone. Specifically, a respective stationary controller may connect to all wristbands in its respective connection zone. Further, in the example of three zones, the connection zone may be set as the largest (e.g., ~15-20 ft). When a respective stationary controller detects a dispensing event (e.g., on the dispenser the respective stationary controller monitors), the respective stationary controller sends one or more messages (e.g., a dispensing message) to all wristbands in the dispensing messaging zone. As discussed in more detail below, this dispensing message triggers the determination of HH event compliance. For example, responsive to a wristband receives the dispensing message and the wristband determining (based on the RSSI value) that the wristband is within the dispensing messaging zone, the wristband starts the HH detection algorithm to determine compliance with one or both of duration of hand rubbing or detection of specific hand movements. In this way, rather than the wristband constantly attempting to review its movements to determine compliance, the wristband may have a trigger (such as based on the wristband receiving the dispensing message from the stationary controller and the wristband determining the wristband received the dispensing message within the dispensing message zone) that allows the wristband to focus its analysis of hand movements and/or duration on a time period for the HH event. Further, the wristband may receive "pings" from the stationary controller (e.g., messages at predetermined intervals), with the wristband determining whether the RSSI signal for the "pings" indicating that the wristband is within the proximity zone. In one or some embodiments, the proximity zone is smaller than the dispensing message zone (e.g., 3-5 feet). Alternatively, the proximity zone is larger than the dispensing message zone.

As discussed above, the location and/or movement of the healthcare provider may be used to identify a HH opportunity. Thus, in one or some embodiments, the electronic device (such as a wristband) associated with the healthcare provider, may determine the movement of the healthcare provider (and in turn identify the HH opportunity). For example, wristbands in the proximity zone may be considered very close to the respective stationary controller. Thus, when a wristband enters/exits a proximity zone of the respective stationary controller, the wristband may receive a "ping" from the respective stationary controller and determine from the signal strength of the "ping" that the wristband is within the proximity zone. In this way, the wristband may determine its location and or associated movement, and then the wristband may determine if there is a hand hygiene opportunity. Thus, in one or some embodiments, communication zones 2330, 2336, 2332, 2334 each comprise a proximity zone for the respective controller. Alternatively, at least one of the communication zones 2330, 2336, 2332, 2334 is different (such as in size) from another of the communication zones 2330, 2336, 2332, 2334.

As one example, the wristband may determine movement from outside of a patient area to an interior of the patient area. In a specific implementation, a first stationary controller (such as controller outside 2320) is positioned at the entrance of a specific patient area and a second stationary controller (controller A 2326, controller B 2322, or controller C 2324) is positioned in an interior of the specific patient area. In moving from outside of the specific patient area to the inside, the first stationary controller (such as controller outside 2320) may send a "ping" to the wristband (with the "ping" from the first stationary controller indicating that it is a message from an electronic device on the exterior of the specific patient area). In turn, the wristband determines that the wristband is within the proximity zone of the first stationary controller that is on the exterior of the specific patient area. As the healthcare provider moves to the interior of the specific patient room, the wristband receives the "ping" from the second stationary controller (controller A 2326, controller B 2322, or controller C 2324) (with the "ping" from the second stationary controller indicating that it is a message from an electronic device in the interior of the specific patient area) and determines that the wristband is within the proximity zone of the zone stationary controller that is in the interior of the specific patient area. Thus, from the series of pings, the wristband may determine movement from outside to inside the patient area. Alternatively, determining movement from outside to inside the patient area may comprise determination of the proximity zone (e.g., 2330) with controller outside 2320 and then the proximity zones (e.g., 2326, 2332, 2334) of at least two interior controllers (e.g., at least two of controller A 2326, controller B 2322, controller C 2324).

Conversely, the wristband may receive a sequence of pings from the second stationary controller (e.g., controller A 2326, controller B 2322, or controller C 2324) and then from the first stationary controller (e.g., controller outside 2320), indicating to the wristband that there was movement from the interior of the specific patient area to the exterior. Alternatively, determining movement from inside to outside the patient area may comprise determination of the proximity zones (e.g., 2326, 2332, 2334) of at least two interior controllers (e.g., at least two of controller A 2326, controller B 2322, controller C 2324) and then the proximity zone (e.g., 2330) with controller outside 2320. Thus, the wristband, analyzing communications with one or more external devices, such as one or more stationary controllers, may determine its respective location and/or its movement.

Figure 24A:
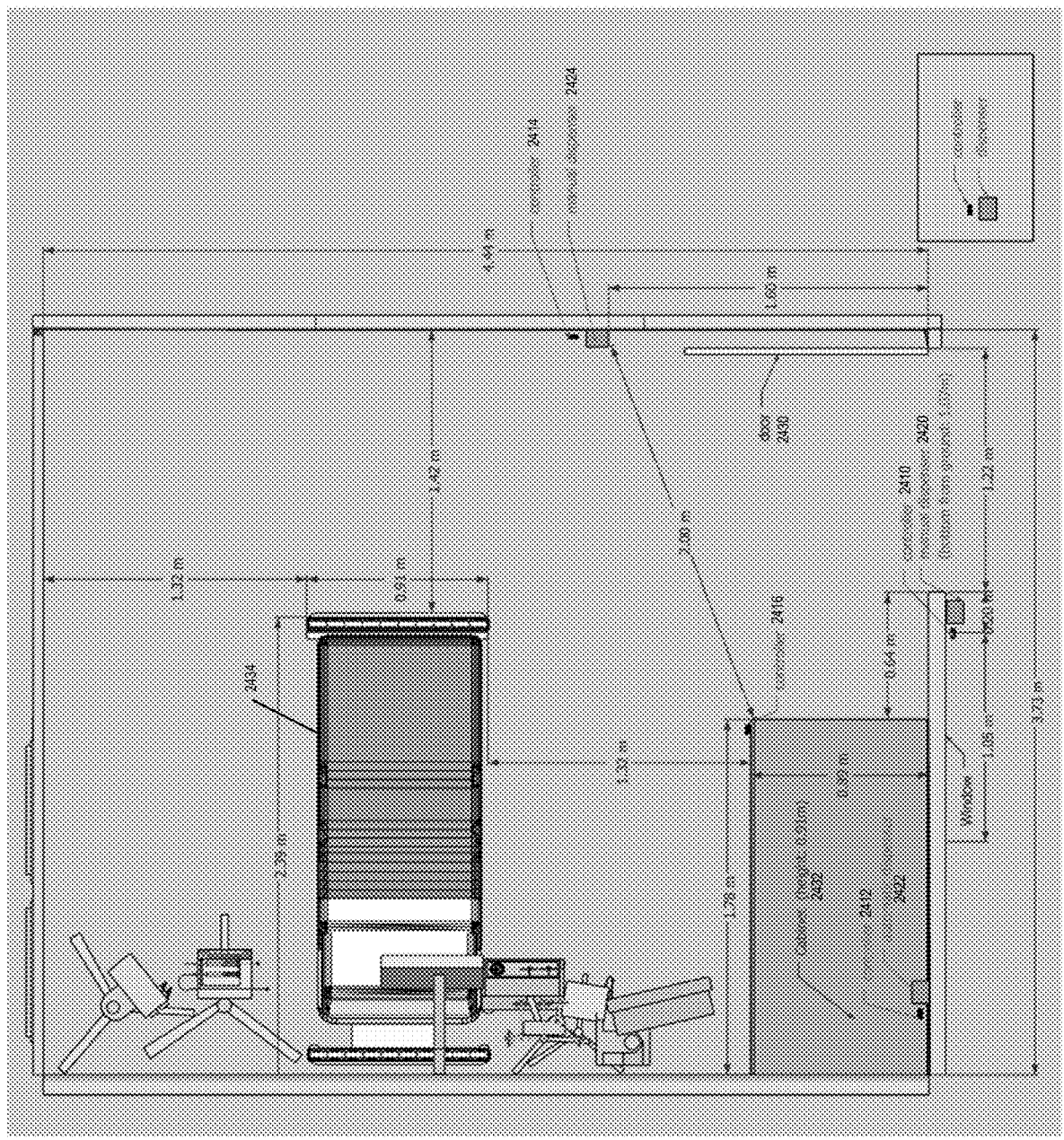
FIG. 24A illustrates a top view of a patient room with sensors and stationary controllers.

FIG. 24A illustrates a top view 2400 of another example of a patient area (e.g., a patient room), with a plurality of stationary controllers 2410, 2412, 2414, 2416, associated dispensers 2420, 2422, 2424, positioned in various areas in the patient area, such as relative to the door 2430, a cabinet 2432, and a bed 2434. As shown, the stationary controller may be associated with dispenser (such as stationary controllers 2410, 2412, 2414 associated with dispensers 2420, 2422, 2424) or may not be associated with any dispenser (such as stationary controller 2416). Further, placement of the stationary controllers in various locations about the patient area enables detection of the HH opportunity and the HH event, as discussed above.

Figure 24B:
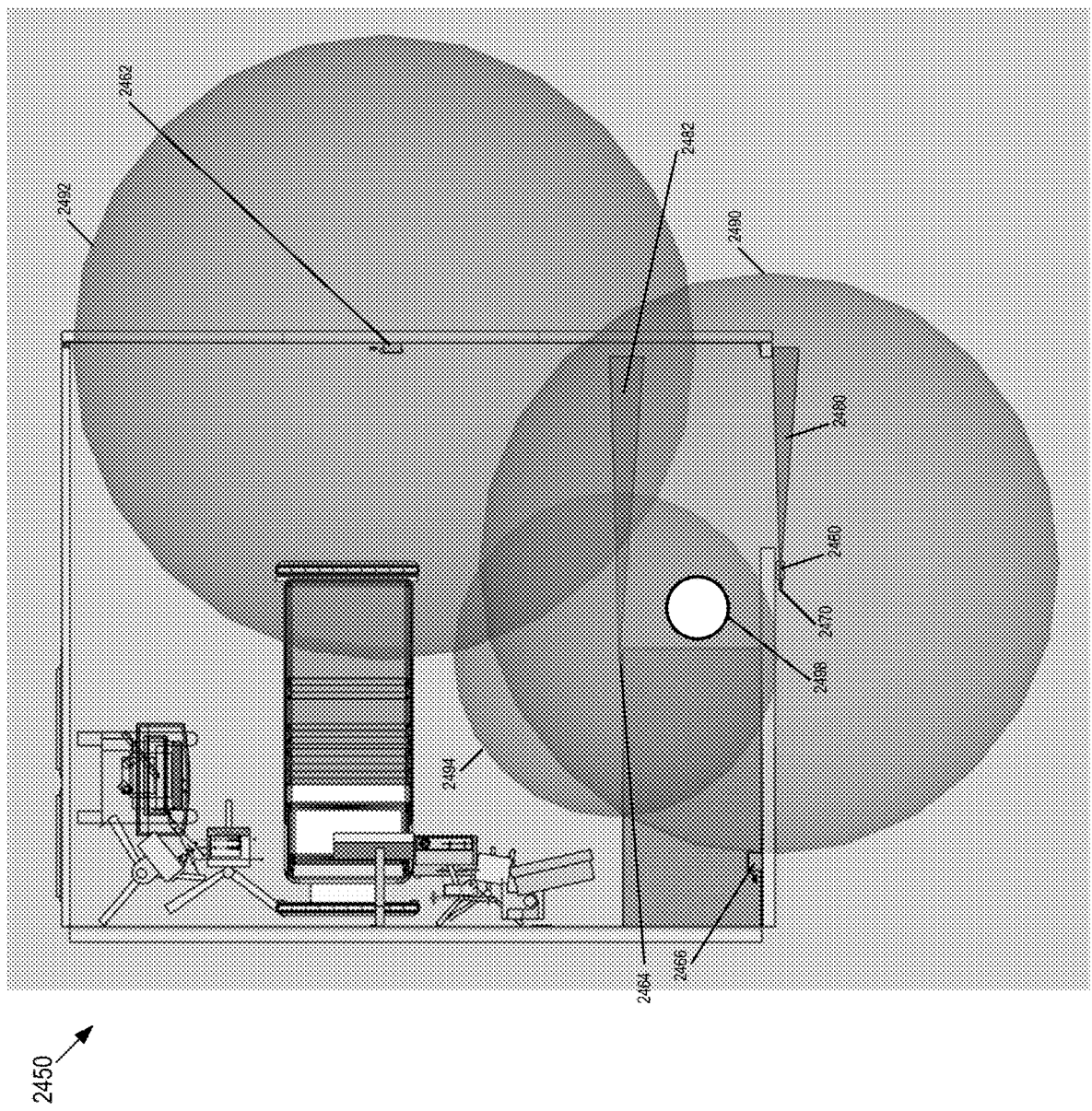
FIG. 24B illustrates a top view of a patient room with sensors, stationary controllers and communication zones.

FIG. 24B illustrates a top view 2450 of yet another example of a patient area with a plurality of stationary controllers 2460, 2462, 2464 (and associated communication zones 2490, 2492, 2494) and one or more sensors 2470. In one or some embodiments, the sensor(s) 2470 may comprise ultrasonic sensors, which may be configured to measure distance from the sensor. As shown, the sensors may have an associated beam 2480, 2482 (with beam 2482 formed by combination controller/sensor 2464). Thus, as a healthcare provider crosses beams 2480, 2482, the sensors 2470 may sense the crossing, and provide the sensor reading(s) to the associated stationary controller (such as 2460, 2464). In this way, based on analyzing the timing of a person crossing beams 2480, 2482, it may be determined whether a healthcare provider is walking into or out of the patient area. For example, in one or some embodiments, the stationary controller(s) may determine, communicating with an associated ultrasonic sensor and with each other, whether the healthcare provider is walking into or out of the patient area. Further, because the stationary controller(s) communicate with the wristband of the healthcare provider (such as communicating in one of the zones, discussed above), the stationary controller(s) may identify which wristband is proximate to the stationary controller(s) when the data indicative of crossing beams 2480, 2482 is sensed. Alternatively, the wristband associated with the healthcare provider may receive the data indicative of crossing beams 2480, 2482, either directly from the ultrasonic sensors or via the stationary controller(s), and determine the movement of the healthcare provider. Further, the patient area may include a trash can 2498 or some other disposal device which is located between beams 2480, 2482, and may be used for disposing PPE. In one or some embodiments, trash can 2498 may further include a sensor (such as an ultrasonic sensor) and/or a stationary controller (for establishing communication with wristbands) in order to identify movement (such as using only its sensor readings and/or its sensor readings with other sensors such as other ultrasonic sensors or communication with other stationary controllers) into and/or out of the patient area. For example, when exiting the patient area, passing beam 2482 (closer to the interior of the patient room) may trigger the start of monitoring movements to remove PPE (e.g., stationary controller may receive the sensor data from passing beam 2482 identifying a crossing and, responsive thereto, send a communication to the wristband to trigger the wristband to monitor PPE movements). After which, detecting dispensing of hand cleaning agent may trigger the start of monitoring hand movements for compliance with hand hygiene (e.g., stationary controller may detect dispensing of hand cleaning agent and, responsive thereto, send a communication to the wristband to trigger the wristband to monitor HH movements).

Figure 25A:
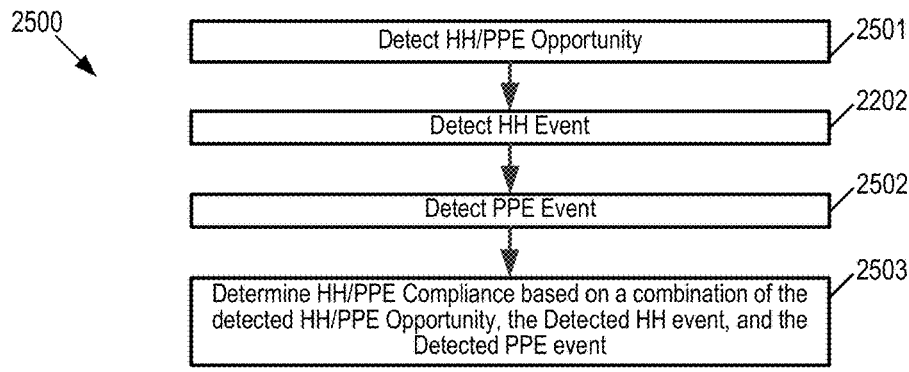
FIG. 25A illustrates is a flow diagram of detecting both the HH/PPE opportunity, the HH event, the PPE event and determining HH compliance based on a combination of the detected HH/PPE opportunity, the HH event and the PPE event.

FIG. 25A illustrates is a flow diagram 2500 of detecting both the HH/PPE opportunity, the HH event, the PPE event and determining HH compliance based on a combination of the detected HH/PPE opportunity, the HH event and the PPE event. At 2501, the HH/PPE opportunity is detected. At 2202, the HH event is detected. At 2502, the PPE event is detected. As discussed above, in one way, the PPE event may be detected on its own, such as by using the proximity sensing-output generating device. In another way, the PPE event may be detected in combination with detecting the HH event. Further, similar to the discussion above, the HH/PPE opportunity may be detected before detecting the HH event or after detecting the HH event (e.g., taking sanitizer in the hallway before entering the room). Thus, while flow diagram 2500 depicts detecting the HH/PPE opportunity before detecting the HH event or the PPE event, the converse may be true.

At 2503, HH/PPE compliance is determined based on a combination of the detected HH/PPE opportunity, the detected HH event, and the detected PPE event. As discussed above, in one or some embodiments, the HH event/PPE event (such as the detection of and/or determined compliance with the HH event/PPE event) is sufficiently connected to the HH/PPE opportunity in order for the compliance with the HH event/PPE event to be associated with or assigned to the HH/PPE opportunity. As discussed further below, the determination of compliance may be based on whether there is sufficient connection (such as connection in time) between the detected HH event/PPE event and the detected HH/PPE opportunity.

Figure 25C:
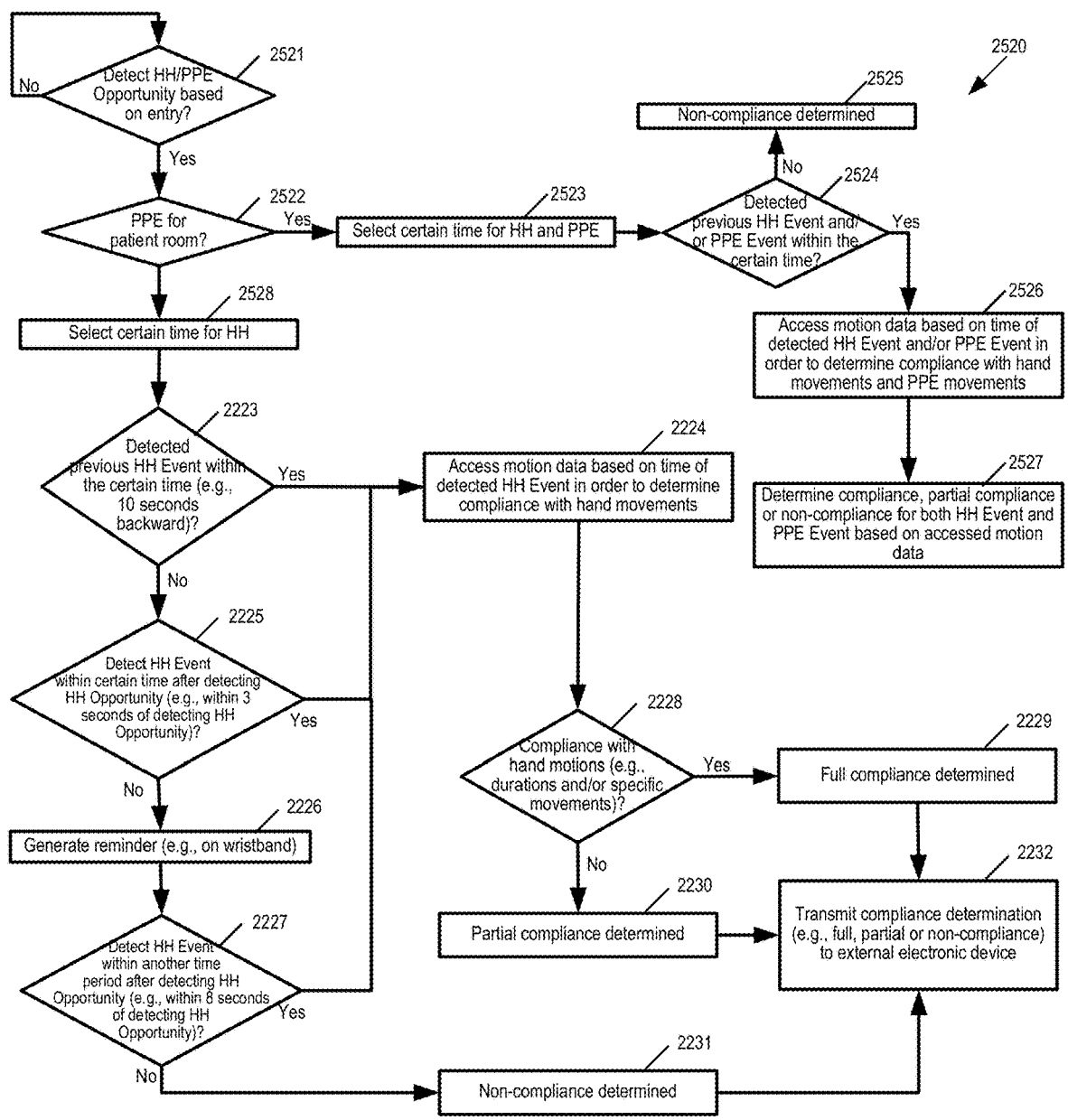
FIG. 25C is a flow diagram of one example of determining whether there is sufficient connection between the detected HH event/PPE event and the detected HH/PPE opportunity when entering a patient area.
Figure 25B:
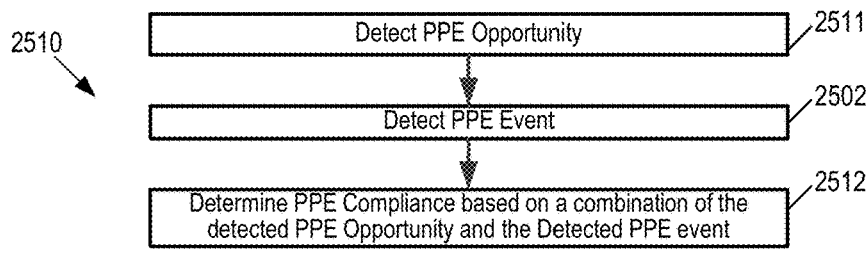
FIG. 25B illustrates is a flow diagram of detecting the PPE opportunity and the PPE event and determining compliance based on a combination of the detected PPE opportunity and the PPE event.

FIG. 25B illustrates is a flow diagram 2510 of detecting the PPE opportunity and the PPE event and determining compliance based on a combination of the detected PPE opportunity and the PPE event. At 2511, the PPE opportunity is detected. At 2502, the PPE event is detected. At 2512, PPE compliance is determined based on a combination of the detected PPE opportunity and the detected PPE event. Though flow diagram 2510 depicts detecting the PPE opportunity before detecting the PPE event, the converse may be true.

FIG. 25C is a flow diagram 2520 of one example of determining whether there is sufficient connection between the detected HH event/PPE event and the detected HH/PPE opportunity when entering a patient area. At 2521, it is determined whether there is a HH/PPE opportunity detected on entry. As discussed above, various ways are contemplated to detect the HH/PPE opportunity, including based on tracking movement of the healthcare provider. Further, various devices are contemplated to detect the HH/PPE opportunity, including one or both of the wristband or the stationary controller.

At 2522, it is determined whether there is a PPE protocol for the patient area (such as the patient room). As discussed above, the PPE protocol may be associated with a patient area. In this regard, a first patient room may have a first PPE protocol, a second patient room may have a second PPE protocol, and a third patient room may have no PPE protocol. In the event that a specific patient room has no PPE protocol (meaning that there is only a hand hygiene opportunity and not a hand hygiene/PPE opportunity), flow diagram 2520 goes to 2528 in order to select a time period to allow for performing hand hygiene prior to the detection of the HH opportunity. In the event that a specific patient room has a PPE protocol (meaning that there is a HH/PPE opportunity), flow diagram 2520 goes to 2523 in order to select a time period to allow for performing hand hygiene and PPE prior to the detection of the HH opportunity. In other words, if the healthcare provider both cleans his/her hands and puts on PPE prior to entering the room (and thus triggering the HH/PPE opportunity), the system provides for a longer time to perform this. In contrast, if the healthcare provider only cleans his/her hands prior to entering the room (and thus triggering the HH opportunity), the system provides for a shorter time to perform this. In this way, the time set at 2528 is shorter than the time set in 2523 (e.g., 10 seconds versus 20 seconds). In particular, the wait time may be dynamic based on the different protocols determined (e.g., dynamic waiting time dependent on whether there is a PPE protocol for the patient room).

At 2524, it is determined whether the HH event and/or PPE event has been detected within the certain time. In the situation in which the healthcare provider enters the room, the PPE is positioned outside of the patient room. Thus, the healthcare provider will have taken the hand cleaning agent outside of the patient room, and then put on the PPE prior to entering the room. In this way, 2524 determines whether one or both of the triggers have been detected (e.g., sensing dispensing of hand sanitizer and/or sensing a cabinet/drawer opening). If not, it is determined that there has been no hand cleaning or PPE donning prior to entry, and at 2525, non-compliance is determined. If so, at 2526, motion data in the wristband may be accessed based on the time of detected HH Event and/or PPE event in order to determine compliance with hand movements and PPE movements. Further, at 2527, compliance, partial compliance or non-compliance for both the HH event and PPE event may be determined based on accessed motion data. As shown in FIG. 25C, flow diagram 2520 after 2528 is similar to FIG. 22B.

Figure 25D:
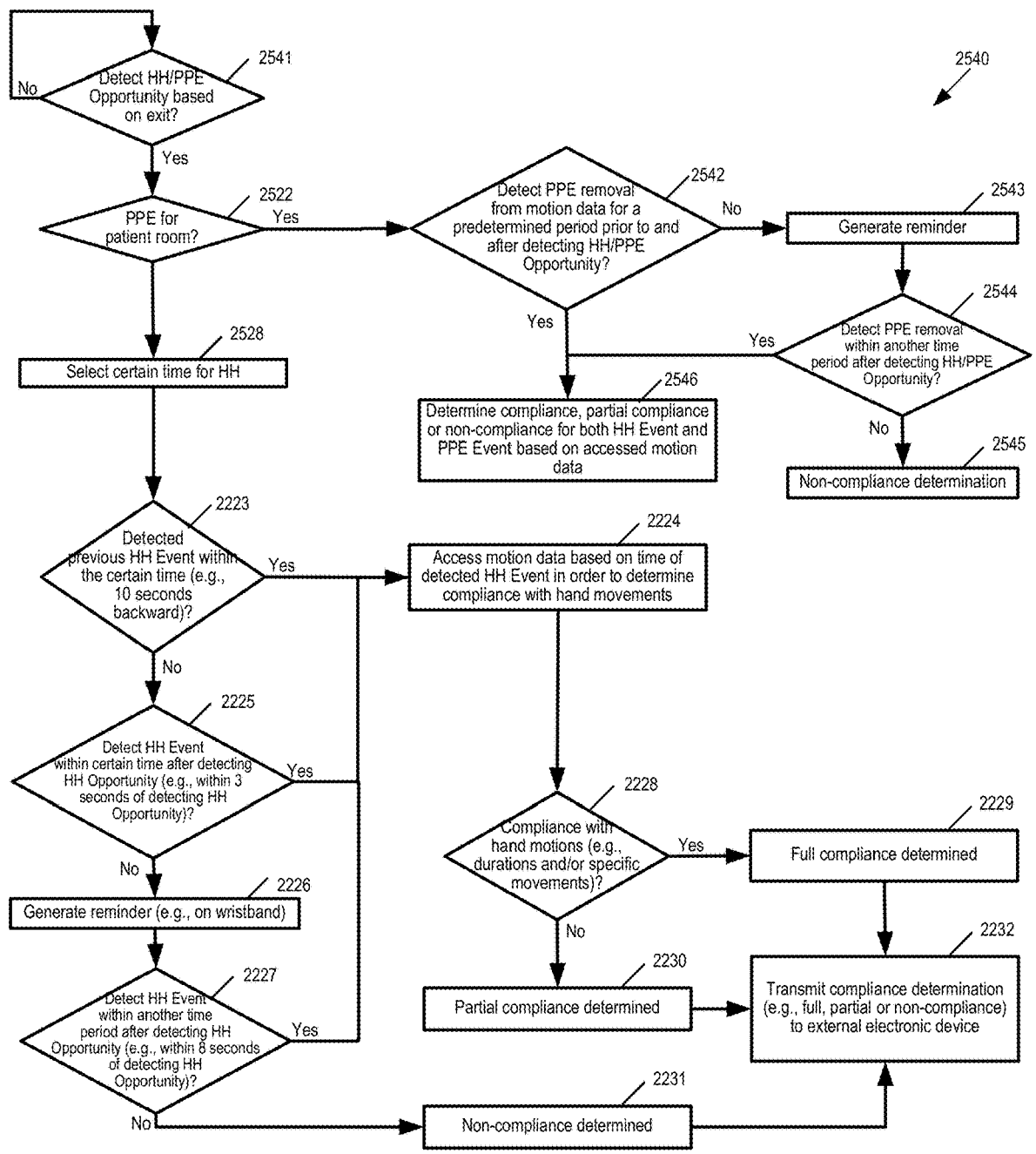
FIG. 25D is a flow diagram of one example of determining whether there is sufficient connection between the detected HH event/PPE event and the detected HH/PPE opportunity when exiting a patient area.

FIG. 25D is a flow diagram 2540 of one example of determining whether there is sufficient connection between the detected HH event/PPE event and the detected HH/PPE opportunity when exiting a patient area. At 2541, it is determined whether there is a HH/PPE opportunity detected on exit. As discussed above, guidelines dictate that PPE is removed prior to hand cleaning. Further, the healthcare provider may begin to remove the PPE prior to or after detecting the HH/PPE opportunity. For example, the healthcare provider may toss the PPE in the trash can 2498 or in a trash can outside of the room. Thus, in detecting whether PPE has been tossed, the motion data both before and after detecting the HH/PPE opportunity may be reviewed. For example, at 2542, it is determined whether PPE removal has been detected from motion data for a predetermined period prior to and after detecting HH/PPE opportunity (e.g., for 2 seconds before and 3 seconds after detecting HH/PPE opportunity). If not, at 2543, a reminder to the healthcare provider (such as via the wristband may be output). The healthcare provider is then given a short time period thereafter to comply with removing PPE and hand hygiene. This is determined at 2544 where it is determined whether PPE removal is detected within another time period after detecting the HH/PPE Opportunity. If it is not determined that PPE removal was detected within the another time period, at 2545, non-compliance is determined (thus meaning that any PPE removal was too remote from the detected HH/PPE Opportunity). Otherwise, at 2546, the accessed motion data is used to determine compliance, partial compliance or non-compliance for one or both of the HH event and PPE event, as discussed above. In this way, the compliance determination for PPE removal and/or hand hygiene is sufficiently proximate to the detected HH/PPE Opportunity.

Figure 26A:
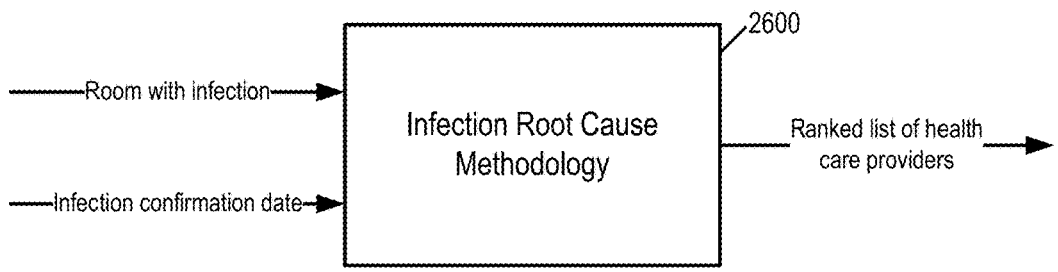
FIG. 26A is an example block diagram of the infection root cause methodology.

FIG. 26A is a block diagram for the infection root cause methodology 2600, which may be programmed to perform the infection root cause analysis. As shown in FIG. 26A, infection root cause methodology 2600 receives as input the area, such as the patient room, with the infection and the infection confirmation date. As output, infection root cause methodology 2600 may generate a ranked list of healthcare providers. In one implementation, infection root cause methodology 2600 may identify some or all visits of hygiene opportunities (such as any of the opportunities discussed above) within a predetermined period (such as a critical time period). For example, the critical period may be 7 days after confirming infection of the patient, although other critical periods are contemplated. As another example, the critical period may be automatically identified based on the type of infection in the area (e.g., different infections have different incubation periods; as such, the critical period may be selected based on the identified incubation period). In this way, an electronic medical record (EMR) may identify when an infection is diagnosed. To determine what caused the infection, the time period before the infection is confirmed may be examined.

Infection root cause methodology 2600 may then identify healthcare providers, associated with the hygiene opportunities, that visited the area during the critical period that may have contributed to the infection in the room. Infection root cause methodology 2600 may, for each provider, analyze compliance for one, some, or all of the opportunities. As discussed above, opportunities may be directed to: entry into the patient area; while in the patient area; and exit from the patient area. Infection root cause methodology 2600 is directed to infection in the patient area. As such, opportunities with regard to exit from the patient area are not considered. In this regard, infection root cause methodology 2600 may analyze for each provider any one or both of: the quantity and/or quality of hygiene when entering a patient area; or the quantity and/or quality of hygiene while in the patient area. As discussed above, one may track the location of the healthcare provider in order to identify when the healthcare provider is entering the patient area. However, tracking activity within the patient area may be more difficult. As such, infection root cause methodology 2600 may estimate a number of opportunities within the patient area based on any one, any combination, or all of: the duration of the visit by the healthcare provider; the role of the healthcare provider (e.g., nurse versus doctor versus custodian); or the patient precautions. Thus, the quantity and/or quality of hygiene within the room for a specific healthcare provider may be estimated based on given the estimated the number of opportunities for the specific healthcare provider multiplied by the historical compliance rate for the specific healthcare provider. Based on the analysis, the infection root cause methodology 2600 may assign each healthcare provider an assessment, such as a score (e.g., poor hygiene quality entering/in a room correlates with a higher score; more frequent hygiene entering/in a room correlates with a higher score). Thus, the score may comprise an objective measure based on a healthcare provider's hygiene opportunity count and performance. In instances where total visit duration is not available due to missing data, visit duration may be estimated to be the population's average.

Alternatively, ranking healthcare providers for infection root cause analysis may be based on one or more criteria, such as any one, any combination, or all of: number of visits; quality of hand hygiene (e.g., full compliance; partial compliance; no compliance); quality of PPE (e.g., compliance with donning and doffing; percentage compliance); total duration of visits (e.g., longer visits tend to indicate a higher likelihood of transmitting infection); or details of each visit (e.g., when healthcare provider entered and/or exited; compliance upon entering versus leaving). In one example, the ranking of the healthcare providers may be based on any one, any combination, or all of: total number of visits; total % compliance of visits; or total duration of visits. For example, the ranking may comprise a local rank. In particular, healthcare providers may be ranked from highest to lowest rank by being assigned a Local Rank score. This score represents a weighted score based on any one, any combination, or all of: visit duration (e.g., total visit duration of a respective healthcare provider in the patient room); hand hygiene compliance (e.g., better hand hygiene compliance translates into a lower (e.g., better) score); PPE compliance (e.g., better PPE compliance translates into a lower (e.g., better) score); Room Precautions (e.g., specific PPE requirements and/or hand hygiene requirements); and confirmation date of infection. The rank is titled "Local Rank" because a score is calculated for one healthcare provider relative to other healthcare providers in the population. In this regard, the Local Rank score in one room with one date range may be different for the same room (or for a different room) with a different date range. Thus, the Local Rank score is tailored to the specific patient area and specific critical time period.

Figure 26B:
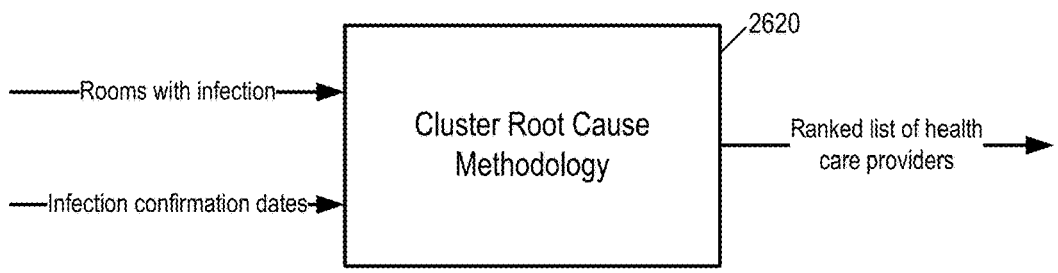
FIG. 26B is an example block diagram of the cluster root cause methodology.

FIG. 26B is a block diagram for the cluster root cause methodology 2620, which may be programmed to perform the cluster root cause analysis. In one or some embodiments, cluster root cause analysis is an extension of the infection root cause analysis. Cluster root cause methodology 2620, like infection root cause methodology 2600, may return a list of providers who may have contributed to an infection. However, cluster root cause methodology 2620 may consider multiple rooms in order to determine how the infection spread from room to room. For example, cluster root cause methodology 2620 may focus on how a pathogen is transmitted from room to room, typically called cross-contamination. Cross-contamination may occur when a provider leaves one identified infection room (representing one opportunity) with poor hygiene, and subsequently enters a second room (representing another opportunity). As discussed above, the opportunities may be connected, such as in time (e.g., a time period between opportunities of less than 60 minutes for pathogen transmission to occur).

As shown in FIG. 26B, cluster root cause methodology 2620 receives as input the areas, such as the patient rooms, with the infections, and the infection confirmation dates. As output, cluster root cause methodology 2620 generates a ranked list of healthcare providers. In one implementation, cluster root cause methodology 2620 may perform root cause analysis in which each healthcare provider is assigned a root cause analysis score. In one or some embodiments, one score is assigned for every input room's hygiene opportunities. Thus, cluster root cause methodology 2620 may assign each provider a cross contamination score (e.g., frequent cross-contamination correlates with a higher score; cross-contamination with worse hygiene correlates with a higher score).

Thus, cluster root cause methodology 2620 may identify some or all visits of healthcare providers to the area within a predetermined period (e.g., a critical period, which may be a predetermined time or dependent on the underlying infection). Cluster root cause methodology 2620 may then rank healthcare providers based on one or more criteria, such as any one, any combination, or all of: number of infected rooms visited; number of visits to each infected room; quality of hand hygiene; quality of PPE; or total duration of visits. In one example, the ranking of the healthcare providers as output may be based on any one, any combination, or all of: total number of visits; total % compliance of visits; or total duration of visits.

Separate from, or in addition to, performing infection analysis to identify higher-risk healthcare providers, the infection analysis may also identify higher-risk patients/patient rooms for potential future infections. In one or some embodiments, future infection analysis may be based on one or more factors, such as one or both of: environmental spread (e.g., healthcare providers pick up pathogens from the environment (air, water, fomites) and, with poor hygiene, may carry these pathogens into a patient room); or cross contamination (e.g., a provider leaves an infected room with poor hygiene and subsequently enters a yet-uninfected room with poor hygiene). In this way, future infection analysis may take one or more forms, such as independent of infections previously diagnosed (e.g., environmental spread) or dependent on infections previously diagnosed (e.g., cross contamination).

Figure 26C:
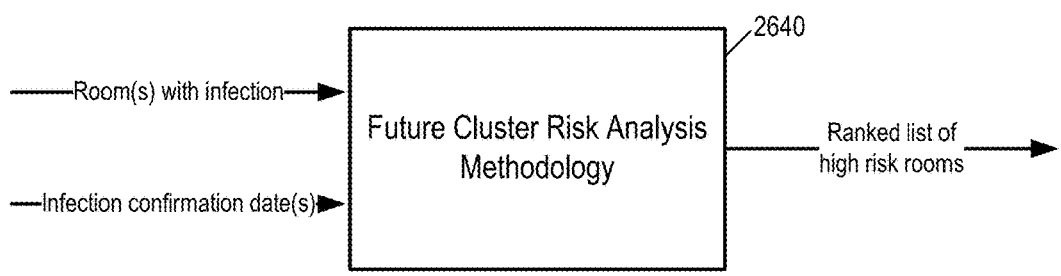
FIG. 26C is an example block diagram of the future cluster risk analysis methodology.

As one example, future infection analysis may be based on infections previously diagnosed in order to determine a future risk that the previously diagnosed infections will spread to other patients/patient areas. This is depicted in FIG. 26C, which is an example block diagram of the future cluster risk analysis methodology 2640, embodying a cross-contamination algorithm, in order to determine future cross contamination risk. As shown, future cluster risk analysis methodology 2640 has as its inputs room(s) with a confirmed infection and associated date(s) of confirmed infection. Future cluster risk analysis methodology 2640 may thus analyze opportunity data, such as compliance data, in order to determine whether an infection, which is confirmed in a first patient area, may spread or be transferred to a second patient area. In this regard, future cluster risk analysis methodology 2640 may divide the analysis infection room by infection room (e.g., infected rooms comprise patient room #2, patient room #8, patient room #12, and patient room #24), and determine for each infected room, a future risk of spread of infection to other (not as-of-yet-infected with the pathogen in the respective room) patient rooms, and determine an overall future risk of spread of infection to the other rooms (e.g., summing the future risk of infection for a respective room due to the spread from all the infected rooms). For example, responsive to identifying an infection in patient room #2 with an associated infection confirmation date, opportunity data (and associated compliance data) may be analyzed to determine other patient rooms connected with patient room #2. Specifically, of note, exit opportunities from a first infected patient room that are connected to entrance opportunities to another patient room (whether the another patient room is generally uninfected or is specifically uninfected with the infections from the first infected patient room).

Figure 26D:
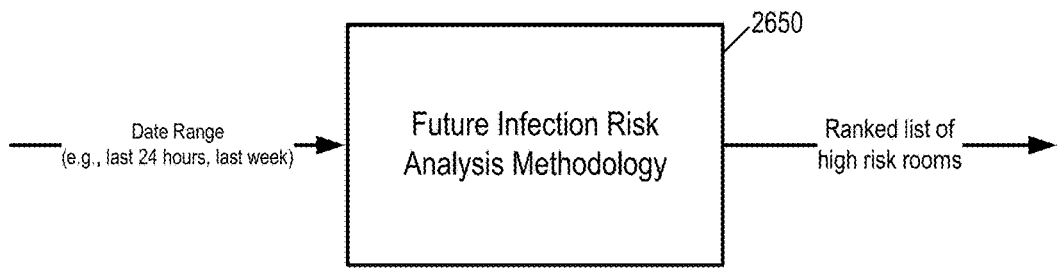
FIG. 26D is an example block diagram of the future infection risk analysis methodology.

FIG. 26D is a block diagram for the future infection risk analysis methodology 2650, embodying an environmental spread algorithm, which may be programmed to perform the future infection risk analysis. In this regard, the future infection risk analysis methodology 2650 may comprise an environmental spread algorithm for environmental spread analysis. Further, in one or some embodiments, future infection risk analysis methodology 2650 receives as input a date range, such as the past 24 hours, the past week, etc., as illustrated in FIG. 26D. Various output(s) generated by future infection risk analysis methodology 2650, such as a ranked list of high-risk rooms, are contemplated.

In one or some embodiments, the environmental spread algorithm (depicted in future infection risk analysis methodology 2650) may identify all hygiene opportunities for one, some, or all of the patient areas (e.g., the patient rooms). For each identified patient area, analyze one or both of: (1) the quantity and/or quality of hygiene entering the room (e.g., one opportunity); or (2) quantity and/or quality of hygiene within the room (e.g., other opportunity). As discussed above, one may estimate the number of opportunities within the room based on any one, any combination, or all of the duration of the visit, provider role, and patient precaution. Each patient area may be assigned an environmental spread score (e.g., poor hygiene quality entering/in the room correlates with a higher score; more frequent hygiene entering/in the room correlates with a higher score).

In one or some embodiments, the cross contamination algorithm (depicted in future cluster risk analysis methodology 2640) may identify cross contamination events between infected rooms and/or yet-uninfected rooms; and assign each room a cross contamination score (e.g., more frequent travel from infected rooms results in a higher score; travel with lower-quality hygiene results in a higher score). Scores may be represented with a table or heat map, such as illustrated in FIG. 26E (e.g., darker colors representing higher scores).

In practice, future cluster risk analysis methodology 2640 and/or future infection risk analysis methodology 2650 identify high-risk patient areas by identifying one or both of: visits performed by high-risk providers; or visits to a given patient area that cross certain risk thresholds (e.g., any one, any combination, or all: high number of visits to a patient area (such as higher than a predetermined number); low hand hygiene and/or PPE compliance throughout visits; or total duration of visits to a patient area). An example of a heat map is illustrated in GUI 2660 of the infection spread analysis in FIG. 26E. Heat map may include different colors, such as a range of colors, depicting the risk to certain patient areas. For example, FIG. 26E shows colors 2662, 2664, 2666, 2668 (with darker colors indicating higher risk) that are associated with different areas of a layout of a floor of a patient area. In one manner, future infection risk scores, such as by cross-contamination and/or environmental spread, may be normalized (e.g., score=0: no chance of infection; score=100: 100% chance of infection). A score over a certain amount or within a certain range may be assigned a certain risk category (e.g., scores 85-100 are designated as high risk). In this way, future cluster risk analysis methodology 2640 and/or future infection risk analysis methodology 2650 may predict other infections even before the infections have been diagnosed.

Alternatively or in addition to generating an output, such as an indication of likely healthcare provider(s) who caused the infection and/or an indication of higher-risk patient area(s), one or more protocols, such as the hand hygiene protocols and/or the PPE protocols, may be modified responsive to the analysis, such as any one, any combination, or all of the infection root cause analysis, cluster root cause analysis, future cluster risk analysis and future infection risk analysis. As one example, responsive to identifying higher-risk patient areas, the hand hygiene protocols and/or the PPE protocols may be modified. In particular, responsive to identifying that a specific healthcare provider likely caused a certain type of infection (e.g., a MRSA infection), the hand hygiene protocols and/or the PPE protocols may be changed in patient rooms where the specific healthcare provider had recently visited even in advance of patients in those higher-risk rooms being diagnosed with the certain type of infection (e.g., change the hand hygiene and PPE protocols to comport with treating a patient with a MRSA infection).

Figure 28A:
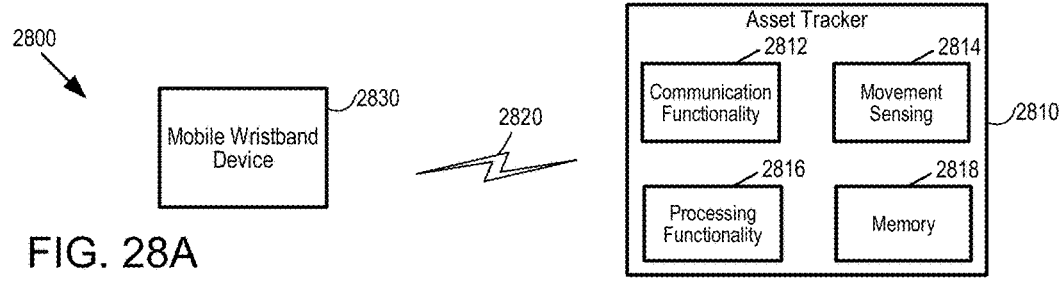
FIG. 28A illustrates one example block diagram of an asset tracker, which may include communication functionality, movement sensing, processing functionality, and memory.

FIG. 28A illustrates one example block diagram 2800 of an asset tracker 2810, which may include communication functionality 2812, movement sensing 2814, processing functionality 2816, and memory 2818. Communication functionality 2812 may comprise one or more wireless communication functionalities, such as Bluetooth or other near-field communication, Wi-Fi, cellular, or the like. In sleep-mode, asset tracker 2810 operates at lower power, including turning off at least part of communication functionality 2812 so that the asset tracker does not wirelessly communicate with external devices. Movement sensing 2814 comprises micro-vibration sensor 312 or the like and is configured to generate a signal responsive to movement. In this regard, movement of at least a part of the asset, such as the entire asset itself or a part of the asset (such as a drawer or a cord of a respirator), results in movement sensing 2814 generating a signal for input to processing functionality 2816. In response, processing functionality 2816 wakes up, including waking up communication functionality 2812, so that asset tracker 2810 may communication wirelessly 2820 with devices proximate, such as via Bluetooth with mobile wristband device 2830 (which may comprise any one, any combination, or all of FIGS. 3A-C). As discussed in more detail below, processing functionality 2816 may monitor one or more aspects, such as who move the asset, when the asset was moved, where the asset was moved, and the like. For example, responsive to asset tracker 2810 sending a communication to mobile wristband device 2830 (or other mobile electronic device associated with the person moving the asset), mobile wristband device 2830 may wake up its CPU (optionally, the mobile wristband device 2830 may be partly asleep (such as its CPU) though the radio transceiver for mobile wristband device 2830 is on to receive the communication; further, the mobile wristband device 2830 may optionally begin monitoring for PPE or the like) and may send a response and include any one, any combination, or all of: (1) an identification of the wristband; (2) a current location of the wristband (e.g., the mobile wristband device 2830 may use a GPS receiver resident on the mobile wristband device 2830 in order to generate the current location); or (3) a current time. Alternatively, asset tracker 2810 may include a GPS receiver in order to generate the current location and a local clock in order to generate the current time. The monitored one or more aspects may be stored in memory 2818, and may optionally be wirelessly transmitted externally of the asset tracker 2810 for storage, such as via Wi-Fi to a back-end server for permanent or semi-permanent storage. Regardless, various aspects of the asset may be tracked, such as the asset's info (any one, any combination, or all of asset type, ID, etc.), the movement of the asset, use of the asset (e.g., the person who opened the drawer of the asset being tracked and/or how long the drawer was opened may be recorded in order to determine time/who dispensed medicine; the person who pulled the plastic tubing from the wall of the patient room and connected to a respirator). After a predetermined time period of no movement of the asset tracker 2810, processing functionality 2816 may return the asset tracker 2810 to sleep mode.

Figure 28B:
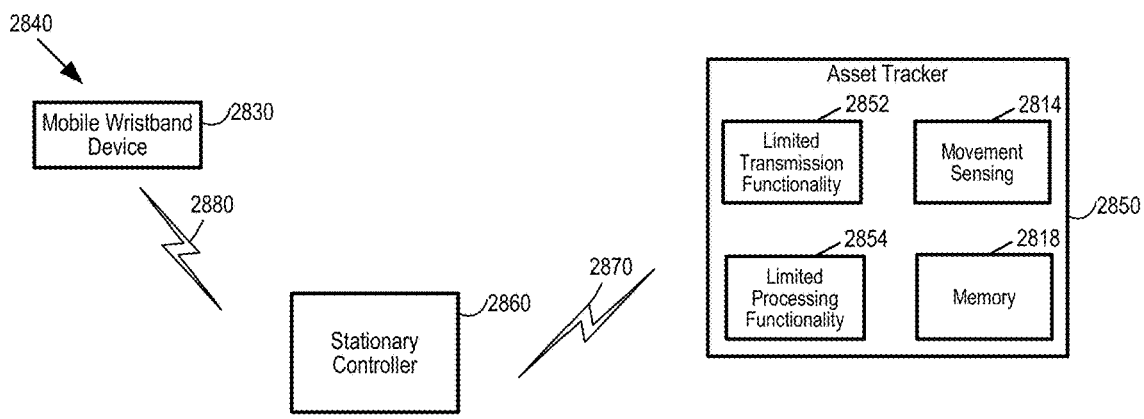
FIG. 28B illustrates another example block diagram of an asset tracker, which may include less functionality than asset tracker illustrated in FIG. 28A.

FIG. 28B illustrates another example block diagram 2840 of an asset tracker 2850, which may include less functionality than asset tracker 2810. In particular, asset tracker 2850 includes limited transmission functionality 2852 and limited processing functionality 2854. For example, responsive to movement sensing 2814 sensing movement, limited processing functionality 2854 wakes up at least a part of asset tracker 2850, such as waking up limited transmission functionality 2852. Limited transmission functionality 2852 includes less communication functionality than communication functionality 2812, such as beacon transmission functionality that transmits a beacon that includes a unique identifier of the asset tracker (which is correlated to the underlying asset) but not wireless receiving capability (such as bi-directional communication via Bluetooth or Wi-Fi). Responsive to movement sensing 2814 sensing movement, asset tracker 2850 uses limited processing functionality 2854 in order to generate the beacon wirelessly via 2870 to stationary controller 2860 via limited transmission functionality 2852. In this regard, limited processing functionality 2854 has less capability than processing functionality 2816, such as being incapable of communicating/processing to identify mobile wristband device 2830. Rather, stationary controller 2860, responsive to receiving the beacon, is configured to communicate wirelessly via 2880 with mobile wristband device 2830. Similar to above, responsive to stationary controller 2860 sending a communication to mobile wristband device 2830, mobile wristband device 2830 may send a response and include any one, any combination, or all of: (1) an identification of the wristband; (2) a current location of the wristband; or (3) a current time. Alternatively, stationary controller 2860 may be preprogrammed with its location (e.g., patient room #10) or include a GPS receiver in order to generate the current location and a local clock in order to generate the current time. Thus, mobile device wristband device 2830 may send its unique identifier (thereby identifying the healthcare provider assigned to mobile wristband device 2830), its location and the like. In turn, stationary controller 2860 (which may comprise any one, any combination, or all of FIGS. 4A-B) may store the unique identifier for local storage and/or for transmission a server (such as back-end server 130). In this regard, in one or some embodiments, the stationary controller 2860 communicates with mobile wristband device 2830 responsive to receiving the beacon. Alternatively, or in addition, stationary controller 2860 may have already communicated with mobile wristband device 2830, such as responsive to the healthcare provider walking into the patient area (e.g., when the mobile wristband device 2830 is within Bluetooth communication with the stationary controller 2860, the stationary controller 2860 may identify the mobile wristband device 2830). Thus, in such an embodiment, the stationary controller 2860 may connect two separate communications (e.g., communicating with the mobile wristband device 2830 in order to identify the mobile wristband device 2830 and receiving the beacon from asset tracker 2850) in order to identify the mobile wristband device 2830 that has moved the asset. As discussed above, the asset tracker (such as asset tracker 2810, 2850) may go back to sleep after no movement for a predetermined amount of time. In one or some embodiments, the asset tracker may send a final beacon indicating that the asset tracker is going back to sleep. The stationary controller 2860 that receives the final beacon (whether in the patient room when the asset tracker awakened or in another patient room) may then determine that this is the present resting position of the asset. For example, the asset may originate in a first room (e.g., ICU room #2) with the stationary controller in the first room receiving the beacon from the asset tracker upon wake-up (responsive to the original movement). Thereafter, the asset may be moved to a second room (e.g., ICU room #5) with the stationary controller in the second room receiving the beacon from the equipment responsive to movement of the equipment into the second room.

Figure 27A:
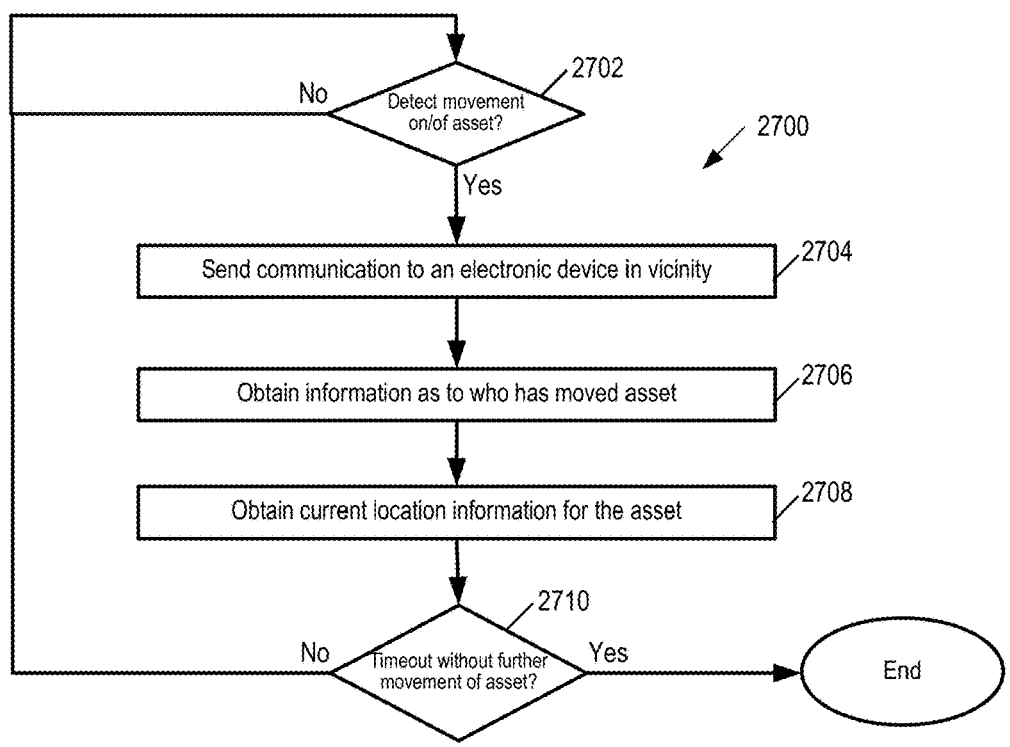
FIG. 27A illustrates a first flow diagram 2700 of asset tracking.

FIG. 27A illustrates a first flow diagram 2700 of asset tracking. At 2702, the asset tracker determines whether there is movement detected on or of the asset. If so, at 2704, the asset tracker sends a communication to an electronic device in its vicinity (e.g., to a proximate wristband or stationary controller). At 2706, information is obtained as to whom as moved the asset (such as by polling the wristband in the vicinity). At 2708, current location information may likewise be obtained. At 2710, the asset tracker may determine whether there has been a timeout without further movement of the asset. If not, flow diagram 2700 goes to 2702. If not, flow diagram 2700 ends.

Figure 27B:
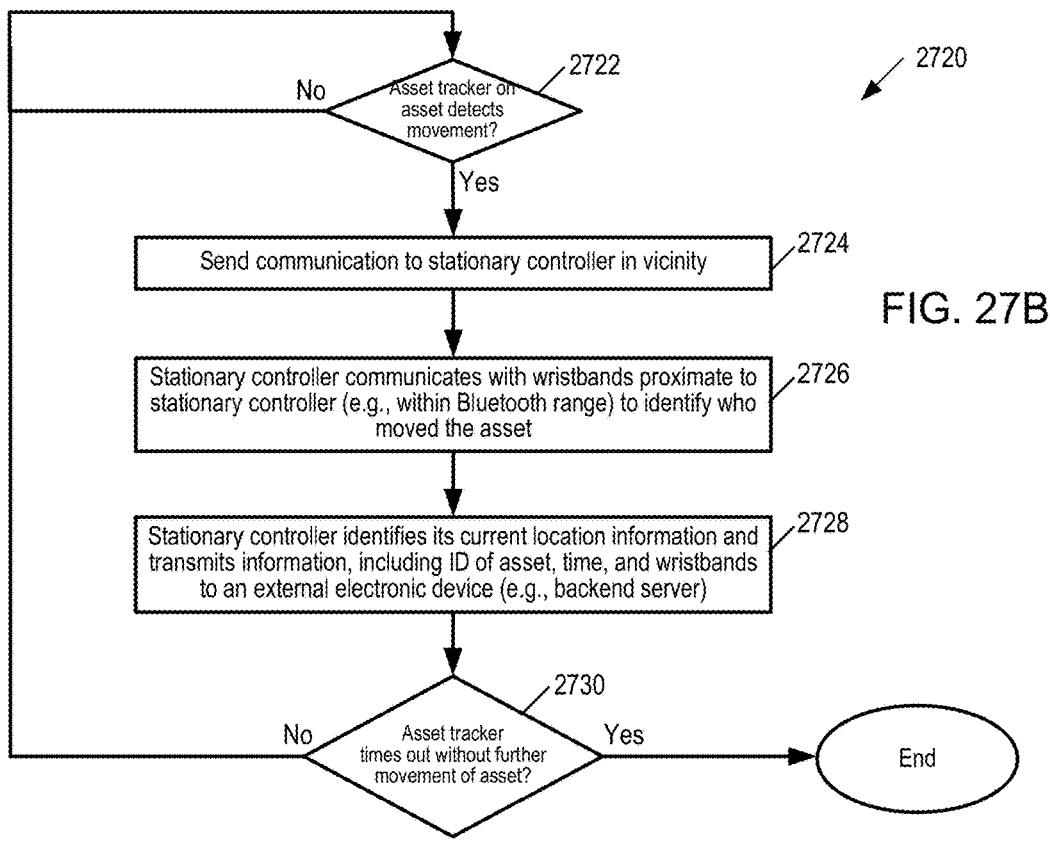
FIG. 27B illustrates a second flow diagram of asset tracking in which the asset tracker communicates with a stationary controller.

FIG. 27B illustrates a second flow diagram 2720 of asset tracking in which the asset tracker communicates with a stationary controller. At 2722, the asset tracker detects movement. At 2724, the asset tracker sends a communication (such as a beacon) to a stationary controller in the vicinity. At 2726, the stationary controller communicates with wristbands proximate to stationary controller (e.g., within Bluetooth range) to identify who moved the asset. At 2728, the stationary controller identifies its current location information (or the current location as sent from the wristband) and transmits information, including ID of the asset, time, and wristbands in proximity to an external electronic device (e.g., backend server). At 2730, the asset tracker determines whether times out has occurred without further movement of the asset.

Figure 27C:
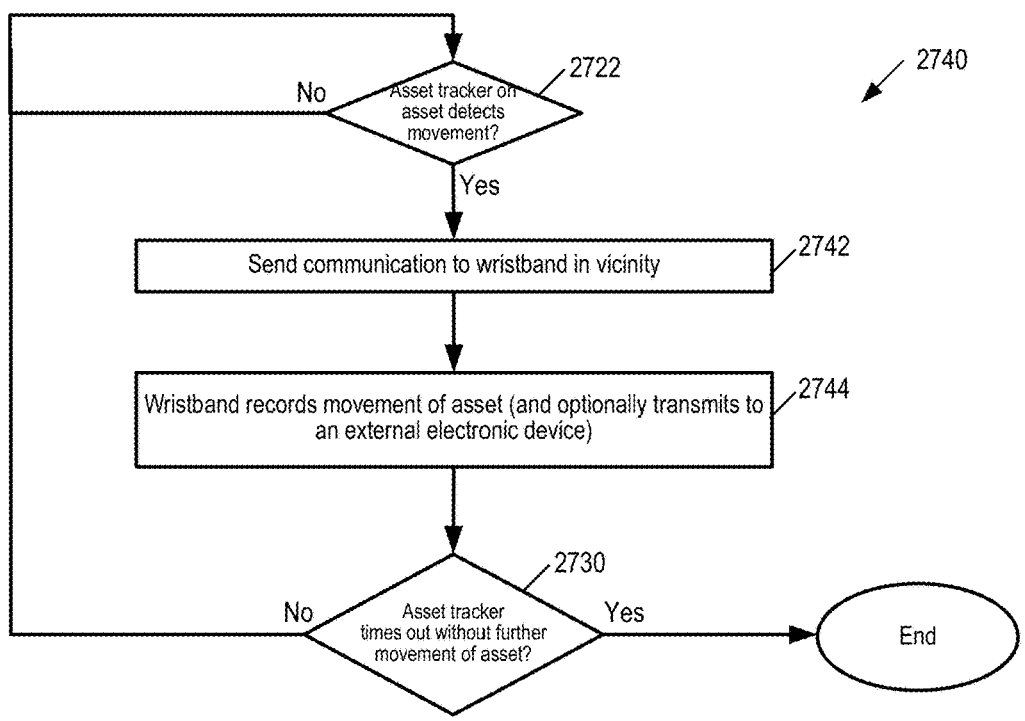
FIG. 27C illustrates a third flow diagram of asset tracking in which the asset tracker communicates with one or more wristbands.

FIG. 27C illustrates a third flow diagram 2740 of asset tracking in which the asset tracker communicates with one or more wristbands. Responsive to the asset tracker detecting movement, at 2742, the asset tracker sends a communication to the wristband(s) in its vicinity. Information, such as any one, any combination or all of when movement occurred, who moved the asset, and current location may be sent. In one or some embodiments, the asset tracker may send the information Alternatively, at 2744, the wristband may record movement of asset (and optionally transmit information to an external electronic device, such as the backend server).

Figure 29:
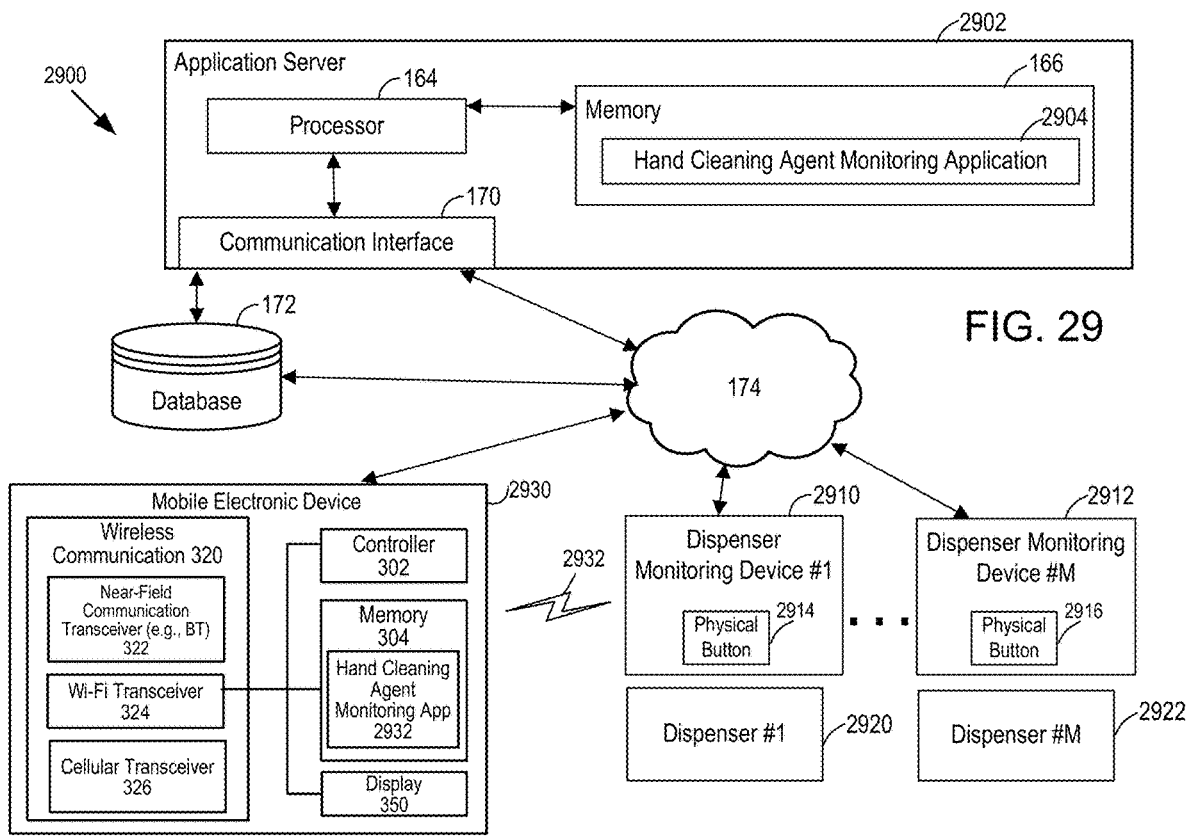
FIG. 29 illustrates a block diagram of a hand cleaning agent monitoring system, which includes an application server, database, network, one or more mobile electronic devices, and one or more dispenser monitor devices and associated dispensers.

FIG. 29 illustrates a block diagram of a hand cleaning agent monitoring system, which includes an application server 2902, database 172, network 174, one or more mobile electronic devices (with one mobile electronic device 2930 illustrated in FIG. 29), and one or more dispenser monitor devices and associated dispensers (with dispenser monitoring device #1 (2910) and associated dispenser #1 (2920), and dispenser monitoring device #2 (2912) and associated dispenser #2 (2922) illustrated in FIG. 29). Application server 2902 includes a hand cleaning agent monitoring application 2904, which may be configured to communicate with one or both of the mobile electronic devices (such as mobile electronic device 2930) and dispenser monitoring devices (such as one or both of dispenser monitoring device #1 (2910) or dispenser monitoring device #2 (2912)). In one or some embodiments, communications with application server 2902 may be directed to refilling of dispensers.

As one example, mobile electronic device 2930 may activate hand cleaning agent monitoring app 2932. In one or some embodiments, hand cleaning agent monitoring app 2932 may generate an output, such as a visual display indicative of a layout illustrating one or more dispensers. A worker using the hand cleaning agent monitoring app 2932 may tap on the screen in order to identify the dispenser subject to refilling (e.g., the tap on the screen identifies the dispenser or the dispenser monitoring device ID). Thus, the hand cleaning agent monitoring app 2932 need not communicate with an external device, such as any monitoring device, in order to identify the dispenser that has been refilled. Alternatively, in order to identify the dispenser for refilling, hand cleaning agent monitoring app 2932 may communicate with a respective dispenser (such as wirelessly communicate via Bluetooth (using near-field communication transceiver 322) or other near-field communication with dispenser monitoring device #1 (2910) in order to obtain the identification of one or both of the dispenser monitoring device (e.g., an ID of dispenser monitoring device #1 (2910)) or the dispenser (e.g., an ID of dispenser #1 (2920)).

Regardless, after identifying the dispenser subject to refilling, and after the worker has replaced the bag of hand cleaning agent (such as replaced in dispenser #1 (2920)), the worker may activate, via hand cleaning agent monitoring app 2932 being executed on the mobile electronic device 2930 (e.g., activate a "refill button" generated by hand cleaning agent monitoring app 2932 on the display 350 of mobile electronic device 2930) in order for the mobile device to transmit a refill communication to application server 2902. In this way, the "refill button" on the display 350 of mobile electronic device 2930 acts as a virtual reset button. The refill communication may be indicative to the application server 2902 that the bag of hand cleaning agent for a dispenser (such as dispenser #1 (2920)) has been replaced. In particular, the refill communication may include any one, any combination, or all of: a field indicating that it is a refill communication; a field indicating the dispenser or the dispenser monitoring device ID that was refilled (e.g., an ID of dispenser monitoring device #1 (2910) and/or an ID of dispenser #1 (2920)); and optionally, a separate field for an ID of the mobile electronic device 2930 and/or an ID of the worker that replaced the bag. In response to receiving the refill communication from the mobile electronic device 2930, the application server 2902 may perform one or both of: (i) update database 172 to indicate that the particular dispenser (such as dispenser #1 (2920)) has been refilled; and (ii) send a communication to the respective monitoring device that its associated dispenser has been refilled (e.g., a server communication sent via Wi-Fi or other farther-field communication methodology, such as farther than near-field communication methodologies such as Bluetooth). In this way, the dispenser monitoring device may communicate with the mobile electronic device 2930 in one wireless manner (e.g., near-field, such as via Bluetooth) and may communicate with application server 2903 in another wireless manner (e.g., farther-field, such as via Wi-Fi). In response to receiving the server communication, the respective monitoring device may reset its indication of the remaining amount of hand cleaning agent in its associated dispenser. For example, the indication may comprise a number value associated with a counter, wherein the number value for the counter indicates the number of dispenses remaining in the dispenser until empty. In practice, the dispenser monitoring device may decrement the number value in the counter every time a dispensing event occurs (e.g., the dispenser dispenses the predetermined amount of hand cleaning agent).

As another example, resetting may be performed using a communication generated by the dispenser monitoring device and transmitted to application server 2902. In particular, responsive to a worker replacing the bag of hand cleaning agent, the worker may provide an input to the dispensing monitoring device. The input may be a manual inputs, such as by pushing physical button 2914 or 2916. Alternatively, the input may be virtual, such as by communicating via an external electronic device, such as mobile electronic device 2930, to transmit the input. Responsive to receiving the input, the dispensing monitoring device may: (i) reset its indication of the remaining amount of hand cleaning agent in its associated dispenser; and/or (ii) generate a dispenser refill communication to transmit to the application server, with the dispenser refill communication comprising any one, any combination, or all of: a field indicating that it is a dispenser refill communication; a field indicating the dispenser or the dispenser monitoring device ID that was refilled; and optionally, a separate field for an ID of the mobile electronic device 2930 and/or an ID of the worker that replaced the bag (which may have been transmitted from the mobile electronic device 2930).

Figure 30C:
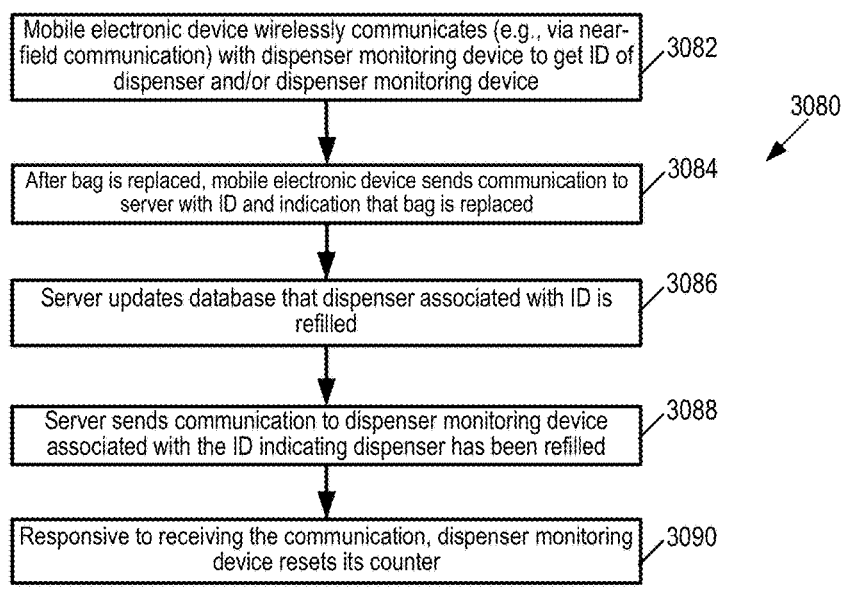
FIG. 30C illustrates a flow diagram 3080 of a mobile electronic device communicating with the dispenser monitoring device and with a backend server.
Figure 30A:
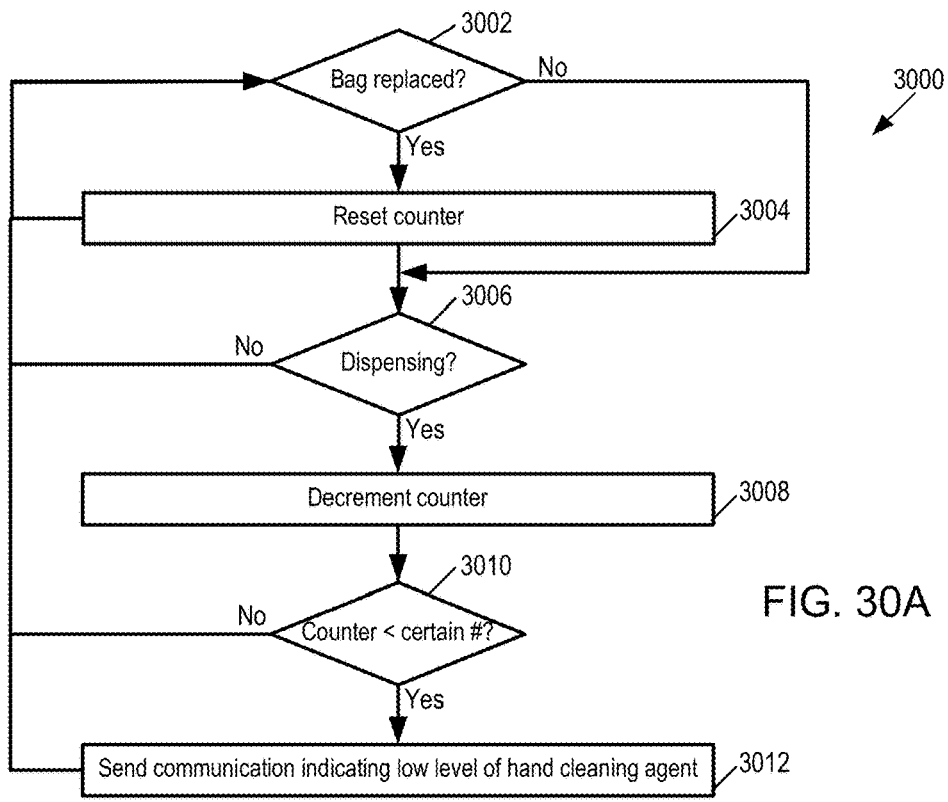
FIG. 30A illustrates a flow diagram of monitoring for a bag (or other type of container) of hand cleaning agent for a respective dispenser.

FIG. 30A illustrates a flow diagram 3000 of monitoring for a bag (or other type of container) of hand cleaning agent for a respective dispenser. At 3002, it is determined whether the bag for the respective dispenser has been replaced. As discussed above, the dispenser monitoring device may receive a direct indication (such as via physical button 2914, 2916) via its interface or a communication, such as from application server 2902, indicating that the bag has been replaced. If so, the value of the counter for the stationary controller associated with the respective dispenser is reset. As discussed above, various indications of the remaining amount of hand cleaning agent in its associated dispenser are contemplated, one of which may comprise a counter. In one or some embodiments, the number for the counter is predetermined (e.g., each bag has 1,000 dispenses so that the number for the counter is always reset back to 1,000). In other embodiments, the number for the counter is dynamic (e.g., a first type of replacement bag has 1,000 dispenses whereas a second type of replacement bag has 500 dispenses; so that, the reset number for the counter is set based on the type of replacement bag). If the bag has not been replaced, flow diagram 3000 moves to 3006, at which the dispenser monitoring device determines whether there has been a dispensing event. As discussed above, the dispenser monitoring device may be part of the stationary controller (e.g., the dispenser monitoring device is integrated with the stationary controller) or work in combination with a stationary controller (e.g., responsive to the stationary controller sensing a dispensing event via its sensor, the stationary controller sends a communication to the dispenser monitoring device). As such, in one embodiment, the stationary controller may be used to determine whether the dispensing event has occurred, as discussed above. Alternatively, the dispenser monitoring device may determine itself whether a dispensing event has occurred. If not, flow diagram 3000 moves to 3002. If so, at 3008, the stationary controller decrements the counter.

Alternatively, or in addition to monitoring dispensing (e.g., decrementing the counter), one or more electronic devices may monitor who dispensed the hand cleaning agent. As one example, people, such as healthcare providers, may wear a mobile electronic device, such as a wristband. The controller resident on the dispenser monitoring device (which may be a controller separate from the stationary controller or may be integrated with the stationary controller) may detect whether a wristband is nearby (e.g., via near-field communication). Responsive to the controller resident on the dispenser monitoring device detecting a wristband, the controller may perform one or both of the following: (1) activate a sensor to detect whether hand cleaning agent is being dispensed (thereby activating the sensor only when a wristband is proximate in order to conserve power); or (2) obtain an identifier from the wristband in order to identify who is taking hand cleaning agent (in order transmit the identifier to the backend server for record keeping).

At 3010, the dispenser monitoring device determines whether the number for the counter is less than or equal to a certain number. If so, at 3012, the dispenser monitoring device sends a communication to the backend server indicating a low level of hand cleaning agent. Again, the communication may be sent via the communication functionality of the stationary controller. Alternatively, the communication may be sent via the communication functionality distinct from any stationary controller. For example, if a bag has 1,000 dispenses, when the counter is less than or equal to 50, a communication is sent. Otherwise, flow diagram 3000 moves to 3002. Instead of (or in addition to) sending the communication, the dispenser monitoring device may cause an output to be generated. As one example, the dispenser monitoring device may include one or both of a speaker or a light, and may cause an aural output to be generated by the speaker or a visual output to be generated by the light. In the instance where the dispenser monitoring device is part of, integrated with or associated with a stationary controller, the dispenser monitoring device may use the speakers/light on the stationary device. As another example, responsive to determining that the amount of hand cleaning agent is low (e.g., below a predetermined amount), the dispenser monitoring device may send a communication to an external device to cause an output to be generated via another device. As one example, the communication sent to the application server 2902 may cause the application server 2902 to send a refill alert message to a mobile electronic device, such as mobile electronic device 2930.

Figure 30B:
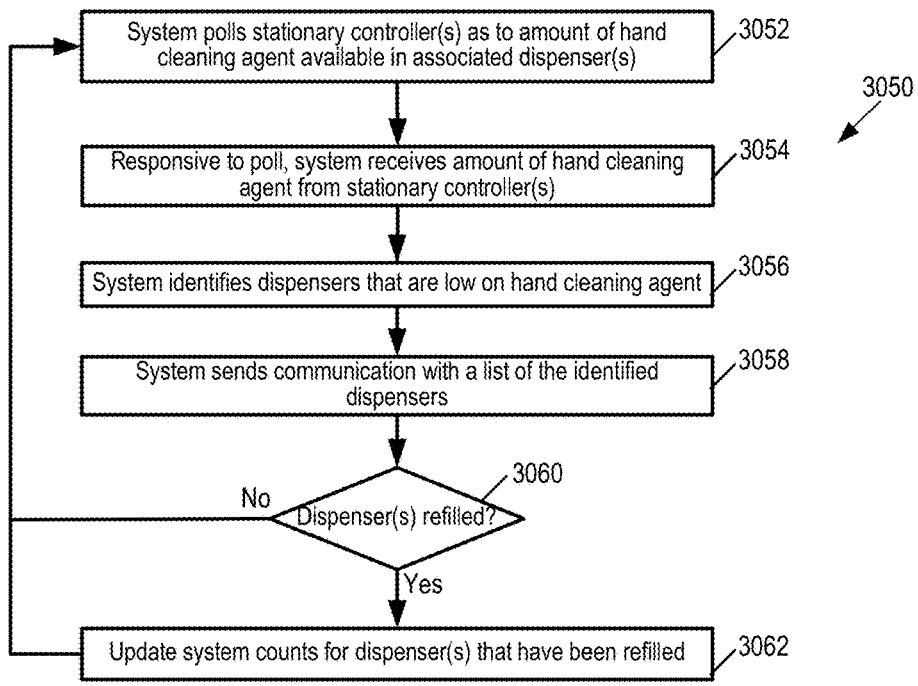
FIG. 30B illustrates a flow diagram 3050 of a backend server (such as an application server) monitoring of amount of hand cleaning agent in dispenser(s).

FIG. 30B illustrates a flow diagram 3050 of a backend server (such as application server 2902) monitoring of amount of hand cleaning agent in dispenser(s). At 3052, the system, such as the backend server, polls one or more stationary controllers as to the amount of hand cleaning agent available in the associated dispensers. Thus, in one embodiment, polling by the backend server may be performed at predetermined intervals (such as once per day). Alternatively, polling by the backend server may be performed responsive to a user request. At 3054, responsive to sending the poll, the system receives the amount of hand cleaning agent from dispenser monitoring device(s). Based on the amount of hand cleaning agent from dispenser monitoring device(s), at 3056, the system identifies the dispenser(s) that are low on hand cleaning agent. At 3058, the system sends a communication with the list of identified dispensers. At 3060, it is determined if the dispenser(s) have been refilled. If so, at 3062, the system updates counts for the dispenser(s) that have been refilled. Otherwise, flow diagram 3050 loops back to 3052.

FIG. 30C illustrates a flow diagram 3080 of a mobile electronic device (such as mobile electronic device 2930) communicating with the dispenser monitoring device (such as dispenser monitoring device #1 (2910)) and with a backend server (such as application server 2902). At 3080, the mobile electronic device wirelessly communicates (e.g., via near-field communication) with the dispenser monitoring device to get an ID of the dispenser and/or the dispenser monitoring device. At 3084, after bag is replaced in the dispenser, the mobile electronic device sends a communication to the server with the ID and the indication that bag is replaced. At 3086, the server updates the database that the dispenser (or dispenser monitoring device) associated with ID is refilled. At 3088, the server sends a communication to the dispenser monitoring device associated with the ID indicating dispenser has been refilled. At 3090, responsive to receiving the communication, the dispenser monitoring device resets its counter. Alternatively, instead of mobile electronic device (such as mobile electronic device 2930) communicating with the dispenser monitoring device (such as dispenser monitoring device #1 (2910)) to obtain the ID of the dispenser and/or the dispenser monitoring device, the mobile electronic device may include a visual layout in order for the worker to identify to the position of the respective dispenser in the visual layout (and thereby obtain the ID of the dispenser and/or the dispenser monitoring device correlated to the position of the respective dispenser in the visual layout).

Figure 31A:
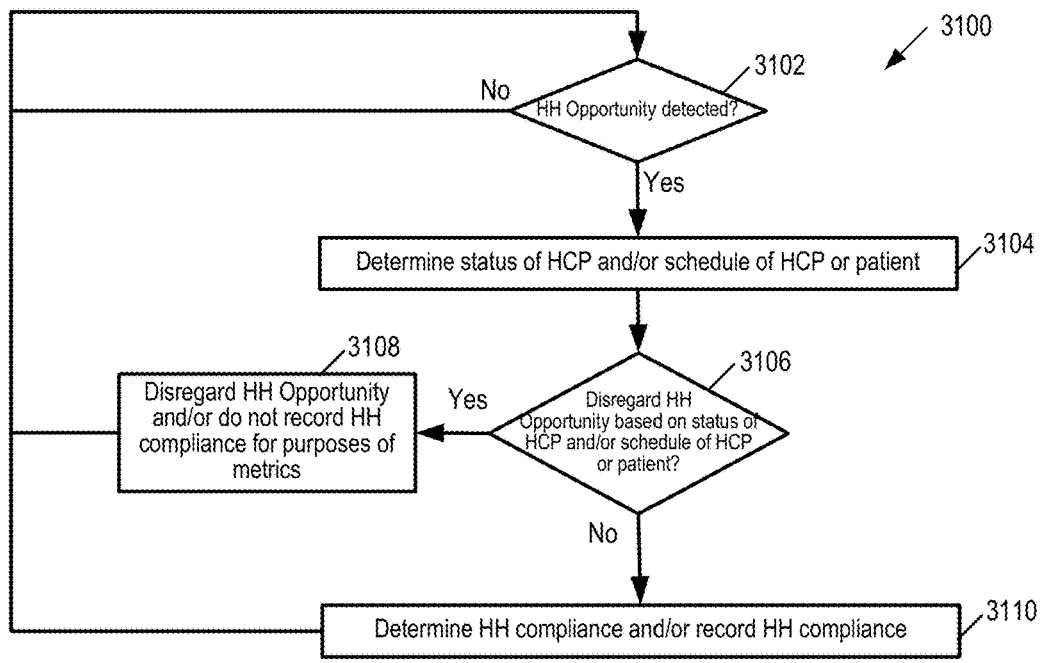
FIG. 31A is a flow diagram for applying rules to determine whether to determine or log compliance with a hand hygiene opportunity.

FIG. 31A is a flow diagram 3100 for applying rules to determine whether to determine or log compliance with a hand hygiene opportunity. At 3102, it is detected that there is a hand hygiene opportunity. At 3104, the status of the healthcare provider (HCP) and/or the patient's or HCP providers schedule is determined. At 3106, it is determined whether to disregard the hand hygiene opportunity based on the status of HCP and/or schedule of HCP or patient. If so, at 3108, the hand hygiene opportunity is disregarded and/or hand hygiene compliance is not recorded for purposes of metrics. If not, at 3110, hand hygiene compliance is determined and/or recorded.

Figure 31B:
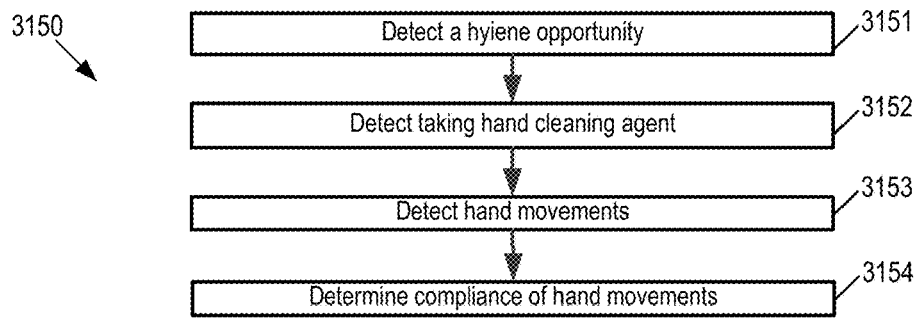
FIG. 31B is a flow diagram for detecting a hygiene opportunity, determining whether hand cleaning agent has been taken, detecting hand movements, and determining compliance based on the hand movements.

FIG. 31B is a flow diagram 3150 for detecting a hygiene opportunity (such as a hand hygiene opportunity), determining whether hand cleaning agent has been taken, detecting hand movements, and determining compliance based on the hand movements. At 3151, the hygiene opportunity is detected. As discussed above, there are various ways in which to detect a hygiene opportunity. As one example, such as in the hospitality industry which may request handwashing periodically (e.g., every 30 minutes), the hygiene opportunity may be determined by a counter, which generates an interrupt or an alarm every 30 minutes. In one or some embodiments, the mobile electronic device, such as the wristband, may house the counter in order to generate the periodic interrupt. At 3152, the taking of hand cleaning agent, such as sanitizer, is detected. For example, the mobile electronic device may determine whether hand cleaning agent has been dispensed. As one example, the mobile electronic device may include a sound sensor, with the sound sensor generating sound data. The mobile electronic device may analyze the sound data in order to determine whether the sound data is indicative of the sound when a dispenser is dispensing sanitizer. As another example, the mobile electronic device may include one or more motion sensors to generate movement data. The mobile electronic device may analyze the motion data in order to determine whether the motion data is indicative of the movements when person moves his/her hand to take sanitizer (e.g., the movement of moving the palm upward). As still another example, the mobile electronic device may communicate with an external electronic device, such as a controller associated with the dispenser, in order to determine whether the hand cleaning agent has been dispensed. In particular, responsive to a dispensing event, the stationary controller may send a near-field communication indicating the dispensing event, with the wristband, in near-field communication range, receiving the communication. Thus, the mobile electronic device may determine the hygiene opportunity (e.g., the hand hygiene opportunity) and determine compliance with the hygiene opportunity. Separate from the hospitality industry, a mobile electronic device associated with a healthcare provider may likewise determine the hygiene opportunity (e.g., based on tracking the healthcare provider) and determine compliance with the hygiene opportunity (e.g., analyze its hand movements to determine compliance).

At 3153, the mobile electronic device may detect hand movements. As discussed above, the mobile electronic device may include one or more motion sensors. As such, responsive to detecting the opportunity and/or responsive to detecting the taking of hand cleaning agent, the mobile electronic device may activate its one or more motion sensors in order to generate motion sensor data. Alternatively, the mobile electronic device may constantly keep its one or more motion sensors active to constantly generate motion sensor data. At 3154, the mobile electronic device may analyze the motion sensor data in order to determine compliance. As discussed above, compliance may be measured in one of several ways, such as based on a duration of hand movements (e.g., at least 20 seconds) and/or based on predefined hand motions.

In this regard, the mobile electronic device may perform one, some, or all of 3151, 3152, 3153, and 3154. Further, the mobile electronic device may determine whether there is full compliance, partial compliance (e.g., taking of sanitizer but not performing the requisite hand movements), or no compliance (e.g., no taking of sanitizer). Alternatively, the mobile electronic device may be configured only to detect the hygiene opportunity and detect whether hand cleaning agent has been taken (e.g., in effect determining whether or not there is partial compliance).

Figure 31C:
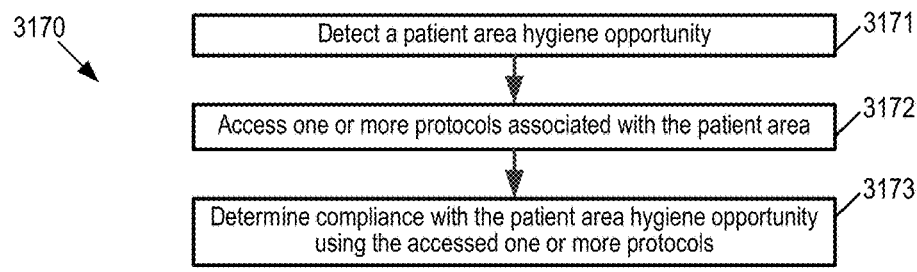
FIG. 31C is a flow diagram for detecting a patient area hygiene opportunity, accessing the protocol(s) associated with the patient area, and determining compliance with the patient area hygiene opportunity using the accessed protocol(s).

FIG. 31C is a flow diagram 3170 for detecting a patient area hygiene opportunity, accessing the protocol(s) associated with the patient area, and determining compliance with the patient area hygiene opportunity using the accessed protocol(s). At 3172, a patient area hygiene opportunity (which is associated with a patient area) is detected. As discussed above, there are a variety of ways in which to detect a patient area hygiene opportunity, such as by tracking a healthcare worker in or about the patient area.

At 3172, one or more protocols associated with the patient area are accessed. As discussed above, the patient area may include one or more protocols, such as one or more HH protocol and/or PPE protocol. Further, the one or more protocols may be predetermined and unchanging (e.g., the same protocol(s) throughout the entire hospital; the mobile electronic device may have prestored therein the same protocol(s); the stationary controller). Alternatively, the one or more protocols may change from one patient area to the next. In this regard, the one or more protocols correlated to the specific patient area subject to the patient area hygiene opportunity may be dynamically determined (e.g., at the server level; at the patient area level; at the server level and the patient area level; by one, some, or all of: the backend server (storing the protocol(s) correlated to the specific patient area); the stationary controller positioned in the specific patient area; or the mobile electronic device in or about the specific patient area). At 3173, compliance is determined for the patient area hygiene opportunity using the accessed one or more protocols.

Figure 32:
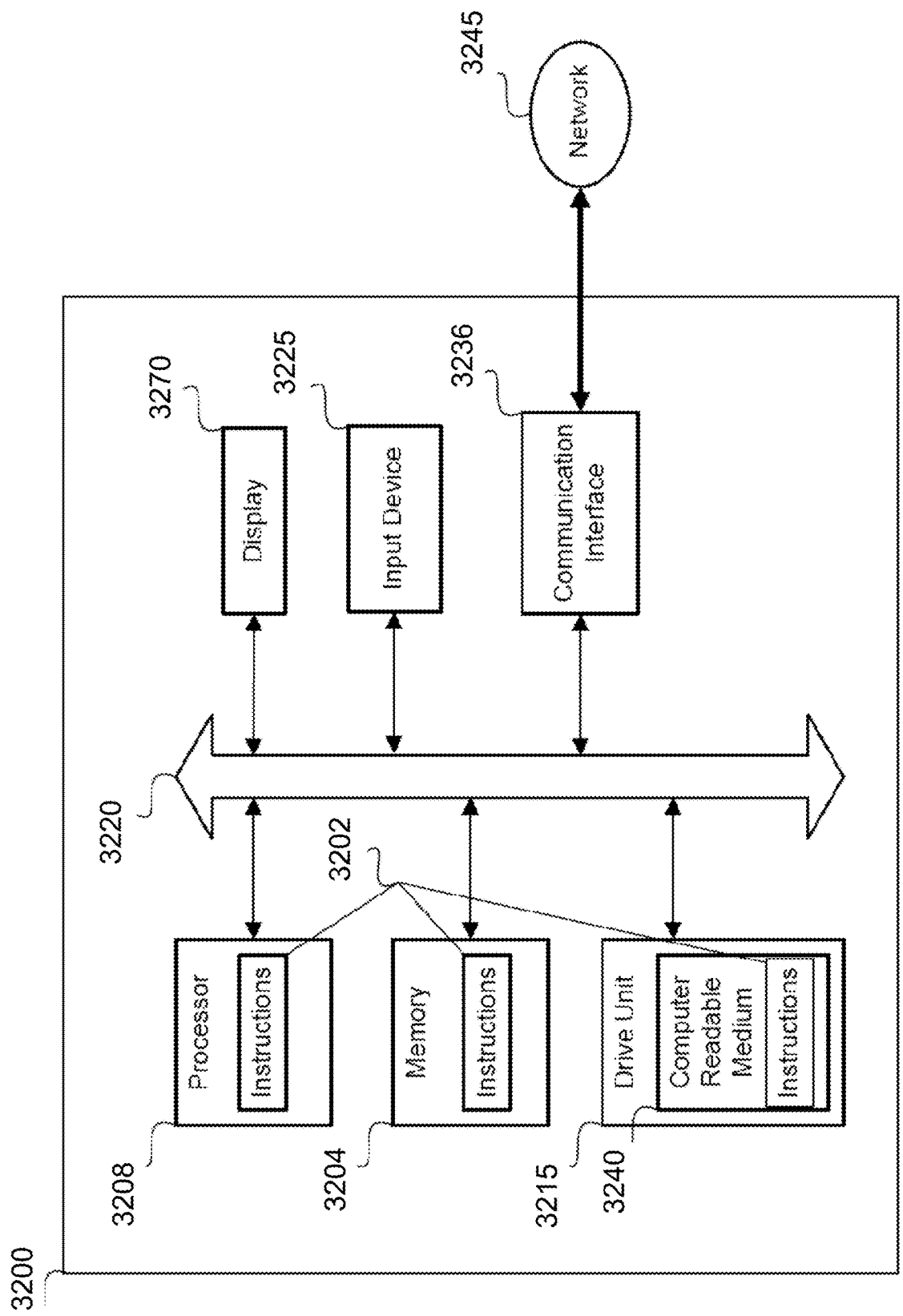
FIG. 32 is a general computer system, programmable to be a specific computer system, which may represent any of the computing devices referenced herein.

FIG. 32 is a general computer system 3200, programmable to be a specific computer system, which may represent any of the computing devices referenced herein, such as the wristband, the stationary controller, or the back-end. The computer system 3200 may include an ordered listing of a set of instructions 3202 that may be executed to cause the computer system 3200 to perform any one or more of the methods or computer-based functions disclosed herein. The computer system 3200 can operate as a stand-alone device or can be connected, e.g., using the network 3245, to other computer systems or peripheral devices.

In a networked deployment, the computer system 3200 can operate in the capacity of a server or as a client-user computer in a server-client user network environment, or as a peer computer system in a peer-to-peer (or distributed) network environment. The computer system 3200 can also be implemented as or incorporated into various devices, such as a personal computer or a mobile computing device capable of executing a set of instructions 3202 that specify actions to be taken by that machine, including and not limited to, accessing the Internet or Web through any form of browser. Further, each of the systems described can include any collection of sub-systems that individually or jointly execute a set, or multiple sets, of instructions to perform one or more computer functions.

The computer system 3200 can include a memory 3204 on a bus 3220 for communicating information. Code operable to cause the computer system to perform any of the acts or operations described herein can be stored in the memory 3204. The memory 3204 can be a random-access memory, read-only memory, programmable memory, hard disk drive or any other type of volatile or non-volatile memory or storage device.

The computer system 3200 can include a processor 3208, such as a central processing unit (CPU) and/or a graphics processing unit (GPU). In one implementation, one example of a processor is a controller. Further, one example of a controller is a microcontroller. The processor 3208 can include one or more general processors, digital signal processors, application specific integrated circuits, field programmable gate arrays, digital circuits, optical circuits, analog circuits, combinations thereof, or other now known or later-developed devices for analyzing and processing data. The processor 3208 can implement the set of instructions 3202 or other software program, such as manually programmed or computer-generated code for implementing logical functions. The logical function or any system element described can, among other functions, process and convert an analog data source such as an analog electrical, audio, or video signal, or a combination thereof, to a digital data source for audio-visual purposes or other digital processing purposes such as for compatibility for computer processing.

The computer system 3200 can also include a disk or optical drive unit 3215. The disk drive unit 3215 can include a computer-readable medium 3240 in which one or more sets of instructions 3202, e.g., software, can be embedded. Further, the instructions 3202 can perform one or more of the operations as described herein. The instructions 3202 can reside completely, or at least partially, within the memory 3204 or within the processor 3208 during execution by the computer system 3200.

The memory 3204 and the processor 3208 also can include computer-readable media as discussed above. A "computer-readable medium," "computer-readable storage medium," "machine readable medium," "propagated-signal medium," or "signal-bearing medium" can include any device that has, stores, communicates, propagates, or transports software for use by or in connection with an instruction executable system, apparatus, or device. The machine-readable medium can selectively be, but not limited to, an electronic, magnetic, optical, electromagnetic, infrared, or semiconductor system, apparatus, device, or propagation medium.

Additionally, the computer system 3200 can include an input device 3225, such as a keyboard or mouse, configured for a user to interact with any of the components of system 3200. It can further include a display 3270, such as a liquid crystal display (LCD), a cathode ray tube (CRT), or any other display suitable for conveying information. The display 3270 can act as an interface for the user to see the functioning of the processor 3208, or specifically as an interface with the software stored in the memory 3204 or the disk drive unit 3215.

The computer system 3200 can include a communication interface 3236 that enables communications via the communications network 3245. The network 3245 can include wired networks, wireless networks, or combinations thereof. The communication interface 3236 network can enable communications via any number of communication standards, such as 802.11, 802.17, 802.20, WiMAX, 802.15.4, cellular telephone standards, or other communication standards, as discussed above. Simply because one of these standards is listed does not mean any one is preferred, as any number of these standards can never actually be adopted in a commercial product.

Block diagrams of different aspects of the system, including FIGS. 1A-5H, 13A, 26A-C, 28A-B, and 29 may be implemented using the computer functionality disclosed in FIG. 32. Further, the flow diagrams, such as those illustrated in FIGS. 5I-6D and 14-20A-F, 22A-B, 25A-D, 27A-C, 30A-C, and 31, may use computer readable instructions that are executed by one or more processors in order to implement the functionality disclosed.

The present disclosure contemplates a computer-readable medium that includes instructions or receives and executes instructions responsive to a propagated signal, so that a device connected to a network can communicate voice, video, audio, images or any other data over the network. Further, the instructions can be transmitted or received over the network via a communication interface. The communication interface can be a part of the processor or can be a separate component. The communication interface can be created in software or can be a physical connection in hardware. The communication interface can be configured to connect with a network, external media, the display, or any other components in system, or combinations thereof. The connection with the network can be a physical connection, such as a wired Ethernet connection or can be established wirelessly as discussed below. In the case of a service provider server, the service provider server can communicate with users through the communication interface.

The computer-readable medium can be a single medium, or the computer-readable medium can be a single medium or multiple media, such as a centralized or distributed database, or associated caches and servers that store one or more sets of instructions. The term "computer-readable medium" can also include any medium that can be capable of storing, encoding or carrying a set of instructions for execution by a processor or that can cause a computer system to perform any one or more of the methods or operations disclosed herein.

The computer-readable medium can include a solid-state memory such as a memory card or other package that houses one or more non-volatile read-only memories. The computer-readable medium also can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an email or other self-contained information archive or set of archives can be considered a distribution medium that can be a tangible storage medium. The computer-readable medium is preferably a tangible storage medium. Accordingly, the disclosure can be considered to include any one or more of a computer-readable medium or a distribution medium and other equivalents and successor media, in which data or instructions can be stored.

Alternatively, or in addition, dedicated hardware implementations, such as application specific integrated circuits, programmable logic arrays and other hardware devices, can be constructed to implement one or more of the methods described herein. Applications that can include the apparatus and systems of various embodiments can broadly include a variety of electronic and computer systems. One or more embodiments described herein can implement functions using two or more specific interconnected hardware modules or devices with related control and data signals that can be communicated between and through the modules, or as portions of an application-specific integrated circuit. Accordingly, the present system can encompass software, firmware, and hardware implementations.

The methods described herein may be implemented by software programs executable by a computer system. Further, implementations may include distributed processing, component/object distributed processing, and parallel processing. Alternatively, or in addition, virtual computer system processing may be constructed to implement one or more of the methods or functionality as described herein.

Although components and functions are described that may be implemented in particular embodiments with reference to particular standards and protocols, the components and functions are not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations described herein are intended to provide a general understanding of the structure of various embodiments. The illustrations are not intended to serve as a complete description of all of the elements and features of apparatus, processors, and systems that utilize the structures or methods described herein. Many other embodiments can be apparent to those of skill in the art upon reviewing the disclosure. Other embodiments can be utilized and derived from the disclosure, such that structural and logical substitutions and changes can be made without departing from the scope of the disclosure. Additionally, the illustrations are merely representational and cannot be drawn to scale. Certain proportions within the illustrations may be exaggerated, while other proportions may be minimized. Accordingly, the disclosure and the figures are to be regarded as illustrative rather than restrictive.

In another implementation, a mobile wearable electronic device is disclosed. The mobile wearable electronic device comprises: at least one mechanical structure configured for attachment onto at least a part of a body of a person; communication functionality configured to communicate with a hand hygiene and/or PPE external electronic device; one or more motion sensors configured to generate sensor data indicative of movement of the person; a radio frequency identification (RFID) tag configured to communicate with an external RFID reader; and a controller in communication with the communication functionality and the one or more sensors, the controller configured to: store the sensor data generated by the one or more motion sensors in order to determine compliance or non-compliance of the movement of the person with regard to a hand hygiene event and/or PPE event.

The mobile wearable electronic device further includes wherein the controller is further configured to: determine, based on the sensor data, the compliance or the non-compliance of the movement of the person with regard to the hand hygiene event and/or PPE event; and transmit the determination of the compliance or the non-compliance to an external device.

The mobile wearable electronic device further includes wherein the mobile wearable electronic device is configured for wear on a wrist of a person.

In another implementation, a mobile wearable electronic device is disclosed. The mobile wearable electronic device comprises: at least one mechanical structure configured for attachment onto at least a part of a body of a person; communication functionality configured to communicate with one or more external devices regarding any one, any combination, or all of hand hygiene, PPE, and access control; one or more motion sensors configured to generate sensor data indicative of movement of the person (indicative of hand hygiene movements and/or PPE movements); an identification of the person; and a controller in communication with the communication functionality and the one or more sensors. The controller is configured to: determine, based on the sensor data generated by the one or more motion sensors, compliance or non-compliance of the movement of the person with regard to a hand hygiene event and/or PPE event; transmit, via the communication functionality, the determination of compliance or non-compliance of the movement of the person with regard to the hand hygiene event and/or PPE event; and transmit, via the communication functionality, the identification of the person to an access control device.

The mobile wearable electronic device further includes wherein the mobile wearable electronic device is a wristband.

The mobile wearable electronic device further includes wherein the controller is configured to transmit the determination of compliance or non-compliance and the identification of the person in a single communication to an external device.

The mobile wearable electronic device further includes wherein the controller is configured to transmit the determination of compliance or non-compliance and the identification of the person in separate communications.

In another implementation, a mobile wearable electronic device is disclosed. The mobile wearable electronic device comprises: at least one mechanical structure configured for attachment onto at least a part of a body of a person; communication functionality configured to communicate with one or more external devices regarding any one, any combination, or all of hand hygiene, PPE and access control; one or more motion sensors configured to generate sensor data indicative of movement of the person (indicative of hand hygiene movements and/or PPE movements); an identification of the person; and a controller in communication with the communication functionality and the one or more sensors, the controller configured to: determine, based on the sensor data generated by the one or more motion sensors, compliance or non-compliance of the movement of the person with regard to a hand hygiene event and/or a PPE event; responsive to determining compliance of the movement of the person, transmit, via the communication functionality, the identification of the person to an access control device; and responsive to determining non-compliance of the movement of the person, do not transmit the identification of the person to the access control device.

The mobile wearable electronic device further includes wherein the mobile wearable electronic device is a wristband electronic device.

In another implementation, a system for instructing hand hygiene and/or PPE is disclosed. The system comprises: a mobile wristband electronic device comprising: a mechanical structure configured for attachment onto a wrist of a user; communication functionality configured to communicate with an electronic instruction display system; one or more motion sensors configured to generate sensor data indicative of user hand motions and/or user PPE motions; and a controller in the mechanical structure and in communication with the communication functionality and the one or more sensors, the controller configured to: responsive to communication with the electronic instruction display system, store sensor data generated by the one or more motion sensors. The system also includes the electronic instruction display system comprising: communication functionality configured to communicate with an electronic instruction display system; a display to display a plurality of hand motions and/or PPE motions; and a controller in communication with the communication functionality and the display, the controller configured to: determine the plurality of hand motions and/or PPE motions; determine a respective time period for each of the plurality of hand motions and/or PPE motions; cause the plurality of hand motions and/or PPE motions to be displayed on the display for the respective times; receive the sensor data, the sensor data indicative of user hand motions and associated respective times for the user hand motions; analyze the sensor data in order to determine a difference between the plurality of hand motions and the user hand motions (and/or between the plurality of PPE motions and the user PPE motions), and a difference between the respective times and the associated respective times for the user hand motions (and/or user PPE motions); and output via the display an indication of the difference between the plurality of hand motions and the user hand motions (and/or between the plurality of PPE motions and the user PPE motions), and a difference between the respective times and the associated respective times for the user hand motions (and/or a difference between the respective times and the associated respective times for the user PPE motions).

The system further includes wherein the controller is configured to output the indication of the difference between the plurality of hand motions and/or PPE motions and the user hand motions by: initially displaying on the display a plurality of indicia; and based on the difference between the plurality of hand motions and the user hand motions (and/or between the plurality of PPE motions and the user PPE motions), removing a number of the plurality of indicia from the display, with a greater difference between the plurality of hand motions and the user hand motions resulting in less removal of the number of the plurality of indicia on the screen for display and with a lesser difference between the plurality of hand motions and the user hand motions resulting in a greater removal of the number of the plurality of indicia on the screen for display (and/or a greater difference between the plurality of PPE motions and the user PPE motions resulting in less removal of the number of the plurality of indicia on the screen for display and with a lesser difference between the plurality of PPE motions and the user PPE motions resulting in a greater removal of the number of the plurality of indicia on the screen for display).

The system further includes wherein the controller is further configured to: compare the difference between the plurality of hand motions and the user hand motions with a previous difference between previous plurality of hand motions and previous user hand motions in a previous training session; and output the comparison via the display. Alternatively, or in addition, the system further includes wherein the controller is further configured to: compare the difference between the plurality of PPE motions and the user PPE motions with a previous difference between previous plurality of PPE motions and previous user PPE motions in a previous training session; and output the comparison via the display.

The above disclosed subject matter is to be considered illustrative, and not restrictive, and the appended claims are intended to cover all such modifications, enhancements, and other embodiments, which fall within the true spirit and scope of the description. Thus, to the maximum extent allowed by law, the scope is to be determined by the broadest permissible interpretation of the following claims and their equivalents, and shall not be restricted or limited by the foregoing detailed description.

The following example embodiments of the invention are also disclosed:

Embodiment 1

A method comprising:
 identifying a personal protective equipment (PPE) event or a PPE opportunity based on interaction of a mobile electronic device and a stationary controller, the mobile electronic device configured to be associated with a person, the stationary controller configured to be associated with a patient area
 responsive to identifying the PPE event or the PPE opportunity, monitoring at least one aspect of the PPE event or the PPE opportunity; and
 determining, based on monitoring the at least one aspect of the PPE event or the PPE opportunity, one or both of compliance or non-compliance with regard to the PPE event or the PPE opportunity.

Embodiment 2

The method of embodiment 1
 wherein the stationary controller is associated with a dispenser configured to dispense hand cleaning agent, the dispenser proximate to an entrance of the patient area.

Embodiment 3

The method of embodiments 1 or 2:
 wherein the PPE comprises a first PPE and a second PPE;
 wherein the PPE opportunity comprises one of a PPE entrance opportunity or a PPE exit opportunity;
 wherein the PPE event comprises one of a PPE entrance event or a PPE exit event;
 wherein the PPE entrance event comprising a first movement associated with putting on the first PPE and a second movement associated with putting on the second PPE, the PPE exit event comprising a third movement associated with taking off the second PPE and a fourth movement associated with taking off the first PPE;
 wherein monitoring at least one aspect of the PPE event or the PPE opportunity comprises monitoring movements of the person; and
 wherein determining one or both of compliance or non-compliance with regard to the PPE event or the PPE opportunity comprises determining whether the movements of the person match one or both of the PPE entrance event or the PPE exit event.

Embodiment 4

The method of any of embodiments 1-3:
 wherein the PPE entrance event comprises a predetermined sequence of the first movement associated with putting on the first PPE being performed prior to the second movement associated with putting on the second PPE;
 wherein the PPE exit event comprises a predetermined sequence of the third movement associated with taking off the second PPE being performed prior to the fourth movement associated with taking off the first PPE; and
 wherein determining one or both of compliance or non-compliance with regard to the PPE event or the PPE opportunity comprises determining whether the movements of the person match the predetermined sequence of the first movement associated with putting on the first PPE being performed prior to the second movement associated with putting on the second PPE or match the predetermined sequence of the third movement associated with taking off the second PPE being performed prior to the fourth movement associated with taking off the first PPE.

Embodiment 5

The method of any of embodiments 1-4:
 wherein the PPE comprises a first PPE and gloves;
 wherein the PPE opportunity comprises an entrance PPE opportunity associated with entering the patient area and an exit PPE opportunity associated with exiting the patient area;
 wherein the PPE event comprises an entrance PPE event associated with entering the patient area and an exit PPE event associated with exiting the patient area;
 wherein the entrance PPE event includes a first PPE putting-on movement associated with putting on the first PPE and a glove putting-on movement associated with putting on the gloves;
 wherein the exit PPE event includes a first PPE taking-off movement associated with taking off the first PPE and a glove taking-off movement associated with taking off the gloves; and
 wherein determining one or both of compliance or non-compliance with regard to the PPE event or the PPE opportunity comprise:

determining whether the first PPE putting-on movement is performed prior to the glove putting-on movement; and determining whether the first PPE taking-off movement is performed after the glove taking-off movement.

Embodiment 6

The method of any of embodiments 1-5:

wherein responsive to determining a first proximity of the mobile electronic device with the stationary controller, determination of compliance of the entrance PPE opportunity is performed; and wherein, responsive to determining a second proximity of the mobile electronic device with the stationary controller, determination of compliance of the exit PPE opportunity is performed, wherein the second proximity is later in time than the first proximity.

Embodiment 7

The method of any of embodiments 1-6:
further comprising:
identifying a hand hygiene (HH) opportunity based on the interaction of the mobile electronic device and the stationary controller;
identifying a HH event;
responsive to identifying the HH opportunity, monitoring at least one aspect of the HH event; and
determining, based on monitoring the at least one aspect of the HH opportunity, one or both of compliance or non-compliance with regard to the HH opportunity.

Embodiment 8

The method of any of embodiments 1-7:
wherein monitoring the at least one aspect of the PPE event comprises monitoring at least one PPE action;
wherein monitoring the at least one aspect of the HH event comprises monitoring at least one HH action; and
further comprising monitoring a sequence of performing the at least one PPE action and the at least one HH action in order to determine whether the person complied or did not comply with a predetermined sequence of performing the at least one PPE action and the at least one HH action.

Embodiment 9

The method of any of embodiments 1-8:
wherein the stationary controller is programmable, based on a specific patient in the patient area, for a specific PPE action; and
further comprising receiving, by the mobile electronic device from the stationary controller, the specific PPE action responsive to identifying the PPE event;
wherein the mobile electronic device includes one or more motion sensors configured to generate motion data;
wherein, responsive to identifying only one of or both of the PPE opportunity or the PPE event, the mobile electronic device stores the motion data generated by the one or more motion sensors; and
wherein the mobile electronic device determines, based on the specific PPE action received from the stationary controller and the stored motion data, one or both of compliance or non-compliance with regard to the PPE opportunity.

Embodiment 10

The method of any of embodiments 1-9:
wherein the mobile electronic device comprises a wristband;
wherein the stationary controller is programmable with a designation of status;
comparing the designation of status with an indication of status as programmed in the mobile electronic device;
responsive to the comparison of the designation of status with the indication of status as programmed in the mobile electronic device, determining whether to output an instruction regarding one or both of the PPE event or the HH event; and
responsive to determining to output the instruction, outputting the instruction on one or both of the wristband or the stationary controller.

Embodiment 11

The method of any of embodiments 1-10:
wherein the designation of status comprises a trainee status; and
responsive to determining that the person, as indicated by the mobile electronic device, is a trainee, determining to output the instruction regarding one or both of the PPE event or the HH event.

Embodiment 12

The method of any of embodiments 1-11:
wherein the at least one aspect of the HH event comprises dispensing hand cleaning agent from a dispenser, the dispenser proximate to an entrance of the patient area; and
wherein responsive to identifying the HH opportunity, the stationary controller monitors whether the hand cleaning agent is dispensed from the dispenser.

Embodiment 13

The method of any of embodiments 1-12:
further comprising generating an output responsive to determining one or both of compliance or non-compliance of the PPE opportunity and responsive to determining one or both of compliance or non-compliance of the HH opportunity.

Embodiment 14

The method of any of embodiments 1-13:
wherein the output responsive to determining one or both of compliance or non-compliance of the PPE opportunity is different from the output responsive to determining one or both of compliance or non-compliance of the HH opportunity.

Embodiment 15

The method of any of embodiments 1-14:
wherein timing for generating the output responsive to determining one or both of compliance or non-compliance of the PPE opportunity is different from timing for generating the output responsive to determining non-compliance of the HH opportunity.

Embodiment 16

The method of any of embodiments 1-15:
  wherein the stationary controller is programmable, based on a location of the patient area, for a specific PPE action; and
  further comprising receiving, by the mobile electronic device from the stationary controller, the specific PPE action responsive to one or both of identifying the PPE opportunity or identifying the PPE event;
  wherein the mobile electronic device includes one or more motion sensors configured to generate motion data;
  wherein, responsive to one or both of identifying the PPE opportunity or identifying the PPE event, the mobile electronic device stores the motion data generated by the one or more motion sensors; and
  wherein the mobile electronic device determines, based on the specific PPE action received from the stationary controller and the stored motion data, one or both of compliance or non-compliance with regard to the PPE event.

Embodiment 17

A mobile wearable electronic device comprising:
  at least one mechanical structure configured for attachment onto at least a part of a body of a person;
  communication functionality configured to communicate with a stationary controller, the stationary controller configured to be associated with a patient area;
  one or more motion sensors configured to generate sensor data indicative of hand movement of the person; and
  a controller in the mechanical structure and in communication with the communication functionality and the one or more motion sensors, the controller configured to:
    responsive to communication with the stationary controller, store sensor data generated by the one or more motion sensors in order to determine compliance or non-compliance of the hand movement of the person with regard to one or both of a personal protective equipment (PPE) event or a PPE opportunity.

Embodiment 18

The method of embodiment 17:
  wherein the controller is further configured to generate an output responsive to one or both of compliance or non-compliance of the hand movement of the person with regard to one or both of the PPE event or the PPE opportunity.

Embodiment 19

The method of any of embodiments 17 or 18:
  further comprising a memory configured to store an indication that the person is a trainee; and
  wherein the controller is further configured to:
    determine, based on accessing the indication in the memory, whether the person is a trainee; and
    responsive to determining that the person is a trainee and responsive to the communication with the stationary controller, output an instruction to the person in order to comply with one or both of the PPE event or the PPE opportunity.

Embodiment 20

The method of any of embodiments 17-19:
  wherein the controller is further configured to determine, based on the stored sensor data, one or both of compliance or non-compliance with one or both of the PPE event or the PPE opportunity.

Embodiment 21

The method of any of embodiments 17-20:
  wherein the stationary controller is associated with a specific patient area that includes specific PPE indicators, the specific PPE indicators indicative of one or both of specific PPE movements or specific PPE for interacting with a specific patient in the specific patient area;
    further comprising a memory configured to:
      store a plurality of PPE indicators, each of the plurality of PPE indicators correlated to one or both of a respective PPE movement or a respective PPE;
      store, for each of the plurality of PPE indicators, respective movement markers, the respective movement markers indicative of the one or both of the respective PPE movement or the respective PPE;
    wherein the mobile wearable electronic device is configured to receive, from the stationary controller, the specific PPE indicators; and
    wherein the controller is further configured to check, based on the specific PPE indicators and using the stored movement markers, for the one or both of the specific PPE movements or the specific PPE for interacting with the specific patient in the specific patient area.

Embodiment 22

The method of any of embodiments 17-21:
  wherein the plurality of PPE indicators comprise a glove indicator, a mask indicator, a gown indicator, a protective eyewear indicator;
    wherein the memory is configured to store glove movements associated with the glove indicator, mask movements associated with the mask indicator, gown movements associated with the gown indicator, and protective eyewear movements associated with the protective eyewear indicator;
    wherein the controller is configured to receive, from the stationary controller, the specific PPE indicators for interacting with the specific patient, the specific PPE indicators consisting of a subset of the glove indicator, the mask indicator, the gown indicator, and the protective eyewear indicator;
    responsive to the controller receiving the specific PPE indicators for interacting with the specific patient, the controller is configured to:
      check, based on the specific PPE indicators and for less than all of the glove movements, the mask movements, the gown movements, and the protective eyewear movements, whether movements of the person comply with a subset of the glove movements, the mask movements, the gown movements, and the protective eyewear movements.

Embodiment 23

The method of any of embodiments 17-22:
  wherein the specific PPE indicators are indicative of a sequence of movements of the person for the subset of the glove movements, the mask movements, the gown movements, and the protective eyewear movements; and wherein the controller is configured to check whether the movements of the person comply with the subset of the glove movements, the mask movements, the gown movements, and the protective eyewear movements in the sequence.

Embodiment 24

The method of any of embodiments 17-23:
wherein a first stationary controller associated with a first patient area for a first patient, interaction with the first patient according to a first PPE protocol, the first PPE protocol comprising a first set of personal protective equipment for a healthcare provider to wear;
a second stationary controller associated with a second patient area for a second patient, interaction with the second patient according to a second PPE protocol, the second PPE protocol comprising a second set of personal protective equipment for the healthcare provider to wear, the second PPE protocol being different from the first PPE protocol such that the PPE for the healthcare provider to wear when interacting with the second patient is different from the PPE for the healthcare provider to wear when interacting with the first patient;
wherein the mobile wearable electronic device is configured to receive, from the first stationary controller, an indication of the first PPE protocol;
wherein, responsive to receiving the indication of the first PPE protocol, the controller is configured to check movements of the person to determine whether the person has complied with the first PPE protocol;
wherein the mobile wearable electronic device is configured to receive, from the second stationary controller, an indication of the second PPE protocol; and
wherein, responsive to receiving the indication of the second PPE protocol, the controller is configured to check the movements of the person to determine whether the person has complied with the second PPE protocol.

Embodiment 25

The method of any of embodiments 17-24:
wherein, responsive to communication with the stationary controller, the controller is further configured to determine, based on the stored sensor data, one or both of compliance or non-compliance with one or both of the PPE event or the PPE opportunity and with one or both of a hand hygiene (HH) event or a HH opportunity.

Embodiment 26

The method of any of embodiments 17-25:
wherein the mobile wearable electronic device is configured to receive one or both of an indication of PPE movements or an indication of a sequence of PPE movements;
wherein the controller is further configured to determine, based on the stored sensor data and the one or both of the indication of a set of PPE movements or the indication of a sequence of the PPE movements, one or both of compliance or non-compliance with one or both of the PPE event or the PPE opportunity; and
wherein the controller is further configured to determine, based on the stored sensor data and without reliance on any indication from the stationary controller of a set of HH movements or the HH movements, one or both of compliance or non-compliance with one or both of the HH event or the HH opportunity.

Embodiment 27

The method of any of embodiments 17-26:
wherein the controller is configured to determine whether the person is entering or exiting the patient area;
wherein, responsive to determining that the person is entering the patient area, the controller is configured to determine compliance based on determining whether the person complies with an entrance sequence of PPE movements and HH movements;
wherein, responsive to determining that the person is exiting the patient area, the controller is configured to determine compliance based on determining whether the person complies with an exit sequence of PPE movements and HH movements; and
wherein the entrance sequence of PPE movements and HH movements is different from the exit sequence of PPE movements and HH movements.

Embodiment 28

The method of any of embodiments 17-27:
wherein the controller is further configured to cause the stored sensor data to be transmitted to the stationary controller for determination by an electronic device, other than the mobile wearable electronic device, of compliance with one or both of the PPE event or the PPE opportunity.

Embodiment 29

A personal protective equipment (PPE) analytics and notification system comprising:
a plurality of electronic device wristbands, the plurality of electronic device wristbands each correlated to a healthcare provider and including one or more motion sensors configured to generate sensor data indicative of movement of a person during one or both of a PPE event or a PPE opportunity;
one or more databases configured to correlate PPE data with the healthcare providers, the PPE data being based on the sensor data and indicative of compliance or non-compliance with one or both of the PPE event or the PPE opportunity;
communication functionality configured to communicate with one or more electronic devices; and
a controller in communication with the one or more databases and the communication functionality, the controller configured to:
analyze the PPE data; and
responsive to the analysis of the PPE data, transmit an alert via the communication functionality to an electronic device.

Embodiment 30

The PPE analytics and notification system of embodiment 29:
wherein the plurality of electronic device wristbands are configured to analyze the sensor data in order to generate the PPE data; and
wherein the PPE data includes compliance, non-compliance, and partial compliance.

Embodiment 31

The PPE analytics and notification system of embodiments 29 or 30:
  wherein the controller is configured to analyze the PPE data by determining a specific healthcare provider suspected of cross-contamination amongst patients.

Embodiment 32

The PPE analytics and notification system of any of embodiments 29-31:
  wherein the controller is configured to analyze the PPE data by determining whether a rate of non-compliant PPE events is lower than a predetermined rate or a number of non-compliant PPE events is lower than a predetermined rate.

Embodiment 33

A mobile wearable electronic device comprising:
  at least one mechanical structure configured for attachment onto at least a part of a body of a person;
  communication functionality configured to communicate with a personal protective equipment (PPE) external electronic device;
  one or more motion sensors configured to generate sensor data indicative of PPE movement of the person;
  a radio frequency identification (RFID) tag configured to communicate with an external RFID reader; and
  a controller in communication with the communication functionality and the one or more sensors, the controller configured to:
    store the sensor data generated by the one or more motion sensors in order to determine compliance or non-compliance of the PPE movement of the person with one or both of a PPE event or a PPE opportunity.

Embodiment 34

The mobile wearable electronic device of embodiment 33:
  wherein the controller is further configured to:
  determine, based on the sensor data, the compliance or the non-compliance of the PPE movement of the person with one or both of the PPE event or the PPE opportunity; and
    transmit the determination of the compliance or the non-compliance to an external device.

Embodiment 35

The mobile wearable electronic device of embodiments 33 or 34:
  wherein the mobile wearable electronic device is configured for wear on a wrist of a person.

Embodiment 36

The mobile wearable electronic device of any of embodiments 33-35:
  wherein the one or more motion sensors are further configured to generate sensor data indicative of hand movement of the person;
  wherein the controller is further configured to:
    determine, based on the sensor data indicative of hand movement of the person, compliance or non-compliance of the hand movement of the person with one or both of a hand hygiene (HH) event or a HH opportunity;
    transmit, via the communication functionality, the determination of compliance or non-compliance of the hand movement of the person with one or both of the HH event or HH opportunity; and
    transmit, via the communication functionality, the identification of the person to an access control device.

Embodiment 37

The mobile wearable electronic device of any of embodiments 33-36:
  wherein the controller is configured to transmit the determination of compliance or non-compliance with one or both of the PPE event or the PPE opportunity, the determination of compliance or non-compliance with one or both of the HH event or the HH opportunity, and the identification of the person in a single communication to the external device.

Embodiment 38

The mobile wearable electronic device of any of embodiments 33-37:
  wherein the controller is configured to transmit the determination of compliance or non-compliance with one or both of the PPE event or the PPE opportunity, the determination of compliance or non-compliance with one or both of the HH event or HH opportunity, and the identification of the person in a separate communications.

Embodiment 39

A mobile wearable electronic device comprising:
  at least one mechanical structure configured for attachment onto at least a part of a body of a person;
  communication functionality configured to communicate with one or more external devices regarding personal protective equipment (PPE) and access control;
  one or more motion sensors configured to generate sensor data indicative of PPE movement of the person;
  an identification of the person; and
  a controller in communication with the communication functionality and the one or more sensors, the controller configured to:
    determine, based on the sensor data generated by the one or more motion sensors, compliance or non-compliance of the PPE movement of the person with one or both of a PPE event or a PPE opportunity;
    transmit, via the communication functionality, the determination of compliance or non-compliance of the PPE movement of the person with one or both of the PPE event or the PPE opportunity; and
    transmit, via the communication functionality, the identification of the person to an access control device.

Embodiment 40

The mobile wearable electronic device of embodiment 39:
  wherein the mobile wearable electronic device is a wristband.

Embodiment 41

The mobile wearable electronic device of embodiments 39 or 40:

wherein the controller is configured to transmit the determination of compliance or non-compliance and the identification of the person in a single communication to an external device.

Embodiment 42

The mobile wearable electronic device of any of embodiments 39-41:
wherein the controller is configured to transmit the determination of compliance or non-compliance and the identification of the person in separate communications.

Embodiment 43

The mobile wearable electronic device of any of embodiments 39-42:
wherein the one or more motion sensors are further configured to generate sensor data indicative of hand movement of the person;
wherein the controller is further configured to:
determine, based on the sensor data indicative of hand movement of the person, compliance or non-compliance of the hand movement of the person with one or both of a hand hygiene (HH) event or a HH opportunity;
transmit, via the communication functionality, the determination of compliance or non-compliance of the hand movement of the person with one or both of the HH event or HH opportunity; and
transmit, via the communication functionality, the identification of the person to an access control device.

Embodiment 44

The mobile wearable electronic device of any of embodiments 39-43:
wherein the controller is configured to transmit the determination of compliance or non-compliance with one or both of the PPE event or the PPE opportunity, the determination of compliance or non-compliance with one or both of the HH event or opportunity, and the identification of the person in a single communication to the external device.

Embodiment 45

The mobile wearable electronic device of any of embodiments 39-44:
wherein the controller is configured to transmit the determination of compliance or non-compliance with one or both of the PPE event or the PPE opportunity, the determination of compliance or non-compliance with one or both of the HH event or HH opportunity, and the identification of the person in a separate communications.

Embodiment 46

A mobile wearable electronic device comprising:
at least one mechanical structure configured for attachment onto at least a part of a body of a person;
communication functionality configured to communicate with one or more external devices regarding personal protective equipment (PPE) and access control;
one or more motion sensors configured to generate sensor data indicative of PPE movement of the person;
an identification of the person; and
a controller in communication with the communication functionality and the one or more sensors, the controller configured to:
determine, based on the sensor data generated by the one or more motion sensors, compliance or non-compliance of the PPE movement of the person with regard to one or both of a PPE event or a PPE opportunity;
responsive to determining compliance of the PPE movement of the person, transmit, via the communication functionality, the identification of the person to an access control device; and
responsive to determining non-compliance of the PPE movement of the person, do not transmit the identification of the person to the access control device.

Embodiment 47

The mobile wearable electronic device of embodiment 46:
wherein the mobile wearable electronic device is a wristband electronic device.

Embodiment 48

The mobile wearable electronic device of embodiments 46 or 47:
wherein the one or more motion sensors are further configured to generate sensor data indicative of hand movement of the person;
wherein the controller is further configured to:
determine, based on the sensor data indicative of hand movement of the person, compliance or non-compliance of the hand movement of the person with regard to one or both of a hand hygiene (HH) event or a HH opportunity;
responsive to determining compliance of the PPE movement of the person and compliance of the hand movement of the person, transmit, via the communication functionality, the identification of the person to an access control device; and
responsive to determining non-compliance of one or both of the PPE movement and the hand movement of the person, do not transmit the identification of the person to the access control device.

Embodiment 49

A system for instructing personal protective equipment (PPE), the system comprising:
a mobile wristband electronic device comprising:
a mechanical structure configured for attachment onto a wrist of a user;
communication functionality configured to communicate with an electronic instruction display system;
one or more motion sensors configured to generate sensor data indicative of user PPE motions; and
a controller in the mechanical structure and in communication with the communication functionality and the one or more sensors, the controller configured to:
responsive to communication with the electronic instruction display system, store sensor data generated by the one or more motion sensors,
the electronic instruction display system comprising:
communication functionality configured to communicate with an electronic instruction display system;

a display to display a plurality of PPE motions; and
a controller in communication with the communication functionality and the display, the controller configured to:
  determine the plurality of PPE motions;
  determine a respective time period for each of the plurality of PPE motions;
  cause the plurality of PPE motions to be displayed on the display for the respective times;
  receive the sensor data, the sensor data indicative of user PPE motions and associated respective times for the user PPE motions;
  analyze the sensor data in order to determine a difference between the plurality of PPE motions and the user PPE motions, and a difference between the respective times and the associated respective times for the user PPE motions; and
  output via the display an indication of the difference between the plurality of PPE motions and the user PPE motions, and a difference between the respective times and the associated respective times for the user PPE motions.

Embodiment 50

The system of embodiment 49:
  wherein the controller is configured to output the indication of the difference between the plurality of PPE motions and the user PPE motions by:
    initially displaying on the display a plurality of indicia; and
    based on the difference between the plurality of PPE motions and the user PPE motions, removing a number of the plurality of indicia from the display, with a greater difference between the plurality of PPE motions and the user PPE motions resulting in less removal of the number of the plurality of indicia on the screen for display and with a lesser difference between the plurality of PPE motions and the user PPE motions resulting in a greater removal of the number of the plurality of indicia on the screen for display.

Embodiment 51

The system of embodiments 49 or 50:
  wherein the controller is further configured to:
  compare the difference between the plurality of PPE motions and the user PPE motions with a previous difference between previous plurality of PPE motions and previous user PPE motions in a previous training session; and
    output the comparison via the display.

Embodiment 52

A mobile wearable electronic device comprising:
  at least one mechanical structure configured for attachment onto at least a part of a body of a person;
  one or more motion sensors configured to generate sensor data indicative of personal protective equipment (PPE) movement of the person;
  a radio frequency identification (RFID) tag configured to communicate with an external RFID reader; and
  a controller in communication with the communication functionality and the one or more sensors, the controller configured to:
    store the sensor data generated by the one or more motion sensors in order to determine compliance or non-compliance of the PPE movement of the person with one or both of a PPE event or a PPE opportunity.

Embodiment 53

The mobile wearable electronic device of embodiment 52:
  wherein the controller is further configured to:
    determine, based on the sensor data, the compliance or the non-compliance of the PPE movement of the person with one or both of the PPE event or the PPE opportunity; and
    transmit the determination of the compliance or the non-compliance to an external device.

Embodiment 54

The mobile wearable electronic device of embodiments 52 or 53:
  wherein the mobile wearable electronic device is configured for wear on a wrist of a person.

Embodiment 55

A computer-implemented method for determining compliance by a person with a patient area hygiene opportunity, the method comprising:
  identifying the patient area hygiene opportunity, the patient area hygiene opportunity indicative of an opportunity to interact with a patient in a patient area;
  responsive to identifying the hygiene opportunity:
    accessing a patient area hygiene protocol, the patient area hygiene protocol comprising one or more protocols for the person to follow in the patient area; and
    determining, based on the accessed patient area hygiene protocol, compliance or non-compliance with the patient area hygiene opportunity.

Embodiment 56

The method of embodiment 55:
  wherein the patient area hygiene opportunity comprises one or both of a patient area hand hygiene (HH) opportunity or a patient area personal protective equipment (PPE) opportunity;
  wherein the patient area hygiene protocol comprises a HH event or PPE event; and
  wherein determining, based on the accessed patient area hygiene protocol, compliance or non-compliance with the patient area hygiene opportunity comprises:
    determining whether there is one or both of a HH event or a PPE event that is sufficiently associated in time or in space with the one or both of the HH opportunity or the PPE opportunity;
    responsive to determining that the one or both of the HH event or the PPE event is sufficiently associated in time or in space with the one or both of the HH opportunity or the PPE opportunity, determining compliance with the one or both of the HH event or the PPE event; and
    responsive to determining that there is no HH event or PPE event that is sufficiently associated in time or in space with the one or both of the HH opportunity or the PPE opportunity, determining non-compliance for the one or both of the HH opportunity or the PPE opportunity.

Embodiment 57

The method of embodiments 55 or 56:
further comprising identifying the one or both of the HH opportunity or the PPE opportunity prior to detecting the one or both of the HH event or the PPE event.

Embodiment 58

The method of any of embodiments 55-57:
further comprising identifying the one or both of the HH opportunity or the PPE opportunity after detecting the one or both of the HH event or the PPE event.

Embodiment 59

The method of any of embodiments 55-58:
wherein determining whether there is one or both of the HH event or the PPE event that is sufficiently associated in time or in space with the one or both of the HH opportunity or the PPE opportunity comprises detecting whether at least one act associated with the HH event is within a time period of the one or both of the HH opportunity or the PPE opportunity.

Embodiment 60

The method of any of embodiments 55-59:
wherein the at least one act associated with the HH event comprises dispensing of hand cleaning agent from a dispenser associated with an area, the one or both of the HH opportunity or the PPE opportunity being associated with the area; and
wherein determining whether the at least one act associated with the HH event is within the time period of the one or both of the HH opportunity or the PPE opportunity comprises:
  detecting the dispensing of hand cleaning agent that is indicative of the HH event;
  determining whether a dispensing time at which the hand cleaning agent is dispensed from the dispenser is either within a first time period after an opportunity time at which the one or both of the HH opportunity or the PPE opportunity is identified or is within a second time period before the opportunity time;
  responsive to determining that the dispensing time is either within the first time period after the opportunity time or is within the second time period before the opportunity time, determining that the dispensing of the hand cleaning agent indicative of the HH event is sufficiently associated with the one or both of the HH opportunity or the PPE opportunity; and
  responsive to determining that the dispensing time is not within the first time period after the opportunity time and is not within the second time period before the opportunity time, determining that the dispensing of the hand cleaning agent indicative of the HH event is not sufficiently associated with the one or both of the HH opportunity or the PPE opportunity.

Embodiment 61

The method of any of embodiments 55-60:
wherein the first time period is different from the second time period.

Embodiment 62

The method of any of embodiments 55-61:
wherein one or both of the first time period or the second time period are predetermined.

Embodiment 63

The method of any of embodiments 55-62:
wherein one or both of the first time period or the second time period are dynamic.

Embodiment 64

The method of any of embodiments 55-63:
wherein the one or both of the first time period or the second time period are dynamic based on hygiene protocols to comply with in a patient area.

Embodiment 65

The method of any of embodiments 55-64:
wherein, responsive to determining that the area is associated with a HH protocol, a first value for the one or both of the first time period or the second time is selected;
responsive to determining that the area is associated with both the HH protocol and a PPE protocol, a second value for the one or both of the first time period or the second time is selected; and
wherein the second value is greater than the first value.

Embodiment 66

The method of any of embodiments 55-65:
wherein a third time period is less than the first time period; and
further comprising, responsive to determining that the dispensing time has not occurred before the opportunity time and has not occurred within the third time period, generating an output indicative to the person to take hand cleaning agent.

Embodiment 67

The method of any of embodiments 55-66:
further comprising identifying the one or both of the HH opportunity or the PPE opportunity based on at least one detected location relative to a designated area.

Embodiment 68

The method of any of embodiments 55-67:
wherein identifying the one or both of the HH opportunity or the PPE opportunity is based on detecting movement of the person relative to the designated area.

Embodiment 69

The method of any of embodiments 55-68:
wherein the designated area comprises a patient area; and
wherein detecting movement of the person relative to a designated area comprises detecting movement of the person either into or out of the patient area.

Embodiment 70

The method of any of embodiments 55-69:
wherein a mobile electronic device is associated with the person;
wherein the patient area includes at least two stationary controllers positioned in fixed relation in or about the patient area;
wherein the at least two stationary controllers each have at least one wireless communication zone; and
wherein the mobile electronic device detects the movement of the person either into or out of the patient area by determining a sequence that the mobile electronic device communicates with the at least one wireless communication zone for the at least two stationary controllers.

Embodiment 71

The method of any of embodiments 55-70:
wherein the patient area includes at least one sensor positioned in fixed relation to the patient area; and
wherein the movement of the person either into or out of the patient area is detected by analyzing sensor output generated by the at least one sensor.

Embodiment 72

The method of any of embodiments 55-71:
wherein a mobile electronic device is associated with the person and includes one or more motion sensors configured to generate motion data; and
further comprising, responsive to determining that there is a HH event, sending a communication to the mobile electronic device in order for the mobile electronic device to begin reviewing the motion data generated by the one or more motion sensor in order to determine compliance with the HH event.

Embodiment 73

The method of any of embodiments 55-72:
wherein dispensing hand cleaning agent is indicative of the HH event;
wherein a stationary controller determines whether a dispenser associated with a patient area has dispensed the hand cleaning agent; and
responsive to the stationary controller determining that the dispenser has dispensed hand cleaning agent, the stationary controller sends the communication to the mobile electronic device in order for the mobile electronic device to begin reviewing the sensor output generated by the one or more motion sensor in order to determine compliance with the HH event.

Embodiment 74

The method of any of embodiments 55-73:
wherein a mobile electronic device is associated with the person and includes one or more motion sensors configured to generate motion data; and
further comprising, responsive to determining that there is a PPE event, sending a communication to the mobile electronic device in order for the mobile electronic device to begin reviewing the motion data generated by the one or more motion sensor in order to determine compliance with the PPE event.

Embodiment 75

The method of any of embodiments 55-74:
wherein an electronic device is associated with a PPE repository and detects movement of the PPE repository;
wherein the movement of the PPE repository is indicative of the HH event; and
responsive to the electronic device detecting the movement of the PPE repository, a communication is sent to the mobile electronic device in order for the mobile electronic device to track sensor output generated by the one or more motion sensor in order to determine compliance with the PPE event.

Embodiment 76

The method of any of embodiments 55-75:
further comprising detecting the HH event;
further comprising:
determining that the HH event is not sufficiently associated in time or in space with any HH opportunity; and
responsive to determining that the HH event is not sufficiently associated in time or in space with any HH opportunity, taking one or more steps to differentiate the HH event not sufficiently associated in time or in space with any HH opportunity with other HH events sufficiently associated in time or in space with any HH opportunity.

Embodiment 77

The method of any of embodiments 55-76:
wherein the one or more steps comprise one, some, or all of:
determining not to analyze motion sensor data in order to determine compliance with the HH event;
determining not to transmit any compliance determination regarding the HH event to a backend server;
determining to transmit the compliance determination regarding the HH event to the backend server and associate an indication to the backend server that the HH event is not associated with any HH opportunity;
responsive to the backend server receiving the indication that the HH event is not associated with any HH opportunity, determining by the backend server not to record the compliance determination regarding the HH event for purposes of analytics associated with one or more healthcare providers; or
responsive to the backend server receiving the indication that the HH event is not associated with any HH opportunity, determining by the backend server to record the compliance determination regarding the HH event along with some indication that the HH event is not associated with any HH opportunity.

Embodiment 78

A method for tracking an asset, the method comprising:
sensing, using an asset tracker that is associated with, connected to or part of the asset, movement of part or all of an asset;
responsive to sensing the movement of part or all of the asset, waking up communication functionality of the asset tracker from a sleep state, wherein, in the sleep state, the asset tracker reduces power to the communication functionality of the asset tracker;

transmitting, using the communication functionality of the asset tracker, an asset tracker communication, the asset tracker communication comprising an asset tracker identification, the asset tracker identification indicative of one or both of the asset tracker or the asset;

responsive to transmitting the asset tracker communication, transmitting, by a mobile electronic device proximate to the asset tracker, a mobile electronic device communication comprising a mobile electronic device identification that is indicative one or both of a unique identifier for the mobile electronic device or of a person assigned to the mobile electronic device;

receiving, by an asset tracking server, one or more communications comprising the asset tracker identification and the mobile electronic device identification; and responsive to the asset tracker determining that the asset tracker has not been moved for a predetermined amount of time, transitioning, by the asset tracker, to the sleep state thereby disabling the communication functionality of the asset tracker.

Embodiment 79

The method of embodiment 78:
wherein the asset tracker communication from the asset tracker is received by a stationary controller, the stationary controller positioned in fixed relation to an area; and
responsive to the stationary controller receiving the asset tracker communication, the stationary controller communicates with the mobile electronic device in order to trigger the mobile electronic device to transmit the mobile electronic device communication.

Embodiment 80

The method of embodiments 78 or 79:
wherein the stationary controller receives the mobile electronic device communication indicative of the identity of the mobile electronic device; and
wherein the stationary controller transmits to the asset tracking server the one or more communications indicative of the asset tracker identification, the mobile electronic device identification, and a stationary controller identification, the stationary controller identification indicative of one or both of a unique identification of the stationary controller or of the area.

Embodiment 81

The method of any of embodiments 78-80:
further comprising moving the asset in proximity of a first stationary controller associated with a first area;
responsive to moving the asset proximate to the first stationary controller:
  the first stationary controller receives the communication from the asset tracker;
  responsive to the first stationary controller receiving the communication, the first stationary controller communicates with the mobile electronic device in order to trigger the mobile electronic device to transmit the mobile electronic device communication; and
  the first stationary controller transmits to the asset tracking server the one or more communications indicative of the asset tracker identification, the mobile electronic device identification, and a first stationary controller identification, the first stationary controller identification indicative of one or both of a unique identification of the first stationary controller or of the first area;

after moving the asset proximate to the first stationary controller wherein responsive to moving the asset proximate to a second stationary controller associated with a second area;
responsive to moving the asset proximate to the second stationary controller:
  the second stationary controller receives the communication from the asset tracker;
  responsive to the second stationary controller receiving the communication, the second stationary controller communicates with the mobile electronic device in order to trigger the mobile electronic device to transmit the mobile electronic device communication; and
  the second stationary controller transmits to the asset tracking server the one or more communications indicative of the asset tracker identification, the mobile electronic device identification, and a second stationary controller identification, the second stationary controller identification indicative of one or both of a unique identification of the second stationary controller or of the second area.

Embodiment 82

The method of any of embodiments 78-81:
wherein the communication from the asset tracker is received by the mobile electronic device; and
responsive to the mobile electronic device receiving the communication, the mobile electronic device:
  accesses location functionality resident on the mobile electronic device in order to determine a current location of the mobile electronic device; and
  transmits to the asset tracking server the one or more communications indicative of the asset tracker identification, the mobile electronic device identification, and the current location of the mobile electronic device.

Embodiment 83

The method of any of embodiments 78-82:
wherein a plurality of the communications from the asset tracker are received by the mobile electronic device responsive to movement of the asset tracker during a time period; and
responsive to the mobile electronic device receiving the plurality of communications, the mobile electronic device:
  determines respective times at which the mobile electronic device received the plurality of communications;
  determines, based on the respective times at which the mobile electronic device received the plurality of communications, the time period of movement of the asset tracker; and
  transmits to the asset tracking server the one or more communications indicative of the asset tracker identification and the determined time period movement of the asset tracker.

Embodiment 84

The method of any of embodiments 78-83:
wherein the asset tracker communicates bidirectionally with the mobile electronic device in order to obtain the mobile electronic device identification from the mobile electronic device; and

Embodiment 85

The method of any of embodiments 78-84:
wherein the asset tracker obtains a current location of the mobile electronic device from the mobile electronic device; and
wherein the asset tracker transmits to the asset tracking server the one or more communications comprising the asset tracker identification, the mobile electronic device identification, and the current location of the mobile electronic device.

Embodiment 86

The method of any of embodiments 78-85:
wherein the communication functionality of the asset tracker is uni-directional that sends a periodic beacon;
wherein the asset tracker includes a vibration sensor that generates movement data indicative of movement of the asset tracker;
wherein the asset tracker stops sending the periodic beacon after the asset tracker determines, based on the movement data, that the asset tracker has not moved for at least the predetermined amount of time; and
wherein in the sleep state, the vibration sensor remains active.

Embodiment 87

The method of any of embodiments 78-85:
wherein the asset tracker senses the movement of only part, but not all, of the asset.

Embodiment 88

An asset tracker comprising:
a movement sensor configured to generate movement data indicative of movement of the asset tracker;
communication functionality configured to transmit an asset tracker communication, the asset tracker communication comprising an asset tracker identification, the asset tracker identification indicative of one or both of the asset tracker or an asset associated with the asset tracker; and
a controller in communication with the movement sensor and the communication functionality, the controller configured to:
responsive to the movement data indicative of the movement of the asset tracker, waking up the communication functionality in order for the communication functionality to transmit the asset tracker communication;
monitoring the movement data in order to determine whether the movement data is indicative of no movement of the asset tracker for a predetermined amount of time; and
responsive to determining that the movement data is indicative of no movement of the asset tracker for at least the predetermined amount of time, transitioning to a sleep state by disabling the communication functionality of the asset tracker.

Embodiment 89

The asset tracker of embodiment 88:
wherein the communication functionality is configured to communicate bidirectionally with a mobile electronic device in order to obtain a mobile electronic device identification from the mobile electronic device; and
wherein the controller is configured to transmit to an asset tracking server one or more communications comprising the asset tracker identification and the mobile electronic device identification.

Embodiment 90

The asset tracker of embodiments 88 or 89:
wherein the controller is configured to receive a current location of the mobile electronic device from the mobile electronic device responsive to transmitting the asset tracker communication; and
wherein the one or more communications transmitted to the asset tracking server comprises the asset tracker identification, the mobile electronic device identification, and the current location of the mobile electronic device.

Embodiment 91

The asset tracker of any of embodiments 88-90:
wherein the communication functionality of the asset tracker is configured to send a uni-directional periodic beacon;
wherein the movement sensor comprises a vibration sensor that generates the movement data indicative of the movement of the asset tracker; and
wherein in the sleep state, the vibration sensor remains active.

Embodiment 92

A stationary controller positioned in fixed relation to an area, the stationary controller comprising:
communication functionality to wirelessly communicate with one or more external devices;
a memory configured to store a stationary controller identification, the stationary controller identification indicative of one or both of a unique identification of the stationary controller or of the area; and
a processor in communication with the communication functionality and the memory, the processor configured to:
receive an asset tracker communication from an asset tracker, the asset tracker configured to sense movement of part or all of an asset and send the asset tracker communication in response to the sensed movement;
responsive receiving the asset tracker communication, communicate with a mobile electronic device proximate to the stationary controller in order to trigger the mobile electronic device to transmit a mobile electronic device communication, the mobile electronic device communication comprising a mobile electronic device identification that is indicative one or both of a unique identifier for the mobile electronic device or of a person assigned to the mobile electronic device; and
transmit to an asset tracking server one or more communications indicative of the asset tracker identification, the mobile electronic device identification, and the stationary controller identification.

Embodiment 93

A dispenser monitoring device integrated or associated with a dispenser, the dispenser, responsive to a request for a
wherein the asset tracker transmits to the asset tracking server the one or more communications comprising the asset tracker identification and the mobile electronic device identification.

dispense of hand cleaning agent, is configured to dispense a premeasured amount of the hand cleaning agent, the dispenser monitoring device comprising:

hand cleaning agent dispensing detector configured to detect whether the dispenser has dispensed the premeasured amount of the hand cleaning agent;

at least one memory configured to store identification of one or both of the dispenser monitoring device or the dispenser;

communication functionality; and a processor in communication with the hand cleaning agent dispensing detector, the memory and the communication functionality, the processor configured to:
receive, from a server, a server communication indicative that the dispenser has been refilled;
responsive to receiving the server communication, reset an indication of a remaining amount of hand cleaning agent in the dispenser;
receive, from the hand cleaning agent dispensing detector, an indication that the dispenser has dispensed the premeasured amount of the hand cleaning agent;
responsive to receiving the indication, revise the indication of the remaining amount of hand cleaning agent in the dispenser;
determine whether the indication of the remaining amount of hand cleaning agent in the dispenser is less than a predetermined number; and
responsive to determining that the indication of the remaining amount of hand cleaning agent in the dispenser is less than the predetermined number, generate an output.

Embodiment 94

The dispenser monitoring device of embodiment 93:
wherein the output comprises a communication to the server, the communication indicative to the server that the remaining amount of hand cleaning agent in the dispenser is less than the predetermined number.

Embodiment 95

The dispenser monitoring device of embodiments 93 or 94:
further comprising a speaker or a light; and
wherein the output comprises an aural output generated by the speaker or a visual output generated by the light.

Embodiment 96

The dispenser monitoring device of any of embodiments 93-95:
wherein the indication of a remaining amount of hand cleaning agent in the dispenser comprises a counter indicative of a remaining number of dispenses from the dispenser; and
wherein revising the indication of the remaining amount of hand cleaning agent in the dispenser comprises decrementing the counter.

Embodiment 97

The dispenser monitoring device of any of embodiments 93-96:
wherein the processor is further configured to:
receive, via the farther-field communication from the server, a polling request, the polling request indicative to the dispenser monitoring device to transmit the indication of a remaining amount of the hand cleaning agent in the dispenser; and
responsive to receiving the polling request, transmit the indication of the remaining amount of the hand cleaning agent in the dispenser.

Embodiment 98

The dispenser monitoring device of any of embodiments 93-97:
wherein the communication functionality comprises near-field communication functionality with a mobile electronic device and for farther-field communication with the server;
wherein the processor further configured to:
receive a request from the mobile electronic device to transmit the identification of one or both of the dispenser monitoring device or the dispenser; and
responsive to receiving the request, transmit, via the near-field communication, the identification of one or both of the dispenser monitoring device or the dispenser; and
wherein the processor is configured to receive, via the farther-field communication from the server, the server communication responsive to the dispenser monitoring device transmitting the identification to the mobile electronic device, which in turn transmits a refill communication to the server, which in turn transmits the server communication.

Embodiment 99

The dispenser monitoring device of any of embodiments 93-98:
wherein the near-field communication comprises Bluetooth communication; and
wherein the farther-field communication comprises Wi-Fi communication.

Embodiment 100

A server configured to communicate with a plurality of dispenser monitoring devices, the dispenser monitoring devices integrated or associated with respective dispensers and configured to monitor an amount of hand cleaning agent in the respective dispensers, the server comprising:
communication functionality configured to communicate with a plurality of dispenser monitoring devices and one or more mobile electronic devices;
at least one memory;
at least one processor in communication with the communication functionality and the at least one memory, the processor configured to:
receive a refill communication from the one or more mobile electronic devices, the refill communication comprising an identification of one or both of a dispenser monitoring device or a respective dispenser, the refill communication indicative that the respective dispenser has been refilled with hand cleaning agent;
responsive to receiving the refill communication:
update the at least one memory to indicate that the hand cleaning agent in the respective dispenser has been refilled; and
send a reset communication to the dispenser monitoring device associated with the identification, the reset communication indicative to the dispenser monitoring device that the respective dispenser has been refilled with hand cleaning agent for purposes of the dispenser monitoring device to monitor the hand cleaning agent in the respective dispenser.

Embodiment 101

The server of embodiment 100:
wherein the identification is obtained by the one or more mobile electronic devices communicating via near-field communication with the dispenser monitoring device.

Embodiment 102

The server of embodiments 100 or 101:
wherein the processor is further configured to:
transmit a polling request to the dispenser monitoring device, the polling request indicative to the dispenser monitoring device to transmit an indication of a remaining amount of the hand cleaning agent in the dispenser; and
responsive to transmitting the polling request, receive from the dispenser monitoring device the indication of the remaining amount of the hand cleaning agent in the dispenser.

Embodiment 103

The server of any of embodiments 100-102:
wherein the identification of the one or both of a dispenser monitoring device or the respective dispenser is obtained by the one or more mobile electronic devices communicating wirelessly with the dispenser monitoring device.

Embodiment 104

A mobile electronic device comprising:
a display;
at least one memory;
communication functionality for near-field communication with a dispenser monitoring device and for farther-field communication with a server; and
a processor in communication with the display, the memory, and the communication functionality, the processor configured to:
output, via the display, a virtual element requesting a user to activate, the virtual element indicative that the user has refilled hand cleaning agent in the dispenser; and
responsive to the user activating the virtual element, transmit a refill communication to the server, the refill communication indicative to the server that the user has refilled hand cleaning agent in the dispenser and comprising an identification of one or both of a dispenser monitoring device or a dispenser, the refill communication in turn prompting the server to transmit a dispenser refill communication to one or both of the dispenser monitoring device or the dispenser, the dispenser refill communication indicative to the dispenser monitoring device or the dispenser to reset an indication of a remaining amount of hand cleaning agent in the dispenser.

Embodiment 105

The mobile device of embodiment 104:
wherein the virtual element comprises a virtual button.

Embodiment 106

The mobile device of embodiments 104 or 105:
wherein the processor is further configured to:
transmit a communication to the dispenser monitoring device requesting the identification of one or both of the dispenser monitoring device or the dispenser; and
responsive to transmitting the communication, receiving the identification of one or both of the dispenser monitoring device or the dispenser in order to include in the refill communication to the server.

Embodiment 107

The mobile device of any of embodiments 104-106:
wherein the processor is further configured to:
output, on the display, a virtual map indicative of one or more dispensers; and
receive input indicative of a location on the virtual map, the input being correlated to the identification of one or both of the dispenser monitoring device or the dispenser in order to include in the refill communication to the server.

Embodiment 108

An opportunity-based infection analysis system comprising:
at least one memory configured to store hygiene opportunity compliance data, the hygiene opportunity compliance data indicative of compliance by one or more healthcare providers of identified hygiene opportunities for interacting with patients in respective patient areas;
at least one output device; and
at least one processor in communication with the memory and the output device, the processor configured to:
access the hygiene opportunity compliance data;
identify some or all of the hygiene opportunity compliance data associated with a patient area during an identified period of time, the identified hygiene opportunity compliance data being segmented into at least two separate opportunities;
identify, based on the hygiene opportunity compliance data associated with the patient area during the identified period of time, the one or more healthcare providers that visited the patient area during the identified period of time;
analyze, for the one or more healthcare providers that visited the patient area during the identified period of time, identified hygiene opportunity compliance data separately for the at least two separate opportunities; and
generate an output based on the analysis.

Embodiment 109

The opportunity-based infection analysis system of embodiment 108:
wherein the opportunities comprise: (1) before touching a patient; (2) before clean/aseptic procedures; (3) after body fluid exposure/risk; (4) after touching a patient; and (5) after touching patient surroundings.

Embodiment 110

The opportunity-based infection analysis system of embodiments 108 or 109:
wherein (1) is identified based on tracking the healthcare provider's movement into the patient area; and
wherein (4) and (5) are identified based on tracking the healthcare provider's movement from the patient area.

Embodiment 111

The opportunity-based infection analysis system of any of embodiments 108-110:

wherein (2) and (3) are estimated based on the tracking of the healthcare provider's movement.

Embodiment 112

The opportunity-based infection analysis system of any of embodiments 108-111:
wherein (2) and (3) are estimated based on:
determining, based on the tracking of the healthcare provider's movement, a duration within the patient area;
determining a status of the healthcare provider; and
estimating a number of hygiene opportunities based on the duration of the healthcare provider within the patient area and the status of the healthcare provider.

Embodiment 113

The opportunity-based infection analysis system of any of embodiments 108-112:
wherein the status of the healthcare provider comprises one of a nurse, doctor, or hospital support staff.

Embodiment 114

The opportunity-based infection analysis system of any of embodiments 108-113:
wherein the at least two separate opportunities analyzed consist of (1), (2) and (3) in order to perform a root cause analysis to identify one or more healthcare workers responsible for an infection in the patient room.

Embodiment 115

The opportunity-based infection analysis system of any of embodiments 108-114:
wherein the identified period of time comprises a predetermined number of days after confirming infection in the patient room.

Embodiment 116

The opportunity-based infection analysis system of any of embodiments 108-115:
wherein the at least two separate opportunities analyzed comprise (1), (2) and (3) in order to perform a root cause analysis for an infection in the patient room.

Embodiment 117

The opportunity-based infection analysis system of any of embodiments 108-116:
wherein the at least two separate opportunities analyzed further comprise (4) or (5) of another patient area, with the opportunities for (4) and (5) of the another patient area are connected in time or space with the opportunities of (1), (2) or (3) in the patient area.

Embodiment 118

The opportunity-based infection analysis system of any of embodiments 108-117:
wherein the compliance data indicative of compliance for the opportunities of the another patient area are imputed to the compliance with the opportunities of (1), (2) or (3) in the patient area depending on whether within the opportunities of the another patient area are imputed to the compliance with the opportunities of (1), (2) or (3) are within a same time window.

Embodiment 119

The opportunity-based infection analysis system of any of embodiments 108-118:
wherein the time window is dynamic depending on the healthcare provider associated with the compliance data.

Embodiment 120

The opportunity-based infection analysis system of any of embodiments 108-119:
wherein the opportunity in the another patient area comprises exiting the another patient area;
wherein the opportunity in the patient area comprises entering the patient area; and
wherein compliance with hand hygiene upon exiting the another patient area is imputed to compliance with hand hygiene upon entering the patient area if the exiting of the another patient area and the entering of the patient area are within the same time window.

Embodiment 121

The opportunity-based infection analysis system of any of embodiments 108-120:
wherein the at least two separate opportunities analyzed comprise (1), (2) and (3) in order to perform a cross contamination analysis to identify one or more healthcare workers responsible for infections in a plurality of patient rooms.

Embodiment 122

The opportunity-based infection analysis system of any of embodiments 108-121:
wherein the processor is configured to analyze the identified hygiene opportunity compliance data separately for the at least two separate opportunities by:
identifying one or more patient areas subject to one or more infections;
identifying the opportunities connecting the one or more patient areas subject to the one or more infections with other patient areas; and
determining future infection risk to the other patient areas.

Embodiment 123

The opportunity-based infection analysis system of any of embodiments 108-122:
wherein the opportunities connected comprise exiting opportunities from the one or more patient areas subject to the one or more infections and entrance opportunities to the other patient areas.

Embodiment 124

The opportunity-based infection analysis system of any of embodiments 108-123:
wherein, responsive to determining that the compliance data associated with the entrance opportunities to the other patient areas indicate non-compliance with the identified hygiene opportunities, the processor is configured to connect the exiting opportunities from the one or more patient areas subject to the one or more infections and the entrance opportunities to the other patient areas.

Embodiment 125

A computer-implemented method for determining whether an identified hand hygiene opportunity is to be used for compliance statistics for a healthcare worker, the method comprising:

responsive to identifying the hand hygiene opportunity, accessing at least one, some or all of a status of the healthcare worker, a schedule of the healthcare worker, or a location of the healthcare worker;

determining, based on the at least one, some or all of a status of the healthcare worker, a schedule of the healthcare worker, or the location of the healthcare worker, whether the hand hygiene opportunity is to be used for compliance statistics for the healthcare worker; and responsive to determining that the hand hygiene opportunity is not to be used for compliance statistics for the healthcare worker, performing at least one action or failing to perform at least one action that results in the hand hygiene opportunity not being used for compliance statistics for the healthcare worker.

Embodiment 126

The method of embodiment 125:

wherein the status of the healthcare worker comprises a physical therapist;

wherein the schedule of the healthcare worker is indicative of performing physical therapy for a patient; and wherein determining whether the hand hygiene opportunity is to be used for compliance statistics for the healthcare worker is based on the status of the healthcare worker being the physical therapist and the schedule of the healthcare worker being indicative of performing physical therapy for the patient.

Embodiment 127

The method of embodiments 125 or 126:

wherein performing the at least one action or failing to perform the at least one action that results in the hand hygiene opportunity not being used for compliance statistics for the healthcare worker comprises a mobile electronic device associated with the healthcare worker determining not to perform a compliance determination for the hand hygiene opportunity.

Embodiment 128

The method of any of embodiments 125-127:

wherein performing the at least one action or failing to perform the at least one action that results in the hand hygiene opportunity not being used for compliance statistics for the healthcare worker comprises:

a mobile electronic device associated with the healthcare worker determining to perform a compliance determination for the hand hygiene opportunity; and the mobile electronic device determining not to transmit the compliance determination to a backend server tasked with compiling data used to perform the compliance statistics for the healthcare worker.

Embodiment 129

The method of any of embodiments 125-128:

wherein performing the at least one action or failing to perform the at least one action that results in the hand hygiene opportunity not being used for compliance statistics for the healthcare worker comprises:

a mobile electronic device associated with the healthcare worker determining to perform a compliance determination for the hand hygiene opportunity; and transmitting, by the mobile electronic device, one or more communications to a backend server, the one or more communications indicative of the compliance determination for the hand hygiene opportunity performed by the mobile electronic device and an indication that the compliance determination is not to be used for compliance statistics for the healthcare worker.

Embodiment 130

The method of any of embodiments 125-129:

wherein the indication that the compliance determination is not to be used for compliance statistics for the healthcare worker is indicative to the backend server not to use the compliance determination for the compliance statistics for the healthcare worker.

Embodiment 131

The method of any of embodiments 125-130:

wherein the location of the healthcare worker comprises a location associated with a contaminated area; and wherein determining that the hand hygiene opportunity is not to be used for compliance statistics for the healthcare worker is responsive to determining that the location of the healthcare worker is the location associated with the contaminated area.

Embodiment 132

A computer-implemented method for determining workload of one or more healthcare providers, the method comprising:

tracking movement or activity of the one or more healthcare providers;

identifying a time period between at least two opportunities for interacting with one or more patients; and determining, based on the time period, the workload for the one or more healthcare providers.

Embodiment 133

The method of embodiment 132:

wherein one of the at least two opportunities comprise an opportunity before touching a patient; and wherein another of the at least two opportunities comprise one or both of an opportunity after touching a patient or an opportunity after touching patient surroundings.

Embodiment 134

The method of embodiments 132 or 133:

wherein tracking movement or activity of the one or more healthcare providers comprising tracking movement of the healthcare provider into and out of a patient area; and wherein the time period is determined as being a period between tracking the movement of the healthcare provider into the patient area and tracking the movement of the healthcare provider out of the patient area.

Embodiment 135

A computer-implemented method for determining infection analysis or workload of one or more healthcare providers, the method comprising:
tracking movement or activity of the one or more healthcare providers;
analyzing entrance opportunities and exit opportunities of the one or more healthcare providers in order to determine durations of interacting with one or more patients;
determining, based on the durations, one or both of the infection analysis or the workload for the one or more healthcare providers.

Embodiment 136

A method of determining hand hygiene compliance in a kitchen area, the method comprising:
identifying a kitchen area hygiene opportunity, the kitchen area hygiene opportunity indicative of interaction of a person in the kitchen area;
responsive to identifying the kitchen area hygiene opportunity:
determining, based on the identified kitchen area hygiene opportunity, a time window in which to comply with the kitchen area hygiene opportunity; and
determining, based on reviewing motion data generated at least partly in the time window by the one or more motion sensors, whether the person complied with the kitchen area hand hygiene opportunity within the time window.

Embodiment 137

The method of embodiment 136:
wherein the kitchen area hygiene opportunity comprises a kitchen area hand hygiene opportunity;
wherein a mobile wearable electronic device, associated with the person, identifies the kitchen area hand hygiene opportunity;
wherein the mobile wearable electronic device determines the time window in which to comply with the kitchen area hygiene opportunity;
wherein the mobile wearable electronic device comprises one or more motion sensors configured to generate the motion data; and
further comprising transmitting, by the mobile wearable electronic device, an indication of whether the person complied with the kitchen area hand hygiene opportunity within the time window.

Embodiment 138

The method of embodiments 136 or 137:
wherein identifying the kitchen area hygiene opportunity is based on tracking movement of the person into or within the kitchen area.

Embodiment 139

The method of any of embodiments 136-138:
wherein tracking the movement of the person into or within the kitchen area is based on interaction between the mobile wearable electronic device and one or more stationary controllers positioned in or about the kitchen area.

Embodiment 140

The method of any of embodiments 136-139:
wherein identifying the kitchen area hygiene opportunity is based on the mobile wearable electronic device identifying whether the person is in, has moved to, or has moved away from a designated area within the kitchen area.

Embodiment 141

The method of any of embodiments 136-140:
wherein the designated area comprises one of a soiled designated area associated with soiled dishes, utensils, or equipment or an aquatic animals area associated with mollusks, shellfish, and crustaceans in display tanks.

Embodiment 142

The method of any of embodiments 136-141:
wherein identifying the kitchen area hygiene opportunity is based on the mobile wearable electronic device communicating with a machine in the kitchen area.

Embodiment 143

The method of any of embodiments 136-142:
further comprising generating a reminder to the person to comply with the kitchen area hygiene opportunity, with the reminder being generated either before whether the person complied with the kitchen area hand hygiene opportunity or after determining whether the person complied with the kitchen area hand hygiene opportunity.

Embodiment 144

The method of any of embodiments 136-143:
wherein the time window is after a time at which the kitchen area opportunity is identified, with the time window being dynamic or predetermined.

Embodiment 145

The method of any of embodiments 136-144:
wherein the time window is before a time at which the kitchen area opportunity is identified.

Embodiment 146

The method of any of embodiments 136-145:
wherein identifying the kitchen area hygiene opportunity comprises the mobile wearable electronic device receiving a signal from a device associated with a glove dispenser, the signal indicative that the person removed gloves from the glove dispenser; and
wherein the mobile wearable electronic device, responsive to receiving the signal, reviews the motion data generated prior to receiving the signal in order to determine compliance with the kitchen area hygiene opportunity.

Embodiment 147

A method comprising:
identifying a patient area hygiene event, the patient area hygiene event for following at least one of patient area personal protective equipment (PPE) protocol associated with a patient area or a patient area hand hygiene (HH) protocol associated with the patient area, the patient area PPE protocol selected from a plurality of PPE protocols, the patient area HH protocol selected from a first hand hygiene protocol or a second hand hygiene protocol;
  responsive to identifying the patient area hygiene event:
  determining at least one of the patient area PPE protocol or the patient area HH protocol associated with the patient area; and
  generating an output indicating the at least one of the patient area PPE protocol or the patient area HH protocol associated with the patient area.

Embodiment 148

The method of embodiment 147:
  wherein the first hand hygiene protocol comprises using hand sanitizer; and
  wherein the second hand hygiene protocol comprises using soap and water.

Embodiment 149

The method of embodiments 147 or 148:
  wherein the patient area hygiene event comprises following both the patient area PPE protocol associated with the patient area and the patient area HH protocol associated with the patient area.

Embodiment 150

The method of any of embodiments 147-149:
  further comprising determining whether a person is entering or exiting the patient area; and
  wherein a sequence for generating the output for the patient area PPE protocol and for the patient area HH protocol is dependent on whether the person is entering or exiting the patient area.

Embodiment 151

The method of any of embodiments 147-150:
  wherein, responsive to determining that the person is entering the patient area, the sequence for generating the output is for the patient area HH protocol and thereafter for the patient area PPE protocol; and
  responsive to determining that the person is exiting the patient area, the sequence for generating the output is for the patient area PPE protocol and thereafter for the patient area HH protocol.

Embodiment 152

The method of any of embodiments 147-151:
  wherein generating the output indicating the at least one of the patient area PPE protocol or the patient area HH protocol is responsive to identifying the patient area hygiene event and prior to determining compliance with the patient area hygiene event.

Embodiment 153

The method of any of embodiments 147-152:
  further comprising determining at least one of full compliance, partial compliance or no compliance with the at least one of the patient area PPE protocol or the patient area HH protocol; and
  wherein generating the output indicating the at least one of the patient area PPE protocol or the patient area HH protocol is responsive to determining partial compliance or no compliance with the patient area hygiene event.

Embodiment 154

The method of any of embodiments 147-153:
  wherein the patient area hygiene event comprises the patient area HH protocol, the patient area HH protocol comprising a minimum time for the person to rub hands; and
  wherein the output generated is for an additional time the person is to rub hands in order to meet the minimum time.

Embodiment 155

The method of any of embodiments 147-154:
  further comprising determining whether the person is entering or exiting the patient area;
  wherein the patient area hygiene event comprises the patient area PPE protocol, the patient area PPE protocol when entering the patient area is to put on a first PPE garment and then a second PPE garment in a first sequence, the patient area PPE protocol when exiting the patient area is to take off the second PPE garment and then the first PPE garment in a second sequence; and
  wherein responsive to determining that the person is entering the patient area:
  output an indication to put on the first PPE garment; and
  thereafter output an indication to put on the second PPE garment; and wherein responsive to determining that the person is exiting the patient area:
  output an indication to take off the second PPE garment; and
  thereafter output an indication to take off the first PPE garment.

Embodiment 156

The method of any of embodiments 147-155:
  wherein outputting the indication to put on the second PPE garment is performed only after sensing movement of the person indicating that the person has put on the first PPE garment; and
  wherein outputting the indication to take off the first PPE garment is performed only after sensing movement of the person indicating that the person has taken off the second PPE garment.

Embodiment 157

The method of any of embodiments 147-156:
  wherein a first output is generated to indicate actions to comply with the patient area PPE protocol; and
  wherein a second output is generated to indicate sufficiency or insufficiency of the actions to comply with the patient area PPE protocol.

Embodiment 158

The method of any of embodiments 147-157:
  wherein the patient area hygiene event is identified based on detecting at least one action associated with the at least one of the patient area PPE protocol or the patient area HH protocol.

Embodiment 159

The method of any of embodiments 147-158:
wherein the at least one action comprises taking hand cleaning agent from a dispenser associated with the patient area.

Embodiment 160

The method of any of embodiments 147-159:
wherein the at least one action comprises taking PPE from a PPE dispenser associated with the patient area.

Embodiment 161

The method of any of embodiments 147-160:
wherein the patient area hygiene event is identified based on interaction of a mobile electronic device and a stationary electronic device, the mobile electronic device associated with a person, the stationary electronic device associated with the patient area.

Embodiment 162

The method of any of embodiments 147-161:
further comprising: responsive to identifying the patient area hygiene event based on interaction of the mobile electronic device and the stationary electronic device, wirelessly receiving, by the mobile electronic device, an indication of the patient area PPE protocol.

Embodiment 163

The method of any of embodiments 147-162:
wherein the output is generated on the mobile electronic device.

Embodiment 164

The method of any of embodiments 147-163:
wherein the output is generated on the stationary electronic device.

Embodiment 165

The method of any of embodiments 147-164:
wherein the output is generated on both the mobile electronic device and the stationary electronic device.

Embodiment 166

The method of any of embodiments 147-165:
further comprising:
determining at least one aspect of the person; and
determining whether to generate the output based on the at least one aspect of the person.

Embodiment 167

The method of any of embodiments 147-166:
wherein the at least one aspect of the person comprises a status of the person.

Embodiment 168

The method of any of embodiments 147-167:
wherein the status of the person comprises one of a trainee or a visitor; and
wherein, responsive to determining that the status of the person as the trainee or the visitor, determining to generate the output.

Embodiment 169

The method of any of embodiments 147-168:
further comprising identifying a patient area opportunity, the patient area opportunity indicative of interaction with a patient in the patient area; and
wherein, responsive to identifying the patient area hygiene event and identifying the patient area opportunity, generating the output indicating the at least one of the patient area PPE protocol or the patient area HH protocol associated with the patient area.

Embodiment 170

A method comprising:
identifying a patient area hygiene event, the patient area hygiene event for following at least one of a patient area personal protective equipment (PPE) protocol associated with a patient area or a patient area hand hygiene (HH) protocol associated with the patient area;
identifying a patient area opportunity, the patient area opportunity indicative of interaction with a patient in the patient area;
responsive to identifying the patient area hygiene event and identifying the patient area opportunity:
accessing at least one of the patient area PPE protocol or the patient area HH protocol; and
generating an output indicating the at least one of the patient area PPE protocol or the patient area HH protocol.

Embodiment 171

The method of embodiment 170:
wherein identifying the patient area opportunity is based on tracking movement of a healthcare provider relative to the patient area.

Embodiment 172

The method of embodiments 170 or 171:
wherein tracking movement of the healthcare provider relative to the patient area comprises:
tracking movement of the healthcare provider either into or out of the patient area; and
responsive to tracking movement of the healthcare provider either into or out of the patient area, identifying the patient area opportunity.

Embodiment 173

The method of any of embodiments 170-172:
wherein the patient area hygiene event is identified based on detecting at least one action associated with the at least one of the patient area PPE protocol or the patient area HH protocol.

Embodiment 174

The method of any of embodiments 170-173:
wherein the at least one action comprises taking hand cleaning agent from a dispenser associated with the patient area.

Embodiment 175

The method of any of embodiments 170-174:
wherein the at least one action comprises taking PPE from a PPE dispenser associated with the patient area.

Embodiment 176

The method of any of embodiments 170-175:
wherein the patient area hygiene event is identified based on interaction of a mobile electronic device and a stationary electronic device, the mobile electronic device associated with a person, the stationary electronic device associated with the patient area.

Embodiment 177

The method of any of embodiments 170-176:
wherein accessing at least one of the patient area PPE protocol or the patient area HH protocol comprises: determining the at least one of the patient area PPE protocol or the patient area HH protocol associated with the patient area.

Embodiment 178

A method comprising:
identifying a patient area opportunity for a healthcare provider, the patient area opportunity indicative of interaction of the healthcare provider with a patient in or about a patient area;
responsive to identifying the patient area opportunity:
determining, based on a status of the healthcare provider or based on a dynamically changing healthcare protocol associated with the patient area based on a diagnosis of the patient in the patient area, whether to output a reminder indicative of the healthcare protocol;
responsive to determining to output the reminder indicative of the healthcare protocol, outputting the reminder to the healthcare provider indicative of the healthcare protocol; and
responsive to determining not to output the reminder indicative of the healthcare protocol, not outputting the reminder to the healthcare provider indicative of the healthcare protocol.

Embodiment 179

The method of embodiment 178:
wherein determining whether to output the reminder indicative of the healthcare protocol is based on whether the healthcare protocol associated with the patient area has changed.

Embodiment 180

The method of embodiments 178 or 179:
wherein the healthcare provider interacts with the patient area at a current time;
wherein the healthcare protocol comprises at least one of a patient area personal protective equipment (PPE) protocol associated with a patient area or a patient area hand hygiene (HH) protocol associated with the patient area;
further comprising determining whether at least one of the patient area PPE protocol or the patient area HH protocol associated with the patient area has changed within a predetermined time period prior to the current time; and
wherein responsive to determining that at least one of the patient area PPE protocol or the patient area HH protocol associated with the patient area has changed within a predetermined time period prior to the current time, determining to output the reminder indicative of the healthcare protocol.

Embodiment 181

The method of any of embodiments 178-180:
wherein determining whether to output the reminder indicative of the healthcare protocol is further based on a number of times that the healthcare provider has been notified of the at least one of the patient area PPE protocol or the patient area HH protocol associated with the patient area that has changed.

Embodiment 182

The method of any of embodiments 178-181:
wherein the patient area comprises a patient room;
wherein the at least one of the patient area PPE protocol or the patient area HH protocol associated with the patient area has changed based on a diagnosis for a patient assigned to the patient room; and
wherein the healthcare provider is provided a set number of times to remind the healthcare provider triggered upon detecting entry of the healthcare provider to the patient area.

Embodiment 183

The method of any of embodiments 178-182:
wherein responsive to determining that the healthcare provider is a trainee, determining to output the reminder indicative of the healthcare protocol.

Embodiment 184

An electronic device configured to determine whether to remind a healthcare worker regarding a healthcare protocol, the electronic device comprising:
at least one memory configured to store a patient area healthcare protocol associated with a patient area, the patient area healthcare protocol associated with the patient area dynamically changeable based on a diagnosis of a patient assigned to the patient area; and
at least one processor in communication with the memory, the processor configured to:
responsive to identifying a healthcare opportunity for a healthcare worker to interact with the patient associated with the patient area, accessing the patient area healthcare protocol associated with the patient area that is dynamically changeable; and
causing an output to be generated, the output indicative to the healthcare worker of the patient area healthcare protocol.

Embodiment 185

The electronic device of embodiment 184:
wherein the processor is further configured to determining whether the patient area healthcare protocol has changed within a predetermined amount of time; and
wherein the processor causes the output to be generated responsive to determining that the patient area healthcare protocol has changed within the predetermined amount of time.

Embodiment 186

The electronic device of embodiments 184 or 185:
wherein the processor is configured to modify the patient area healthcare protocol responsive to the diagnosis for the patient.

Embodiment 187

The electronic device of any of embodiments 184-186:
wherein the electronic device comprises a server; and
further comprising communication functionality configured to communicate with a separate electronic device, the separate electronic device configured to identify the healthcare opportunity for the healthcare worker to interact with the patient associated with the patient area.

Embodiment 188

The electronic device of any of embodiments 184-187:
wherein the separate electronic device is configured to identify the healthcare opportunity for the healthcare worker to interact with the patient associated with the patient area by tracking movement of the healthcare worker relative to the patient area.

The invention claimed is:

1. A method for identifying and performing a compliance determinations for a healthcare worker with hygiene opportunities, the method comprising:
   automatically detecting a specific hygiene opportunity, the specific hygiene opportunity indicative of interaction with a patient in a patient area for which compliance is to be monitored, the compliance requiring one or more hygiene actions;
   automatically detecting at least one action, the at least one action comprising at least one of the one or more hygiene actions;
   automatically determining, proximate to the patient, whether at least one criterion associated with the at least one action is within a criterion amount of automatically detecting the specific hygiene opportunity in order to determine whether there is sufficient connection between the at least one action and the specific hygiene opportunity;
   responsive to automatically determining that the at least one criterion associated with the at least one action is within the criterion amount of the specific hygiene opportunity, automatically using, proximate to the patient, the at least one action for the compliance determination for the specific hygiene opportunity; and
   transmitting, to a server, information for storage, the information indicative of the compliance determination and the specific hygiene opportunity.

2. The method of claim 1, wherein the at least one criterion associated with the at least one action comprises time; and
   wherein automatically determining whether the at least one criterion associated with the at least one action is within the criterion amount of the specific hygiene opportunity comprises determining whether the at least one action is performed within one or more times of detecting the specific hygiene opportunity.

3. The method of claim 1, wherein the at least one criterion associated with the at least one action comprises space; and
   wherein automatically determining whether the at least one criterion associated with the at least one action is within the criterion amount of the specific hygiene opportunity comprises determining whether the at least one action is performed within a predetermined space at which the specific hygiene opportunity is determined.

4. The method of claim 1, wherein determining compliance or non-compliance with the specific hygiene opportunity comprises:
   responsive to determining that the at least one action is performed within the criterion amount of the specific hygiene opportunity, determining compliance of performing the at least one action with regard to the specific hygiene opportunity; and
   responsive to determining that the at least one action is not performed within the criterion amount of the specific hygiene opportunity, determining non-compliance with regard to the specific hygiene opportunity.

5. The method of claim 1, wherein the specific hygiene opportunity comprises at least one of: before touching a patient; before clean/aseptic procedures; after body fluid exposure/risk; after touching a patient; and after touching patient surroundings.

6. The method of claim 1, wherein automatically detecting the specific hygiene opportunity comprises automatically monitoring at least one action of the healthcare worker in a patient area associated with the patient.

7. The method of claim 1, wherein automatically detecting the specific hygiene opportunity comprises automatically tracking movement of the healthcare worker relative to a patient area including into the patient area, out of the patient area, or within the patient area.

8. The method of claim 7, wherein the patient area comprises one or more electronic devices associated with the patient area; and
   wherein automatically tracking movement of the healthcare worker into or out of the patient area comprises the one or more electronic devices determining the movement into or out of the patient area.

9. The method of claim 8, wherein the patient area has a first stationary electronic device associated with an interior of the patient area and a second stationary electronic device associated with an entrance of the patient area; and
   wherein automatically tracking movement of the healthcare worker into or out of the patient area is based on both the first stationary electronic device and the second stationary electronic device.

10. The method of claim 9, wherein automatically tracking movement of the healthcare worker into or out of the patient area is based on a mobile electronic device associated with the healthcare worker communicating with both the first stationary electronic device and the second stationary electronic device.

11. The method of claim 9, wherein the specific hygiene opportunity comprises before touching a patient; and
    wherein automatically tracking movement of the healthcare worker comprises at least one of:

tracking the movement of the healthcare worker toward a defined border of the patient area;
tracking the movement crossing the defined border of the patient area; or
tracking the movement within the patient area after crossing the defined border of the patient area.

12. The method of claim 1, wherein the specific hygiene opportunity comprises a hand hygiene opportunity;
wherein the compliance with the hand hygiene opportunity comprises taking hand cleaning agent from a dispenser;
wherein the at least one action comprises taking the hand cleaning agent from the dispenser;
wherein automatically determining whether the at least one action is within the criterion amount of detecting the specific hygiene opportunity comprises determining whether taking the hand cleaning agent from the dispenser is performed within a first predetermined time before detecting the hand hygiene opportunity or within a second predetermined time after detecting the hand hygiene opportunity;
responsive to determining that the hand cleaning agent was taken from the dispenser within the first predetermined time before detecting the hand hygiene opportunity or within the second predetermined time after detecting the hand hygiene opportunity, determining compliance of hand cleaning agent from the dispenser with regard to the hand hygiene opportunity; and
responsive to determining that the hand cleaning agent was not taken from the dispenser within the first predetermined time before detecting the hand hygiene opportunity and was not taken from the dispenser within the second predetermined time after detecting the hand hygiene opportunity, determining non-compliance with regard to the hand hygiene opportunity.

13. The method of claim 1, wherein automatically detecting the specific hygiene opportunity is performed prior to automatically detecting the at least one action; and
further comprising determining whether to generate an output to remind the healthcare worker to perform the at least one action.

14. The method of claim 13, wherein the specific hygiene opportunity comprises a hand hygiene opportunity;
wherein the compliance with the hand hygiene opportunity comprises taking hand cleaning agent from a dispenser within a first predetermined time since detecting the hand hygiene opportunity;
wherein the at least one action comprises taking the hand cleaning agent from the dispenser; and
wherein determining whether to generate the output to remind the healthcare worker to perform the at least one action comprises:
determining whether the healthcare worker has failed to take hand cleaning agent with a second predetermined time since detecting the hand hygiene opportunity, wherein the second predetermined time is shorter than the first predetermined time; and
responsive to determining that the healthcare worker has failed to take hand cleaning agent with the second predetermined time since detecting the hand hygiene opportunity, generating the output.

15. The method of claim 1, wherein automatically detecting the specific hygiene opportunity is performed after automatically detecting the at least one action;
wherein the compliance with the specific hygiene opportunity comprises detecting the specific hygiene opportunity within a first predetermined time since performing the at least one action; and
wherein responsive to determining that the specific hygiene opportunity was not detected within the first predetermined time since performing the at least one action, the at least one action is not used for compliance for a later detected hygiene opportunity that was detected after the first predetermined time.

16. The method of claim 1, wherein the specific hygiene opportunity comprises a personal protective equipment hygiene opportunity.

17. The method of claim 1, further comprising accessing a patient area hygiene protocol, the patient area hygiene protocol comprising one or more protocols for the healthcare worker to follow in the patient area associated with the patient, the one or more protocols including the one or more hygiene actions; and
wherein determining compliance or non-compliance for the specific hygiene opportunity is based on the accessed patient area hygiene protocol.

18. The method of claim 17, wherein the at least one criterion associated with the at least one action comprises time;
wherein automatically determining whether the at least one criterion associated with the at least one action is within the criterion amount of the specific hygiene opportunity comprises determining whether the at least one action is performed within one or more predetermined times of detecting the specific hygiene opportunity; and
wherein the one or more predetermined times are dependent on the accessed patient area hygiene protocol.

19. The method of claim 18, wherein responsive to determining that the accessed patient area hygiene protocol comprises a hand hygiene protocol, a first value for the one or more predetermined times is selected; and
wherein responsive to determining that the accessed patient area hygiene protocol comprises a personal protective equipment protocol, a second value for the one or more predetermined times is selected; and
wherein the second value is greater than the first value.

20. The method of claim 18, wherein automatically determining whether the at least one action is performed within the one or more predetermined times of detecting the specific hygiene opportunity comprises determining whether the at least one action is within a predetermined time window, the predetermined time window defined around a time at which the specific hygiene opportunity is detected; and
responsive to determining that the at least one action is within the predetermined time window, using the at least one action to determine compliance with the specific hygiene opportunity.

21. The method of claim 1, wherein the at least one action comprises taking hand cleaning agent from a dispenser;
wherein a stationary controller is associated with the dispenser and tasked with detecting taking of hand cleaning agent from the dispenser; and
wherein automatically detecting the specific hygiene opportunity is based on a mobile electronic device associated with the healthcare worker communicating with the stationary controller associated with the dispenser.

22. The method of claim 1, wherein automatically detecting the at least one action is performed by a first device; and wherein automatically detecting the specific hygiene opportunity is determined by a second device that is separate from the first device.

23. The method of claim 22, wherein the at least one action comprises taking of hand cleaning agent from a dispenser;
 wherein the first device comprises a stationary controller that automatically detects the taking of hand cleaning agent from the dispenser; and
 wherein the second device comprises a mobile electronic device associated with the healthcare worker.

24. The method of claim 1, wherein automatically detecting the specific hygiene opportunity is determined based on a mobile electronic device associated with the healthcare worker interacting with at least two stationary controllers associated with the patient area.

* * * * *